(12) United States Patent
Brunstedt et al.

(10) Patent No.: US 7,622,290 B2
(45) Date of Patent: Nov. 24, 2009

(54) FUNGAL LIPOLYTIC ENZYMES, NUCLEIC ACIDS ENCODING, AND USES THEREOF

(75) Inventors: Janne Brunstedt, Roskilde (DK); Jørn Dalgaard Mikkelsen, Hvidovre (DK); Henrik Pedersen, Østbirk (DK); Jørn Borch Søe, Tilst (DK)

(73) Assignee: Danisco A/S, Copenhagen (DK)

( * ) Notice: Subject to any disclaimer, the term of this patent is extended or adjusted under 35 U.S.C. 154(b) by 0 days.

(21) Appl. No.: 11/519,734

(22) Filed: Sep. 12, 2006

(65) Prior Publication Data

US 2008/0038404 A1    Feb. 14, 2008

Related U.S. Application Data

(63) Continuation-in-part of application No. PCT/IB2005/000875, filed on Mar. 10, 2005.

(60) Provisional application No. 60/559,149, filed on Apr. 2, 2004.

(30) Foreign Application Priority Data

Mar. 12, 2004    (GB) ................ 0405637.0

(51) Int. Cl.
| | | |
|---|---|---|
| C12P 1/00 | (2006.01) |
| C12N 9/00 | (2006.01) |
| C12N 1/20 | (2006.01) |
| C12N 15/00 | (2006.01) |
| C07H 21/04 | (2006.01) |

(52) U.S. Cl. .................. 435/198; 435/41; 435/183; 435/252.3; 435/320.1; 536/23.2

(58) Field of Classification Search ............... 435/183, 435/198, 252.3, 320.1; 536/23.2
See application file for complete search history.

(56) References Cited

U.S. PATENT DOCUMENTS

| | | |
|---|---|---|
| 2,888,385 A | 5/1959 | Grandel |
| 3,260,606 A | 7/1966 | Azuma |
| 3,368,903 A | 2/1968 | Johnson |
| 3,520,702 A | 7/1970 | Menzi |
| 3,634,195 A | 1/1972 | Melaschouris |
| 3,652,397 A | 3/1972 | Pardun |
| 3,677,902 A | 7/1972 | Aunstrup |
| 3,852,260 A | 12/1974 | Knutsen |
| 3,973,042 A | 8/1976 | Kosikowski |
| 4,034,124 A | 7/1977 | Van Dam |
| 4,065,580 A | 12/1977 | Feldman |
| 4,160,848 A | 7/1979 | Vidal |
| 4,202,941 A | 5/1980 | Terada |
| 4,399,218 A | 8/1983 | Gauhl |
| 4,567,046 A | 1/1986 | Inoue |
| 4,683,202 A | 7/1987 | Mullis |
| 4,689,297 A | 8/1987 | Good |
| 4,707,291 A | 11/1987 | Thom |
| 4,707,364 A | 11/1987 | Barach |
| 4,708,876 A | 11/1987 | Yokoyama |
| 4,798,793 A | 1/1989 | Eigtved |
| 4,808,417 A | 2/1989 | Masuda |
| 4,810,414 A | 3/1989 | Huge-Jensen |
| 4,814,331 A | 3/1989 | Kerkenaar |
| 4,818,695 A | 4/1989 | Eigtved |
| 4,826,767 A | 5/1989 | Hansen |
| 4,865,866 A | 9/1989 | Moore |
| 4,904,483 A | 2/1990 | Christensen |
| 4,916,064 A | 4/1990 | Derez |
| 5,112,624 A | 5/1992 | Johna |
| 5,213,968 A | 5/1993 | Castle |
| 5,219,733 A | 6/1993 | Myojo |
| 5,219,744 A | 6/1993 | Kurashige |
| 5,232,846 A | 8/1993 | Takeda |
| 5,264,367 A | 11/1993 | Aalrust |
| 5,273,898 A | 12/1993 | Ishii |
| 5,288,619 A | 2/1994 | Brown |
| 5,290,694 A | 3/1994 | Nakanishi |
| 5,378,623 A | 1/1995 | Hattori |
| 5,523,237 A | 6/1996 | Budtz |
| 5,536,661 A | 7/1996 | Boel |
| 5,558,781 A | 9/1996 | Buchold |

(Continued)

FOREIGN PATENT DOCUMENTS

AR    249546    12/1996

(Continued)

OTHER PUBLICATIONS

Chica et al. Curr Opin Biotechnol. Aug. 2005;16(4):378-84.*

(Continued)

Primary Examiner—Christian L Fronda
(74) Attorney, Agent, or Firm—Frommer Lawrence & Haug LLP; Thomas J. Kowalski

(57) ABSTRACT

A fungal wild-type lipolytic enzyme having a higher ratio of activity on polar lipids compared with triglycerides, wherein the enzyme preferably has a phospholipid:triglyceride activity ratio of at least 4. Preferably, the lipolytic enzyme according to the present invention has a glycolipid:triglyceride hydrolyzing activity ratio of at least 1.5. In one embodiment, the fungal lipolytic enzyme according to the present invention comprises an amino acid sequence as shown in SEQ ID NO: 1 or SEQ ID No. 2 or SEQ ID No. 4 or SEQ ID No. 6 or an amino acid sequence which has at least 90% identity thereto. The present invention further encompasses a nucleic acid encoding a fungal lipolytic enzyme, which nucleic acid is selected from the group consisting of: (a) a nucleic acid comprising a nucleotide shown in SEQ ID No. 3, SEQ ID No. 5 or SEQ ID No. 7; (b) a nucleic acid which is related to the nucleotide sequence of SEQ ID No. 3, SEQ ID No. 5 or SEQ ID No. 7 by the degeneration of the genetic code; and (c) nucleic acid comprising a nucleotide sequence which has at least 90% identity with the nucleotide sequence shown in SEQ ID No. 3, SEQ ID No. 5 or SEQ ID No. 7.

13 Claims, 28 Drawing Sheets

U.S. PATENT DOCUMENTS

| | | | |
|---|---|---|---|
| 5,650,188 | A | 7/1997 | Gaubert |
| 5,677,160 | A | 10/1997 | Oester |
| 5,695,802 | A | 12/1997 | Van Den Ouweland |
| 5,763,383 | A | 6/1998 | Hashida |
| 5,766,912 | A | 6/1998 | Boel |
| 5,776,741 | A | 7/1998 | Pedersen |
| 5,814,501 | A | 9/1998 | Becker |
| 5,821,102 | A | 10/1998 | Berka |
| 5,827,719 | A | 10/1998 | Sandal |
| 5,830,736 | A | 11/1998 | Oxenboll |
| 5,834,280 | A | 11/1998 | Oxenboll |
| 5,856,163 | A | 1/1999 | Hashida |
| 5,863,759 | A | 1/1999 | Boel |
| 5,869,438 | A | 2/1999 | Svendsen |
| 5,874,558 | A | 2/1999 | Boel |
| 5,879,920 | A | 3/1999 | Dale |
| 5,892,013 | A | 4/1999 | Svendsen |
| 5,914,306 | A | 6/1999 | Svendsen |
| 5,916,619 | A | 6/1999 | Miyazaki |
| 5,919,746 | A | 7/1999 | Hirayama |
| 5,929,017 | A | 7/1999 | Gormsen |
| 5,965,384 | A | 10/1999 | Boel |
| 5,965,422 | A | 10/1999 | Loffler |
| 5,976,855 | A | 11/1999 | Svendsen |
| 5,989,599 | A | 11/1999 | Chmiel |
| 5,990,069 | A | 11/1999 | Andre |
| 6,001,586 | A | 12/1999 | Schellenberger |
| 6,001,640 | A | 12/1999 | Loeffler |
| 6,020,180 | A | 2/2000 | Svendsen |
| 6,066,482 | A | 5/2000 | Steffens |
| 6,074,863 | A | 6/2000 | Svendsen |
| 6,103,505 | A | 8/2000 | Clausen |
| 6,110,508 | A | 8/2000 | Olesen |
| 6,140,094 | A | 10/2000 | Loffler |
| 6,143,543 | A | 11/2000 | Michelsen |
| 6,143,545 | A | 11/2000 | Clausen |
| 6,146,869 | A | 11/2000 | Harris |
| 6,156,548 | A | 12/2000 | Christensen |
| 6,180,406 | B1 | 1/2001 | Stemmer |
| 6,254,645 | B1 | 7/2001 | Kellis |
| 6,344,328 | B1 | 2/2002 | Short |
| 6,350,604 | B1 | 2/2002 | Hirayama |
| 6,358,543 | B1 | 3/2002 | Soe |
| 6,361,974 | B1 | 3/2002 | Short |
| 6,365,204 | B1 | 4/2002 | Spendler |
| 6,432,898 | B1 | 8/2002 | Rey |
| 6,495,357 | B1 | 12/2002 | Fuglsang |
| 6,506,588 | B2 | 1/2003 | Tsutsumi |
| 6,509,182 | B2 | 1/2003 | Tsutsumi |
| 6,511,837 | B2 | 1/2003 | Tsutsumi |
| 6,514,739 | B1 | 2/2003 | Udagawa |
| 6,558,715 | B1 | 5/2003 | Rey |
| 6,582,942 | B1 | 6/2003 | Christensen |
| 6,624,129 | B1 | 9/2003 | Borch |
| 6,645,749 | B2 | 11/2003 | Vind |
| 6,682,922 | B2 | 1/2004 | Berka |
| 6,686,189 | B2 | 2/2004 | Rey |
| 6,726,942 | B2 | 4/2004 | Soe et al. |
| 6,730,346 | B2 | 5/2004 | Rey |
| 6,815,190 | B1 | 11/2004 | Abo |
| 6,852,346 | B2 | 2/2005 | Soe |
| 6,936,289 | B2 | 8/2005 | Olsen et al. |
| 6,967,035 | B2 | 11/2005 | Bojsen et al. |
| 7,226,771 | B2 | 6/2007 | Gramatikova et al. |
| 2002/0098536 | A1 | 7/2002 | Norinobu |
| 2002/0110854 | A1 | 8/2002 | Tsutsumi |
| 2002/0142434 | A1 | 10/2002 | Tsutsumi |
| 2002/0168746 | A1 | 11/2002 | Tsutsumi |
| 2003/0003561 | A1 | 1/2003 | Vind |
| 2003/0028923 | A1 | 2/2003 | Lardizabal |
| 2003/0040450 | A1 | 2/2003 | Rey |
| 2003/0074695 | A1 | 4/2003 | Farese |
| 2003/0100092 | A1 | 5/2003 | Berka |
| 2003/0119164 | A1 | 6/2003 | Udagawa |
| 2003/0148495 | A1 | 8/2003 | Hastrup |
| 2003/0180418 | A1 | 9/2003 | Rey |
| 2003/0185939 | A1 | 10/2003 | Nielsen |
| 2003/0215544 | A1 | 11/2003 | Nielsen |
| 2004/0005399 | A1 | 1/2004 | Chakrabarti |
| 2004/0235106 | A1 | 11/2004 | Kapeller-Libermann |
| 2005/0059130 | A1 | 3/2005 | Bojsen |
| 2005/0059131 | A1 | 3/2005 | Bisgard-Frantzen |
| 2005/0118697 | A1 | 6/2005 | Budolfsen |
| 2005/0142647 | A1 | 6/2005 | Wassell |

FOREIGN PATENT DOCUMENTS

| | | |
|---|---|---|
| AR | P000105426 | 10/2000 |
| AR | P040101441 | 4/2004 |
| AT | 110 768 | 8/1987 |
| AU | 570720 | 9/1984 |
| AU | 723031 | 4/1998 |
| AU | 754470 | 11/1999 |
| BR | 8404421-7 | 4/1984 |
| CA | 1270781 | 6/1990 |
| CA | 2012723 | 9/1990 |
| CA | 2134597 | 10/1994 |
| CA | 2224143 | 12/1996 |
| CA | 2 403 025 | 4/2004 |
| DE | 2817087 | 11/1978 |
| DE | 19620649 | 11/1997 |
| DE | 69129988 | 3/1999 |
| DE | 69330066 | 10/2001 |
| DE | 69527835 | 4/2003 |
| DE | 69528070 | 6/2003 |
| DE | 69904161 | 7/2003 |
| DE | 69716711 | 9/2003 |
| DE | 69531538 | 6/2004 |
| DE | 69819782 | 9/2004 |
| DK | 3106.200 | 1/1989 |
| DK | 157560 | 1/1990 |
| DK | PA0888/92 | 7/1992 |
| DK | 0217/94 | 2/1994 |
| DK | PA0830/95 | 7/1995 |
| DK | PA1096/95 | 9/1995 |
| DK | 152763 | 3/1998 |
| DK | PA0543/98 | 4/1998 |
| DK | PA199801572 | 11/1998 |
| DK | PA5677000 | 12/1998 |
| DK | PA199801604 | 12/1998 |
| DK | PA199901736 | 12/1999 |
| DK | PA200000989 | 6/2000 |
| DK | PA200000991 | 6/2000 |
| DK | PA200100285 | 2/2001 |
| DK | PA200100843 | 5/2001 |
| DK | EP659049 | 6/2001 |
| DK | EP0784674 | 11/2002 |
| DK | EP0869167 | 1/2003 |
| DK | EP1073339 | 1/2003 |
| DK | PA200300634 | 4/2003 |
| DK | EP0746608 | 10/2003 |
| DK | EP1042458 | 3/2004 |
| EP | 0064855 | 11/1982 |
| EP | 0010296 | 12/1982 |
| EP | 0109244 | 5/1984 |
| EP | 0130064 | 1/1985 |
| EP | 0140542 | 5/1985 |
| EP | 0167309 | 1/1986 |
| EP | 0171995 | 2/1986 |
| EP | 0205208 | 12/1986 |
| EP | 0206390 | 12/1986 |
| EP | 0257388 | 3/1988 |
| EP | 0260573 | 3/1988 |
| EP | 0334462 | 9/1989 |

| | | | | | | |
|---|---|---|---|---|---|---|
| EP | 0195311 | 6/1990 | | EP | 1 624 047 A1 | 2/2006 |
| EP | 0375102 | 6/1990 | | EP | 1 624 047 B1 | 10/2006 |
| EP | 0426211 | 5/1991 | | ES | 535608 | 9/1984 |
| EP | 0445692 | 9/1991 | | ES | 535602 | 10/1984 |
| EP | 0449375 | 10/1991 | | ES | 535609 | 3/1985 |
| EP | 0468731 | 1/1992 | | GB | 1086550 | 10/1967 |
| EP | 0513709 | 11/1992 | | GB | 1442418 | 7/1976 |
| EP | 0542351 | 5/1993 | | GB | 1577933 | 10/1980 |
| EP | 0558112 | 9/1993 | | GB | 2 264 429 | 9/1993 |
| EP | 0258068 | 11/1993 | | GB | 0028701.1 | 11/2000 |
| EP | 0238023 | 12/1993 | | GB | 2358784 | 8/2001 |
| EP | 0575133 | 12/1993 | | GB | 0301117.8 | 1/2003 |
| EP | 0580252 | 1/1994 | | GB | 0301118.6 | 1/2003 |
| EP | 0258068 | 8/1994 | | GB | 0301119.4 | 1/2003 |
| EP | 0622446 | 11/1994 | | GB | 0301120.2 | 1/2003 |
| EP | 0652289 | 5/1995 | | GB | 0301121.0 | 1/2003 |
| EP | 0654527 | 5/1995 | | GB | 0301122.8 | 1/2003 |
| EP | 0396162 | 9/1995 | | GB | 2379165 | 3/2003 |
| EP | 0585988 | 3/1996 | | GB | 2267033 | 11/2003 |
| EP | 0721981 | 7/1996 | | GB | 0330016.7 | 12/2003 |
| EP | 0776604 | 6/1997 | | JP | 59183881 | 4/1960 |
| EP | 0531104 | 8/1997 | | JP | 55131340 | 10/1980 |
| EP | 0808903 | 11/1997 | | JP | 60-78529 | 5/1985 |
| EP | 0682116 | 12/1997 | | JP | 60078529 | 5/1985 |
| EP | 0812910 | 12/1997 | | JP | 62118883 | 11/1985 |
| EP | 0305216 | 3/1998 | | JP | 63042691 | 8/1986 |
| EP | 0847701 | 6/1998 | | JP | 62061590 | 3/1987 |
| EP | 0548228 | 8/1998 | | JP | 62285749 | 12/1987 |
| EP | 0 869 167 | 10/1998 | | JP | 10203974 | 8/1988 |
| EP | 0702712 | 12/1998 | | JP | 1252294 | 10/1989 |
| EP | 0882797 | 12/1998 | | JP | 2-49593 | 2/1990 |
| EP | 0897667 | 2/1999 | | JP | 2-153997 | 6/1990 |
| EP | 0913092 | 5/1999 | | JP | 04075592 | 3/1992 |
| EP | 0913468 | 5/1999 | | JP | 6014773 | 3/1992 |
| EP | 0321811 | 12/1999 | | JP | 4121186 | 4/1992 |
| EP | 1131416 | 6/2000 | | JP | 15626492 | 6/1992 |
| EP | 0739985 | 11/2000 | | JP | 04200339 | 7/1992 |
| EP | 1057415 | 12/2000 | | JP | 4300839 | 10/1992 |
| EP | 1071734 | 1/2001 | | JP | 4327536 | 11/1992 |
| EP | 1073339 | 2/2001 | | JP | 5211852 | 8/1993 |
| EP | 0659049 | 3/2001 | | JP | 6345800 | 12/1994 |
| EP | 1103606 | 5/2001 | | JP | 8268882 | 4/1995 |
| EP | 1108360 | 6/2001 | | JP | 7231788 | 9/1995 |
| EP | 1138763 | 10/2001 | | JP | 7330794 | 12/1995 |
| EP | 1145637 | 10/2001 | | JP | 8143457 | 6/1996 |
| EP | 0191217 | 2/2002 | | JP | 8266213 | 10/1996 |
| EP | 0869167 | 2/2002 | | JP | 9040689 | 2/1997 |
| EP | 1193314 | 4/2002 | | JP | 10155493 | 6/1998 |
| EP | 0746618 | 8/2002 | | JP | 10155493 A | 6/1998 |
| EP | 1233676 | 8/2002 | | JP | 11290078 | 10/1999 |
| EP | 0648263 | 9/2002 | | JP | 2000226335 | 8/2000 |
| EP | 0784674 | 9/2002 | | JP | 3553958 | 5/2004 |
| EP | 1275711 | 1/2003 | | KR | 93-700773 | 3/1993 |
| EP | 1285969 | 2/2003 | | KR | 94-10252 | 10/1994 |
| EP | 1298205 | 4/2003 | | KR | 95-700043 | 1/1995 |
| EP | 0635053 | 6/2003 | | KR | 95-702583 | 6/1995 |
| EP | 0675944 | 6/2003 | | KR | 96-704602 | 8/1996 |
| EP | 0817838 | 6/2003 | | KR | 2001-7012115 | 9/2001 |
| EP | 1280919 | 6/2003 | | KR | 2003-7008997 | 10/2003 |
| EP | 0746608 | 8/2003 | | NL | 0784674 | 12/2002 |
| EP | 0851913 | 5/2004 | | NL | 0869167 | 1/2003 |
| EP | 1262562 | 6/2004 | | NL | 1073339 | 2/2003 |
| EP | 1433852 | 6/2004 | | NL | 0746608 | 11/2003 |
| EP | 0977869 | 7/2004 | | RU | 2140751 | 6/1997 |
| EP | 0743017 | 9/2004 | | RU | 2235775 | 11/1999 |
| EP | 0675949 | 10/2004 | | RU | 2001117497 | 6/2001 |
| EP | 0880590 | 10/2004 | | TR | 200101551 | 12/1999 |
| EP | 0897423 | 10/2004 | | WO | 88/02775 | 4/1988 |
| EP | 1466980 | 10/2004 | | WO | 88/03365 | 5/1988 |
| EP | 0839186 | 11/2004 | | WO | 89/01969 | 3/1989 |
| EP | 1162889 | 2/2005 | | WO | 89/06803 | 7/1989 |
| EP | 1559788 | 8/2005 | | WO | 91/00920 | 1/1991 |
| EP | 1363506 | 11/2005 | | WO | 91/06661 | 5/1991 |

| | | | | | | |
|---|---|---|---|---|---|---|
| WO | 91/14772 | 10/1991 | | WO | 01/16308 | 3/2001 |
| WO | 92/05249 | 4/1992 | | WO | 01/27251 | 4/2001 |
| WO | 92/14830 | 9/1992 | | WO | 01/29222 | 4/2001 |
| WO | 92/18645 | 10/1992 | | WO | 01/34835 | 5/2001 |
| WO | 93/01285 | 1/1993 | | WO | 01/39602 | 6/2001 |
| WO | 93/11249 | 6/1993 | | WO | 01/42433 | 6/2001 |
| WO | 93/12812 | 7/1993 | | WO | 01/47363 | 7/2001 |
| WO | 94/01541 | 1/1994 | | WO | 01/66711 | 9/2001 |
| WO | 94/04035 | 3/1994 | | WO | 01/78524 | 10/2001 |
| WO | 94/14940 | 7/1994 | | WO | 01/83559 | 11/2001 |
| WO | 94/14951 | 7/1994 | | WO | 01/83770 | 11/2001 |
| WO | 94/26883 | 11/1994 | | WO | 01/92502 | 12/2001 |
| WO | 95/06720 | 3/1995 | | WO | 02/00852 | 1/2002 |
| WO | 95/09909 | 4/1995 | | WO | 02/03805 | 1/2002 |
| WO | 95/22606 | 8/1995 | | WO | 02/06457 | 1/2002 |
| WO | 95/22615 | 8/1995 | | WO | WO 02/00852 | 1/2002 |
| WO | 95/22625 | 8/1995 | | WO | WO 02/03805 | 1/2002 |
| WO | 95/29996 | 11/1995 | | WO | 02/14490 | 2/2002 |
| WO | 95/30744 | 11/1995 | | WO | 02/24881 | 3/2002 |
| WO | 96/09772 | 4/1996 | | WO | 02/30207 | 4/2002 |
| WO | 96/13578 | 5/1996 | | WO | 02/055679 | 7/2002 |
| WO | 96/13579 | 5/1996 | | WO | 02/062973 | 8/2002 |
| WO | 96/13580 | 5/1996 | | WO | 02/065854 | 8/2002 |
| WO | 96/27002 | 9/1996 | | WO | 02/066622 | 8/2002 |
| WO | 96/28542 | 9/1996 | | WO | 02/094123 | 11/2002 |
| WO | 96/30502 | 10/1996 | | WO | WO 02/094123 | 11/2002 |
| WO | 96/32472 | 10/1996 | | WO | 03/020923 | 3/2003 |
| WO | 96/39851 | 12/1996 | | WO | 03/040091 | 5/2003 |
| WO | 97/04079 | 2/1997 | | WO | 03/060112 | 7/2003 |
| WO | 97/05219 | 2/1997 | | WO | 03/070013 | 8/2003 |
| WO | 97/07202 | 2/1997 | | WO | 03/089260 | 10/2003 |
| WO | 97/07205 | 2/1997 | | WO | WO 03/089620 | 10/2003 |
| WO | 97/11083 | 3/1997 | | WO | 03/097825 | 11/2003 |
| WO | 97/14713 | 4/1997 | | WO | 03/099016 | 12/2003 |
| WO | 97/27237 | 7/1997 | | WO | 03/100044 | 12/2003 |
| WO | 97/27276 | 7/1997 | | WO | 03/102118 | 12/2003 |
| WO | 97/41212 | 11/1997 | | WO | 2004/004467 | 1/2004 |
| WO | 97/41735 | 11/1997 | | WO | 2004/018660 | 3/2004 |
| WO | 97/41736 | 11/1997 | | WO | 2004/053039 | 6/2004 |
| WO | 98/08939 | 3/1998 | | WO | 2004/053152 | 6/2004 |
| WO | 98/14594 | 4/1998 | | WO | 2004/059075 | 7/2004 |
| WO | 98/18912 | 5/1998 | | WO | 2004/064537 | 8/2004 |
| WO | 98/26057 | 6/1998 | | WO | 2004/064987 | 8/2004 |
| WO | 98/31790 | 7/1998 | | WO | 2004/097012 | 11/2004 |
| WO | WO 98/31790 | 7/1998 | | WO | 2004/111216 | 12/2004 |
| WO | 98/41623 | 9/1998 | | WO | WO 2004/111216 | 12/2004 |
| WO | 98/44804 | 10/1998 | | WO | 2005/003339 | 1/2005 |
| WO | 98/45453 | 10/1998 | | WO | 2005/005977 | 1/2005 |
| WO | 98/50532 | 11/1998 | | WO | 2005/056782 | 6/2005 |
| WO | 98/51163 | 11/1998 | | WO | 2005/066347 | 7/2005 |
| WO | 98/59028 | 12/1998 | | WO | 2005/066351 | 7/2005 |
| WO | 99/33964 | 7/1999 | | WO | 2005/080540 | 9/2005 |
| WO | 99/34011 | 7/1999 | | WO | 2005/087918 | 9/2005 |
| WO | 99/37782 | 7/1999 | | WO | 2006/008508 | 1/2006 |
| WO | 99/42566 | 8/1999 | | WO | 2006/008653 | 1/2006 |
| WO | 99/50399 | 10/1999 | | WO | 2006/032279 | 3/2006 |
| WO | 99/53001 | 10/1999 | | WO | WO 2008/094847 | 8/2008 |
| WO | 99/53769 | 10/1999 | | | | |
| WO | 99/55883 | 11/1999 | | | OTHER PUBLICATIONS | |
| WO | 00/05396 | 2/2000 | | | | |
| WO | 00/28044 | 5/2000 | | Seffernick et al. J Bacteriol. Apr. 2001; 183 (8): 2405-10.* | | |
| WO | 00/32758 | 6/2000 | | Witkowski et al. Biochemistry. Sep. 7, 1999; 38(36): 11643-50.* | | |
| WO | 00/34450 | 6/2000 | | Sen et al. Appl Biochem Biotechnol. Dec. 2007;143(3):212-23.* | | |
| WO | 00/36114 | 6/2000 | | Uwe T. Bornscheuer, et al., Optimizing Lipases And Related | | |
| WO | WO 00/32758 | 6/2000 | | Enzymes For Efficient Application; Trends in Biotechnology (2002) | | |
| WO | 00/43036 | 7/2000 | | vol. 20, No. 10, p. 433-437. | | |
| WO | 00/49164 | 8/2000 | | Klaus A. Dugi, et al., Human Hepatic And Lipoprotein Lipase: The | | |
| WO | 00/58517 | 10/2000 | | Loop Covering The Catalytic Site Mediates Lipase Substrate Speci- | | |
| WO | 00/59307 | 10/2000 | | ficity, The Journal of Biological Chemistry (1995) vol. 270, No. 43, | | |
| WO | 00/60063 | 10/2000 | | p. 25396-25401. | | |
| WO | 00/61771 | 10/2000 | | Ching T. Hou, pH Dependence And Thermostability Of Lipases | | |
| WO | 00/71808 | 11/2000 | | From Cultures From The ARS Culture Collection, Journal Of Indus- | | |
| WO | 00/75295 | 12/2000 | | trial Microbiology (1994) vol. 13, p. 242-248. | | |

Mary G. McCoy, et al., Characterization Of The Lipolytic Activity Of Endothelial Lipase, Journal of Lipid Research (2002) vol. 53, p. 921-929.

Manfred T. Reetz, Lipases As Practical Biocatalysts, Current Opinion In Chemical Biology (2002) vol. 6, p. 145-150.

Jinichi Toida, et al., Purification And Characterization Of A Lipase From *Aspergillus oryzae*, Biosci. Biotech. Biochem. (1995) vol. 59, No. 7, p. 1199-1203.

U.S. Appl. No. 60/039,791, filed Mar. 4, 1997, Clausen.

U.S. Appl. No. 60/189,780, filed Mar. 16, 2000, Soe.

U.S. Appl. No. 60/489,441, filed Jul. 23, 2003, Kreij.

Acker, L. "Die Lipide des Getreides, ihre Zusammense und inre Bedeutung", Getreide Mehl Brot (1974) 28:181-187.

Adamzcak, Marek, et al., "Application of Enzymatic Glycerolysis for Production of Monoglycerides from Waste Fats", Polish Journal of Food and Nutrition Science, Mar. 1994.

Adhikari, B., et al., "Stickiness in Foods: A Review of Mechanisms and Test Methods", International Journal of Food Properties, vol. 4, No. 1, 2001.

Agarwal et al., "Lipase Activity of Some Fungi Isolated from Groundnut", Current Science, Dec. 5, 1984, vol. 53, No. 23.

Aires-Barros et al (1994) Isolation and purification of lipases, Cambridge Unversity Press.

Aisaka, Kazuo et al., "Production of Lipoprotein Lipase and Lipase by *Rhizopus japonicu*", Agri. Biol. Chem., vol. 43, No. 10, pp. 2125-2129, 1979.

Akoh, Casimir C., et al., "GDSL family of serine esterases/lipases" Progress in Lipid Research, vol. 43, 2004, pp. 534-552.

Allan Svendsen et al., "Biochemical properties of cloned lipases from the Pseudomonas family", Biochimica et Biophysica Acta, vol. 1259, 1995, pp. 9-17.

Al-Obaidy, K A, Dissertation Abstracts International B (1987) vol. 47(9) 3597, order No. DA8624641, pp. 266.

Amano Enzyme Inc. (2004). Http://www.amano-enzyme.co.jp/english/productuse/oil_fat.html. Dato 21.06.04.

Amano Enzymes "Enzymes for Gastrointestinal Digestion" Oct. 1997.

Amano Enzymes, Amano Enzyme Europe Ltd, Sep. 1994.

Amin, Neelam S., et al., "Direct transformation of site-saturation libraries in *Bacillus subtilis*", BioTechniques, Dec. 2003, 35:1134-1140.

Amino acid composition of lipases.

Andersson, L., et al., "Hydrolysis of galactolipids by human pancreatic lipolytic enzymes and duidenal contents", Journal of Lipid Research, 1995, vol. 36, pp. 1392-1400.

Andreas Sander, Eberhand Eilers, Andrea Heilemann, Edith von Kreis.Fett/lipid 99 (1997) Nr. 4, 115-120.

Angelino, S.A.G.F., et al., "The first European Symposium on Enzymes and Grain Processing".

An-I Yeh et al., "Effects of Oxido-reductants on rheological properties of wheat flour dough and comparison with some characteristics of extruded noodles", Cereal Chemistry, 1999, vol. 76, no. 5, pp. 614-620.

Application of F. oxysporum phospholipase (FoL) in baking.

Arbige, Michael A et al, Novel lipase for cheddar cheese flavor development.

Archer, David B., et al., "Proteolytic degradation of heterologous proteins expressed in *Aspergillus niger*", Biotechnology Letter, vol. 14, No. 5, May 1992, pp. 357-362.

Arcos J.A. et al, "Quantative Enzymatic Production of 6.O-Acylglucose Esters", Biotechnology and Bioengineering 1998 57(5).

Arpigny Jean Louis et al, "Bacterial lipolytic enzymes: Classification and properties", Biochemical Journal, vol. 343, No. 1, Oct. 1, 1999, pp. 177-183, XP002375631.

Assignment Document for Enzymatisk detergent additiv, detergent og vaskemetode.

Atomi, et al.; "Microbial Lipases—from Screening to Design"; pp. 49-51.

August C.A.P.A. et al. "The use of genetic engineering to obtain efficient production of porcine pancreatic phospholipase A2", Biochimica et Biophysica Acta, vol. 1089, 1991, pp. 345-351.

Aunstrup, Knud et al., "Production of Microbiol Enzymes", Microbiol Technology, vol. 1.

Ausubel, Frederick M., et al., "Short Protocols in Molecular Biology-A Compendium of Methods from Current Protocols in Molecular Biology", 1995, John Wiley & Sons, Inc.

Bachmatova, I., et al., "Lipase of Pseudomonas mendocina 3121-1 and its Substrate Specificty", Biologija, 1995.

Bailey's Industrial Oils and Fat Products, vol. 2, 4th Edition, John Wiley and Sons, New York pp. 97-173.

Bakezyme PH 800.

Balashev, Konstantin, Surface studies of enzymes using Atomic force microscopy (AFM).

Balcao V.M., Pavia A.L. Malcata F.X., Enzyme Microb Technhol, May 1, 1996; 18(6):392-416.

Balcao, Victor M and Malcata F. Xavier (1998), Biotechnology Advances, vol. 16, No. 2, pp. 309-341.

Ballance, D.J., et al., "Transformation of *Aspergillus nidulans* by the orotidine-5'-phosphate decarboxylase gene of *Neurospora crassa*", Biochemical and biophysical Research Communications, vol. 112, No. 1, 1983, pp. 284-289.

Ballance, Molecular Industrial Mycology, Systems and Applications for Filamentous Fungi, Leong and Berka (eds.), Marcel Dekker Inc, New York 1991, pp. 1-29.

Barbesgaard, Peder et al Applied Microbiology and Biotechnology (1992) 36: 569-572.

Barnes, P.J., "Lipids in Cereal Technology", Food and Science Technology, Academic Press, 1983.

Basrl, M., et al., "Amidination of Lipase with Hyrdophobic Imidoesters", JAOCS, vol. 69, No. 6, Jun. 1992.

Bateman A and Haft DH (2002) Brief Bioinform 3, 236-245.

Bateman A et al, (2002) Nucleic Acids Res. 30, 276-280.

Becker T. "Separation and Purification Processes for Recovery of Industrial Enzymes" in R.K. Singh, S.S.H. Rizvi (eds): Bioseparation processess in Foods, Marcel Dekker, New York, pp. 427-445.

Bedre Brod med nyt enzym.

Bekkers et al, The use of genetic engineering to obtain efficient production of porcine pancreatic phospholipase A2 by *Saccharomyces cerevisiae*, (1991) Biochim Biophys Acta 1089(3), 345-51.

Bengtsson Olivecrona Gunilla et al. Phospholipase activity of milk lipoprotein lipase, Methods in Enzymology, vol. 197, 1991.

Bentley S D et al, Complete genome sequence of the model actinomycete *Streptomyces coelicolor* A3(2), Nature vol. 417, 2002, pp. 141-147.

Berger K.G. (1990) Recent developments in palm oil. In Oleagineux 45:437-443.

Berks, Ben C., "A common export pathway for proteins binding complex redox cofactors?" Molecular Microbiology, 1996, vol. 22, pp. 393-404.

Beucage S.L. et al, (1981) Tetrahedron Letters 22, p. 1859-1869.

Bieleski R.L., Chapter 5, Sugar Alcohols.

Bilyk, Alexander, et al., "Lipase-catalyzed triglyceride Hydrolysis in Organic Solvent", pp. 320-323, JAOCS, vol. 68, No. 5, May 1991.

Biocatalysts, Limited, Product Sheet for Lipomod(TM) 627P-L627P.

Biotekkomet falder hardt til jorden.

Birch et al., "Evidence of Multiple Extracellular Phospholipase Activities of *Aspergillus fumigatus*", Infection and Immunity, Mar. 1996, vol. 64, No. 3, 1996.

Birgitte Hugh-Jensen et al., "Rhizomucor miehei Triglyceride Lipase is Processed and Secreted from Transformed *Aspergillus oryzae*", Lipids, vol. 24, No. 9, 1989.

Biswas, et al., "Interfacial Behavior of Wheat Puroindolines: Study of Adsorption at the Air-Water Interface from Surface Tension Measurement Using Wilhelmy Plate Method", Journal of Colloid and Interface Science, vol. 244, pp. 245-253, 2001.

Bjorkling, F., et al., "Lipase Catalyzed Organic Synthesis", S. Servie (ed.), Microbial Reagents in Organic Synthesis, pp. 249-260, 1992.

Bjorkling, Frederik, et al., "Lipase Catalyzed Synthesis of Perozycarboxylic Acids and Lipase Mediated Oxidations", Tetrahedron, vol. 48, No. 22, pp. 4587-4592, 1992.

Bjorkling, Frederik, et al., "Lipase -mediated Formation of Peroxycarboxylic acids used in Catalytic Epoxidation of Alkenes", J. Chem. Soc., Chemical Communications, Issue 19, 1990.

Bjurlin et al. Identification of carboxylesterase activities of commercial triacylglycerol hydrolase (lipase) preparations, Eur. J. Lipid Sci. Technol. 104 (2002) 143-155.

Blain JA et al, The Nature of Mycelial Lipolytic enzymes in filamentous fungi, Ferns Microbiol. Lett., 1978, vol. 3, 85-87.

Blecker et al, Improved emulsifying and foaming of whey proteins after enzymic fat hydrolysis, (1997) J Food Science, vol. 62, No. 1.

Blumenthal, Cynthia Z., "Production of toxic metabolites in *Aspergillus niger, Aspergillus oryzae*, and *Trichoderma reesei*: justification of mycotoxin testing in food grade enzyme preparations derived from the three fungi", Regulatory Toxicology and Pharmacology, vol. 39, 2004, p. 214-228.

Boel, Esper, et al.; "*Rhizomucor miehei* Triglyceride Lipase is Synthesized as a Precursor"; Novo Research Institute; vol. 23; No. 7; Jul. 1988.

Bornscheuer U T et al, Trends in Biotechnology, Elsevier Publications, Cambridge GB, vol. 20, No. 10, Oct. 1, 2002, pp. 433-437.

Bornscheuer, Uwe T., Lipase-catalyzed syntheses of monoacylglycerols, Enzyme and Microbiol Technology, vol. 17, pp. 578-586, 1995.

Brady, Leo, et al., "A serine protease triad forms the catalytic centre of a triacylglycerol lipase", Nature, vol. 343, 1990.

Brockerhoff, Hans, et al., "Lipolytic Enzymes", Academic Press, 1974.

Brumlik, Michael J., et al., "Identification of the Catalytic Triad of the Lipase/Acyltransferase from *Aeromonas hydrophila*", Journal of Bacteriology, Apr. 1996, vol. 178, No. 7, pp. 2060-2064.

Brzozowski, A.M., et al., "A model for interfacial activation in lipases from the structure of a fungal lipase-inhibitor complex", Nature, vol. 351, 1991.

Buckley J. Thomas et al, Journal of Biological Chemistry, vol. 257, No. 6, pp. 3320-3325, 1982.

Buckley, Biochemistry 1983, 22, 5490-5493.

Bulkacz J et al, Biochim. Biophys. Acta (1981) vol. 664, pp. 148-155.

Bulletin of the IDF 294: 1994.

Burdge, Graham C., et al., "A method for separation of phosphatidylcholine, triacylglycerol, non-esterified fatty acids and cholesterol esters from plasma by solid-phase extraction", British Journal of Nutrition, 2000, vol. 84, pp. 281-787.

Butcher, Bronwyn G., et al., Microbiology, 2002, vol. 148, pp. 3983-3992.

Buxton et al, Gene, 1985, 37:207-214.

Cao, Shu-Gui, et al., "Enzymatic Preparation of Monoglycerides via Glycerolysis of Fats and Oils Catalyzed by Lipase from Pseudomonas Species" National Laboratory of Enzyme Engineering.

Carriere et al, "Pancreatic Lipase Structure- Function Relationships by Domain Exchange", American Chemical Society-Biochemistry (1997), 36, pp. 239-248.

Carriére, Frédéric, et al., "Structural basis for the substrate selectivity of pancreatic lipases and some related proteins", Biochemica et Biophysica Acta, vol. 1376, pp. 417-432, 1998.

Caruthers MH et al (1980) Nuc Acids Res Symp Ser 215-23.

Casimir C A et al Progress in Lipid Research, 2004, pp. 534-552.

Castello, P., et al., "Technological and Biochemical effects of exogenous lipases in breadmaking", 2nd European Symposium on enzymes in Grain Processing.

Castello, Phillippe, et al., "Effect of exogenous lipase on dough lipids during mixing of wheat flours", Cereal Chemistry, 1998, vol. 75, No. 5, pp. 595-601.

Castello, Phillippe, et al., "Effects of mixing conditions and wheat flour dough composition on lipid hydrolysis and oxidation levels in the presence of exogenous lipase", Cereal Chemistry, 1999, vol. 76, No. 4. pp. 476-482.

Chakravarti DN et al, Biol. Abstracts, 1981, vol. 72, abstract No. 012592.

Cheng Cheng et al., "Transformation of *Trichoderma viride* using the *Neurospora crassa* pyr4 gene and its use in the expression of a Taka-amylase A gene from *Aspergillus oryzae*", Curr. Genet., 18: 453-456, 1990.

Christensen et al, "A new and simple method to immobilise lipases by means of granulation", 1998 Nachwachsende Rohstoff 10, 98-105.

Christie, William et al., "New Procedures for Rapid Screening of Leaf Lipid Components from *Arabidopsis*", Phytochemical Analysis, vol. 9, pp. 53-57, 1998.

Christophersen, Claus, et al., "Enzymatic Characterisation of Novamyl a Thermostable α-Amylase", Starch/Sturke, vol. 50, 1998.

Chung O K et al, "Defatted and Reconstituted wheat flours. VI. Response to shortening addition and Lipid Removal in Flours that vary in Bread-making Quality" Cereal Chemistry (1980), vol. 57(2), p. 111-117.

Chung OK et al, "Recent Research on Wheat Lipids" Bakers Digest Oct. 1981.

Ciuffreda, Pierangela, et al., "Spectrophotometric Assay of Lipase Activity: A New 40nitrophenyl Ester of a Dialkylglycerol Suitable as a Chromogenic Substrate of *Pseudomonas cepacia* Lipase", Biocatalysis and Biotransformation, vol. 21, No. 3, pp. 123-127, 2003.

Claesson et al., "Techniques for measuring surface forces", Advances in Colloid and Interface Science, vol. 67, 1996, pp. 119-183.

Clausen, Kim, "Enzymatic oil-degumming by a novel microbial phospholipase", European Journal of Lipid Science and Technology, vol. 103, 2001, pp. 333-340.

Clausen, Kim, "New enzyme for degumming", Oils and Fats International, vol. 17, No. 4, Jun. 2001, pp. 24-25.

Cloning of rad51 and rad52 homologues from *Aspergillus oryzae* and the effect of their overexpression on homologous recombination.

Collar C, et al, "Lipid binding fresh and stored formulated wheat breads. Relationships with dough and bread technological performance", Lab de Cereales Inst de Agroquimica y Tec de Alimentos, CSIC, Food Science and Technology International 2001, vol. 7(6), p. 501-510.

Colombo, Diego, et al., "Optically Pure 1-0- and 3-0-β-D-Glucosylk- and Galactosyl-sn-glycerols through Lipase-catalyzed Transformations", Tetrahedron Letters, vol. 36, No. 27, pp. 2865-4868, 1995.

Conference May 6-8, 1999 in Santorini, Greece—Lipases & Lipids Structure, Function and Biotechnological Applications—Slides presented by Charlotte Poulsen.

Cordle et al, "The hydrophobic surface of colipase influences lipase activity at an oil-water interface", Journal of Lipid Research, vol. 39 (1998), 1759-1767.

Coteron, A., et al., "Reactions of Olive Oil and Glycerol over Immobilized Lipases", JAOCS, vol. 75, No. 5, 1998.

Council Directive of Dec. 21, 1988 (89/107/EEC).

Council Regulation (EC) No. 2991/94 May 12, 1994 Official Journal of the European Communities, Sep. 12 1994, No. L316/2-7.

Courtin, Christophe M., et al., "Recent Advances in Enzymes in Grain Processing".

Creveld, Lucia D, et al., "Identification of Functional and Unfolding Motions of Cutinase as Obtained from Molecular Dynamics Computer Simulations", Proteins: Structure, Function, and Genetics, 33:253-264, 1998.

Cromie, Susan. Psychrotrophs and their Enzyme residues in cheese milk, The Australian Journal of Dairy Technology, vol. 47, Nov. 1992.

Cui et al., "Purification and characterization of an intracellular carboxylesterase from Arthrobacter viscosus NRRL B-1973", Enzyme and Microbial Technology, vol. 24, pp. 200-208, 1999.

Daboussi et al, Heterologous expression of the *Aspergillus nidulans* regulatory gene nirA in *Fusarium oxysporum*, (1991) Gene 109(1), 155-60.

Daboussi et al., "Transformation of seven species of filamentous fungi using the nitrate reductase gene of *Aspergillus nidulans*", Curr. Genet., 15:453-456, 1989.

Daftary, R.D., et al., "Functional Bread-Making Properties of Wheat Flour Lipids", Food Technology, vol. 22, No. 237, Mar. 1968-1979.

Dahlquist, Anders, et al., "Phospholipid: diacylglycerol acyltransferase: An enzyme that catalyzes the acyl-CoA-independent formation of triacylglycerol in yeast and plants", PNAS, vol. 97, No. 12, pp. 6487-6492, 2000.

Dalrymple, Brian D., et al., "Three Neocallimastic patriciarum esterases associated with the degradation of complex polysaccharides are members of a new family of hydrolases", Microbiology, vol. 142, pp. 2605-2614, 1997.

Danisco, "Unique Chance for Better Bread" *Direct, A Newsletter from Danisco Ingredients* (1996).
Danisco, Hexose oxidase—nyt enzym med mange mulingheder (advert).
Darnell et al., Eds., "Synthetic Peptide and Nucleotide Sequences: Their Use in Isolating and Identifying Genes", in *Molecular Cell Biology*, Chapter 6, Manipulating Macromolecules, 1990, Scientific American Books, Baltimore.
Database accession No. P10480 -& Database UniProt 'Online!, Jul. 1, 1989.
Database accession No. Q44268 -& Database UniProt 'Online! Nov. 1, 1996.
Database accession No. Q9F7Y6 Database UniProt 'Online!, Mar. 1, 2001.
Database FSTA International Food Information Service (IFIS), Frankfurt/Main, De Mine Y:"Application of the enzymatic methods to the determination of contaminated yolk in egg white." XP002077295 see abstract & Food Research International, vol. 29, No. 1, 1996, pp. 81-84.
Database FSTA International Food Information Service (IFIS), Frankfurt/Main, De Nicolas J:"Action of oxidoreductases in breadmaking. Maturation of soft wheat flours and kneading of doughs." XP002077286 see abstract & Annales De Technologie Agricole, vol. 28, No. 4, 1979, pp. 445-468.
Database FSTA International Food Information Service (IFIS), Frankfurt/Main, De Qi Si J: "New enzymes for the baking industry" XP002077284 see abstract & Food Tech Europe vol. 3, No. 1, 1996, pp. 60-64, Novo Nordisk Ferment Ltd.
Database FSTA International Food Information Service (IFIS), Frankfurt/Main, De Weipert D:"Rheologie von Roggenteigen. II. Der einfluss der enzyme unterschiedlicher spezifitat auf das rheologische verhalten des teiges." XP002077285 see abstract & Getreide, Mehl Und Brot, vol. 26, No. 10, 1972, pp. 275-280.
Database Uniprotke Jun. 1, 2003, S. Omura et al: "putative secreted hydrolase from *Streptomyces avermitilis*" XP002376340 retrieved from Ebi, Hinxton, UK Database accession No. Q828T4 abstract.
Database Uniprotkb May 1, 2000, S.D. Bentley et al: "Putative Secreted Hydrolase from *Streptomyces coelicolor*" XP002376339 retrieved from Ebi, Hinxton, UK Database accession No. Q9S2A5 abstract.
Davies, Progress in Industrial Microbiology, Martinelli and Kinghorn (eds.), Elsevier, Amsterdam 1994, 29:525-560.
De Haas GH et al, "Purification and Properties of Phospholipase A from Porcine Pancreas" Biochim. Biophys. ACTA, 1968, vol. 139, pp. 103-117.
Declaration by Clive Graham Phipps Walter (Dec C).
Declaration by Dr Jorn Borch Soe (Dec F).
Declaration by Dr M Turner.
Declaration by Dr Mark Turner (Dec G).
Declaration by Henrik Pedersen (Dec A).
Declaration by Henrik Pedersen, Masoud Rajabi Zargahi and Clive Graham Phipps Walter (Dec 2).
Declaration by Janne Brunstedt (Dec D).
Declaration by Kazuko Kato, Henrik Pedersen, Masoud Rajabi Zaghari, Clive Phipps Walter, and Janne Brunstedt (Dec I).
Declaration by Kim Borch.
Declaration by Luise Erlandsen.
Declaration by Masoud Rajabi Zargahi (Dec B).
Declaration by Masoud Rajabi Zargahi (Dec E).
Declaration by Tina Spendler.
Delcros, Jean-Francois, et al., "Effect of mixing conditions on the behavior of lipoxygenase, peroxidase, and catalase in wheat flour doughs", Cereal Chemistry, 1998, vol. 75, No. 1, pp. 85-93.
Dellaporta, et al.; "A Plant DNA Minipreparation Version II"; Plant Molecular Biology Reporter(1983); vol. 1(4); pp. 19-21.
Derewenda et al, "The crystal and molecular structure of the *Rhizomuxor miehei* Triacylglyceride Lipase at 1-9 Å Resolution", J. Mol. Biol. 1992, 227:818-839.
Derewenda, Urszula, et al., "Catalysis at the Interface: The Anatomy of a Conformational Change in a Triglyceride Lipase", Biochemistry, vol. 31, pp. 1532-1541, 1992.
Dictionary of Biochemistry and Molecular Biology, Second Edition, p. 16.

Dinkci. N, Mucor miehei den elde edilen lipaz.
Direct, A Newsletter from Danisco Ingredients, Sep. 1996.
Directive 2000/36/EC. Http://europa.eu.int/scadplus/leg/en/Ivb/121122b.htm. Dato: 16.06.04.
Drost-Lustenberger, C and Spendler T Lipopan F BG—Application and Mechanism of a new lipase for baking, Novozymes.
Drost-Lustenberger, Cornelia, et al., "Lipopan F BG-application and mechanism of a new lipase for bread baking", Cereal Food, 2003.
Drost-Lustenberger, Cornelia, et al., "Lipopan F BG-unlocking the natural strengthening potential in dough", Cereal Food, 2004.
Duan, Rui Dong, Fat Digestion and Absorption (2000), p. 25-46, publisher AOCS Press, Champaign III CODEN 69ACBA Conference; general review written in English.
Dubreil, Laurence, et al., "Localization of Puroinoline-a and Lipids in Bread Dough Using Confocal Scanning Laser Microscopy", J. Agric. Food Chem., 2002, vol. 50, pp. 6078-6085.
Ducancel, Frederic, et al., "Complete amino acid sequence of a PLA2 from the tiger snake Notechis sculatus scutatus as deduced from a complementary DNA", Nucleic Acids Research, vol. 16, No. 18, 1988.
Dugi KA et al, "Human hepatic and lipoprotein lipase: the loop covering the catalytic site mediates lipase substrate specificity", Journal of Biological Chemistry (1995), vol. 270, pp. 25, 396-pp. 25, 401.
Dugruix (Edited by) Crystallization of Nucleic Acids and Proteins A Practical Approach.
Dutilh & Groger, "Improvement of Product Attributes of Mayonnaise by Enzymic Hydrolysis of Egg Yolk with Phospholipase A2", 1981 J. Sci. Food Agric. 32, 451-458.
Dybdal, L., et al., "Enzymes in Cereals Processing".
Eddine et al, "Cloning and expression analysis of NhL1, a gene encoding an extracellular lipase from the fungal pea pathogen *Nextria haematococca* MP VI (Fusarium solani f. sp. pisi) that is expressed in planta", Mol. Genet. Genomics (2001) 265: 215-224.
EFEMA Index of Food Emulsifiers Jan. 2004, 4th Edition.
Efthymiou CC et al. Development of domestic feta cheese.
Eliasson et al., "Cereals in Breadmaking- A molecular colloidal approach".
Ellaiah et al., "Production of lipase by immobilized cells of *Aspergillus niger*", Process Biochemistry, vol. 39, 2004, pp. 525-528.
Elyk, Alexander, et al., "Lipase-Catalyzed—", JAOCS, vol. 08, No. May 1991, pp. 320-323.
Engelhorn and Raab, "Rapid Electroblotting of Small DNA Fragments from Polyacrylamide Gels", Biotechniques (1991) 11(5):594-6.
Engelhorn et al., "Rapid Electroblotting of Small DNA Fragments from Polyacrylamide Gels"; Biotechniques (1991); vol. 11(5); pp. 594-596.
Enzymes in food processing (3rd Ed.), Academic press 1993.
EPO, Mobay Chemical Corporation—Decision of the Technical Board of Appeal 3.3.1 dated Jul. 1, 1982, *Official Journal EPO*, Oct. 1982, pp. 394-402.
Ettinger, William F. et al., "Structure of Cutinase Gene, cDNA, and the Derived Amino Acid Sequence from Phytopathogenic Fungi", Biochemistry, vol. 26, pp. 7883-7892, 1987.
Euromonitor International, "The World Market for Dairy Products—Introduction, Executive Summary, Operating Environment, World Market Overview, Key Trends and Developments" in *Euromonitor, Strategy 2000*, Feb. 2001.
European Parliament and Council Directive No. 95/2/EC of Feb. 20, 1995 on food additives other than colours and sweeteners.
European Parliament and Council Directive No. 98/72/EC of Oct. 15, 1998 amending Directive 95/2/EC on food additives other than colours and sweeteners.
Eurpean Journal of Biochemistry, vol. 166, 1987, Published by Springer International on behalf of the Federation of European Biochemical Societies.
Ezra, David, et al., "Coronamycins, peptide antibiotics produced by a verticillate *Streptomyces* sp. (MSU-2110) endophytic on *Monstera* sp.", Microbiology, 2004, vol. 150, p. 785-793.
Fauvel, et al.; "Purification of Two Lipases With High Phospholipase A, Activity from Guinea-Pig Pancreas"; Biochimica et Biophysica Acta(1981); vol. 663; pp. 446-456.

Fennema, Owen F., "Food Chemistry Second Edition, Revised and Expanded".

Fernandez-Garcia et al., "The use of lipolytic and proteolytic enzymees in the manufacture of manchego type cheese from ovine and bovine milk", 1994 J. Dairy Sci. 77: 2139-2149.

Fernandez-Lafuente, Roberto, et al., The coimmobilization of D-amino acid oxidase and catalase enables the quantitative transformation of D-amino acids (D-phenylalanine) into α-keto acids (phenylpyruvic acid), Enzyme and Microbial Technology, vol. 23, pp. 28-33, 1998.

Ferrer et al, 2000, J. Chem. Technol. Biotechnol. 75, 569-576.

Finizym Technical Information, Novo Enzymes, 1981.

Fødevarenubusteriet (2003). Bekendtgørelse om indhold af transfedtsyrer I olier og fedtstoffer. Bekendtgørelse nr. 160 af Nov. 3, 2003.

Food Enzymes: Stalingase L, Gist-brocades Food Ingredients.

Food R&D. Dairy fields ingredient technology section.

Forman, Todd, "Enzymes Used in Bread Baking: An Application Update", Technical Bulletin, vol. XXVI, Issue 10, Oct. 2004.

Fox, et al.; "Isolation and some Properties of Extracellular Heat-Stable Lipases: from *Pseudomonas Fluorescens* Strain AFT 36"; Journal of Dairy Research (1988); vol. 50; pp. 77-89.

Frenken N. et al (1992) Appl. Envir. Microbiol. 58 3787-3791.

Freshzyme, Product Sheet.

Frohman, et al.;"Rapid Production of Full-Length cDNAs from Rare transcripts: Amplification using a single gene-specific oligonucleotide primer"; Proc. Natl. Acad. Sci. USA (1988); vol. 85; pp. 8998-9002.

Frost & Sullivan, U.S. Market for Enzymes for food Applications.

Fugman, Douglas A et al Biochemica et Biophysica acia 795 (1984) 191-195.

Functional Bread-Making Properties of Lipids.

Galliard T and Dennis S (1974) Phytochemistry vol. 13, pp. 1731-1735.

Galliard, "The Enzymic Breakdown of Lipids in Potato Tuber by Phospholipid- And Galactolipid- Acyl Hydrolase Activities and by Lipoxygenase", Phytochemistry, 1970, vol. 9, pp. 1725-1734.

Gan, Z. et al., "Rapid Communication- Antisera agains: Wheat Diacylgalactosylglycerol (MGDG) and Diacyldigalactosylglycerol (DGDG)", Journal of Cereal Science, vol. 18, pp. 207-210, 1993.

Ganghro AB & Dahot MU, Sci Int. (Lahore), 1992, vol. 4, pp. 169-172.

Gemel, Joanna et al., "Comparison of galactolipase activity and free fatty acid levels in chloroplasts of chill-sensitive and chill resistant plants", European Journal of Biochemistry, vol. 166, 1987.

Geus et al (1987) Nucleic Acids Research 15(9) p. 3743-3759.

Gilbert, E. Jane, et al., "Purification and properties of extracellular lipase from *Pseudomonal aeruginosa* EF2", Journal of General Microbiology, 1991, vol. 137, pp. 2223-2229.

Gillian, B., Turgeon et al., "*Cochliobolus heterostrophus* using the *Aspergillus nidulans* amdS gene", Mol Gen Genet, 201: 450-453, 1985.

Gist-brocades, Amylase P Information Sheet.

Godfrey, Tony, et al., "Industrial Enzymology Second Edition".

Goodey et al, Yeast Biotechnology, Berry et al (eds.), Allen and Unwin, London 1987, pp. 401-429.

Graille J, Lipid Technology, vol. 5, No. 1, 1993, pp. 11-16.

GRAS Notification dated Apr. 11, 2001 by Novozymes for Lecitase$^R$ and Lipopan™ F.

Greenough et al (1996) Food Chem Toxicology 34:161-166 and PubMed abstract in respect thereof.

Greenough R J et al, Food and Chemical Toxicology, vol. 34(2), 1996, pp. 161-166.

Grindsted Products, Grindsted Bakery News.

Grindsted, "Emulsifiers for the baking industry".

Grindsted, "Grindamyl Fungal Alpha-Amylase".

Hass and Berka, 1991, Gene, 109:107-113.

Haas, et al., "Enzymatic Phosphatidylcholine Hydrolysis in Organic Solvents: An Examination of Selected Commercially Available Lipases", JAOCS, vol. 71, No. 5, May 1994, pp. 483-490.

Haas, et al.; "Lipases of the Genera *Rhizopus* and *Rhizomucor*: Versatile Catalysts in Nature and the Laboratory"; Food Biotechnology Micro-organisims (1995); pp. 549-588.

Haggag H F et al. Egypt J Food Sci vol. 22, No. 1 pp. 99-107 (1994).

Hamer, Rob J., et al., "Interaction: The Keys to Cereal Quality", American Association of Cereal.

Hanlin, Richard T., "Illustrated Genera of Ascomycetes"; The American Phytopathological Society.

Hansen, Chr., Danisco and Novozymes, Apr. 3, 2002, Food Ingredients day, R&D—the main ingredients for growth.

Hara, et al.; "Comparative Study of Comercially Available Lipases in Hydrolysis Reaction of Phosphatidylcholine"; JAOCS (1997); vol. 74; No. 9, pp. 1129-1132.

Hawker, Kim L., et al., "Heterologous expression and regulation of the *Neurospora crassa* nit-4 pathway-specific regularotry gene for nitrate assimilation in *Aspergillus nidulans*", Gene., vol. 100, pp. 237-240, 1991.

Hedin, Eva M.K., et al., "Selective reduction and chemical modification of oxidized lipase cysteine mutants".

Helmsing, "Purification and Properties of Galactolipase", Biochim., Biophys., Acta, vol. 178, pp. 519-533, 1969.

Henderson, H.E., et al., "Structure-function relationships of lipoprotein lipase: mutation analysis and mutagenesis of the loop region", Journal of Lipid Research, vol. 34, 1993, pp. 1593-1602.

Henke, Erik, et al., "Activity of Lipases and Esterases towards Tertiary Alcohols: Insights into Structure-Function Relationships", Angew. Chem. Int. Ed., 2002, vol. 41, No. 17.

Hernquist L & Anjou K (1993) Diglycerides as a stabilizer of the β'-crystal form in margarines and fats, in Fette Seifen Anstrichmittel 2:64-66.

Hernquist L. Herslof B. Larsson K & Podlaha O. (1981) Polymorphism of rapeseed oil with low content of erucic acid and possibilities to stabilize the β-crystal form in fats, in Journal of Science and Food Agriculture 32:1197-1202.

Hilton S et al, Biochemistry vol. 29, No. 38, 1990, pp. 9072-9078.

Hilton S, Buckley JT, J Bid Chem. Jan. 15, 1991; 266(2): 997-1000.

Hirayama O et al, Biochim Biophys Acta. 1975, vol. 384(1), p. 127-37.

Hirose, Yoshihiko et al., "Characteristics of Immobilized Lipase PS on Chemically Modified Ceramics", Amano Pharmaceutical.

Hjorth, Annegrethe, et al., "A Structural Domain (the lid) Found in Pancreatic Lipases is Absent in the Guinea Pic (Phospho) lipase", Biochemistry, vol. 32, pp. 4702-4704, 1993.

Höfelmann et al, J. Food Sci., 1985, 50:1721-1731.

Holmquist et al., "Lipases from *Rhizomucor miehei* and *Humicola lanuginosa*: Modification of the Lid covering the active site alters enantioselectivity", Journal of Protein Chemistry, vol. 12, No. 6, 1993.

Holmquist et al., "Probing a Functional Role of Glu87 and Trp89 in the Lid of *Humicola lanuginosa* Lipase through Transesterification Reactions in Organic Solvent", Journal of Protein Chemistry, 1995, vol. 14, No. 4, pp. 217-224.

Holmquist et al., "Trp89 in the Lid of *Humicola lanuginosa* Lipase is Important for Efficient Hydrolysis of Tributyrin", Lipids, vol. 29, No. 9, 1994.

Horn T et al, (1980) Nuc Acids Res Symp Ser 225-232.

Hoshino, et al.; "Calcium Ion Regulates the Release of Lipase of *Fusarium oxysporum*"; J. Biochem (1991); vol. 110; pp. 457-461.

Hoshino, et al.; "Purification and Some Characteristics of Extracellular Lipase from *Fusarium oxysporum f. sp. lini*"; Biosci. Biotech. Biochem (1992); pp. 660-664.

Hoshino, Tamotsu, et al., "Purfication and Some Characteristics of Extracellular Lipase from *Fusarium oxysporum*", Biosci. Biotech. Biochem., vol. 56, No. 4, pp. 660-664, 1992.

Hossen, Monjur and Hernandez, Ernesto, Lipids, vol. 39, Aug. 2004, pp. 777-782.

Hou Ching T, Journal of Industrial Microbiology, vol. 13, No. 4, 1994, pp. 242-248.

Hübner et al., "Interactions at the lipid-water interface", Chemistry and physics of Lipids, vol. 96, 1998, pp. 99-123.

Hugh-Jensen, Birgitte, et al., "*Rhizomucor miehei* Triglyceride Lipase is Processed and Secreted from Transformed *Aspergillus oryzae*", Lipids, vol. 24, No. 9, pp., 1989.

Humum et al., "Enzyme Catalysed Synthesis in Ambient Temperature Ionic Liquids", Biocatalysis and Biotransformation, vol. 19, pp. 331-338.

Icard-Verniere, Christele, et al., "Effects of mixing conditions on pasta dough development on biochemical changes", Cereal Chemistry, 1999, vol. 76, No. 4, pp. 558-565.

Igrejas, Gilberto, et al., "Genetic and Environmental Effects on Puroindoline-a and Puroindoline -b Content and their Relationship to Technological Properties in French Bread Wheats", Journal of Cereal Science, vol. 34, 2001, pp. 37-47.

Ikeda H et al, Nature Biotech, vol. 21, 2003, p. 526-531.

Industrial enzymology (2nd Ed.), The Macmillan press 1996.

Ishihara et al Biochimica et Biophysica Acta 388 (1975) 413-422.

Isobe and Nokihara, Febs. Lett., 1993, 320:101-106.

Isobe K et al, Journal of Molecular Catalysis B: Enzymatic 1 (1995), pp. 37-43.

Iwai and Tsujisaka (in Lipases, Borgström and Brockman (eds.), Elsevier, Amsterdam, 1984, pp. 443-468.

Iwai, Mieko, et al., "Hydrolytic and Esterifying Actions of Crystalline Lipase of *Aspergillus niger*", Osaka Municipal Technical Research Institute, Osaka, Japan.

Izco et al. Adv Food Sci vol. 21 N 3/4, (10-116) 1999.

Jacob, Jules S., et al., "The Effects of Galactolipid Depletion on the Structure of a Photosynthetic Membrane", The Journal of Cell Biology, vol. 103, Oct. 1986, pp. 1337-1347.

Jacobsberg B. & Oh C.H. (1976) Studies in Palm Oil Crystallisation, in Journal of the American Oil Chemist Society 53:609-616.

jan-Willem F. A. Simons et al., "Cloning, purification and characterisation of the lipase from *Staphylococcus epidermidis*", Eur. J. Biochem., vol. 253, pp. 675-683, 1998.

Jeng-yen Lin, Matthew, "Wheat Polar Lipids- A Theseis Submitted to the Graduate Faculty of the North Dakota State University of Agriculture and Applied Science", May 1972.

Jensen B et al "Effect and Activity of Lipases in Dough and Bread" Translation.

Jensen, B., et al., "Effekt and Wirksamkeit von Lipasen in Teig und Brot".

JJ Owens. Lecithinase Positive Bacteria in milk.

Joerger et al., "Alteration of Chain Length Selectivity of a Rhizopus delemar Lipase through Site-Directed Mutagenesis", Lipids, vol. 29, No. 6, 1994, pp. 377-384.

Jong et al.; "American Type Culture Collection Catalogue of Filamentous Fungi"; Eighteenth edition (1991).

Joshi, et al.; "Specificity of Fungal Lipase in Hydrolytic Cleavage of Oil"; Acta Microbiologica Hungarica (1987); vol. 34(2); pp. 111-114.

Joshi, Sunita, et al., "Specificity of Lipase isolated from *Fusarium oxysporum*", Department of Chemistry, Indian Institute of Technology, vol. 25, No. 1 & 2, pp. 76-78.

Juffer, A.H., et al., "Adsorption of Proteins onto Charged Surfaces: A Monte Carlo Approach with Explicit Ions", Journal of Computational Chemistry, vol. 17, No. 16, pp. 1783-1803, 1996.

Jurgens, Catharina, et al., "Directed evolution of a $(\beta\alpha)8$-barrel enzyme to catalyze related reactions in two different metabolic pathways", PNAS, Aug. 29, 2000, vol. 97, No. 18, pp. 9925-9930.

Kaniuga Z, Acta Biochim Pol. (1997), vol. 44(1), p. 21-35.

Kapur J & Sood ML, J. Parasit., 1986, vol. 72, pp. 346-347.

Kasai, Naoya, et al., "Chiral C3 epoxides and halophydrins: Their preparation and synthetic application", Journal of Molecular Catalysis B: Enzymatic, vol. 4, 1998, pp. 237-252.

Kasai, Naoya, et al., "Optically Active Chlorohydrins as Chiral C3 and C4 Building Units: Microbial Resolution and Synthetic Applications", Chirality, vol. 10, pp. 682-692.

Kawamura and Doi, J. of Bacteriology Oct. 1984, p. 442-444.

Keller, R.C.A., et al., "Competitive Adsorption Behaviour of Wheat Flour Components and Emulsifiers at an Air-Water Interface", Journal of Cereal Science, vol. 25, 1997, pp. 175-183.

Keum J S et al. Korean J Dairy Sci 15 (2): 103-117 1993.

Kim, Hyung Kwoun, et al., Expression and characterization of Ca2=-independent lipase from *Bacillus pumilus* B26, Biochimica et Biophysica Acta, vol. 1583, 2002, pp. 205-212.

Kim, Myo-Jeong, et al., "Thermal Inactivation Kinetics and Application of Phospho and Galactolipid-Degrading Enzymes for Evaluation of Quality Changes in Frozen Vegetables", J. Agric. Food Chem., 2001, vol. 49, pp. 2241-2248.

Kimura, Yoshiharu, et al., "Application of Immobilized Lipase to Hydrolysis of Triacylglyceride", Eur J. Appl Microbiol Biotechnol, 1983, vol. 17, pp. 107-112.

Kindstedt et al, Rapid Quantative test for free oil (Oiling off) in melted Mozzarella cheese.

King et al, Molecular and Cell Biology of Yeasts, Walton and Yarronton (eds.), Blackie, Glasgow, 1989, pp. 107-133.

Kirk, Ole, et al., "Fatty Acid Specificity in Lipase-Catalyzed Synthesis of Glucoside Esters" Biocatalysis, 1992, vol. 6, pp. 127-134.

Klein, Robert R., et al., "Altered Acyl Chain Length Specificity of Rhizopus delemar Lipase Through Mutagenesis and Molecular Modeling", Lipids, 1997, vol. 32, No. 2, pp. 123-130.

Klein, Robert R., et al., "Additive Effects of Acyl-Binding Site Mutations on the Fatty Acid Selectivity of Rhizopus delemar Lipase", JAOCS, vol. 74, No. 11, 1997.

Kocak et al, Effect of lipase enzyme (palatase A 750 L) on the ripening of tulum cheese.

Kocak et al, Milchwissenschaft 51(1), 1996.

Kochubei et al Role of lipids in the organization of the closest surroundings of the reaction centers(1976) Institute of Plant Physiology.

Kochubei S M et al, Biophysics (1981), vol. 26(2), p. 299-304.

Kochubei S M et al, Mol Biol (Mosk) (1975), vol. 9(2), (p. 190-3) p. 150-153.

Kochubei SM et al, Mol Biol (Mosk) (1978),(vol. 1, p. 47-54) p. 32-37.

Kolkovski et al (1991) Fish Nutrition in Practice, Biarritz (France), Jun. 24-27.

Kostal, Jan, et al., "Enhanced Arsenic Accumulation in Engineered Bacterial Cells Expressing ArsR", Applied and Environmental Microbiology, Aug. 2004, pp. 4582-4587.

Kouker, et al.; "Specific and Sensitive Plate Assay for Bacterial Lipases"; Applied and Environmental Microbiology (1987); vol. 53(1); pp. 211-213.

Krishna, Sajja Hari, et al., "Enantioselective transesterification of a tertiary alcohol by lipase A from *Candida antarctica*", Tetrahedron: Asymmetry, vol. 13, 2002, pp. 2693-2696.

Kristensen A.C.J. (2004) Preparation of margarine and spreads by enzyme-generated emulsifiers. Master thesis, The Royal Veterinary and Agricultural University, Frederiksberg, Copenhagen.

Krog, Cereal Foods World, The American Association of Cereal Chemists, p. 10, Jan. 1979, vol. 24, No. 1, pp. 10-11.

Krupa, Zbigniew et al., "Requirement of Galactolipids for Photosystem J Activity in Lyophilized Spinach Chloroplasts", Biochimica et Biophysica Acta, 408, pp. 26-34, 1975.

KSV-5000.

Kuipers, Oscar P., et al., "Enhanced Activity and Altered Specificity of Phospholipase A2 by Deletion of a Surface Loop", Science, vol. 244, 1989.

Richardson, Toby H., et al., "A Novel, High Performance Enzyme for Starch Liquefaction", The Journal of Biological Chemistry, vol. 277, No. 29, Issue of Jul. 19, pp. 25501-26507, 2002.

Roberts et al. (1992) Gene 122(1), 155-61.

Roberts, et al.; "Extracellular Lipase Production by Fungi from Sunflower Seed"; Mycologia(1987); vol. 79(2); pp. 265-273.

Roberts, Ian N., et al., Heterologous gene expression in *Aspergillus niger*: a glucoamylase-porcine pancreatic prophospholipase A2 fusion protein is secreted and processed to yield mature enzyme.

Robertson et al, Journal of Biological Chemistry, 1994, 2146-2150.

Rodrigues, et al.;"Short Communication: Bioseparations with Permeable Particles"; Journal of Chromatography & Biomedical Applications(1995); vol. 655; pp. 233-240.

Rogalska, Ewa, et al., "Stereoselective Hydrolysis of Triglycerides by Animal and Microbial Lipases", Chirality, vol. 5, pp. 24-30, 1993.

Rose, et al.;"CODEHOP (Consensus-Degenerate Hybrid Oligonucleotide Primer) PCR primer design"; Nucleic Acids Research(2003); vol. 31(13); pp. 3763-3766.

Rousseau, Derick, et al., "Tailoring the Textural Attributes of Butter Fat/Canola Oil Blends via *Rhizopus arrhizus* Lipase-Catalyzed Interesterification. 2. Modifications of Physical Properties", J. Agric. Food Chem., vol. 1998, vol. 46, pp. 2375-2381.

Rydel, Timothy J. et al., "The Crystal Structure, Mutagenesis and Activity Studies Reveal that Patatin Is A Lipid Acyl Hydrolase with a Ser-Asp Catalytic Dyad", Biochemistry, 2003, vol. 42, pp. 6696-6708.

Sahsah, Y., et al., "Enzymatic degradation of polar lipids in *Vigna unguiculata* leaves and influence of drought stress", Physiologia Plantarum, vol. 104, pp. 577-586, 1998.

Sahsah, Y., et al., "Purification and characterization of a soluble lipolytic acylhydrolase from Cowpea (*Vigna unguiculata* L.) leaves", Biochimica et Biophysica Acta, vol. 1215, pp. 66-73, 1994.

Saiki R.K. et al Science (1988) 239, pp. 487-491.

Saito, Kunihiko, et al., "Phospholipase B from *Penicillium notatum*", Methods in Enzymology, vol. 197.

Sakai, Norio, et al., "Human glactocerebrosidase gene: promoter analysis of the 5'-flanking region and structural organization", Biochimica et Biophysica Acta, vol. 1395, pp. 62-67, 1998.

Sakaki T et al, Advanced Research on Plant Lipids, Proceedings of the International Symposium on Plant Lipids, 15th, Okazaki, Japan, May 12-17, 2002 (2003) p. 291-294, Publisher Kluwer Academic Publishers.

Sales Range for Baking Improver and Premix Manufacturers from DSM Bakery Ingredients.

Sambrook et al, Chapters 1, 7, 9, 11, 12 and 13—Molecular Cloning a laboratory manual, Cold Spring Harbor Laboratory Press (1989).

Sambrook, J., et al. "A Laboratory Manual, Second Edition", Plasmid Vectors, 1989.

Sanchez et al., ."Solution and Interface Aggregation States of Crotalus atrox Venom Phospholipase A2 by Two-Photon Excitation Fluorescence Correlation Spectroscopy", Biochemistry, 2001, vol. 40, pp. 6903-6911.

Sarney Douglas B. et al, "Enzymatic Synthesis of Sorbitan Esters Using a Low-Boiling-Point Azeotrope as Reaction Solvent", Biotechnology and Bioengineering, 1997, vol. 54(4).

Saxena, et al.; "Purification Strategies for Microbial Lipases"; Journal of Microbilogical Methods (2003); pp. 1-18.

Scheib et al.; "Stereoselectivity of Mucorales lipases toward triradylglycerols—A simple solution to a complex problem"; Protein Science (1999); vol. 8; pp. 215-221.

Schiller, Jurgen, et al., "Lipid analysis of human spermatozoa and seminal plasma by MALDI-TOF mass spectrometry and NMR spectroscopy—effects of freezing and thawing" Chemistry and Physics of Lipids, vol. 106, 2000, pp. 145-156.

Schofield, J. David, "Wheat Structure, Biochemistry and Functionality", Department of Food Science and Technology.

Scopes, Robert K., "Section 8.4: Ultrafiltration" in *Protein Purification Principles and Practice, Third Edition* (1994) Springer-Verlag, New York, p. 267-9.

Sequence alignment of the nucleotide sequences of SEQ ID No. 2 of EP'167 and SEQ ID No. 7 of D20 and the amino acid sequences of SEQ ID No. 2 of EP'167 and SEQ ID No. 8 of D20.

Shehata PhD Thesis.

Shillcock, Julian C., et al., "Equilibrium structure and lateral stress distribution of amphiphilic bilayers from dissipative particle dynamics simulations", Journal of Chemical Physics, vol. 117, No. 10, Sep. 8, 2002.

Shillcock, Julian C., et al., "Tension-induced fusion of bilayer membranes and vesicles", Advance Online Publication.

Shimada et al, J. of Bioscience and Bioengineering vol. 91, No. 6, 529-538 (2001).

Shimada et al, J. of Fermentation and Bioengineering vol. 75, No. 5, 349-352 (1993).

Shimada et al, JAOCS vol. 71, No. 9, (Sep. 1994).

Shin, et al.; "Butyl-Toyopearl 650 as a New Hydrophobic Adsorbent for Water-Soluable Enzyme Proteins"; Analytical Biochemistry(1984); vol. 138; pp. 259-261.

Shogren, M.D., et al., "Functional (Breadmaking) and Biochemical Properties of Wheat Flour Components. I. Solubilizing Gluten and Flour Protein", Cereal Chemistry, vol. 46, No. 2, Mar. 1969.

Si, Joan Qi, "Enzymes, Baking, Bread-Making".

Si, Joan Qi, "Synergistic Effect of Enzymes for Breadbaking".

Si, Joan Qi, et al. "Enzymes for bread, noodles and non-durum pasta".

Si, Joan Qi, et al., "Novamyl—A true Anti-Staling Enzyme", Cereal Food, p. 1, No. 20.

Si, Joan Qi, et al., "Synergistic Effect of Enzymes for Breadbaking".

Si, Joan Qi; "New Enzymes for the Baking Industry"; Food Tech Europe (1996) pp. 60-64.

Sias B et al, Biochemistry, (2004), vol. 43(31), p. 10138-48.

Siew W.L. & Ng W.L. (1999) Influence of diglycerides on crystalisation of palm oil, in Journal of Science of Food and Agriculture 79:722-726.

Siew W.L. & Ng W.L. (2000) Differential scanning thermograms of palm oil triglycerides in the presence of diglycerides, in Journal of Oil Palm Research 12:107.

Siew W.L. (2001) Understanding the Interactions of Diacylglycerols with oil for better product performance, paper presented at the 2001 PIPOC International Palm Oil Congress—Chemistry and Technology Conference Aug. 20-23, 2001, Kuala Lumpur, Malaysia.

Skovgaard, et al.;"Comparison of Intra- and extraclluealr isozyme banding patterns of *Fusarium oxysporum*"; Mycol. Res. (1998); vol. 102(9); pp. 1077-1084.

Slotboom et al Chem. Phys. Lipids 4 (1970) 15-29.

Smith, George P.; "The Progeny of sexual PCR"; Nature; vol. 370; No. 18; Aug. 4, 1994.

Smith, Timothy L., et al., "The promoter of the glucoamylase-encoding gene of *Aspergillus niger* functions in *Ustilago maydis*", Gene. 88, 259-262, 1990.

Soe, J.B., "Analyses of Monoglycerides and Other Emulsifiers by Gaschromatography".

Solares, Laura F., et al., "Enzymatic resolution of new carbonate intermediates for the synthesis of (S)-(=)-zopiclone", Tetrahedron: Asymmetry, vol. 13, 2002, pp. 2577-2582.

Sols and De Le Fuente, "On the substrate specificity of glucose oxidase", Biochem et Biophysica Acta (1957) 24:206-7.

Sonntag N.O.V. (1982a) Glycerolysis of Fats and methyl esters—status, review and critique, in Journal of American Oil Chemist Society 59:795-802A.

Soragni, Elisabetta, et al., "A nutrient-regulated, dual localization phospholipase A2 in the symbiotic fungus" The EMBO Journal, vol. 20, No. 18, pp. 5079-5090, 2001.

Sorensen, H.R., et al., "Effects of added enzymes on the physicochemical characteristics on fresh durum-pasta".

Sosland, Josh, "Alive and kicking", Milling & Baking News, Feb. 24, 2004.

Soumanou, Mohamed M., et al., "Two-Step Enzymatic Reaction for the Synthesis of Pure Structured Triacylglycerides", JAOCS, vol. 75, No. 6, 1998.

Spargeon, Brad, "In China, a twist: Forgers file patents".

Spendler, et al., "Functionality and mechanism of a new 2nd generation lipase for baking industry"—Abstract. 2001 AACC Annual Meeting; Symposia at Charlotte, NC. Oct. 14-18, 2001.

Spradlin J E, Biocatalysis in Agric. Technol., ACS Symposium, 389(3), 24-43 (1989).

Sreekrishna K et al (1988) J Basic Microbiol. 28(4), 265-78.

Stadler et al., "Understanding Lipase Action and Selectivity", CCACAA, vol. 68, No. 3, pp. 649-674, 1995.

Steinstraesser, et al., "Activity of Novispirin G10 against *Pseudomonas aeruginosa* In Vitro and in Infected Burns", Antimicrobial Agents and Chemotherapy, Jun. 2002, vol. 46, No. 6, pp. 1837-1844.

Stemmer, Willem P.C.; "DNA shuffling by random fragmentation and reassembly: In vitro recombination for molecular evolution"; Proc. Natl. Acad. Sci. USA, vol. 91, pp. 10747-10751; Oct. 1994.

Stemmer, Willem P.C.; "Rapid evolution of a protein in vitro by DNA shuffling"; Affymax Research Institute, Nature, vol. 370, Aug. 4, 1994.

Sternberg, M., "Purification of Industrial Enzymes with Polyacrylic Acids", Process Biochemistry, Sep. 1976.

Strickland, James A., et al., "Inhibition of Diabrotica Larval Growth by Patatin, the Lipid Acyl Hydrolase from Potato Tubers", Plant Physiol, vol. 109, pp. 667-674, 1995.

Sudbery et al (1988) Biochem Soc Trans. 16(6), 1081-3.

Sugatani, Junko, et al., "Studies of a Phospholipase B from Penicillium Notatum Substrate Specificity and Properties of Active Site", Biochimica et Biophysica Acta, vol. 620, 1980, pp. 372-386.

Sugimoto et al., Agric. Biol. Chem. 47(6), 1201-1206 (1983).

Sugiyama et al., "Molecular cloning of a second phospholipase B gene, caPLB2 from *Candida albicans*", Medical Mycology, vol. 37, 1999.

Svendsen, A. "Engineered lipases for practical use", INFORM (1994) 5(5):619-623.

Svendsen, Allan, "Lipase protein engineering" Biochimica et Biophysica Acta, vol. 1543, 2000, pp. 223-238.

Svendsen, Allan, et al., "Biochemical properties of cloned lipases from the Pseudomonas family", Biochimica et Biophysica Acta, vol. 1259, 1995, pp. 9-17.

Sweigard, James A., et al., "Cloning and analysis of CUT1, a cutinase gene from *Magnaporthe grisea*", Mol. Gen. Genet., 232:174-182, 1992.

Swinkels et al (1993) Antonie van Leeuwenhoek 64, 187-201.

Sztajer H et al Acta Biotechnol, vol. 8, 1988, pp. 169-175.

Talker-Huiber, Cynthia Z., et al., "Esterase EstE from *Xanthomonas vesicatoria* (Xv_EstE) is an outer membrane protein capable of hydrolyzing long-chain polar esters", Appl. Microbiol Biotechnol, 61:479-487, 2003.

Terasaki, Masaru, et al., "Glycerolipid Acyl Hydrolase Activity in the Brown Alga *Cladosiphon okamuranus* Tokida", Biosci. Biotechnol. Biochem., vol. 67, No. 9, pp. 1986-1989, 2003.

The First European Symposium of Enzymes on Grain Processing—Proceedings.

The New Enzyme Operatives, Ingredient Technology, 50, Aug. 1997.

Thommy L-G; Carlson, "Law and Order in Wheat Flour Dough; Colloidal Aspects of the Wheat Flour Dough and its Lipid and Protein Constitutents in Aqueous Media", Fortroligt, Lund 1981.

Thornton et al 1988 Biochem. Et Biophys. Acta. 959, 153-159.

Tiss, Aly, et al., "Effects of Gum Arabic on Lipase Interfacial Binding and Activity", Analytical Biochemistry, vol. 294, pp. 36-43, 2001.

Toida J et al, Bioscience, Biotechnology, and Biochemistry, Jul. 1995, vol. 59, No. 7, pp. 1199-1203.

Tombs and Blake, Biochim. Biophys (1982) 700:81-89.

Topakas, E., et al. "Purification and characterization of a feruloyl esterase from *Fusarium oxysporum* catalyzing esterification of phenolic acids in ternary water—organic solvent mixtures", Journal of Biotechnology, vol. 102, 2003, pp. 33-44.

Torossian and Bell (Biotechnol. Appl. Biochem., 1991, 13:205-211.

Tsao et al. (1973) J Supramol Struct. 1(6), 490-7.

Tsuchiya, Atsushi et al, Fems Microbiology Letters, vol. 143, pp. 63-67.

Tsuneo Yamane et al., "Glycerolysis of Fat by Lipase", Laboratory of Bioreaction Engineering, vol. 35, No. 8, 1986.

Tsychiya, Atsushi, et al., "Cloning and nucleotide sequence of the mono- and diacylglycerol lipase gene (mdlB) of *Aspergillus oryzae*", FEMS Microbiology Letters, vol. 143, pp. 63-67, 1996.

Turnbull, K.M., et al., "Early expression of grain hardness in the developing wheat endosperm", Planta, 2003, vol. 216, pp. 699-706.

Turner, Nigel A., et al., "At what temperature can enzymes maintain their catalytic activity?", Enzyme and Microbial Technology, vol. 27, 2000, pp. 108-113.

Turner, Progress in Industrial Microbiology, Martinelli and Kinghorn (eds.), Elsevier, Amsterdam, 1994, 29:641-666.

Unknown, "Appendix: Classification and Index of Fungi mentioned in the Text" in *Unknown*, p. 599-616.

Unknown, "Section I: Structure and Growth—Chapter 1: An Introduction to the Fungi" in *Unknown* pp. 1-16.

Unknown, *Studies on Lipase* (1964) p. 21.

Uppenberg, Jonas, et al., "Crystallographic and Molecular-Modeling Studies of Lipase B from *Candida antarctia* Reveal a Stereospecificity Pocket for Secondary alcohols", Biochemistry, 1995, vol. 34, pp. 16838-16851.

Uppenberg, Jonas, et al., "The Sequence, crystal structure determination and refinement of two crystal forms of lipase B from *Candida antarctica*", Structure 1994, vol. 2, No. 4.

Upton C et al TIBS Trends in Biochemical Sciences, Elsevier Publication (1995), vol. 20, pp. 178-179.

USDA, "Production of an Industrially Useful Fungal Lipase by a Genetically Altered Strain of *E. coli*", New Technology.

Uusitalo et al. (1991) J Biotechnol. 17(1), 35-49.

Uwajima T et al, Agricultural and Biological Chemistry, 43(12), pp. 2633-2634, 1979.

Uwajima T et al, Agricultural and Biological Chemistry, 44(9), pp. 2039-2045, 1980.

Uwajima T et al, Methods in Enzymology, 89(41), pp. 243-248.

Vaidehi, et al.; "Lipase Activity of Some Fungi Isolated from Groundnut"; Current Science (1984); vol. 53(23); p. 1253.

van Binsbergen, Jan, et al., "Substitution of PHE-5 and ILE-9, Amino Acids Involved in the Active Site of Phospholipase A2 (PLA), and Chemical Modification of Enzymatically Generated (LYS-6)-PLA.", Proceedings of the 20th European Peptide Symposium, Sep. 4-9, 1988, University of Tubingen.

Van Den Berg. G, Regulatory status and use of lipase in various countries.

van Gemeren, I.A., et al., "Expression and Secretion of Defined Cutinase Variants by *Aspergillus awamori*" Applied and Environmental Microbiology, vol. 64, No. 8, pp. 2794-2799, Aug. 1998.

van Kampen, M.D., et al., "The phospholipase activity of *Staphylococcus hyicus* lipase strongly depends on a single Ser to Val mutation", Chemistry and Physics of Lipids, vol. 93, 1998, pp. 39-45.

van Nieuqenhuyzen, "Open Doors to baked goods".

van Oort, Maarten G et al, Biochemistry 1989 9278-9285.

van Solingen, Pieter, et al., "The cloning and characterization of the acyltransferase gene of penicillium chrysogenum", Agricultural University, Wageningen, The Netherlands.

Vaysse et al J. of Biotechnology 53 (1997) 41-46.

Villenueva, Inform, vol. 8, No. 6, Jun. 1997.

Vujaklija, Dušica, et al., "A novel streptomycete lipase: cloning, sequencing and high-level expression of the *Streptomyces rimosus* GDS (L)-lipase gene", Arch. Microbiol, vol. 178, pp. 124-130, 2002.

Wahnelt S.V., Meusel D, & Tülsner M, (1991) Zur kenntnis des diglyceride influsses auf das kristallisationsverhalten von Fetten, in Fat Science Technology 4:117-121.

Waninge, Rianne, et al., "Milk membrane lipid vesicle structures studied with Cryo-TEM", Colloids and Surfaces B: Biointerfaces 31 (2003), pp. 257-264.

Warmuth et al, 1992, Bio Forum 9, 282-283.

Watanabe et al. Bio sci Biochem 63(5) 820-826, 1999.

Watanabe, Yasuo et al., "Cloning and sequencing of phospholipase B gene from the yeast *Torulaspora delbrueckii*", FEMS Microbiology Letters, vol. 124, 1994, pp. 29-34.

Webb EC, Enzyme Nomenclature, 1992, p. 310.

Weber et al. J Agric Food Chem 1985, 33, 1093-1096.

Welter, et al; "Identification of Recombinant DNA"; pp. 424-431.

Wen-Chen Suen et al., "Improved activity and thermostability of *Candida antarctica* lipase B by DNA family shuffling", Protein Engineering, Design & Selection, vol. 17, No. 2, pp. 133-140, 2004.

West S.; "Olive and Other Edible Oils"; Industrial Enzymology (1996); pp. 295-299.

Whitaker, John R., et al., "Biocatalysis in Agricultural Biotechnology", ACS Symposium Series.

Whitehead, Michael, et al., "Transformation of a nitrate reductase deficient mutant of *Penicillium chrysogenum* with the corresponding *Aspergillus niger* and *A. nidulans* niaD genes", Mol Gen Genet, 216: 408-411, 1989.

Wihlem et al., "A Novel Lipolytic Enzyme Located in the Outer Membrane of *Pseudomonas aeruginosa*", Journal of Bacteriology, vol. 181, No. 22, Nov. 1999, pp. 6977-6986.

Williams et al Protein Analysis by Integrated Sample Preparation, Chemistry, and Mass Spectrometry, Edited by Meyers.

Winnacker, Chapter 11, pp. 424-431 In From genes to clones: introduction to gene technology, VCH (1987).

Winnacker, E. "Chapter 11: Identification of Recombinant DNA" in *From Genes to Clones: Introduction to Gene Technology*, 1987 John Wiley & Sons.

Winther, Ole, et al., "Teaching computers to fold proteins", Physical Review, vol. 70, No. 030903, 2004.

wirkung von Phospholipiden, "Struktur-Wirkungsbezehungen von Phospholipiden in Backwaren".

Withers-Martinez, Chrislaine, et al., "A pancreatic lipase with a phospholipase A1 activity: crystal structure of a chimeric pancreatic lipase-related protein 2 from guinea pig", Structure, 1996, vol. 4, No. 11.

Witt, Wolfgang et al., "Secretion of Phospholipase B From *Saccharomyces cerevisiae*", Biochimica et Biophysica Acta, vol. 795, 1984, pp. 117-124.

Wood et al., Eds., "Biomass, Part B, Lignin, Pectin, and Chitin", Methods in Enzymology (1988) vol. 161, Academic Press, San Diego.

Woolley et al., "Lipases their structure, biochemistry and application", Cambridge University Press.

WPI Acc No. 93-298906(38) and JP05211852 Preparation of low fat content cream-by adding lipase to mixture of fat and water.

Xu, Jun, et al., "Intron requirement for AFP gene expression in *Trichoderma viride*", Microbiology, 2003, vol. 149, pp. 3093-3097.

Yamaguchi et al, 1991, Gene 103:61-67.

Yamane et al., "High-Yield Diacylglycerol Formation by Solid-Phase Enzymatic Glycerolysis of Hydrogenated Beef Tallow", JAOCS, vol. 71, No. 3, Mar. 1994.

Yamano Y, Surface activity of lysophosphatidyl choline from soybean.

Yamauchi, Asao et al., "Evolvability of random polypetides through functional selection within a small library", Protein Engineering, vol. 15, No. 7, pp. 619-626, 2002.

Yang, Baokang, et al., "Control of Lipase-Mediated Glycerolysis Reactions with Butteroil in Dual Liquid Phase Media Devoid of Organic Solvent", J. Agric. Food Chem., 1993, vol. 41, pp. 1905-1909.

Yount, Nannette Y., et al., "Multidimensional signatures in antimicrobial peptides".

Zaks, Aleksey, et al., "Enzyme-catalyzed processes in organic solvents", Proc. Natl. Acad. Sci. USA, vol. 82, pp. 3192-3196, May 1985.

Zaks, Aleksey, et al., "The Effect of Water on Enzyme Action in Organic Media", The Journal of Biological Chemistry, vol. 263, No. 17, Issue of Jun. 15, pp. 8017-8021, 1988.

Zangenbert, Niels Honberg, et al., "A dynamic in vitro lipolysis model 1. Controlling the rate of lipolysis by continuous addition of calcium", European Journal of Pharmaceutical Sciences, vol. 14, 2001, pp. 115-122.

Zangenbert, Niels Honberg, et al., "A dynamic in vitro lipolysis model II. Evaluation of the model", European Journal of Pharmaceutical Sciences, vol. 14, 2001, pp. 237-244.

Zhang, Hong, et al., "Modification of Margarine Fats by Enzymatic Interesterification: Evaluation of a Solid-Fat-Content-Based Exponential Model with Two Groups of Oil Blends", JAOCS, vol. 81, No. 1, 2004.

Kunze, Hans, et al., "On the mechanism of lysophospholipase activity of secretory phospholipase A2 (EC 3.1.1.4): deacylation of monoacylphosphoglycerides by intrinsic sn-1 specificity and Ph-dependent acyl migration in combination with sn-2 specificity", Biochimica et Biophysica Acta, vol. 1346, 1997, pp. 86-92.

Kuwabara, et al., "Purification and Some Properties of Water-soluble Phospholipase B from *Torulaspora delbrueckii*", J. Biochem., vol. 104, pp. 236-241, 1988.

Kuwabara, et al., "Purification and Some Properties of Water-soluble Phospholipase", Agric. Biol. Chem., vol. 52, No. 10, pp. 2451-2458, 1988.

Kweon et al., "Phospholipid Hydolysate and Antistaling Amylase Effects on Retrogradation of Starch in Bread", Journal of Food Science, vol. 59, No. 5, 1994.

Larchenkova LP et al. Effect of starter and souring temperature on reproduction of *E coli* and lactobacili in milk.

Larsen N G et al, Journal of Cereal Science (1990), vol. 12(2), p. 155-164.

Lecointe et at Biotechnology Letters, vol. 18, No. 8 (August) pp. 869-874.

Lee, Keun Hyeung, et al., "Identification and characterization of the antimicrobial peptide corresponding to C-terminal B-sheet domain of tenecin 1, an antibacterial protein of larvae of *Tenebrio molitor*", Biochem. J., 1996, vol. 334, pp. 99-105.

Lee, Kyung S., et al., The *Saccharomyces cerevisiae* PLB1 Gene Encodes a Protein Required for Lysophospholipase and Phospholipase B Activity, The Journal of Biological Chemistry, vol. 269, No. 31, Issue of Aug. 5, pp. 19725-19730.

Leggio, Leila Lo, et al., "The 1.62 A structure of *Thermoascus aurantiacus* endoglucanase: completing the structural picture of subfamilies in glycoside hydrolase family 5", FEBS Letters, vol. 523, 2002, pp. 103-108.

Leidich et al., "Cloning and Disruption of caPLB1, a Phospholipase B Gene Involved in the Pathogenicity of *Candida albicans*", The Journal of Biological Chemistry, vol. 273, No. 40, oo. 26078-26086, 1998.

Li, W., et al., "Surface properties and locations of gluten proteins and lipids revealed using confocal scanning laser microscopy in bread dough", Journal of Cereal Science, vol. 39, 2004, pp. 403-411.

Lih-ling Wang et al, J Agric. Food. Chem. (1993), 41, 1000-1005.

Lima, Vera L.M., et al., "Lecithin-cholesterol acyltransferase (LCAT) as a plasma glycoprotein: an overview", Carbohydrate Polymers, vol. 55, 2004, pp. 179-191.

Lin M J Y et al, Cereal Chemistry (1974), vol. 51(1), p. 34-45.

Lin S et al, Enzyme and Microbial Technology 18 (1996), pp. 383-387.

Lipase A "Amano" 6 Assay Note and Product Specification from Armano Pharmaceutical Co Ltd Nagoya Japan, Dec. 16, 1985.

Lipase A "Amano" 6 Assay Note and Product Specification from Armano Pharmaceutical Co Ltd Nagoya Japan, Aug. 27, 1985.

Lipase A "Amano" 6 product sheet, Apr. 1, 1999.

Lipase SP677 as a Baking Enzyme, from Novo Nordisk, Denmark, Mar. 17, 1994.

Liomod L338P.

Lipopan F: Keep the quality—cut your costs 2000 Novozymes A/S. www.enzymes.novo.dk/cgl-bin/bvisapi.dll/biotimes/one_article. jsp?id=16947&lang=en&t=b1.

Litthauer, Derek, et al., "*Pseudomonas luteola* lipase: A new member of the 320- residue *Pseudomonas* lipase family", Enzyme and Microbial Technology, vol. 30, pp. 209-215, 2002.

Llustenberger, Cornelia, et al., "Application of Noopazyme in Asian Noodles and Non-Durum Pasta", Cereal Food, 2002-18584-01, p. 1, vol. 11.

Llustenberger, Cornelia, et al., "Enzymes in Frozen Dough and Parbaked Bread", Cereal Food, 2001-17056-01, p. 1, vol. 19.

Lo Y-C et al. Crystal structure of *Escherichia coli* Thioesterase I/Proteasel/Lysophospholipase L1: Consensus sequence blocks constitute the catalytic center of SGNH-hydrolases through a conserved hydrogen bond network. Journal of Molecular Biology, London, GB, vol. 330, No. 3, 539-551.

Longhi, Sonia, et al., "Atomic Resolution (1.0 Å) Crystal Structure of *Fusarium solani* Cutinase: Stereochemical Analysis" J. Mol. Biol. vol. 268, pp. 779-799, 1997.

Lozano et al., "Over-stabilization of *Candida antarctica* lipase B by ionic liquids in ester synthesis", Biotechnology Letters, vol. 23, pp. 1529-1533, 2001.

Lustenberger Abstract.

Luzi, Paola et al, Genomics (1995), vol. 26(2), p. 407-9.

Madsen J.S. & Qvist K.B. (1997) J. Food Sci. 62, 579-582.

Mao, Cungui, et al., "Cloning and Characterization of a *Saccharomyces cerevisiae* Alkaline Ceramidase with Specificity for Dihydroceramide", The Journal of Biological Chemistry, vol. 275, No. 40, 2000, pp. 31369-31378.

Maria Teres Neves Petersen, PhD, "Total Internal Reflection Fluorescence Flow System with Electrochemical Control", TIRF-EC Flow System, Sep. 2002.

Marion D et al—Chapter 6, pp. 131-p. 167 of "Interactions the Keys to Cereal Quality" 1998 ISBN 0 913250-99-6 (ed. Hamer & Hoseney).

Marion D et al pp. 245-260 of Wheat Structure Biochemistry & Functionality (ed Schofield JP) ISBN 085404777-8 published in 2000—(It states that it is the Proceedings of Conference organised by Royal Soc of Chemistry Food Chemistry Group held on Apr. 10-12, 1995, in Reading, UK. However, it is unclear why there was such a delay).

Marsh, Derek, et al., "Derivatised lipids in membranes. Physicochemical aspexts of N-biotinyl phosphatidylethanolamines and N-acyl ethanolamines", Chemistry and Physics of Lipids, vol. 105, 2000, pp. 43-69.

Martinelle et al., "The Role of Glu87 and Trp89 in the lid of *Humicola lanuginosa* lipase", Protein Engineering, vol. 9, No. 6, 1996, pp. 519-524.

Martinez, Chrislaine, et al., "Engineering cysteine mutants to obtain crystallographic phases with a cutinase from *Fusarium solani* pisi", Protein Engineering, vol. 6, No. 2, pp. 157-165, 1993.

Martinez, Diego, et al., "Genome sequence of the lignocellulose degrading fungus *Phanerochaete chrysosporium* strain RP78", Nature Biology, May 2, 2004.

Mase et al., "Purification and Characterization of a new Lipase from *Fusarium* sp. TM-30", Biosci. Biotech. Biochem., vol. 59, No. 9, pp. 1771-1772, 1995.

Mason, Research Disclosure, Kenneth Mason Publications, Westbourne GB No. 390, Oct. 1996, pp. 661-662.

Masuda, Naoko, et al., "Primary structure of protein moiety of *Penicillium notatum* phospholipase B deduced from the Cdna", Eur. J. Biochem., vol. 202, pp. 783-787, 1991.

Matos AR, Lipid Catabolism: Lipid Degradation, 2000, p. 779-781.

Matos, A.R., et al., "A patatin-like protein with galactolipase activity is induced by drought stress in *Vigna unguiculata* leaves", Biochemical Society Transactions, vol. 28, part 6, 2000.

Matos, AR et al, Febs Letters, 491 (2001) p. 188-192.

Matsuda H et al, Biochim Biophys Acta, (1979), vol. 573(1), p. 155-65.

Matsuoka, et al.; "Purification and properties of a Phospholipase C That has High Activity toward Sphingomyelin from *Aspergillus saitor*"; Biotiechonology and Applied Biochemistry (1987); vol. 9, pp. 401-409.

Matthes et al, (1984) EMBO J. 3, p. 801-805.

Max-Planck-Institut fur Kohlenforschung et al., "Controlling the enantioselectivity of enzymes by directed evolution: Practical and theoretical ramifications".

McAuley, Katherine E., et al., "Structure of a feruloyl esterase from *Aspergillus niger*", Acta Crystallographica, Section D, pp. 878-887, 2004.

McCoy M G et al, Journal of Lipid Research (2002), vol. 43, pp. 921-929.

McNeill G.P. & Berger R.G. (1993) Enzymatic glycerolysis of palm oil fractions and palm oil based model mixture: Relationship between fatty acid composition and monoglyceride yield, in Food Biotechnology 7: 75-87.

McNeill, Gerald P., et al., "Further Improvements in the Yield of Monoglycerides During Enzymatic Glycerolysis of Fats and Oils".

McNeill, Gerald P., et al., "High-Yield Enzymatic Glycerolysis of Fats and Oils", JAOCS, vol. 68, No. 1, Jan. 1991.

McNeill, Gerald P., et al., "Selective Distribution of Saturated Fatty Acids into the Monoglyceride Fraction During Enzymatic Glycerolysis", JAOCS, vol. 69, No. 11, Nov. 1992.

McNeill, Gerald P., et al., "Solid Phase Enzymatic Glycerolysis of Beef Tallow Resulting in a High Yield of Monoglyceride".

Mechanism studies of the new lipase, Article, p. 1, No. 14.

Memo: From Charlotte Johanson?, "Short introduction/ status on Ferulic Acid Esterases and Acetyl Xylan Esterases", Jan. 9, 2004.

Meyer, V., et al., "Transcriptional regulation of the Antifungal Protein in *Aspergillus giganteus*", Mol Genet Genomics, 2002, vol. 266, pp. 747-757.

Meyers, Robert A., "Molecular Biology and Biotechnology—A Comprehensive Desk Reference".

Michalski et al., "Photosynthetic apparatus in chilling-sensitive plants. VII. Comparison of the effect of galactolipase treatment of chloroplasts and cold-dark storage of leaves on photosynthetic electron flow", Biochimica et Biophysica Acta, vol. 589, pp. 84-99, 1980.

Mielgo, I., et al., "Covalent immobilisation of manganese peroxidases (MnP) from *Phanerochaete chrysosporium* and *Bjerkandera* sp. BOS55", Enzyme and Microbial Technology, vol. 32, 2003, pp. 769-775.

Miller, Byron S., et al., "A Comparison of Cereal, Fungal, and Bacterial Alpha-Amylases as Supplements for Breadmaking", Food Technology, Jan. 1953.

Mine Y, Food Research International, 29(1), 1996, pp. 81-84.

Ministerio da Ciencia e Tecnologia, *Diario Oficial da Uniao*, Jul. 15, 2003.

Mogensen, Jesper E., et al., "Activation, Inhibition, and Destabilization of *Thermomyces lanuginosus* Lipase by Detergents", Biochemistry, vol. 44, pp. 1719-1730, 2005.

Mohsen et al., "Specificity of Lipase Produced by Rhyopus Delemar and Its Utilization in Bread Making", Egypt. J Food. Sci. vol. 14, No. 1, pp. 175-182.

Molecular Biological Methods for Bacillus—Chapter 3 (Ed. C.R. Harwood and S.M. Cutting) 1990, John Wiley and Sons Ltd, Chichester, UK.

Mølgaard, Anne, et al., "*Rhamnogalacturonan acetylesterase* elucidates the structure and function of a new family of hydrolases", Structure, vol. 9, No. 4, 2000.

Molochnaya Promyshlennost 1980 No. 11 21-25, 47—abstract from Food Sci & Tech Abs.

Monick John A., Alcohols, Their Chemistry, Properties and Manufacture.

Monographs for Emulsifiers for Foods, EFEMA Nov. 1985 2nd Edition.

Moore, Charles M., et al., "Metal ion homeostasis in *Bacillus subtilis*", Current Opinion in Microbiology, 2005, vol. 8, pp. 188-195.

Morgan, Keith R., et al., "Stalling in Starch Breads: The Effect of Antistaling α-Amylase", Starch/Stärke, vol. 49, 1997, pp. 59-66.

Morgan-Jones, Gareth; "Notes on Coelomycetes.II. Concerning the Fusicoccum Anamorph of *Botryosphaneria ribis*"; vol. Xxx, pp. 117-125; Oct.-Dec. 1987.

Morinaga et al Biotechnology (1984) 2, p. 636-639.

Morten, T. & A., Letter, Rodovre, Jul. 2004.

Mukherjee, Kumar D. et al., "Enrichment of y-linolenic acid from fungal oil by lipase-catalysed reactions", Appl. Microbiol Biotechnol (1991), vol. 35, pp. 579-584.

Murakami, Mototake, et al., "Transesterification of Oil by Fatty Acid-Modified Lipase", Technical Research Institute.

Murakami, Nobutoshi, et al., "Enzymatic Transformation of Glyceroglycolipids into sn-1 and sn-2 Lysoglyceroglycolipids by use of *Rhizopus arrhizus* Lipase", Tetrahedron, vol. 50, No. 7, pp. 1993-2002, 1994.

Mustranta, Annikka, et al., "Comparison of Lipases and Phosphlipases in the Hydrolysis of Phospholipids", Process Biochemistry, vol. 30, No. 5, pp. 393-401, 1995.

N.V. Nederlandsch Octrooibureau Terms and Conditions.

Nagano, et al.; "Cloning and Nucleotide Sequence of cDNA Encoding a Lipase from *Fusarium keteroporum*"; J. Biochem (1994); vol. 116; pp. 535-540.

Nagao et al, J. Biochem 124, 1124-1129, 1998.

Nagao et al, J. of Bioscience and Bioengineering vol. 89, No. 5, 446-450, 2000.

Nagao et al, J. of Molecular Catalysis B: Enzymatic 17 (2002) 125-132.

Nagao et al, JAOCS vol. 78, No. 2, 2001.

Nagao, Toshihiro et al., "Cloning and Nucleotide Sequence of CDNA Encoding a Lipase from *Fusarium heterosporum*", J. Biochem., vol. 116, pp. 535-540, 1994.

Nagao, Toshihiro et al., "Expression of Lipase cDNA from *Fusarium heterosporum* by *Saccharomyces cereviisiae*: High-Level Production and Purification", Journal of Fermentation and Bioengineering, 1996, vol. 81, No. 6, pp. 488-492.

Nagodawlthana et al., "Enzymes in Food Processing", Third Edition, 1993, Academic Press, Inc.

National Research Council (U.S.) Committee on Specifications of the Food Chemicals Codex, "Lipase Activity" in *Food Chemicals Codex* (1981) National Academy Press, Washington, D.C. pp. 492-493.

Needleman & Wunsch (1970), J. of Molecular Biology 48, 443-453.

Nelson and Long, Analytical Biochemistry (1989), 180, p. 147-151.

Nerland A H, Journal of Fish Diseases, vol. 19, No. 2, 1996, pp. 145-150.

Néron, et al., "Effects of lipase and the phosphlipase on the lipids hydrolysis during mixing in correlation with the oxygen consumption by wheat flour dough during kneading" available at http://www.cnam.fr/biochimie.

Ness, Jon. E., et al., "DNA shuffling of subgenomic sequences of subtilisin" Nature Biotechnology, vol. 17, Sep. 1999.

Nestle Research Center, Brochure for "Food Colloids 2006" in Montreux, Switzerland, Apr. 23-26, 2006.

Neugnot Virginie et al, European Journal of Biochemistry, 2002, vol. 269, pp. 1734-1745.

Newport, G., et al., "KEX2 Influences *Candida albicans* Proteinase Secretion and Hyphal Formation", The Journal of Biological Chemistry, 1997, vol. 272, No. 46, pp. 28954-28961.

Nicolas, Anne, et al., "Contribution of Cutinase Serine 42 Side Chain to the Stabilization of the Oxyanion Transition State", Biochemistry, vol. 35, pp. 398-410, 1996.

Nielsen et al., "Lipases A and B from the yeast *Candida antarctica*".

Nierle W et al, Fette Seifen Anstrichmittel (1981), vol. 83(10), p. 391-395.

Nierle, Von W. et al. "Weizenlipide: Funktion und Einfluß bei der Verarbeitung des Mehles".

Nierle, W., et al., "Versuche zur Verlangerung der Haltbarkeit von Dartoffelprodukten", Chem. Mikrobiol. Technol. Lebensm., 1975, vol. 3, pp. 172-175.

Nobutoshi M et al, Tetrahedron Letters (1991), vol. 31(1), p. 1331-4.

Novozymes data dated Jul. 17, 2005 entitled "Baking performance of prior art lipases from *Humicola lanuginosa, Aspergillus tubigensis, Rhizopus delemar* and *Rhizomucor miehei*, and their activity on galactolipids in dough".

Novozymes Memo—Test of lipases for EP1193314B1, Jul. 6, 2005.

Novozymes Report 2002 Annual Report.

Novozymes, "Biowhitening—a new concept for steamed bread", *BioTimes*, Jan. 2005.

Novozymes, "Breakthrough: Less Fattening Fried Food" *BioTimes*, Jun. 2001, No. 2.

Novozymes, "Enzymes for dough strengthening", 2001.

Novozymes, "Lipopan F BG- application and mechanism of a new lipase for bread baking" (Draft) *Cereal Food* (2003) (Author: Drost-Lustenberger, C. et al.).

Novozymes, "Lipopan F BG", *Cereal Foods*.

Novozymes, "Mechanism studies of the new lipase".

Novozymes, "Product Sheet for Lipopan F BG", *Cereal Food*, (2001).

Novozymes, "Product Sheet for Lipopan FS BG", *Cereal Food* (2002).

Novozymes, "Product Sheet for Lipopan S BG", *Cereal Food* (2002).

Novozymes, "Product Sheet for Noopazyme".

Novozymes, "Product Sheet for Novozym 27016" (draft);

Novozymes, "Product Sheet for Novozym 27041" (draft).

Novozymes, "Product Sheet for Novozym 27019" (draft).

Novozymes, "Product Sheet for Novozym 27080".

Novozymes, "Product Sheet for Novozym 27106".

Novozymes, "Product Sheet: Enzyme Business, Noopazyme" (draft).

Novozymes, "Product Sheet: Enzyme Business, Novozym 27019" (draft).

Novozymes, "Product Sheet: Enzyme Business, Novozym 677 BG".

Novozymes, "Revolutionizing baking", *BioTimes* (2002) pp. 6-7.

Novozymes, "Strong sales for lipase that makes dough stronger" *BioTimes*, Dec. 2003.

Novozymes, "The Novozyme Touch: Make your mark on the future".

Novozymes, "The perfect roll every time for steers", *BioTimes*, Sep. 2003.

Novozymes, "The value of innovation", *BioTimes*, Mar. 2004.

Novozymes, "The vital role of technical service in baking", *BioTimes*, Jun. 2004.

Novozymes, Lipopan 50 BG, Product Sheet.

Novozymes, Lipopan F BG, Product Specification.

Novozymes, Lipopan F BG, Product Data Sheet.

Novozymes, Lipopan FS BG, Product Sheet.

Novozymes. Enzymes at work.

NY metode til aktivitetsbestemme fedtnedbrydende vaskemiddelenzy.

Nylander et al., "Interaction between lipids and lipases A collection of papers presented at the European Meeting on lipid and lipase interaction at Lund University".

Ognjenovic Radomir et al, Acceleration of ripening of semi-hard cheese by proteolytic and lipolytic enzymes.

Ohm, J.B., et al., "Relationships of Free Lipids with Quality Factors in Hard Winter Wheat Flours", Cereal Chem., vol. 79, No. 2, pp. 274-278, 2002.

Ohta, S. et al., "Application of Enzymatic Modification of Phospholipids on Breadmaking", Abstract from AACC 68th Annual Meeting in Kansas City, MO, Oct. 30-Nov. 3, 1983, published in Cerial Foods World, p. 561.

Ohta, Yoshifumi, et al., "Inhibition and Inactivation of Lipase by Fat Peroxide in the Course of Batch and Continuous Glycerolyses of Fat by Lipase", Agric. Biol. Chem., vol. 53, No. 7, pp. 1885-1890, 1989.

Okiy D.A. (1977) Partial glycerides and palm oil Crystallisation, in Journal of Science and Food Agriculture 28:955.

Okiy D.A. (1978) Interaction of triglycerides and diglycerides of palm oil, in Oleagineux 33:625-628.

Okiy D.A., Wright, W.B., Berger, K.G. & Morton I.D. (1978), The physical properties of modified palm oil, in Journal of Science of Food and Agriculture 29:1061-1068.

Oluwatosin, Yemisi E., et al., "Phenotype: a Possible Role for the Kex2 Endoprotease in Vacuolar Acidification", Molecular and Cellular Biology, 1998, pp. 1534-1543.

Oluwatosin, Yemisi E., et al., "Mutations in the Yeast KEX2 Gene Cause a Vma-Like Phenotype: a Possible Role for the Kex2 Endoprotease in Vacuolar Acidification", Molecular and Cellular Biology, vol. 18, No. 3, pp. 1534-1543, Mar. 1998.

O'Mahony et al. Hydrolysis of the lipoprotein fractions of milk by Phospholipase C.

Orberg, Marie-Louise, "Self-assembly Structures Formed by Wheat Polar Lipids and their Interaction with Lipases", Master of Scient Thesis, Apr. 2005.

Orskov, Janne, et al., "Solubilisation of poorly water-soluble drugs during in vitro lipolysis of medium- and long-chain triacylglycerols", European Journal of Pharmaceutical Sciences, vol. 23, 2004. pp. 287-296.

Osman, Mohamed, et al., "Lipolytic activity of Alternaria alternate and *Fusarium oxysporum* and certain properties of their lipids", Microbios Letters, vol. 39, pp. 131-135, 1988.

Ostrovskaya L K et al, Dokl Akad Nauk SSSR, (vol. 186(4), p. 961-3) p. 59-61.

O'Sullivan et al, J Plant Physiol, vol. 313, (1987) p. 393-404.

Outtrup, Günther H., et al., "Properties and Application of a Thermostable Maltogenic Amylase Produced by a Strain of *Bacillus* Modified by Recombinant-DNA Techniques", Starch/Starke, vol. 36, No. 12, pp. 405-411.

Palomo, Jose M., et al., "Enzymatic production of (3S, 4R)-(−)-4-(4'-fluorophenyl)-6-oxo-piperidin-3-carboxylic acid using a commerical preparation of lipase A from *Candida antarctica*: the role of a contaminant esterase" Tetrahedron: Asymmetry, vol. 13, 2002, pp. 2653-2659.

Palomo, Jose M., et al., "Enzymatic resolution of (±)-glycidyl butyrate in aqueous media. Strong modulation of the properties of the lipase from *Rhizopus oryzae* via immobilization techniques", Tetrahedron: Asymmetry, vol. 15, 2004, pp. 1157-1161.

Palomo, Jose M., et al., "Modulation of the enantioselectivity of *Candida antarctica* B lipase via conformational engineering: kinetic resolution of (±)-α-hydroxy-phenylacetic acid derivatives", Tetrahedron: Asymmetry, vol. 13, 2002, pp. 1337-1345.

Pariza, Michael, et al., "Evaluating the safety of Microbiol Enzyme Preparations Used in Food Processing: Update for a New Century", Regulatory Toxicology and Pharmacology, vol. 33, pp. 173-186.

Patent Abstracts of Japan vol. 016, No. 528 (C-1001), Oct. 29, 1992 & JP 04 200339 A see abstract.

Patent Abstracts of Japan vol. 095, No. 001, Feb. 28, 1995 & JP 06 296467 A see abstract.

Peelman F, et al, Protein Science Mar. 1998; 7(3): 587-99.

Penninga et al, Biochemistry (1995), 3368-3376.

Persson, Mattias, et al., "Enzymatic fatty acid exchange in digalactosyldiacylglycerol", Chemistry and Physics of Lipids, vol. 104, 2000, pp. 13-21.

Peters, G.H., et al., "Active Serine Involved in the Stabilization of the Active Site Loop in the *Humicola lanuginosa* Lipase", Biochemistry, 1998, vol. 37, pp. 12375-12383.

Peters, G.H., et al.; "Dynamics of *Rhizomucor miehei* lipase in a lipid or aqueous environment: Functional role of glycines"; Dept. of Biochemistry and Molecular Biology, University of Leeds.

Peters, G.H., et al.; "Essential motions in lipases and their relationship to the biological function".

Peters, Günther H., et al., "Theoretical Investigation of the Dynamics of the Active Site Lid in *Rhizomucor miehei* Lipase", Biophysical Journal, vol. 71, 1996, pp. 119-129.

Philippine Patent Application Serial No. 31068.

*Phytochemical Dictionary* "Chapter 4, Sugar Alcohols and Cyclitols".

Picon et al. Biotechnology letters vol. 17 nr 10 pp. 1051-1056.

Plijter J and JHGM Mutsaers, The surface rheological properties of dough and the influence of lipase on it, Gist-brocades, Bakery Ingredients Division, Oct. 1994.

Plou et al, J. Biotechnology 92 (2002) 55-66.

Ponte J G, Cereal Chemistry (1969), vol. 46(3), p. 325-29.

Poulsen, C.H., et al., "Effect and Functionality of Lipases in Dough and Bread", The British Library.

Poulsen, Charlotte, et al. "Purification and Characterization of a Hexose Oxidase with Excellent Strenghening Effects in Bread".

Product Data Sheet, Bakezyme P 500 BG, DSM Food Specialties.

Product Description PD 40084-7a Grindamyl Exel 16 Bakery Enzyme.

Product Sheet B1324a-GB—Lecitase$^R$ Novo, Novo Nordisk.

Product Sheet, Lipozyme® 10.000 L, Novo Nordisk.

Punt and van den Hondel, Meth. Enzym., 1992, 216:447-457.

Pyler, E.J., "Baking Science and Technology Third Edition", vol. 1, 1988.

Pyler, E.J., "Baking Science and Technology Third Edition", vol. II, 1988.

Queener et al. (1994) Ann N Y Acad Sci. 721, 178-93.

Rambosek and Leach, CRC Crit. Rev. Biotechnol., 1987, 6:357-393.

Rapp, Peter, et al., "Formation of extracellular lipases by filamentous fungi, yeasts, and bacteria", Enzyme Microb. Technol., 1992, vol. 14, November.

Rapp, Peter; "Production, regulation, and some properties of lipase activity from *Fusarium oxysporum* f. sp. *vasinfectum*"; Enzyme and Microbial Technology(1995); vol. 17; pp. 832-838.

Reetz M.T., Jaeger K.E. Chem Phys Lipids. Jun. 1998; 93(1-2): 3-14.

Reetz Manfred T, Current Opinion in Chemical Biology, Apr. 2002, vol. 6, No. 2, pp. 145-150.

Reiser J et al. (1990) Adv Biochem Eng Biotechnol. 43, 75-102.

Richardson & Hyslop, pp. 371-476 in Food Chemistry, 1985, second edition, Owen R. Fennema (ed), Manel Dekker, Inc, New York and Basel.

Richardson and Hyslop, "Enzymes: XI—Enzymes Added To Foods During Processing" in *Food Chemistry*, Marcel Dekker, Inc., New York, NY 1985.

Arskog and Joergensen, "Baking performance of prior art lipases from *Candida cylindracea* and *Aspergillus foeditus* and their actiivty on galactolipids in dough", Novozymes Report 2005.

Arskog and Joergensen, "Baking performance of prior art lipases from *Humicola lanuginosa, Aspergillus tubigensis, Rhizopus delemar* and *Rhizomucor miehei*, and their actiivty on galactolipids in dough", Novozymes Report 2005.

Delphine Briand et al., "Substrate Specificity of the Lipase from *Candida parapsilosis*", Lipids, 1995, vol. 30, No. 8.

"Definition of Recombined Milk", International Dairy Federation, 1979, doc. 116, p. 5.

Stryer, L., Biochemistry, 1981, $2^{nd}$ Edition, W H Freeman and Co., San Francisco.

"AOCS Introduction to the Processing of Fats and Oils", American Oil Chemists Society, 2003, pp. III 16-19.

Hajime Seino et al., "Enzymatic Synthesis of Carbohydrate Esters of Fatty Acid (1) Esterification of Sucrose, Glucose, Fructose and Sorbitol", JAOCS, Nov. 1984, vol. 61, No. 11.

Anna Maria V. Garzillo et al., "Production, purification and characterization of glucose oxidase from *Penicillium variabile* P16$^1$", Biotechnol, Appln. Biochem., 1995, vol. 22, pp. 169-178.

Patent Abstracts of Japan; Publication No. 07-079687; Publication Date Mar. 28, 1995.

Patent Abstracts of Japan; Publication No. 04-370055; Publication Date Dec. 12, 1992.

Patent Abstracts of Japan; Publication No. 48016612; Publication Date May 23, 1973.

"Purifine Enzyme", Verenium Corporation leaflet, Jan. 2008.

Sequence alignment of database accession No. Q44268 with Seq. ID No. 16.

Sequence alignment of database accession No. Q44268 with Seq. ID No. 70.

Nerland A.H., "The Nucleotide Sequence of the Gene Encoding GCAT from *Aeromonas salmonicida SSP. Salmonicida*", Journal of Fish Diseases, 1996, vol. 19, No. 2, pp. 145-150, XP008049669.

Nerland A.H., "Glycerophospholipid-cholesterol acyltransferase precursor", SwissProt, Feb. 11, 2005, XP002318368.

Buckley J. Thomas, "Substrate specificity of bacterial glycerophospholipid" Cholesterol Acyltransferase, Biochemistry, 1982, vol. 21, pp. 6699-6703.

Sen, et al., Developments in Directed Evolution for Improving Enzyme Functions, Appl. Biochem. Biotechnol (2007) vol. 143, No. 3, p. 212-223.

* cited by examiner 8  9  10  11  12  13  14  15  P  std.
P:Pool #172-174 100U/mL diluted 1:10
Std. Standard protein series

```
                    1                                                50
CBS Peptides   (1)  ---------------------------------AVGVTSTDFTNFKFYIQH
F. het-Nagao   (1)  MMLVLSLLSIIAFTAAGPVPSVDENTRVLEHRAVTVTTQDLSNFRFYLQH
                                                     ** **. * .**.**.**
                    51                                               100
CBS Peptides   (19) GAAAYCNSGTAAGAKITCSNNGCPTIESNGVTVVASFTGSKTGIGGYVST
F. het-Nagao   (51) ADAAYCNFNTAVGKPVHCSAGNCPDIEKDAAIVVGSVVGTKTGIGAYVAT
                    . ***** ** * . **   ** **  . **-* *.*****.**.*
                    101                                              150
CBS Peptides   (69) DSSRKEIVVAIRGSSNIRNWLTNLDFDQSDCSLVSGCGVHSGFQNAWAEI
F. het-Nagao  (101) DNARKEIVVSVRGSINVRNWITNFNFGQKTCDLVAGCGVHTGFLDAWEEV
                    * .******..*** *.***.**  *  *  * **.*****.** ** *.
                    151                                              200
CBS Peptides  (119) SAQASAAVAKARKANPSFKVVATGHSLGGAVATLSAANLRAAGTPVDIYT
F. het-Nagao  (151) AANVKAAVSAAKTANPTFKFVVTGHSLGGAVATIAAAYLRKDGFPFDLYT
                    .*.   ***. *- ***.** * ************..-** ** * *.**
                    201                                              250
CBS Peptides  (169) YGAPRVGNAALSAFISNQAGGEFRVTHDKDPVPRLPPLIFGYRHTTPEYW
F. het-Nagao  (201) YGSPRVGNDFFANFVTQQTGAEYRVTHGDDPVPRLPPIVFGYRHTSPEYW
                    **.*****  . *...* *-*.**** ******** ****** **** ****
                    251                                              300
CBS Peptides  (219) LSGGGGDKVDYAISDVKVCEGAANLMCNGGTLGLDIDAHLHYFQATDACN
F. het-Nagao  (251) LNGGP-LDKDYTVTEIKVCEGIANVMCNGGTIGLDILAHITYFQSMATCA
                    * **     ** ....***** **.****** **** **. ***.    *
                    301              334
CBS Peptides  (269) AGGFSWR---------------------------
F. het-Nagao  (300) PIAIPWKRDMSDEELEKKLTQYSEMDQEFVKQMI
                        *
```

FIG. 7

```
              M   R   F   P   S   I   F   T   A   V   L   F   A   A   S   S   A   L   A   A   P   V   N                      23
    AATTCAAACGATGAGATTCCCATCCATCTTTACCGCTGTTCTGTTCGCCGCTTCCTCCGCCCTGGCTGCCCCAGTCAACA                                           80
                    ───────► alpsynt
      T   T   T   E   D   E   T   A   Q   I   P   A   E   A   V   I   G   Y   S   D   L   E   G   D   F   D   V              50
    CTACCACTGAGGACGAGACTGCTCAGATTCCAGCTGAGGCTGTCATCGGTTACTCTGACCTGGAGGGTGACTTCGATGTT                                          160

A   V   L   P   F   S   N   S   T   N   N   G   F   L   F   I   N   T   T   I   A   S   I   A   A   K   E              77
    GCTGTTTTGCCATTCTCCAACTCCACCAACAACGGTTTCTTGTTCATCAACACTACCATTGCCTCCATTGCTGCCAAGGA                                          240

Y
      E   G   V   S   L   D   K   R   A   V   G   V   T   S   T   D   F   T   N   F   K   F   Y   I   Q   H                 103
    GGAAGGTGTTTCCTTGGACAAGAGAGCCGTTGGAGTGACCTCTACTGACTTCACTAACTTTAAGTTCTACATTCAGCATG                                          320
                                                                      ───────► alps.cbss
    ◄─────────────────────────────────── cbss.alps
      G   A   A   A   Y   C   N   S   G   T   A   A   G   A   K   I   T   C   S   N   N   G   C   P   T   I   E             130
    GTGCTGCCGCATACTGTAACTCCGGTACCGCCGCAGGTGCAAAGATCACTTGTTCGAATAACGGTTGCCCTACTATCGAG                                          400

S   N   G   V   T   V   V   A   S   F   T   G   S   K   T   G   I   G   G   Y   V   S   T   D   S   S   R             157
    TCCAACGGCGTGACTGTGGTCGCCTCCTTCACTGGTTCGAAGACTGGCATCGGCGGTTACGTGTCCACCGATAGCTCGAG                                          480

K   E   I   V   V   A   I   R   G   S   S   N   I   R   N   W   L   T   N   L   D   F   D   Q   S   D                 183
    AAAAGAGATCGTGGTCGCAATCAGAGGTTCCAGCAACATCCGGAATTGGCTGACTAATCTTGACTTTGACCAGTCCGACT                                          560

C   S   L   V   S   G   C   G   V   H   S   G   F   Q   N   A   W   A   E   I   S   A   Q   A   S   A   A             210
    GTTCCCTTGTTTCGGGCTGTGGTGTTCACTCCGGTTTCCAGAACGCTTGGGCCGAGATCTCCGCACAGGCCTCGGCTGCC                                          640

V   A   K   A   R   K   A   N   P   S   F   K   V   V   A   T   G   H   S   L   G   G   A   V   A   T   L             237
    GTGGCAAAAGCTAGAAAGGCCAACCCATCCTTCAAGGTTGTCGCCACTGGCCACTCGCTCGGCGGCGCTGTGGCGACCCT                                          720

S   A   A   N   L   R   A   A   G   T   P   V   D   I   Y   T   Y   G   A   P   R   V   G   N   A   A                 263
    GTCCGCTGCCAACCTTCGAGCTGCAGGTACTCCAGTCGACATCTACACTTATGGTGCACCTAGAGTTGGCAACGCCGCAC                                          800

L   S   A   F   I   S   N   Q   A   G   G   E   F   R   V   T   H   D   K   D   P   V   P   R   L   P   P             290
    TGTCTGCTTTCATCTCGAACCAAGCAGGCGGTGAATTTAGAGTCACTCACGACAAGGACCCAGTGCCTCGGCTTCCACCT                                          880

L   I   F   G   Y   R   H   T   T   P   E   Y   W   L   S   G   G   G   D   K   V   D   Y   A   I   S                 317
    CTGATCTTCGGTTACAGACACACTACCCCAGAGTACTGGCTGTCAGGTGGCGGCGGAGACAAGGTGGACTACGCAATCTC                                          960

D   V   K   V   C   E   G   A   A   N   L   M   C   N   G   G   T   L   G   L   D   I   D   A   H   L                 343
    CGACGTGAAGGTCTGCGAGGGAGCCGCAAACCTCATGTGTAACGGCGGTACACTGGGACTGGACATCGACGCACACTTGC                                         1040

H   I   F   Q   A   T   D   A   C   N   A   G   G   F   S   W   R                                                     360
    ACTACTTCCAGGCAACTGATGCTTGCAACGCCGGAGGTTTCTCCTGGAGATAGGCCATGGAGAGAATTGGATCCT                                              1115
                                  cbss.t ◄──────────────────────────
```

FIG. 8

A.
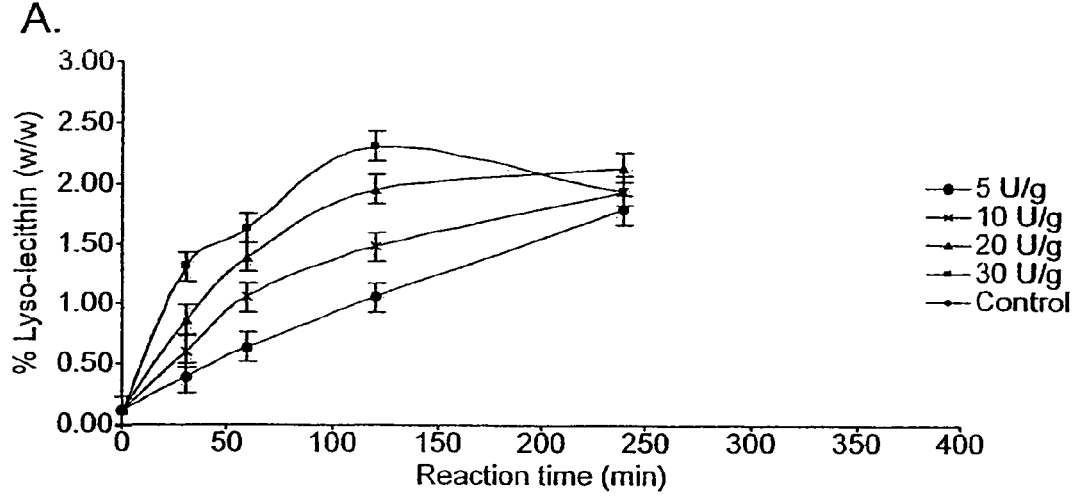
B.
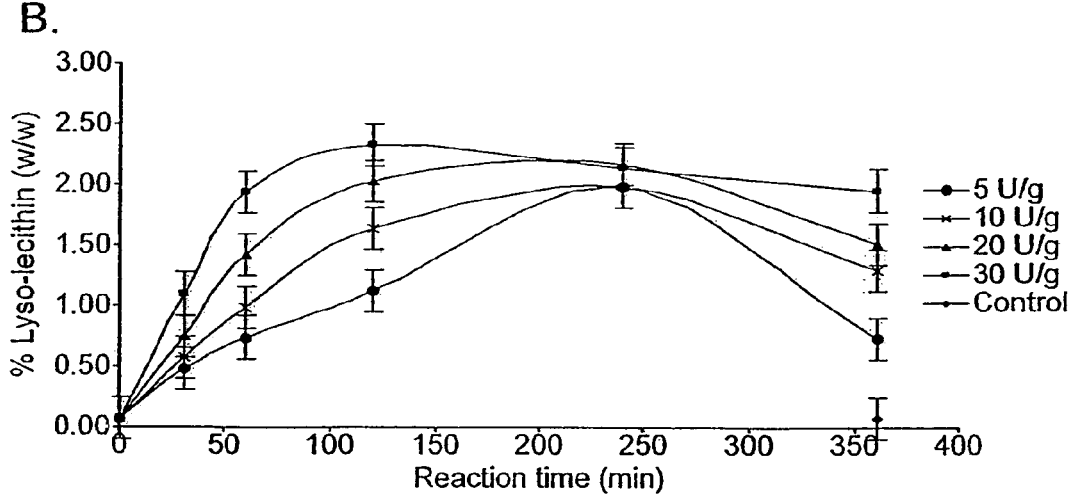
C.
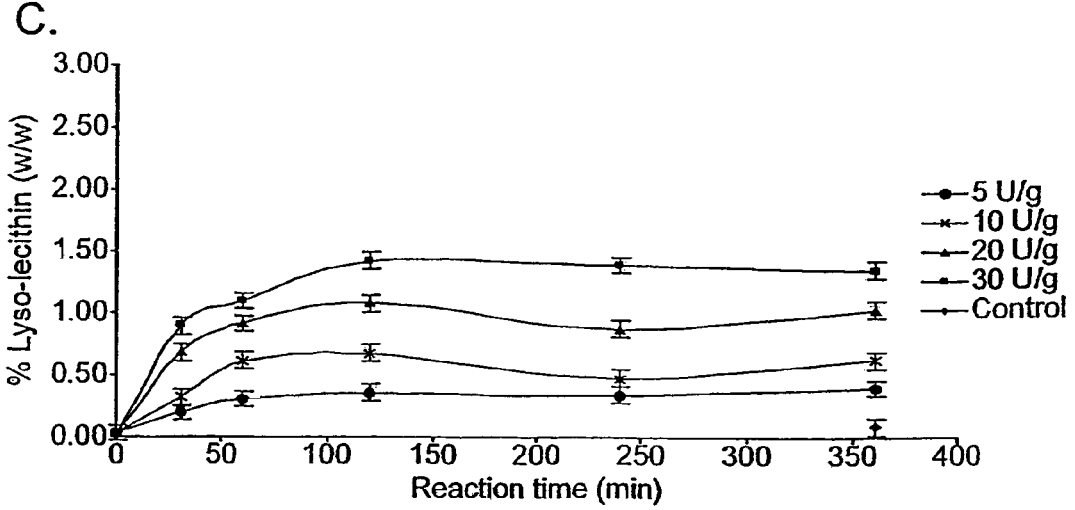
FIG. 22

1. Control
2. Lipolytic enzyme
3. Lecitase® Ultra

```
                                                                              80
GGGGGGGATATCTTCGCCAGTTTCAGTGTTCAGTATCCTTTCTGAGGGAGTCGCACTTGTCACAGCTTGTCTATCACTTA
                         M  R  V  L  S  L  L  S  V  A  T  F  A  V  A  S  P   17
TACCCTTGATCCATACCCTTGCCTGTCAAGATGCGTGTCCTGTCACTCCTCTCAGTTGCCACCTTTGCTGTGGCCAGTCC 160
  L  S  V  E  D  Y  A  K  A  L  D  E  R  A  V  A  V  S  N  G  D  F  G  N  F  K   43
TCTGAGCGTAGAGGACTACGCCAAGGCTCTCGATGAAAGAGCTGTTGCTGTCTCCAACGGTGACTTTGGTAACTTCAAGT 240
  F  Y  I  Q  H  G  A  A  S  Y  C  N  S  N  A  A  A  G  A  K  I  T  C  G  N  N  G   70
TCTACATCCAGCACGGTGCTGCTTCATACTGCAACTCCAATGCCGCAGCTGGTGCAAAGATCACCTGTGGAAACAATGGC 320
  C  P  T  V  Q  S  N  G  A  T  I  V  A  S  F  T  G  S  K  T  G  I  G  G  Y  V  S   97
TGTCCAACAGTCCAGTCCAACGGTGCTACTATCGTCGCATCCTTCACTGGTTCCAAGACTGGCATCGGCGGTTACGTTTC 400
  T  D  S  S  R  K  E  I  V  L  S  V  R  G  S  I  N  I  R  N  W  L  T  N  L  D   123
GACCGACTCTTCACGAAAGGAAATCGTCCTCTCCGTTCGAGGCAGCATAAACATTCGAAACTGGCTCACCAACCTCGACT 480
  F  G  Q  E  D  C  S  L  T  S  G  C  G  V  H  S  G  F  Q  N  A  W  K  E  I  S  A   150
TCGGCCAGGAGGACTGCAGCTTGACCTCAGGTTGTGGAGTACACAGCGGTTTCCAGAATGCCTGGAAAGAGATTTCCGCT 560
  A  A  T  A  A  V  A  K  R  K  A  N  P  S  F  K  V  I  A  T  G  H  S  L  G  G   177
GCAGCAACCGCTGCTGTCGCAAAGGCCCGCAAGGCGAACCCTTCGTTCAAGGTCATTGCCACAGGCCACTCCCTTGGTGG 640
  A  V  A  T  L  A  G  A  N  L  R  V  G  G  T  P  V  D  I  Y  T  Y  G  S  P  R   203
TGCCGTCGCTACACTCGCCGGCGCAAATCTTCGAGTTGGTGGAACACCCGTTGACATCTACACCTACGGCTCCCCCCGAG 720
  V  G  N  S  Q  L  A  G  F  I  S  N  Q  A  G  G  E  F  R  V  T  N  A  K  D  P  V   230
TTGGAAACTCCCAGCTCGCTGGCTTCATCTCGAACCAAGCTGGTGGAGAGTTCCGCGTTACCAATGCCAAGGACCCTGTT 800
  P  R  L  P  P  L  V  F  G  Y  R  H  T  S  P  E  Y  W  L  S  G  A  G  G  D  K  V   257
CCCAGACTTCCCCCTCTGGTCTTTGGTTACCGACACACATCCCCCGAGTACTGGCTGTCTGGTGCGGGAGGTGACAAGGT 880
  D  Y  T  I  N  D  I  K  V  C  E  G  A  A  N  L  K  C  N  G  G  T  L  G  L  D   283
TGACTACACCATCAATGACATCAAGGTCTGTGAGGGTGCTGCCAACCTCAAGTGCAACGGTGGAACCCTTGGATTGGATA 960
  I  D  A  H  L  H  Y  F  Q  E  T  D  A  C  S  G  G  G  I  S  W  R  S  R  R  Y  R   310
TTGATGCTCACCTGCACTACTTCCAGGAGACTGATGCTTGCTCTGGTGGCGGTATCTCTTGGAGAAGCCGAAGATACAGA 1040
  S  A  K  R  E  D  I  S  E  R  A  A  P  M  T  D  A  E  L  E  K  K  L  N  N  Y  V   337
AGCGCCAAGCGTGAGGACATCTCTGAGAGGGCTGCTCCTATGACGGATGCTGAGCTTGAGAAGAAGCTCAACAACTATGT 1120
  E  M  D  K  E  Y  V  K  N  N  A  A  R  T  S                                    352
CGAGATGGATAAGGAGTATGTCAAGAACAATGCCGCACGCACGTCATAGTATGACATTTACGCAGTAATGATATACCACG 1200
AATAATAAGAATCACAAAATAAAAAAAAAAAAAAAA                                            1236
```

FIG. 33

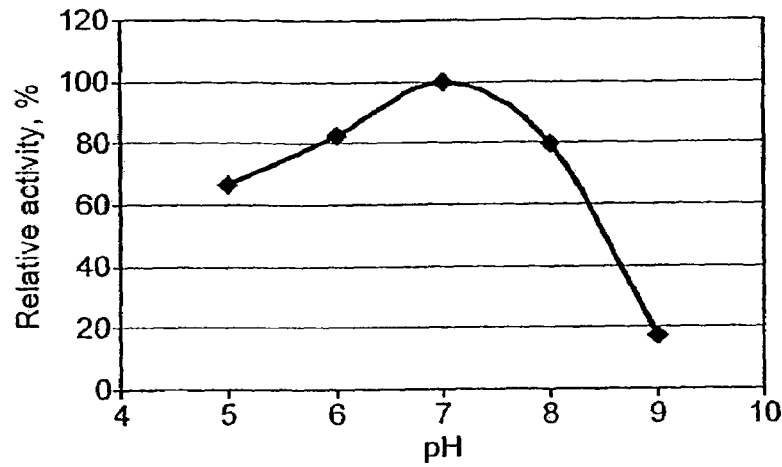

FIG. 36

(SEQ ID No. 1)
```
  1 avgvtstdft nfkfyiqhga aaycnsgtaa gakitcsnng cptiesngvt vvasftgskt
 61 giggyvstds srkeivvair gssnirnwlt nldfdqsdcs lvsgcgvhsg fqnawaeisa
121 qasaavakar kanpsfkvva tghslggava tlsaanlraa gtpvdiytyg aprvgnaals
181 afisnqagge frvthdkdpv prlpplifgy rhttpeywls ggggdkvdya isdvkvcega
241 anlmcnggtl gldidahlhy fqatdacnag gfswr
```
FIG. 37

(SEQ ID No. 2)
```
  1 mrfpsiftav lfaassalaa pvntttedet aqipaeaviq ysdleqdfdv avlpfsnstn
 61 ngflfintti asiaakeeqv sldkravgvt stdftnfkfy iqhgaaaycn sgtaagakit
121 csnngcptie sngvtvvasf tgsktgiggy vstdssrkei vvairgssni rnwltnldfd
181 qsdcslvsgc gvhsgfqnaw aeisaqasaa vakarkanps fkvvatghsl ggavatlsaa
241 nlraagtpvd iytygaprvg naalsafisn qaggefrvth dkdpvprlpp lifgyrhttp
301 eywlsggggd kvdyaisdvk vcegaanlmc nggtlgldid ahlhyfqatd acnaggfswr
361 *
```
FIG. 38

(SEQ ID No. 3)
```
  1 gccgttggag tgacctctac tgacttcact aactttaagt tctacattca gcatggtgct
 61 gccgcatact gtaactccgg taccgccgca ggtgcaaaga tcacttgttc gaataacggt
121 tgccctacta tcgagtccaa cggcgtgact gtggtcgcct ccttcactgg ttcgaagact
181 ggcatcggcg gttacgtgtc caccgatagc tcgagaaaag agatcgtggt cgcaatcaga
241 ggttccagca acatccggaa ttggctgact aatcttgact ttgaccagtc cgactgttcc
301 cttgtttcgg gctgtggtgt tcactccggt ttccagaacg cttgggccga gatctccgca
361 caggcctcgg ctgccgtggc aaaagctaga aaggccaacc catccttcaa ggttgtcgcc
421 actggccact cgctcggcgg cgctgtggcg accctgtccg ctgccaacct tcgagctgca
481 ggtactccag tcgacatcta cacttatggt gcacctagag ttggcaacgc cgcactgtct
541 gctttcatct cgaaccaagc aggcggtgaa tttagagtca ctcacgacaa ggacccagtg
601 cctcggcttc cacctctgat cttcggttac agacacacta cccagagta ctggctgtca
661 ggtggcggcg gagacaaggt ggactacgca atctccgacg tgaaggtctg cgagggagcc
721 gcaaacctca tgtgtaacgg cggtacactg ggactggaca tcgacgcaca cttgcactac
781 ttccaggcaa ctgatgcttg caacgccgga ggtttctcct ggaga
```

FIG. 39

(SEQ ID No. 4)
```
  1 MRVLSLLSVA TFAVASPLSV EDYAKAEDER AVAVSNGDFG NFKFIIQHGA ASTCKSNAAA
 61 GAFITCGNNG CPTVQSNGAT IVASFTGSKT GIGGYVSTDS SRKEIVLSVR GSINIRNWLT
121 NLDFGQEDCS LFSGCGVHSG FQNAWKEISA AATAAVAKAR KANPSFKVIA TGHSLGGAVA
181 TLAGANLRVG GTPVDIYTYG SPRVGNSQLA GFISNQAGGE FRVTNAKDPV PRLPPLVFGY
241 RHTSPEYWLS GAGGDKVDYA INDIKVCEGA ANLKCNGGTL GLDIDAHLHY FQETDACSGG
301 GISWRSRRYR SAKREDISER AAPMTDAELE KKLNNYVEMD KEYVKNNAAR TS
```

FIG. 40

(SEQ ID No. 5)
```
   1 gggggggata tcttcgccag tttcagtgtt cagtatcctt tctgagggag tcgcacttgt
  61 cacagcttgt ctatcactta tacccttgat ccatacccTt gcctgtcaag atgcgtgtcc
 121 tgtcactcct ctcagttgcc acctttgctg tggccagtcc tctgagcgta gaggactacg
 181 ccaaggctct cgatgaaaga gctgttgctg tctccaacgg tgactttggt aacttcaagt
 241 tctacatcca gcacggtgct gcttcatact gcaactccaa tgccgcagct ggtgcaaaga
 301 tcacctgtgg aaacaatggc tgtccaacag tccagtccaa cggtgctact atcgtcgcat
 361 ccttcactgg ttccaagact ggcatcggcg gttacgtttc gaccgactct tcacgaaagg
 421 aaatcgtcct ctccgttcga ggcagcataa acattcgaaa ctggctcacc aacctcgact
 481 tcggccagga ggactgcagc ttgacctcag gttgtggagt acacagcggt ttccagaatg
 541 cctggaaaga gatttccgct gcagcaaccg ctgctgtcgc aaaggcccgc aaggcgaacc
 601 cttcgttcaa ggtcattgcc acaggccact cccttggtgg tgccgtcgct cactcgccg
 661 gcgcaaatct tcgagttggt ggaacacccg ttgacatcta cacctacggc tccccccgag
 721 ttggaaactc ccagctcgct ggcttcatct cgaaccaagc tggtggagag ttccgcgtta
 781 ccaatgccaa ggacctgttc ccagacttcc ccctctggt ctttggttac cgacacacat
 841 cccccgagta ctggctgtct ggtgcgggag tgacaaggt tgactacacc atcaatgaca
 901 tcaaggtctg tgagggtgct gccaacctca agtgcaacgg tggaacccTt ggattggata
 961 ttgatgctca cctgcactac ttccaggaga ctgatgcttg ctctggtggc ggtatctctt
1021 ggagaagccg aagatacaga agcgccaagc gtgaggacat ctctgagagg gctgctccta
1081 tgacggatgc tgagcttgag aagaagctca caactatgt cgagatggat aaggagtatg
1141 tcaagaacaa tgccgcacgc acgtcatagt atgacattta cgcagtaatg atataccacg
1201 aataataaga atcacaaaat aaaaaaaaaa aaaaaa
```

FIG. 41

(SEQ ID No. 6)
```
   1 EAEAAVGVTS TDFTNFKFYI QHGAAAYCNS GTAAGAKITC SNNGCPTIES
  51 NGVTVVASFT GSKTGIGGYV STDSSRKEIV VAIRGSSNIR NWLTNLDFDQ
 101 SDCSLVSGCG VHSGFQNAWA EISAQASAAV AKARKANPSF KVVATGHSLG
 151 GAVATLSAAN LRAAGTPVDI YTYGAPRVGN AALSAFISNQ AGGEFRVTHD
 201 KDPVPRLPPL IFGYRHTTPE YWLSGGGGDK VDYAISDVKV CEGAANIMCN
 251 GGTLGLDIDA HLHYFQATDA CNAGGFSWR
```

FIG. 42

(SEQ ID No. 7)
```
   1 agaattcaaa cgatgagatt cccatccatc tttacogctg ttctgttcgc cgcttcctcc
  61 gccctggctg ccccagtcaa cactaccact gaggacgaga ctgctcagat tccagctgag
 121 gctgtcatcg gttactctga cctggagggt gacttcgatg ttgctgtttt gccattctcc
 181 aactccacca acaacggttt cttgttcatc aacactacca ttgcctccat tgctgccaag
 241 gaggaaggtg tttccttgga caagagagct gttgctgtct ccaacggtga ctttggtaac
 301 ttcaagttct acatccagca cggtgctgct tcatactgca actccaatgc cgcagctggt
 361 gcaaagatca cctgtggaaa caatggctgt ccaacagtcc agtccaacgg tgctactatc
 421 gtcgcatcct tcactggttc caagactggc atcggcggtt acgtttcgac cgactcttca
 481 cgaaaggaaa tcgtcctctc cgttcgaggc agcataaaca ttcgaaactg gctcaccaac
 541 ctcgacttcg gccaggagga ctgcagcttg acctcaggtt gtggagtaca cagcggtttc
 601 cagaatgcct ggaaagagat ttccgctgca gcaaccgctg ctgtcgcaaa ggcccgcaag
 661 gcgaaccctt cgttcaaggt cattgccaca ggccactccc ttggtggtgc cgtcgctaca
 721 ctcgccggcg caaatcttcg agttggtgga acaccgttg acatctacac ctacggctcc
 781 cccgagttg gaaactccca gctcgctggc ttcatctcga accaagctgg tggagagttc
 841 cgcgttacca atgccaagga ccctgttccc agacttcccc ctctggtctt tggttaccga
 901 cacacatccc ccgagtactg gctgtctggt gcgggaggtg acaaggttga ctacaccatc
 961 aatgacatca aggtctgtga gggtgctgcc aacctcaagt gcaacggtgg aaccttgga
1021 ttggatattg atgctcacct gcactacttc caggagactg atgcttgctc tggtggcggt
1081 atctcttgga gaagccgaag atacagaagc gccaagcgtg aggacatctc tgagagggct
1141 gctcctatga cggatgctga gcttgagaag aagctcaaca actatgtcga gatggataag
1201 gagtatgtca agaacaatgc cgcacgcacg tcatagtatg acatttacgc ggatcct
```

FIG. 43

FUNGAL LIPOLYTIC ENZYMES, NUCLEIC ACIDS ENCODING, AND USES THEREOF

REFERENCE TO RELATED APPLICATIONS

This application is a continuation-in-part of International Patent Application PCT/IB2005/000875 filed Mar. 10, 2005 and published as WO 2005/087918 on Sep. 22, 2005, which claims priority from GB Application No. 0405637.0 filed Mar. 12, 2004 and U.S. Provisional Patent Application No. 60/559,149 filed Apr. 2, 2004.

Each of the above referenced applications, and each document cited in this text ("application cited documents") and each document cited or referenced in each of the application cited documents, and any manufacturer's specifications or instructions for any products mentioned in this text and in any document incorporated into this text, are hereby incorporated herein by reference; and, technology in each of the documents incorporated herein by reference can be used in the practice of this invention.

It is noted that in this disclosure, terms such as "comprises", "comprised", "comprising", "contains", "containing" and the like can have the meaning attributed to them in U.S. Patent law; e.g., they can mean "includes", "included", "including" and the like. Terms such as "consisting essentially of" and "consists essentially of" have the meaning attributed to them in U.S. Patent law, e.g., they allow for the inclusion of additional ingredients or steps that do not detract from the novel or basic characteristics of the invention, i.e., they exclude additional unrecited ingredients or steps that detract from novel or basic characteristics of the invention, and they exclude ingredients or steps of the prior art, such as documents in the art that are cited herein or are incorporated by reference herein, especially as it is a goal of this document to define embodiments that are patentable, e.g., novel, non-obvious, inventive, over the prior art, e.g., over documents cited herein or incorporated by reference herein. And, the terms "consists of" and "consisting of" have the meaning ascribed to them in U.S. Patent law; namely, that these terms are closed ended.

FIELD OF THE INVENTION

The present invention relates to novel fungal lipolytic enzymes and to one or more polynucleotides encoding one or more novel fungal lipolytic enzymes. The invention also relates to methods of producing fungal lipolytic enzymes, and uses thereof. The present invention further relates to the preparation of an improved foodstuff, in particular to the preparation of improved bakery products. Specifically, the invention provides novel fungal lipolytic enzymes, which enzymes are capable of conferring improved characteristics to food products, including bakery products.

TECHNICAL BACKGROUND

The beneficial use of lipolytic enzymes (E.C. 3.1.1.x) in food and/or feed industrial applications has been known for many years.

For instance, in EP 0 585 988 it is claimed that lipase addition to dough resulted in an improvement in the antistaling effect. It is suggested that a lipase obtained from *Rhizopus arrhizus* when added to dough can improve the quality of the resultant bread when used in combination with shortening/fat. WO94/04035 teaches that an improved bread softness can be obtained by adding a lipase to dough without the addition of any additional fat/oil to the dough. Castello, P. ESEGP 89-10 December 1999 Helsinki, shows that exogenous lipases can modify bread volume.

The substrate for lipases in wheat flour is 1.5-3% endogenous wheat lipids, which are a complex mixture of polar and non-polar lipids. The polar lipids can be divided into glycolipids and phospholipids. These lipids are built up of glycerol esterified with two fatty acids and a polar group. The polar group contributes to surface activity of these lipids. Enzymatic cleavage of one of the fatty acids in these lipids leads to lipids with a much higher surface activity. It is well known that emulsifiers, such as DATEM, with high surface activity are very functional when added to dough.

Lipolytic enzymes hydrolyse one or more of the fatty acids from lipids present in the food which can result in the formation of powerful emulsifier molecules within the foodstuff which provide commercially valuable functionality. The molecules which contribute the most significant emulsifier characteristics are the partial hydrolysis products, such as lyso-phospholipids, lyso-glycolipids and mono-glyceride molecules. The polar lipid hydrolysis products, namely lyso-phospholipids and lyso-glycolipids, are particularly advantageous. In bread making, such in situ derived emulsifiers can give equivalent functionality as added emulsifiers, such as DATEM.

However, the activity of lipolytic enzymes has also been found to result in accumulation of free fatty acids, which can lead to detrimental functionality in the foodstuff. This inherent activity of lipolytic enzymes limits their functionality.

The negative effect on bread volume is often explained by overdosing. Overdosing can lead to a decrease in gluten elasticity which results in a dough which is too stiff and thus results in reduced volumes. In addition, or alternatively, such lipases can degrade shortening, oil or milk fat added to the dough, resulting in off-flavour in the dough and baked product. Overdosing and off-flavour have been attributed to the accumulation of free fatty acids in the dough, particularly short chain fatty acids.

The presence of high levels of free fatty acids (FFA) in raw materials or food products is generally recognised as a quality defect and food processors and customers will usually include a maximum FFA level in the food specifications. The resulting effects of excess FFA levels can be in organoleptic and/or functional defects.

In EP 1 193 314, the inventors discovered that the use of lipolytic enzymes active on glycolipids was particularly beneficial in applications in bread making, as the partial hydrolysis products the lyso-glycolipids were found to have very high emulsifier functionality, apparently resulting in a higher proportion of positive emulsifier functionality compared to the detrimental accumulation of free fatty acids. However, the enzymes were also found to have significant non-selective activity on triglycerides which resulted in unnecessarily high free fatty acid.

This problem of high triglyceride activity was addressed in WO 02/094123, where the inventors discovered that by selecting lipolytic enzymes which were active on the polar lipids (glycolipids and phospholipids) in a dough, but substantially not active on triglycerides or 1-mono-glycerides, an improved functionality could be achieved.

A commercially preferred source of lipase enzymes is filamentous fungi, such as *Aspergillus* spp. and *Fusarium* spp. Lipases isolated from filamentous fungi have been found to have industrially applicable characteristics and also have been found to be routine to express in heterologous production systems, such as in *Aspergillus oryzae, Fusarium* and yeast.

A lipase from *Fusarium oxysporum* was identified in EP 0 130 064, and the application of *F. oxysporum* lipases in food applications has been suggested in Hoshino et al. (1992) Biosci. Biotech. Biochem 56: 660-664.

EP 0 869 167 describes the cloning and expression of a *Fusarium oxysporum* lipase and its use in baking. The enzyme is described as having phospholipase activity. This enzyme is now sold by Novozymes A/S (Denmark) as Lipopan F™.

WO 02/00852 discloses five lipase enzymes and their encoding polynucleotides, isolated from *F. venenatum, F. sulphureum*, A. berkeleyanum, *F. culmorum* and *F. solani*. All five enzymes are described as having triacylglycerol hydrolysing activity, phospholipase and galactolipase activity. Three of the enzymes have equivalent activity to the *F. oxysporum* enzyme taught in EP 0 869 167: *F. venenatum, F. sulphureum, F. culmorum*.

Therefore, it is apparent that some *Fusarium* lipases, including Lipopan F™ have been found to have side activity on polar lipids, including phospholipids and glycolipids. Although described as a phospholipase in EP 0 869 167, the lipase from *Fusarium oxysporum* has high lipase activity. The enzyme also has glycolipase activity. However, despite the significant activity on polar lipids, the functionality achieved by use of the enzyme is limited due to the high lipase (i.e. triglyceride) activity.

Nagao et al (J. Biochem 116 (1994) 536-540) describes a lipase from *F. heterosporum*; which enzyme predominantly functions as a lipase (E.C. 3.1.1.3) to hydrolyse triglycerides. This is very different from the enzymes according to the present invention.

Lipolytic enzyme variants, with specific amino acid substitutions and fusions, have been produced some of which have an enhanced activity on the polar lipids compared to the wild-type parent enzymes. WO01/39602 describes such a variant, referred to as SP979, which is a fusion of the *Thermomyces lanuginosus* lipase, and the *Fusarium oxysporum* lipase described in EP 0 869 167. This variant has been found to have a significantly high ratio of activity on phospholipids and glycolipids compared to triglycerides.

However, prior to the present invention, natural fungal lipolytic enzymes, particularly from *Fusarium* spp., having a high ratio of activity on polar lipids compared with triglycerides had not been taught.

SUMMARY OF THE INVENTION

In a broad aspect the present invention relates to a fungal lipolytic enzyme having a higher ratio of activity on polar lipids (phospholipids and/or glycolipids) as compared with triglycerides, in particular a higher ratio of activity on glycolipids as compared with triglycerides.

In a further broad aspect the present invention relates to a wild-type fungal lipolytic enzyme having a higher ratio of activity on polar lipids (phospholipids and/or glycolipids) as compared with triglycerides, in particular a higher ratio of activity on glycolipids as compared with triglycerides.

In a yet further broad aspect the present invention relates to a nucleic acid encoding a novel fungal lipolytic enzyme as taught herein.

In one broad aspect the present invention relates to a method of preparing a foodstuff, preferably an egg-based foodstuff, the method comprising adding a fungal lipolytic enzyme of the present invention to one or more ingredients of the foodstuff.

The present invention relates to a method of preparing a dough, the method comprising adding a fungal lipolytic enzyme of the present invention to one or more ingredients of the dough and mixing to form a dough.

Another broad aspect of the present invention relates to a method of preparing a baked product from a dough, the method comprising adding a fungal lipolytic enzyme of the present invention to the dough.

There is also provided a method of preparing a fungal lipolytic enzyme according to the present invention, the method comprising transforming a host cell with a recombinant nucleic acid comprising a nucleotide sequence coding for the fungal lipolytic enzyme, the host cell being capable of expressing the nucleotide sequence coding for the polypeptide of the fungal lipolytic enzyme, cultivating the transformed host cell under conditions where the nucleic acid is expressed and harvesting the fungal lipolytic enzyme.

In a further broad aspect, the invention provides a lipolytic enzyme which retains activity at low temperatures, i.e. is a low temperature lipolytic enzyme.

Aspects of the present invention are presented in the claims and in the following commentary.

Other aspects concerning the nucleotide sequences which can be used in the present invention include: a construct comprising the sequences of the present invention; a vector comprising the sequences for use in the present invention; a plasmid comprising the sequences for use in the present invention; a transformed cell comprising the sequences for use in the present invention; a transformed tissue comprising the sequences for use in the present invention; a transformed organ comprising the sequences for use in the present invention; a transformed host comprising the sequences for use in the present invention; a transformed organism comprising the sequences for use in the present invention. The present invention also encompasses methods of expressing the nucleotide sequence for use in the present invention using the same, such as expression in a host cell; including methods for transferring same. The present invention further encompasses methods of isolating the nucleotide sequence, such as isolating from a host cell.

Other aspects concerning the amino acid sequence for use in the present invention include: a construct encoding the amino acid sequences for use in the present invention; a vector encoding the amino acid sequences for use in the present invention; a plasmid encoding the amino acid sequences for use in the present invention; a transformed cell expressing the amino acid sequences for use in the present invention; a transformed tissue expressing the amino acid sequences for use in the present invention; a transformed organ expressing the amino acid sequences for use in the present invention; a transformed host expressing the amino acid sequences for use in the present invention; a transformed organism expressing the amino acid sequences for use in the present invention. The present invention also encompasses methods of purifying the amino acid sequence for use in the present invention using the same, such as expression in a host cell; including methods of transferring same, and then purifying said sequence.

For the ease of reference, these and further aspects of the present invention are now discussed under appropriate section headings. However, the teachings under each section are not necessarily limited to each particular section.

DETAILED DISCLOSURE OF INVENTION

In one aspect, the present invention provides a wild-type fungal lipolytic enzyme having a higher ratio of activity on polar lipids compared with triglycerides.

In one aspect, the present invention provides a fungal lipolytic enzyme comprising an amino acid sequence as shown as SEQ ID No. 1, SEQ ID No. 2, SEQ ID No. 4, or SEQ ID No. 6 or an amino acid sequence which has at least 90% identity thereto.

In a further aspect the present invention provides a nucleic acid encoding a fungal lipolytic enzyme comprising an amino acid sequence as shown in SEQ ID No. 1, SEQ ID No. 2, SEQ ID No. 4 or SEQ ID No. 6 or an amino acid sequence which has at least 90% identity therewith.

SEQ ID No. 1 is shown in FIG. 37, SEQ ID No. 2 is shown in FIG. 38, SEQ ID No. 4 is shown in FIG. 40 and SEQ ID No. 6 is shown in FIG. 42.

In a further aspect the present invention provides a nucleic acid encoding a fungal lipolytic enzyme, which nucleic acid is selected from the group consisting of:
 a) a nucleic acid comprising a nucleotide sequence shown in SEQ ID No. 3, SEQ ID No. 5 or SEQ ID No. 7;
 b) a nucleic acid which is related to the nucleotide sequence of SEQ ID No. 3, SEQ ID No. 5 or SEQ ID No. 7 by the degeneration of the genetic code; and
 c) a nucleic acid comprising a nucleotide sequence which has at least 90% identity with the nucleotide sequence shown in SEQ ID No. 3, SEQ ID No. 5 or SEQ ID No. 7.

SEQ ID No. 3 is shown in FIG. 39; SEQ ID No. 5 is shown in FIG. 41; and SEQ ID No. 7 is shown in FIG. 43.

In another aspect the present invention provides the use of a fungal lipolytic enzyme according to the present invention in the manufacture of a foodstuff, such as for instance a dough, a baked product, an egg, an egg-based product, a noodle product, a cheese product, a tortilla product, an animal feed product, a vegetable oil or an edible oil. Advantageously, the addition of an enzyme of the present invention to the foodstuff may lead to improved emulsification with lower accumulation of free fatty acids.

In a further aspect the present invention provides the use of a fungal lipolytic enzyme according to the present invention in the manufacture of a dough and/or a baked product, comprising adding said lipolytic enzyme to a dough, and (optionally) baking the dough to make a baked product for one or more of the following: reducing stickiness of the dough; improving machinability of the dough; reducing blistering during baking of the baked product; improving bread volume and/or softness; prolonging shelf life of the baked product and/or dough; improving antistaling effect of the baked product and/or dough; improving crumb structure of the baked product; reducing pore heterogeneity of the baked product; improving pore homogeneity of the baked product; reducing mean pore size of the baked product; enhancing the gluten index of the dough; improving flavour and/or odour of the baked product, improving the colour of the crust of the baked product.

Advantageously, the enzyme according to the present invention may have a higher activity than conventional lipolytic enzymes at a low pH and so may be more advantageously suited for use in a low pH sour dough environment than conventional lipolytic enzymes.

In another aspect of the present invention there is provided a method of making a dough and/or a baked product comprising adding a fungal lipolytic enzyme according to the present invention to a dough and (optionally) baking the dough to make the baked product.

In a further aspect of the present invention provides the use of a fungal lipolytic enzyme according to the present invention in the manufacture of egg-based products for improving texture, reducing mean particle size, reducing mean particle distribution, improving heat stability, improving microwave performance and/or stability.

In another aspect of the present invention, there is provided a method of treating egg or egg-based product, which method comprises adding a fungal lipolytic enzyme according to the present invention to an egg or egg-based product.

In another aspect of the invention, there is provided a method of making noodles, or a noodle dough or a noodle-based product, which method comprises adding a fungal lipolytic enzyme according to the present invention to the noodle, noodle dough or noodle-based product.

In one aspect of the present invention, there is provided a use of a fungal lipolytic enzyme according to the present invention in the manufacture of a noodle or a noodle-based product for one or more of improving colour/yellowness, stabilising colour characteristics, reducing brightness, reducing fat content, improving texture and bite (chewiness), reducing water activity, reducing breakage, increasing core firmness and improving shape retention during processing In another aspect of the invention, there is provided a method of making a tortilla or tortilla dough, which method comprises adding a fungal lipolytic enzyme according to the present invention to the tortilla or tortilla dough A further aspect of the present invention provides the use of a fungal lipolytic enzyme according to the present invention in the manufacture of a tortilla or a tortilla dough for improving the rollability of a tortilla, increasing pliability of a tortilla, improving antistaling properties of the tortilla and/or tortilla dough, improving softness and/or reducing off-flavour in the tortilla and/or tortilla dough.

The functionality of the lipolytic enzyme in tortilla and/or noodles may be improved by combination with emulsifiers such as DATEM.

In another aspect of the invention, there is provided a method of treating milk, cheese milk, cheese or a cheese-based product, which method comprises adding a fungal lipolytic enzyme according to the present invention to the cheese or cheese-based product.

The present invention yet further provides use of a fungal lipolytic enzyme according to the present invention in the manufacture of a cheese or a cheese-based product for one or more of improving flavour, texture and/or stability, decreasing in the oiling-off effect in cheese and/or to increase cheese yield in cheese production.

In another aspect of the invention, there is provided a method of treating animal feed, which method comprises adding a fungal lipolytic enzyme according to the present invention to the animal feed.

The present invention further provides the use of a fungal lipolytic enzyme according to the present invention in the manufacture of animal feed for enhancing one or more of: feed utilisation and/or conversion efficiency, body weight gain, digestibility nitrogen uptake, metabolisability of dry matter and palatability.

In a further aspect of the present invention provides the use of a fungal lipolytic enzyme according to the present invention in a process of preparing a lyso-phospholipid, for example lysolecithin by treatment of a phospholipid (e.g. lecithin) with the enzyme to produce the partial hydrolysis product, i.e. the lyso-phospholipid.

In another aspect of the present invention there is provided a process of preparing a lyso-phospholipid, for example lysolecithin, which process comprises treating a phospholipid (e.g. lecithin) with the fungal lipolytic enzyme according to the present invention.

In a further aspect of the present invention provides the use of a fungal lipolytic enzyme according to the present invention in a process of preparing a lyso-glycolipid, (for example digalactosyl monoglyceride (DGMG) or monogalactosyl monoglyceride (MGMG)) by treatment of a glycolipid (e.g. digalactosyl diglyceride (DGDG) or monogalactosyl diglyceride (MGDG)) with the lipolytic enzyme according to the present invention to produce the partial hydrolysis product, i.e. the lyso-glycolipid.

In a yet further aspect there is provided a process of preparing a lyso-glycolipid (for example digalactosyl monoglyceride (DGMG) or monogalactosyl monoglyceride (MGMG)), which process comprising treating a glycolipid (e.g. digalactosyl diglyceride (DGDG) or monogalactosyl diglyceride (MGDG)) with a fungal lipolytic enzyme according to the present invention.

The present invention also provides a process of enzymatic degumming of vegetable or edible oils, comprising treating the edible or vegetable oil with fungal lipolytic enzyme according to the present invention so as to hydrolyse a major part of the polar lipids (e.g. phospholipid and/or glycolipid).

For the avoidance of doubt, a person of ordinary skill in the art would be aware of methodology suitable for carrying out the enzymatic treatment of edible oils (for instance see EP 0 869 167). Known method may suitably be used when carrying out the present invention, with the proviso that the known enzyme is replaced with the enzyme according to the present invention.

In a further aspect the present invention provides the use of a fungal lipolytic enzyme according to the present invention in the manufacture of a vegetable oil or edible oil for reducing the amount phospholipid in the vegetable oil or edible oil whilst maintaining the triglyceride content of the oil and/or preventing or reducing the accumulation of free fatty acids.

In a yet further aspect the present invention provides the use of a fungal lipolytic enzyme according to the present invention in a process comprising treatment of a phospholipid so as to hydrolyse fatty acyl groups.

In another aspect the present invention provides the use of a fungal lipolytic enzyme according to the present invention in a process for reducing the content of a phospholipid in an edible oil, comprising treating the oil with the fungal lipolytic enzyme according to the present invention so as to hydrolyse a major part of the phospholipid, and separating an aqueous phase containing the hydrolysed phospholipid from the oil.

In a further aspect the invention provides a lipolytic enzyme which retains activity at low temperatures, i.e. a low temperature lipolytic enzyme. Further aspects of the invention include the use of a low temperature lipolytic enzyme in the methods and uses describes herein, i.e. of the fungal lipolytic enzyme of the present invention.

Preferably, the fungal lipolytic enzyme according to the present invention has a higher ratio of activity on polar lipids (e.g. glycolipids and/or phospholipids) than on triglycerides.

Preferably, the fungal lipolytic enzyme according to the present invention has a higher ratio of activity on phospholipids than on triglycerides.

Preferably, the fungal lipolytic enzyme according to the present invention has a higher ratio of activity on glycolipids than on triglycerides.

Suitably, the fungal lipolytic enzyme according to the present invention may have a higher ratio of activity on both glycolipids and phospholipids than on triglycerides.

More preferably, the fungal lipolytic enzyme according to the present invention has a higher ratio of activity on digalactosyl diglyceride (DGDG) than on triglycerides.

Preferably the fungal lipolytic enzyme according to the present invention hydrolyses DGDG or MGDG to DGMG or MGMG, respectively.

The term "higher ratio of activity on polar lipids" as referred to herein means that the fungal lipolytic enzyme according to the present invention has a polar lipid:triglyceride hydrolysing activity ratio which is higher when compared with a commercial enzyme Lipopan F™ (Novozymes A/S, Denmark).

The term "polar lipids" as used herein means phospholipids and/or glycolipids. Preferably, the term "polar lipids" as used herein means both phospholipids and glycolipids.

The terms "higher ratio of activity on glycolipids" and "higher ratio of activity of phospholipids" as referred to herein means that the fungal lipolytic enzyme according to the present invention has a glycolipid:triglyceride hydrolysing activity ratio or a phospholipid:triglyceride hydrolysing activity ratio, respectively, which is higher than the corresponding ratio achieved with the commercial enzyme Lipopan F™ (Novozymes A/S, Denmark).

Preferably, the lipolytic enzyme according to the present invention may have a polar lipid:triglyceride hydrolysing activity ratio of at least 4. Suitably, the polar lipid:triglyceride hydrolysing activity ratio may be greater than 5. Suitably, the polar lipid:triglyceride hydrolysing activity ratio may be greater than 8, preferably greater than 9, more preferably greater than 10, even more preferably greater than 15.

Preferably, the fungal lipolytic enzyme according to the present invention may have a phospholipid:triglyceride hydrolysing activity ratio of at least 4. Suitably, the polar lipid:triglyceride hydrolysing activity ratio may be greater than 5. Suitably, the polar lipid:triglyceride hydrolysing activity ratio may be greater than 8, preferably greater than 9, more preferably greater than 10, even more preferably greater than 15.

Preferably, the fungal lipolytic enzyme according to the present invention may have a glycolipid:triglyceride hydrolysing activity ratio of at least 1.5, preferably at least 1.8, preferably at least 2, preferably at least 3, preferably at least 4. Suitably, the glycolipid:triglyceride hydrolysing activity ratio may be greater than 4. Suitably, the glycolipid:triglyceride hydrolysing activity ratio may be greater than 5.

In a further aspect the present invention provides a fungal lipolytic enzyme having a polar lipid:triglyceride hydrolysing activity ratio of at least 4. Suitably, the polar lipid:triglyceride hydrolysing activity ratio may be greater than 5. Suitably, the polar lipid:triglyceride hydrolysing activity ratio may be greater than 8, preferably greater than 9, more preferably greater than 10, even more preferably greater than 15.

In another aspect the present invention provides a fungal lipolytic enzyme having a phospholipid:triglyceride hydrolysing activity ratio of at least 4. Suitably, the polar lipid:triglyceride hydrolysing activity ratio may be greater than 5. Suitably, the polar lipid:triglyceride hydrolysing activity ratio may be greater than 8, preferably greater than 9, more preferably greater than 10, even more preferably greater than 15.

In a yet further aspect, the present invention provides a fungal lipolytic enzyme having a glycolipid:triglyceride hydrolysing activity ratio of at least 1.5, preferably at least 1.8, preferably at least 2, preferably at least 3, preferably at least 4, preferably greater than 5, preferably greater than 10, preferably greater than 15.

Preferably the fungal lipolytic enzyme according to the present invention has at least 1.5 times more activity against polar lipids (e.g. phospholipase A2 (E.C. 3.1.1.4) activity and/or phospholipase A1 (E.C. 3.1.1.32) activity and/or glycolipase (E.C. 3.1.1.26) activity) as compared with triglyceride lipase activity (E.C. 3.1.1.3), more preferably at least 2-times, more preferably at least 3-times, more preferably at least 4-times.

Preferably the fungal lipolytic enzyme according to the present invention has at least 1.5 times more glycolipase (E.C. 3.1.1.26) activity as compared with triglyceride lipase activity (E.C. 3.1.1.3), more preferably at least 2-times, more preferably at least 3-times, more preferably at least 4-times.

Preferably at the dosage that provides the optimal bread volume using the minibaking assay detailed in example 3, the ratio of hydrolysis of DGDG to triglyceride (TG) ratio is at least 1.7%, preferably at least 1.8%, preferably at least 2% preferably at least 3%, preferably at least 4%, preferably at least 5%, preferably at least 10%, preferably at least 20%, preferably at least 40%, preferably at least 50%.

The term "glycolipase activity" as used herein encompasses "galactolipase activity".

The glycolipase activity, phospholipase activity and triacylglyceride lipase activity of an enzyme can be determined using the assays presented hereinbelow.

Determination of Galactolipase Activity (Glycolipase Activity Assay):

Substrate:
0.6% digalactosyldiglyceride (Sigma D 4651), 0.4% Triton-X 100 (Sigma X-100) and 5 mM CaCl$_2$ was dissolved in 0.05M HEPES buffer pH 7.

Assay Procedure:
400 µL substrate was added to an 1.5 mL Eppendorf tube and placed in an Eppendorf Thermomixer at 37° C. for 5 minutes. At time t=0 min, 50 µL enzyme solution was added. Also a blank with water instead of enzyme was analyzed. The sample was mixed at 10*100 rpm in an Eppendorf Thermomixer at 37° C. for 10 minutes. At time t=10 min the Eppendorf tube was placed in another thermomixer at 99° C. for 10 minutes to stop the reaction.

Free fatty acid in the samples was analyzed by using the NEFA C kit from WAKO GmbH.

Enzyme activity GLU at pH 7 was calculated as micromoles of fatty acid produced per minute under assay conditions.

Determination of Phospholipase Activity (Phospholipase Activity Assay):

Phospholipase activity was measured using two different methods which give comparable results. Either of these methods can be used to determine phospholipase activity in accordance with the present invention. Preferably, the PLU assay is used for determining the phospholipase activity of any enzyme.

"PLU Assay" for Determination of Phospholipase Activity

Substrate:
0.6% L-α Phosphatidylcholine 95% Plant (Avanti #441601), 0.4% Triton-X 100 (Sigma X-100) and 5 mM CaCl$_2$ was dissolved in 0.05M HEPES buffer pH 7.

Assay Procedure:
400 µL substrate was added to an 1.5 mL Eppendorf tube and placed in an Eppendorf Thermomixer at 37° C. for 5 minutes. At time t=0 min, 50 µL enzyme solution was added. Also a blank with water instead of enzyme was analyzed. The sample was mixed at 10*100 rpm in an Eppendorf Thermomixer at 37° C. for 10 minutes. At time t=10 min the Eppendorf tube was placed in another thermomixer at 99° C. for 10 minutes to stop the reaction.

Free fatty acid in the samples was analyzed by using the NEFA C kit from WAKO GmbH.

Enzyme activity PLU-7 at pH 7 was calculated as micromoles of fatty acid produced per minute under assay conditions "TIPU Assay" for Determination of Phospholipase Activity 1 TIPU (Titration Phospholipase Unit) is defined as the amount of enzyme, which liberates 1 µmol free fatty acid per minute at the assay conditions.

Phospholipase A1 and A2 catalyse the conversion of lecithin to lyso-lecithin with release of the free fatty acid from position 1 and 2, respectively. Phospholipase activity can be determined by continuous titration of the fatty acids liberated from lecithin during enzymation, since the consumption of alkali equals the amount of fatty acid liberated.

Substrate:
4% lecithin, 4% Triton-X 100, and 6 mM CaCl2: 12 g lecithin powder (Avanti Polar Lipids #44160) and 12 g Triton-X 100 (Merck 108643) was dispersed in approx. 200 ml demineralised water during magnetic stirring. 3.0 ml 0.6 M CaCl2 (p.a. Merck 1.02382) was added. The volume was adjusted to 300 mL with demineralised water and the emulsion was homogenised using an Ultra Thurax. The substrate was prepared freshly every day.

Assay Procedure:
An enzyme solution was prepared to give a slope on the titration curve between 0.06 and 0.18 ml/min with an addition of 300 µL enzyme.

A control sample of known activity is included.

The samples were dissolved in demineralised water and stirred for 15 min. at 300 rpm. 25.00 ml substrate was thermostatted to 37.0° C. for 10-15 minutes before pH was adjusted to 7.0 with 0.05 M NaOH. 300 µL enzyme solution was added to the substrate and the continuous titration with 0.05 M NaOH was carried out using a pH-Stat titrator (Phm 290, Mettler Toledo). Two activity determinations are made on each scaling. After 8 minutes the titration is stopped and the slope of the titration curve is calculated between 5 and 7 minutes. The detection limit is 3 TIPU/ml enzyme solution.

Calculations:
The phospholipase activity (TIPU/g enzyme) was calculated in the following way:

$$TIPU/g = \frac{\alpha \cdot N \cdot 10^6 \frac{\mu mol}{mol} \cdot 10^{-3} \frac{l}{ml} \cdot V_1}{m \cdot V_2} = \frac{\alpha \cdot N \cdot 10^3 \cdot V_1}{m \cdot V_2}$$

Where:
α is the slope of the titration curve between 5 and 7 minutes of reaction time (ml/min)
N is the normality of the NaOH used (mol/l)
$V_1$ is the volume in which the enzyme is dissolved (ml)
m is the amount of enzyme added to $V_1$ (g)
$V_2$ is the volume of enzyme solution added to the substrate (ml)

Determination of Triacylglyceride Lipase Activity: Assay Based on Triglyceride (Tributyrin) as Substrate (LIPU):

Lipase activity based on tributyrin is measured according to Food Chemical Codex, Forth Edition, National Academy Press, 1996, p 803, with the modifications that the sample is dissolved in deionized water instead of glycine buffer, and the pH stat set point is 5.5 instead of 7.

1 LIPU is defined as the quantity of enzyme which can liberate 1 mol butyric acid per minute under assay conditions.

Based on the assays for activity on galactolipid (GLU), phospholipid (PLU) and triglyceride (LIPU) it is possible to calculate the ratios PLU/LIPU and GLU/LIPU.

The analysis of Lipopan F™ and a lipolytic enzyme according to the present invention derived from *Fusarium heterosporum* (sample 209) (see Example 3) gave the following results.

The relative activity ratios for Lipopan F™ and Sample 209 are

|  |  | Lipopan F | Sample 209 |
|---|---|---|---|
| Phospholipid/triglyceride | PLU/LIPU | 3 | 9 |
| Galactolipid/triglyceride | GLU/LIPU | 1 | 4 |

Suitably the terms "synergy" or "synergistic effect" as used herein means that the combination produces a better effect than when each component (i.e. enzyme) is used separately. Synergy may be determined by making a product, e.g. a dough and/or baked product, with the addition of each component (i.e. enzyme) separately and in combination, and comparing the effects.

The term "fungal lipolytic enzyme" as used herein means that the naturally-occurring source of the enzyme is a fungus. For the avoidance of doubt, however, this term may include a fungal enzyme which is isolated from a fungus, one which is expressed in a fungal host (either the native or non-native fungus) or one which is expressed in a non-fungal host (e.g. in a bacterial or yeast for instance).

Preferably, the fungal lipolytic enzyme according to the present invention is a wild type enzyme.

The terms "natural" and "wild type" as used herein mean a naturally-occurring enzyme. That is to say an enzyme expressed from the endogenous genetic code and isolated from its endogenous host organism and/or a heterologously produced enzyme which has not been mutated (i.e. does not contain amino acid deletions, additions or substitutions) when compared with the mature protein sequence (after co- and post-translational cleavage events) endogenously produced. Natural and wild-type proteins of the present invention may be encoded by codon optimised polynucleotides for heterologous expression, and may also comprise a non-endogenous signal peptide selected for expression in that host.

The term "non-endogenous signal peptide" as used herein means a signal peptide not naturally present in the nascent polypeptide chain of the lipolytic enzyme prior to co-translational cleavage. In the lipolytic enzyme according to the present invention, part or whole of the non-endogenous signal peptide, for example a pro-peptide, may remain attached to the mature polypeptide—this is encompassed by the term "wild-type" as used herein.

As mentioned above, the terms "natural" and "wild type" as used herein mean a naturally-occurring enzyme. However, this does not exclude the use of a synthetic or chemically synthesised polypeptide comprising of the same polypeptide sequence as the naturally occurring mature lipolytic enzyme.

The term "variant" as used herein means a protein expressed from a non-endogenous genetic code resulting in one or more amino acid alterations (i.e. amino acid deletions, additions or substitutions) when compared with the natural or wild-type sequence within the mature protein sequence.

Preferably the fungal lipolytic enzyme according to the present invention is a lipolytic enzyme which retains activity at a low temperature, i.e. is a low temperature lipolytic enzyme.

The term "a low temperature lipolytic enzyme" means an enzyme which has significant activity at 5-15° C., preferably an enzyme which has significant activity at 10° C.

In one embodiment the low temperature lipolytic enzyme according to the present invention is not a lipolytic enzyme comprising the amino acid sequence motif GDSX as disclosed in WO2004/064987 wherein X is one or more of the following amino acid residues: L, A, V, I, F, Y, H, Q, T, N, M or S.

A low temperature lipolytic enzyme according to the present invention may be an enzyme which has a relative activity of at least 5%, preferably at least 7%, more preferably at least 10%, on lecithin substrate at 10° C., at a pH within 20% of the optimal pH of the lipolytic enzyme, as determined by the determination of free fatty acids by the NEFA C method (see Example 5, performed at pH 7). Example 6 provides a method for determining the pH optima for a lipolytic enzyme.

A low temperature lipolytic enzyme according to the present invention may be an enzyme which has a relative activity of at least 10%, preferably at least 15%, more preferably at least 20%, more preferably at least 25% and most preferably at least 30% on lecithin substrated at 20° C., at a pH within 20% of the optimal pH of the lipolytic enzyme, as determined by the determination of free fatty acids by the NEFA C method (see Example 5, performed at pH 7). Example 6 provides a method for determining the pH optima for a lipolytic enzyme.

A low temperature lipolytic enzyme according to the present invention may also show significant activity of egg yolk lecithin at 5° C., characterised in that it is capable of releasing at least 1%, preferably at least 1.5%, more preferably at least 2% of free fatty acid after a reaction time of 480 minutes at an enzyme dosage equivalent to 20 U/g egg yolk, using the assay described in Example 9 and illustrated in FIGS. 24 and 25.

Preferably, the fungal lipolytic enzyme according to the present invention may be obtainable (preferably obtained) from a filamentous fungus. More preferably, the fungal lipolytic enzyme is obtainable (preferably obtained) from *Fusarium* spp. Preferably, the fungal lipolytic enzyme according to the present invention may be obtainable (preferably obtained) from *Fusarium heterosporum* or *Fusarium semitectum*. Suitably, the fungal lipolytic enzyme according to the present invention may be obtainable (preferably obtained) from *Fusarium heterosporum* (CBS 782.83) or *Fusarium semitectum* (IBT 9507).

Thus in one aspect, preferably the lipolytic enzyme according to the present invention is a filamentous fungal lipolytic enzyme, preferably a filamentous fungal wild-type lipolytic enzyme.

Preferably, the fungal lipolytic enzyme according to the present invention comprises an amino acid sequence which has at least 90%, preferably at least 95%, preferably at least 98%, preferably at least 99% identity with the amino acid sequence shown as SEQ ID No. 1 or SEQ ID No. 2, SEQ ID No. 4 or SEQ ID No. 6.

Preferably, the nucleic acid encoding the fungal lipolytic enzyme according to the present invention comprises a nucleotide sequence which has at least 90%, preferably at least 95%, preferably at least 98%, preferably at least 99% identity with the nucleotide sequence shown in SEQ ID No. 3, SEQ ID No. 5 or SEQ ID No. 7.

Preferably, the fungal lipolytic enzyme according to the present invention is not a fusion protein comprising an amino acid sequence from a *Thermomyces* protein or part thereof fused with an amino acid sequence from a *Fusarium* protein or part thereof. In particular, preferably the fungal lipolytic enzyme according to the present invention is not a fusion protein comprising an amino acid sequence from a *Thermomyces lanuginosa* protein or a part thereof fused with an amino acid sequence from a *Fusarium oxysporum* protein or part thereof.

Preferably, the fungal lipolytic enzyme according to the present invention is not obtained from *Thermomyces lanuginosa* and/or is not a variant of an enzyme obtained from *Thermomyces lanuginosa*.

Preferably, the fungal lipolytic enzyme according to the present invention is isolated from a fermentation broth of *Fusarium heterosporum* CBS 782.83 or *Fusarium semitectum* (IBT 9507).

Suitably, the enzyme may be purified by liquid chromatography.

The amino acid sequence of the purified fungal lipolytic enzyme may be determined by Edman degradation and MALDI-TOF analysis.

A partly purified lipolytic enzyme from *Fusarium heterosporum* CBS 782.83 has been tested in mini scale baking tests and in pilot scale baking tests with very good results.

The baking effects of the fungal lipolytic enzyme from *F. heterosporum* CBS 782.83 were found to be superior to Lipopan F™ and this correlated to a increased ratio of activity on polar lipids, in particular glycolipids, such as digalactosyl diglyceride (DGDG), compared to triglycerides.

Additionally, a lipolytic enzyme from *Fusarium semitectum* IBT 9507 has been tested for activity on flour lipids in dough slurry with very good results.

The lipolytic enzyme from *F. semitectum* IBT 9507 was shown to have significant activity on galactolipids in a dough and relatively less activity on triglyceride compared with Lipopan F™.

Suitably, the term "foodstuff" as used herein means a substance which is suitable for human and/or animal consumption.

Suitably, the term "foodstuff" as used herein may mean a foodstuff in a form which is ready for consumption. Alternatively or in addition, however, the term foodstuff as used herein may mean one or more food materials which are used in the preparation of a foodstuff. By way of example only, the term foodstuff encompasses both baked goods produced from dough as well as the dough used in the preparation of said baked goods.

In a preferred aspect the present invention provides a foodstuff as defined above wherein the foodstuff is selected from one or more of the following: eggs, egg-based products, including but not limited to mayonnaise, salad dressings, sauces, ice creams, egg powder, modified egg yolk and products made therefrom; baked goods, including breads, cakes, sweet dough products, laminated doughs, liquid batters, muffins, doughnuts, biscuits, crackers and cookies; confectionery, including chocolate, candies, caramels, halawa, gums, including sugar free and sugar sweetened gums, bubble gum, soft bubble gum, chewing gum and puddings; frozen products including sorbets, preferably frozen dairy products, including ice cream and ice milk; dairy products, including cheese, butter, milk, coffee cream, whipped cream, custard cream, milk drinks and yoghurts; mousses, whipped vegetable creams; edible oils and fats, aerated and non-aerated whipped products, oil-in-water emulsions, water-in-oil emulsions, margarine, shortening and spreads including low fat and very low fat spreads; dressings, mayonnaise, dips, cream based sauces, cream based soups, beverages, spice emulsions and sauces.

In one aspect the foodstuff in accordance with the present invention may be a dough product or a baked product, such as a bread, a fried product, a snack, cakes, pies, brownies, cookies, noodles, instant noodles, tortillas, snack items such as crackers, graham crackers, pretzels, and potato chips, and pasta.

In another aspect, the foodstuff in accordance with the present invention may be an animal feed.

In one aspect preferably the foodstuff is selected from one or more of the following: eggs, egg-based products, including mayonnaise, salad dressings, sauces, ice cream, egg powder, modified egg yolk and products made therefrom.

In some of the applications mentioned herein, particularly the food applications, such as the bakery applications, the lipolytic enzyme according to the present invention may be used with one or more conventional emulsifiers, including for example monoglycerides, diacetyl tartaric acid esters of mono- and diglycerides of fatty acids, sodium stearoyl lactylate (SSL) and lecithins.

The lipolytic enzyme according to the present invention is especially preferred in bread recipes with added fat; this is considered to be due to the low activity of the lipolytic enzyme according to the present invention on triglycerides which results in a reduced free fatty acid accumulation and, with respect to short chain triglycerides, reduced or avoidance of off odour.

In the present context, the term "added fat" is used to indicate no lipid or fat is added to the flour dough.

In addition or alternatively, the enzyme according to the present invention may be used with one or more other suitable food grade enzymes. Thus, it is within the scope of the present invention that, in addition to the lipolytic enzyme of the present invention, at least one further enzyme may be added to the baked product and/or the dough. Such further enzymes include starch degrading enzymes such as endo- or exoamylases, pullulanases, debranching enzymes, hemicellulases including xylanases, cellulases, oxidoreductases, e.g. glucose oxidase, pyranose oxidase, sulfhydryl oxidase or a carbohydrate oxidase such as one which oxidises maltose, for example hexose oxidase (HOX), lipases, phospholipases and hexose oxidase, proteases, and acyltransferases (such as those described in WO04/064987 for instance).

It is particularly preferred that the lipolytic enzyme of the invention is used in combination with alpha amylases in producing food products. In particular, the amylase may be a non-maltogenic amylase, such as a polypeptide having non-maltogenic exoamylase activity, in particular, glucan 1,4-alpha-maltotetrahydrolase (EC 3.2. 1.60) activity (as disclosed in WO05/003339). A suitable non-maltogenic amylase is commercially available as Powersoft™ (available from Danisco A/S, Denmark). Maltogenic amylases such as Novamyl™ (Novozymes A/S, Denmark) may also be used. In one embodiment, the combined use of alpha amylases and the lipolytic enzyme of the invention may be used in a dough, and/or the production of a baked product, such as bread, cakes, doughnuts, cake doughnuts or bagels. The combination of alpha amylases and the lipolytic enzyme of the invention is also considered as preferable for use in methods of production of tortillas, such as wheat and/or maize tortillas.

In another preferred embodiment, the lipolytic enzyme according to the present invention may be used in combination with a xylanase in producing food products. GRIND-AMYL™ and POWERBake 7000 are examples of commercially available xylanase enzymes available from Danisco A/S. Other examples of xylanase enzymes may be found in WO03/020923 and WO01/42433

Preferably, the lipolytic enzyme according to the present invention may be used in combination with a xylanase and an alpha amylase. Suitably the alpha amylase may be a maltogenic, or a non-maltogenic alpha amylase (such as GRIND-AMYL™ or POWERSoft, commercially available from Danisco A/S), or a combination thereof.

The lipolytic enzyme of the invention can also preferably be used in combination with an oxidising enzyme, such as a maltose oxidising enzyme (MOX), for example hexose oxidase (HOX). Suitable methods are described in WO03/099016. Commercially available maltose oxidising enzymes GRINDAMYL™ and SUREBake are available from Danisco A/S.

Optionally an alpha-amylase, such as a non-maltogenic exoamylase and/or a maltogenic amylases, and/or a maltose oxidising enzyme (MOX) in combination with the enzyme according to the present invention may be used in methods of preparing a dough, a baked product, tortilla, cake, instant noodle/fried snack food, or a dairy product such as cheese.

The lipolytic enzyme according to the present invention is typically included in the foodstuff or other composition by methods known in the art. Such methods include adding the lipolytic enzyme directly to the foodstuff or composition, addition of the lipolytic enzyme in combination with a stabilizer and/or carrier, and addition of a mixture comprising the lipolytic enzyme and a stabilizer and/or carrier.

Suitable stabilizers for use with the present invention include but is not limited to inorganic salts (such as NaCl, ammonium sulphate), sorbitol, emulsifiers and detergents (such as Tween 20, Tween 80, Panodan AB100 without triglycerides, polyglycerolester, sorbitanmonoleate), oil (such as rape seed oil, sunflower seed oil and soy oil), pectin, trehalose and glycerol.

Suitable carriers for use with the present invention include but is not limited to starch, ground wheat, wheat flour, NaCl and citrate.

Gluten index may be measured by means of a Glutomatic 2200 from Perten Instruments (Sweden). To measure the gluten index: immediately after proofing, 15 g of dough may be scaled and placed in the Glutomatic and washed with 500 ml 2% NaCl solution for 10 min. The washed dough may then be transferred to a Gluten Index Centrifuge 2015 and the two gluten fractions scaled and the gluten index calculated according to the following equation:

Gluten index=(weight of gluten remaining on the sieve×100)/total weight of gluten Preferably the gluten index in the dough is increased by at least 5%, relative to a dough without addition of the polypeptide, the gluten index may be determined by means of a Glutomatic 2200 apparatus mentioned above Further preferable aspects are presented in the accompanying claims and the in the following description and examples.

Advantages

Surprisingly and unexpectedly it has been found that fungal lipolytic enzymes according to the present invention have a much higher ratio of activity on polar lipids (phospholipids and/or glycolipids):triglycerides, compared with previously identified lipolytic enzymes (particularly LipopanF™) from fungi. This is particularly surprising because prior to the present invention none of the known wild type lipolytic enzymes from fungi showed this activity. Although research had been carried out to investigate lipolytic enzyme variants (i.e. ones which had been exposed to non-natural mutagenesis and/or in some other way altered), it had not been envisaged that a natural, wild-type enzyme from fungi could have possessed these highly beneficial characteristics.

The enzymes identified have been found to have superior functionality when used in baking applications. The use of the fungal lipolytic enzyme according to the present invention advantageously results in significantly improved properties to the dough and/or baked products compared with other lipolytic enzymes from fungi, particularly LipopanF™.

Advantageously lipolytic enzyme which retains activity at lower temperatures, i.e. a low temperature lipolytic enzyme, may be suitable for use in low temperature applications, thus removing the need to heat a substrate. This may be of particular advantage in applications such as enzymatic treatment of egg yolk, enzymatic degumming of edible oils, and in treatment of milk or dairy products, for example treatment of cheese milk prior to cheese manufacture. A further advantage of using a low temperature lipolytic enzyme may be found in foodstuffs and/or animal feeds, where the retention of significant activity at low operating temperatures allows for enzymatic treatment to be performed with reduced risk of microbial, particularly bacterial, contamination. In addition, when the stability of the enzyme is greater at lower temperatures; this allows for efficient dosage of enzyme and longer effective working life of the enzyme in industrial applications.

Technical Effects

For baked products, such as bread, steam buns and US white pan bread, for example, the addition of a lipolytic enzyme of the present invention may result in one or more of the following: improved bread volume and softness, prolonged shelf life and/or an antistaling effect, improved crumb structure, reduced pore heterogeneity, reduced mean pore size, enhanced gluten index, improved flavour and/or odour, and improved colour of the crust.

Advantageously, the enzyme according to the present invention may be used to replace emulsifiers in foodstuffs, such as dough and/or baked products.

The lipolytic enzyme according to the present invention may have synergy with emulsifiers such as DATEM, SSL, CSL, monoglyceride, polysorbates and Tween. Thus, the lipolytic enzyme according to the present invention may be used in combination with one or more emulsifiers. Advantageously, the use of the lipolytic enzyme according to the present invention in combination with one or more emulsifiers may reduce the overall amount of emulsifier used compared with the amount needed when no enzyme according to the present invention is used.

The lipolytic enzyme according to the present invention may also have synergy with hydrocolloids, Guar, xanthum and pectin, and with maltose oxidising enzymes such as hexose oxidase.

For doughnuts, cake doughnuts, bagels, snack cakes and muffins, for example, the use of a lipolytic enzyme of the present invention may result in a synergistic effect when used in combination with one or more of alpha-amylases, maltogenic alpha-amylase and non-maltogenic alpha-amylase.

For cakes, sponge cakes and palm cakes, for example, the use of the lipolytic enzyme of the present invention may result in a synergistic effect when used in combination with one or more of hydrocolloids such as Guar, and/or one or more emulsifiers such as DATEM.

For biscuits, for example, use of a lipolytic enzyme according to the present invention confers improved rollability and handling properties, particularly when cold (cold rollability).

Advantageously, in mayonnaise and other egg-based products, for example, use of a lipolytic enzyme according to the present invention may lead to improved texture, reduced mean particle size, and/or reduced mean particle distribution, improved heat stability, improved microwave performance and/or stability.

In cakes, use of the present invention advantageously leads to improved softness, volume, improved keeping properties and shelf life.

For noodles or noodle-products, e.g. instant noodles, for example, the lipolytic enzyme of the present invention may confer one or more of the following characteristics: improved colour/yellowness, more stable colour characteristics, reduced brightness, reduced fat content, improved texture and bite (chewiness), reduced water activity, reduced breakage, increased core firmness and improved shape retention during processing.

Preferably, the lipolytic enzyme of the present invention may be used to reduce the fat content of a noodle or a noodle product, for instance an instant noodle.

In tortilla, for example, use of the enzyme according to the present invention may result in one or more of the following: reduced rollability of the tortilla, for instance by increasing pliability, improved antistaling properties, improving softness and/or reducing off flavour.

Advantageously, improved rollability and/or pliability may lead to a reduced likelihood of the tortilla splitting when rolled.

In cheese and/or cheese-based products, for example, the use of the enzyme according to the present invention may result in one or more of the following: an improved flavour, texture and/or stability, a decrease in the oiling-off effect in cheese and/or an increase in cheese yield.

The term "oiling off effect" as used herein refers to the free oil released when cheese is melted.

The lipolytic enzyme according to the present invention may be used to produce a low fat cheese. Advantageously, the enzyme of the present invention may stabilise fat in milk and/or may enhance flavour.

One advantageous of the present invention is that the enzyme functions (and indeed has a high functionality) at a low temperature. This can have a number of advantages depending upon the use to which the enzyme is put. For instance, in cheese manufacture this functionality may reduce the risk of microbial contamination and microbial growth during enzymatic treatment. The reason for this may be that the cheese can remain chilled during the enzymatic treatment. Thus, the lipolytic enzyme according of the present invention may be particularly suitable for maturation of cheese at low temperature for improved flavour.

In animal feed, for example, the enzyme according to the present invention advantageously may result in one or more the following: enhanced feed utilisation/conversion efficiency within the animal, improved body weight gain of the animal, improved digestibility of the feed, improved nitrogen uptake by the animal, e.g. from the feed, improved metabolisability of dry matter of the feed and improved palatability of feed.

In degumming of an edible oil, such as a vegetable oil, the lipolytic enzyme of the present invention has a high activity at low temperature. This advantageously may reduce the requirement to heat oil prior to or during enzyme treatment. This has the advantageous effect of reducing the amount of energy needed effect the treatment. The enzyme according to the present invention may improve selectivity the reduction of phospholipids compared with triglycerides. The enzyme according to the present invention in an edible oil (such as a vegetable oil) may there have reduced hydrolytic activity on triglycerides compared to phospholipids. This may lead to less of the triglyceride being hydrolysed (compared with a conventional/phospholipase enzyme) and this may lead to fewer losses in the oil yield and/or a reduced free fatty acid accumulation in the oil (compared with a conventional lipolytic/phospholipase enzyme).

Uses

The enzyme according to the present invention has many applications.

In particular, the fungal lipolytic enzymes according to the present invention may be useful in the preparation of a foodstuff.

For example, the fungal lipolytic enzymes according to the present invention may be particularly useful in the treatment of egg or egg-based products.

Phospholipases, particularly phospholipase A2 (E.C. 3.1.1.4), have been used for many years for the treatment of egg or egg-based products (see U.S. Pat. No. 4,034,124 and Dutihl & Groger 1981 J. Sci. Food Agric. 32, 451-458, for example). The phospholipase activity during the treatment of egg or egg-based products results in the accumulation of polar lysolecithin, which can act as an emulsifier.

Treatment of egg or egg-based products with a fungal lipolytic enzyme according to the present invention can improve the stability, thermal stability under heat treatment such as pasteurisation and result in substantial thickening. Egg-based products may include, but are not limited to cakes, mayonnaise, salad dressings, sauces, ice creams and the like.

The fungal lipolytic enzymes according to the present invention are particularly useful in the preparation of baked products, such as those prepared from a dough, including breads, cakes, sweet dough products, laminated doughs, liquid batters, muffins, doughnuts, biscuits, crackers and cookies.

The fungal lipolytic enzymes according to the present invention may also be used in bread-improving additive, e.g. dough compositions, dough additive, dough conditioners, pre-mixes and similar preparations conventionally added to the flour and/or the dough during processes for making bread or other baked products to provide improved properties to the bread or other baked products.

Thus, the present invention further relates to a bread-improving composition and/or a dough-improving composition comprising a fungal lipolytic enzyme according to the present invention; and also to a dough or baked product comprising such a bread-improving and/or dough-improving composition.

The bread-improving composition and/or dough-improving composition may comprise, in addition to a fungal lipolytic enzyme according to the present invention, other substances, which substances are conventionally used in baking to improve the properties of dough and/or baked products.

The bread-improving composition and/or dough-improving composition may comprise one or more conventional baking agents, such as one or more of the following constituents:

A milk powder, gluten, an emulsifier, granulated fat, an oxidant, an amino acid, a sugar, a salt, flour or starch.

Examples of suitable emulsifiers are: monoglycerides, diacetyl tartaric acid esters of mono- and diglycerides of fatty acids, sugar esters, sodium stearoyl lactylate (SSL) and lecithins.

The bread and/or dough improving composition may further comprise another enzyme, such as one or more other suitable food grade enzymes, including starch degrading enzymes such as endo- or exoamylases, pullulanases, debranching enzymes, hemicellulases including xylanases, cellulases, oxidoreductases, e.g. glucose oxidase, pyranose oxidase, sulfhydryl oxidase or a carbohydrate oxidase such as one which oxidises maltose, for example hexose oxidase (HOX), lipases, phospholipases and hexose oxidase, proteases and acyltransferases (such as those described in WO04/064987 for instance).

The term "improved properties" as used herein means any property which may be improved by the action of the fungal lipolytic enzymes of the present invention. In particular, the use of a fungal lipolytic enzyme according to the present invention results in one or more of the following characteristics: increased volume of the baked product; improved crumb structure of the baked product; anti-staling properties in the baked product; increased strength, increased stability, reduced stickiness and/or improved machinability of the dough.

The improved properties are evaluated by comparison with a dough and/or a baked product prepared without addition of the lipolytic enzyme according to the present invention.

The term "baked product" as used herein includes a product prepared from a dough. Examples of baked products (whether of white, light or dark type) which may be advantageously produced by the present invention include one or more of the following: bread (including white, whole-meal and rye bread), typically in the form of loaves or rolls or toast, French baguette-type bread, pita bread, tortillas, tacos, cakes, pancakes, biscuits, crisp bread, pasta, noodles and the like.

The dough in accordance with the present invention may be a leavened dough or a dough to be subjected to leavening. The dough may be leavened in various ways such as by adding sodium bicarbonate or the like, or by adding a suitable yeast culture such as a culture of Saccharomyces cerevisiae (baker's yeast).

The present invention further relates to the use of fungal lipolytic enzymes in accordance with the present invention to produce a pasta dough, preferably prepared from durum flour or a flour of comparable quality.

The fungal lipolytic enzymes according to the present invention are suitable for use in the enzymatic degumming of vegetable or edible oils. In processing of vegetable or edible oil the edible or vegetable oil is treated with a fungal lipolytic enzyme according to the present invention so as to hydrolyse a major part of the polar lipids (e.g. phospholipid and/or glycolipid). Preferably, the fatty acyl groups are hydrolysed from the polar lipids. The degumming process typically results in the reduction of the content of the polar lipids, particularly of phospholipids, in an edible oil due to hydrolysis of a major part (i.e. more than 50%) of the polar lipid, e.g. glycolipid and/or phospholipid. Typically, the aqueous phase containing the hydrolysed polar lipid (e.g. phospholipid and/or glycolipid) is separated from the oil. Suitably, the edible or vegetable oil may initially (pre-treatment with the enzyme according to the present invention) have a phosphorus content of 50-250 ppm.

Furthermore, the present invention is directed to the use of a lipolytic enzyme according to the present invention for treatment of cheese products.

The lipolytic enzyme according to the present invention is also particularly suitable for use in the preparation of an animal feed.

As the skilled person is aware, the term "degumming" as used herein means the refining of oil by converting phosphatides (such as lecithin, phospholipids and occluded oil) into hydratable phosphatides. Oil which has been degummed is more fluid and thus has better handling properties than oil which has not been degummed.

The following table is merely for general guidance and provides an overview of the dosage level for a lipolytic enzyme according to the present invention which may be needed in different applications. The table further provides guidance in respect of the dosage level for a lipolytic enzyme according to the present invention when used in combination with an emulsifier for example. Of course, as would be apparent to the person of ordinary skill in the art optimisation of enzyme dosage, reaction temperature and reaction time may be readily determined, using routine experimentation, for any given application.

| Application | "Optimal" dosage, TIPU/ kg of flour | Optimal dosage in combination with emulsifier | Dosage range, TIPU/KG of flour |
| --- | --- | --- | --- |
| Crusty rolls | 400 | 120 | 300-800 |
| Straight dough toast bread | 400 | 120 | 300-800 |
| Straight dough long fermentation | 120 | | 75-250 |
| High speed mixing - Tweedy procedure | | 120 | 300-800 |
| US sponge & dough pan bread on top of DATEM | | 120 | 75-400 |
| Wheat tortilla | 700 | Contains emulsifiers | 400-2500 |
| Cakes - sponge cakes | 2000 | Contains cake emulsifiers | 1000-4000 |
| Retarded dough (24 hours) | 120 | Contains emulsifiers | 75-250 |
| Steam buns | 200 | | 150-500 |
| Instant fried noodles | | | 200-10,000 |

Isolated

In one aspect, preferably the sequence is in an isolated form. The term "isolated" means that the sequence is at least substantially free from at least one other component with which the sequence is naturally associated in nature and as found in nature.

Purified

In one aspect, preferably the sequence is in a purified form. The term "purified" means that the sequence is in a relatively pure state—e.g. at least about 90% pure, or at least about 95% pure or at least about 98% pure.

Nucleotide Sequence

The scope of the present invention encompasses nucleotide sequences encoding enzymes having the specific properties as defined herein.

The term "nucleotide sequence" as used herein refers to an oligonucleotide sequence or polynucleotide sequence, and variants, homologues, fragments and derivatives thereof (such as portions thereof). The nucleotide sequence may be of genomic or synthetic or recombinant origin, which may be double-stranded or single-stranded whether representing the sense or anti-sense strand.

The term "nucleotide sequence" in relation to the present invention includes genomic DNA, cDNA, synthetic DNA, and RNA. Preferably it means DNA, more preferably cDNA sequence coding for the present invention.

In a preferred embodiment, the nucleotide sequence when relating to and when encompassed by the per se scope of the present invention does not include the native nucleotide sequence according to the present invention when in its natural environment and when it is linked to its naturally associated sequence(s) that is/are also in its/their natural environment. For ease of reference, we shall call this preferred embodiment the "non-native nucleotide sequence". In this regard, the term "native nucleotide sequence" means an entire nucleotide sequence that is in its native environment and when operatively linked to an entire promoter with which it is naturally associated, which promoter is also in its native environment. However, the amino acid sequence encompassed by scope the present invention can be isolated and/or purified post expression of a nucleotide sequence in its native organism. Preferably, however, the amino acid sequence encompassed by scope of the present invention may be expressed by a nucleotide sequence in its native organism but wherein the nucleotide sequence is not under the control of the promoter with which it is naturally associated within that organism.

Preparation of the Nucleotide Sequence

Typically, the nucleotide sequence encompassed by scope of the present invention is prepared using recombinant DNA techniques (i.e. recombinant DNA). However, in an alternative embodiment of the invention, the nucleotide sequence could be synthesised, in whole or in part, using chemical methods well known in the art (see Caruthers M H et al., (1980) *Nuc Acids Res Symp Ser* 215-23 and Horn T et al., (1980) *Nuc Acids Res Symp Ser* 225-232).

A nucleotide sequence encoding an enzyme which has the specific properties as defined herein may be identified and/or isolated and/or purified from any cell or organism producing said enzyme. Various methods are well known within the art for the identification and/or isolation and/or purification of nucleotide sequences. By way of example, PCR amplification techniques to prepare more of a sequence may be used once a suitable sequence has been identified and/or isolated and/or purified.

By way of further example, a genomic DNA and/or cDNA library may be constructed using chromosomal DNA or messenger RNA from the organism producing the enzyme. If the amino acid sequence of the enzyme or a part of the amino acid sequence of the enzyme is known, labelled oligonucleotide probes may be synthesised and used to identify enzyme-encoding clones from the genomic library prepared from the organism. Alternatively, a labelled oligonucleotide probe containing sequences homologous to another known enzyme gene could be used to identify enzyme-encoding clones. In the latter case, hybridisation and washing conditions of lower stringency are used.

Alternatively, enzyme-encoding clones could be identified by inserting fragments of genomic DNA into an expression vector, such as a plasmid, transforming enzyme-negative bacteria with the resulting genomic DNA library, and then plating the transformed bacteria onto agar plates containing a substrate for the enzyme (e.g. maltose for a glucosidase (maltase) producing enzyme), thereby allowing clones expressing the enzyme to be identified.

In a yet further alternative, the nucleotide sequence encoding the enzyme may be prepared synthetically by established standard methods, e.g. the phosphoroamidite method described by Beucage S. L. et al., (1981) *Tetrahedron Letters* 22, p 1859-1869, or the method described by Matthes et al., (1984) *EMBO J.* 3, p 801-805. In the phosphoroamidite method, oligonucleotides are synthesised, e.g. in an automatic DNA synthesiser, purified, annealed, ligated and cloned in appropriate vectors.

The nucleotide sequence may be of mixed genomic and synthetic origin, mixed synthetic and cDNA origin, or mixed genomic and cDNA origin, prepared by ligating fragments of synthetic, genomic or cDNA origin (as appropriate) in accordance with standard techniques. Each ligated fragment corresponds to various parts of the entire nucleotide sequence. The DNA sequence may also be prepared by polymerase chain reaction (PCR) using specific primers, for instance as described in U.S. Pat. No. 4,683,202 or in Saiki R K et al., (*Science* (1988) 239, pp 487-491).

Due to degeneracy in the genetic code, nucleotide sequences may be readily produced in which the triplet codon usage, for some or all of the amino acids encoded by the original nucleotide sequence, has been changed thereby producing a nucleotide sequence with low homology to the original nucleotide sequence but which encodes the same, or a variant, amino acid sequence as encoded by the original nucleotide sequence. For example, for most amino acids the degeneracy of the genetic code is at the third position in the triplet codon (wobble position) (for reference see Stryer, Lubert, Biochemistry, Third Edition, Freeman Press, ISBN 0-7167-1920-7) therefore, a nucleotide sequence in which all triplet codons have been "wobbled" in the third position would be about 66% identical to the original nucleotide sequence. However, the amended nucleotide sequence would encode for the same, or a variant, primary amino acid sequence as the original nucleotide sequence.

Therefore, the present invention further relates to any nucleotide sequence that has alternative triplet codon usage for at least one amino acid encoding triplet codon, but which encodes the same, or a variant, polypeptide sequence as the polypeptide sequence encoded by the original nucleotide sequence.

Furthermore, specific organisms typically have a bias as to which triplet codons are used to encode amino acids. Preferred codon usage tables are widely available, and can be used to prepare codon optimised genes. Such codon optimisation techniques are routinely used to optimise expression of transgenes in a heterologous host.

Amino Acid Sequences

The scope of the present invention also encompasses amino acid sequences of enzymes having the specific properties as defined herein.

As used herein, the term "amino acid sequence" is synonymous with the term "polypeptide" and/or the term "protein". In some instances, the term "amino acid sequence" is synonymous with the term "peptide". In some instances, the term "amino acid sequence" is synonymous with the term "enzyme".

The amino acid sequence may be prepared/isolated from a suitable source, or it may be made synthetically or it may be prepared by use of recombinant DNA techniques.

The enzyme encompassed in the present invention may be used in conjunction with other enzymes. Thus the present invention also covers a combination of enzymes wherein the combination comprises the enzyme of the present invention and another enzyme, which may be another enzyme according to the present invention.

Preferably the amino acid sequence when relating to and when encompassed by the per se scope of the present invention is not a native enzyme. In this regard, the term "native enzyme" means an entire enzyme that is in its native environment and when it has been expressed by its native nucleotide sequence.

Identity/Homology

The present invention also encompasses the use of homologues of any amino acid sequence of an enzyme or of any nucleotide sequence encoding such an enzyme.

Here, the term "homologue" means an entity having a certain homology with the amino acid sequences and the nucleotide sequences. Here, the term "homology" can be equated with "identity". These terms will be used interchangeably herein.

In the present context, a homologous amino acid sequence is taken to include an amino acid sequence which may be at least 92% identical, preferably at least 95, 96, 97, 98 or 99% identical to the sequence. Typically, the homologues will comprise the same active sites etc.—e.g. as the subject amino acid sequence. Although homology can also be considered in terms of similarity (i.e. amino acid residues having similar chemical properties/functions), in the context of the present invention it is preferred to express homology in terms of sequence identity.

Preferably, an homologous amino acid sequence according to the present invention is one which has at least 90% identity, more preferably at least 95, 96, 97, 98 or 99% identity, over a region of at least 30, more preferably 40, contiguous amino acids.

In the present context, an homologous nucleotide sequence is taken to include a nucleotide sequence which may be at least 92% identical, preferably at least 95, 96, 97, 98 or 99% identical to a nucleotide sequence encoding an enzyme of the present invention (the subject sequence). Typically, the homologues will comprise the same sequences that code for the active sites etc. as the subject sequence. Although homology can also be considered in terms of similarity (i.e. amino acid residues having similar chemical properties/functions), in the context of the present invention it is preferred to express homology in terms of sequence identity.

Preferably, an homologous nucleotide sequence according to the present invention is one which has at least 90% identity, more preferably at least 95, 96, 97, 98 or 99% identity, over a region of at least 30, preferably 40, more preferably 60 contiguous nucleotides.

For the amino acid sequences and the nucleotide sequences, homology comparisons can be conducted by eye, or more usually, with the aid of readily available sequence comparison programs. These commercially available computer programs can calculate % homology between two or more sequences.

% homology may be calculated over contiguous sequences, i.e. one sequence is aligned with the other sequence and each amino acid in one sequence is directly compared with the corresponding amino acid in the other sequence, one residue at a time. This is called an "ungapped" alignment. Typically, such ungapped alignments are performed only over a relatively short number of residues.

Although this is a very simple and consistent method, it fails to take into consideration that, for example, in an otherwise identical pair of sequences, one insertion or deletion will cause the following amino acid residues to be put out of alignment, thus potentially resulting in a large reduction in % homology when a global alignment is performed. Consequently, most sequence comparison methods are designed to produce optimal alignments that take into consideration possible insertions and deletions without penalising unduly the overall homology score. This is achieved by inserting "gaps" in the sequence alignment to try to maximise local homology.

However, these more complex methods assign "gap penalties" to each gap that occurs in the alignment so that, for the same number of identical amino acids, a sequence alignment with as few gaps as possible—reflecting higher relatedness between the two compared sequences—will achieve a higher score than one with many gaps. "Affine gap costs" are typically used that charge a relatively high cost for the existence of a gap and a smaller penalty for each subsequent residue in the gap. This is the most commonly used gap scoring system. High gap penalties will of course produce optimised alignments with fewer gaps. Most alignment programs allow the gap penalties to be modified. However, it is preferred to use the default values when using such software for sequence comparisons. For example when using the GCG Wisconsin Bestfit package the default gap penalty for amino acid sequences is −12 for a gap and −4 for each extension.

Calculation of maximum % homology therefore firstly requires the production of an optimal alignment, taking into consideration gap penalties. A suitable computer program for carrying out such an alignment is the GCG Wisconsin Bestfit package (Devereux et al 1984 Nuc. Acids Research 12 p 387). Examples of other software than can perform sequence comparisons include, but are not limited to, the BLAST package (see Ausubel et al., 1999 *Short Protocols in Molecular Biology*, $4^{th}$ Ed—Chapter 18), FASTA (Altschul et al., 1990 *J. Mol. Biol.* 403-410) and the GENEWORKS suite of comparison tools. Both BLAST and FASTA are available for offline and online searching (see Ausubel et al., 1999, *Short Protocols in Molecular Biology*, pages 7-58 to 7-60).

However, for some applications, it is preferred to use the GCG Bestfit program. A new tool, called BLAST 2 Sequences is also available for comparing protein and nucleotide sequence (see *FEMS Microbiol Lett* 1999 174(2): 247-50; *FEMS Microbiol Lett* 1999 177(1): 187-8 and tatiana@ncbi.nlm.nih.gov).

Although the final % homology can be measured in terms of identity, the alignment process itself is typically not based on an all-or-nothing pair comparison. Instead, a scaled similarity score matrix is generally used that assigns scores to each pairwise comparison based on chemical similarity or evolutionary distance. An example of such a matrix commonly used is the BLOSUM62 matrix—the default matrix for the BLAST suite of programs. GCG Wisconsin programs generally use either the public default values or a custom symbol comparison table if supplied (see user manual for further details). For some applications, it is preferred to use the public default values for the GCG package, or in the case of other software, the default matrix, such as BLOSUM62.

Alternatively, percentage homologies may be calculated using the multiple alignment feature in DNASIS™ (Hitachi Software), based on an algorithm, analogous to CLUSTAL (Higgins D G & Sharp P M (1988), *Gene* 73(1), 237-244).

Once the software has produced an optimal alignment, it is possible to calculate % homology, preferably % sequence identity. The software typically does this as part of the sequence comparison and generates a numerical result.

The sequences may also have deletions, insertions or substitutions of amino acid residues which produce a silent change and result in a functionally equivalent substance. Deliberate amino acid substitutions may be made on the basis of similarity in amino acid properties (such as polarity, charge, solubility, hydrophobicity, hydrophilicity, and/or the amphipathic nature of the residues) and it is therefore useful to group amino acids together in functional groups. Amino acids can be grouped together based on the properties of their side chain alone. However it is more useful to include mutation data as well. The sets of amino acids thus derived are likely to be conserved for structural reasons. These sets can be described in the form of a Venn diagram (Livingstone C. D. and Barton G. J. (1993) "Protein sequence alignments: a strategy for the hierarchical analysis of residue conservation" *Comput. Appl Biosci.* 9:745-756) (Taylor W.R. (1986) "The classification of amino acid conservation" *J. Theor. Biol.* 119; 205-218). Conservative substitutions may be made, for example according to the table below which describes a generally accepted Venn diagram grouping of amino acids.

| | SET | SUB-SET | |
|---|---|---|---|
| Hydrophobic | F W Y H K M I L V A G C | Aromatic | F W Y H |
| | | Aliphatic | I L V |
| Polar | W Y H K R E D C S T N Q | Charged | H K R E D |
| | | Positively charged | H K R |
| | | Negatively charged | E D |
| Small | V C A G S P T N D | Tiny | A G S |

The present invention also encompasses homologous substitution (substitution and replacement are both used herein to mean the interchange of an existing amino acid residue, with an alternative residue) that may occur i.e. like-for-like substitution such as basic for basic, acidic for acidic, polar for polar etc. Non-homologous substitution may also occur i.e. from one class of residue to another or alternatively involving the inclusion of unnatural amino acids such as ornithine (hereinafter referred to as Z), diaminobutyric acid ornithine (hereinafter referred to as B), norleucine ornithine (hereinafter referred to as O), pyriylalanine, thienylalanine, naphthylalanine and phenylglycine.

Replacements may also be made by unnatural amino acids.

Variant amino acid sequences may include suitable spacer groups that may be inserted between any two amino acid residues of the sequence including alkyl groups such as methyl, ethyl or propyl groups in addition to amino acid spacers such as glycine or β-alanine residues. A further form of variation, involves the presence of one or more amino acid residues in peptoid form, will be well understood by those skilled in the art. For the avoidance of doubt, "the peptoid form" is used to refer to variant amino acid residues wherein the α-carbon substituent group is on the residue's nitrogen atom rather than the α-carbon. Processes for preparing peptides in the peptoid form are known in the art, for example Simon R J et al., *PNAS* (1992) 89(20), 9367-9371 and Horwell D C, *Trends Biotechnol.* (1995) 13(4), 132-134.

The nucleotide sequences for use in the present invention may include within them synthetic or modified nucleotides. A number of different types of modification to oligonucleotides are known in the art. These include methylphosphonate and phosphorothioate backbones and/or the addition of acridine or polylysine chains at the 3' and/or 5' ends of the molecule. For the purposes of the present invention, it is to be understood that the nucleotide sequences described herein may be modified by any method available in the art. Such modifications may be carried out in order to enhance the in vivo activity or life span of nucleotide sequences of the present invention.

The present invention also encompasses the use of nucleotide sequences that are complementary to the sequences presented herein, or any derivative, fragment or derivative thereof. If the sequence is complementary to a fragment thereof then that sequence can be used as a probe to identify similar coding sequences in other organisms etc.

Polynucleotides which are not 100% homologous to the sequences of the present invention but fall within the scope of the invention can be obtained in a number of ways.

Other variants of the sequences described herein may be obtained for example by probing DNA libraries made from a range of individuals, for example individuals from different populations. In addition, other homologues may be obtained and such homologues and fragments thereof in general will be capable of selectively hybridising to the sequences shown in the sequence listing herein. Such sequences may be obtained by probing cDNA libraries made from or genomic DNA libraries from other species, and probing such libraries with probes comprising all or part of any one of the sequences in the attached sequence listings under conditions of medium to high stringency. Similar considerations apply to obtaining species homologues and allelic variants of the polypeptide or nucleotide sequences of the invention.

Variants and strain/species homologues may also be obtained using degenerate PCR which will use primers designed to target sequences within the variants and homologues encoding conserved amino acid sequences within the sequences of the present invention. Conserved sequences can be predicted, for example, by aligning the amino acid sequences from several variants/homologues. Sequence alignments can be performed using computer software known in the art. For example the GCG Wisconsin PileUp program is widely used.

The primers used in degenerate PCR will contain one or more degenerate positions and will be used at stringency conditions lower than those used for cloning sequences with single sequence primers against known sequences.

Alternatively, such polynucleotides may be obtained by site directed mutagenesis of characterised sequences. This may be useful where for example silent codon sequence changes are required to optimise codon preferences for a particular host cell in which the polynucleotide sequences are being expressed. Other sequence changes may be desired in order to introduce restriction enzyme recognition sites, or to alter the property or function of the polypeptides encoded by the polynucleotides.

Polynucleotides (nucleotide sequences) of the invention may be used to produce a primer, e.g. a PCR primer, a primer for an alternative amplification reaction, a probe e.g. labelled with a revealing label by conventional means using radioactive or non-radioactive labels, or the polynucleotides may be cloned into vectors. Such primers, probes and other fragments will be at least 15, preferably at least 20, for example at least 25, 30 or 40 nucleotides in length, and are also encompassed by the term polynucleotides of the invention as used herein.

Polynucleotides such as DNA polynucleotides and probes according to the invention may be produced recombinantly, synthetically, or by any means available to those of skill in the art. They may also be cloned by standard techniques.

In general, primers will be produced by synthetic means, involving a stepwise manufacture of the desired nucleic acid sequence one nucleotide at a time. Techniques for accomplishing this using automated techniques are readily available in the art.

Longer polynucleotides will generally be produced using recombinant means, for example using a PCR (polymerase chain reaction) cloning techniques. The primers may be designed to contain suitable restriction enzyme recognition sites so that the amplified DNA can be cloned into a suitable cloning vector.

Biologically Active

Preferably, the variant sequences etc. are at least as biologically active as the sequences presented herein.

As used herein "biologically active" refers to a sequence having a similar structural function (but not necessarily to the same degree), and/or similar regulatory function (but not necessarily to the same degree), and/or similar biochemical function (but not necessarily to the same degree) of the naturally occurring sequence.

Hybridisation

The present invention also encompasses sequences that are complementary to the nucleic acid sequences of the present invention or sequences that are capable of hybridising either to the sequences of the present invention or to sequences that are complementary thereto.

The term "hybridisation" as used herein shall include "the process by which a strand of nucleic acid joins with a complementary strand through base pairing" as well as the process of amplification as carried out in polymerase chain reaction (PCR) technologies.

The present invention also encompasses the use of nucleotide sequences that are capable of hybridising to the sequences that are complementary to the sequences presented herein, or any derivative, fragment or derivative thereof.

The term "variant" also encompasses sequences that are complementary to sequences that are capable of hybridising to the nucleotide sequences presented herein.

Preferably, the term "variant" encompasses sequences that are complementary to sequences that are capable of hybridising under stringent conditions (e.g. 50° C. and 0.2×SSC {1×SSC=0.15 M NaCl, 0.015 M Na$_3$citrate pH 7.0}) to the nucleotide sequences presented herein.

More preferably, the term "variant" encompasses sequences that are complementary to sequences that are capable of hybridising under high stringent conditions (e.g. 65° C. and 0.1×SSC {1×SSC=0.15 M NaCl, 0.015 M Na$_3$citrate pH 7.0}) to the nucleotide sequences presented herein.

The present invention also relates to nucleotide sequences that can hybridise to the nucleotide sequences of the present invention (including complementary sequences of those presented herein).

The present invention also relates to nucleotide sequences that are complementary to sequences that can hybridise to the nucleotide sequences of the present invention (including complementary sequences of those presented herein).

Also included within the scope of the present invention are polynucleotide sequences that are capable of hybridising to the nucleotide sequences presented herein under conditions of intermediate to maximal stringency.

In a preferred aspect, the present invention covers nucleotide sequences that can hybridise to the nucleotide sequence of the present invention, or the complement thereof, under stringent conditions (e.g. 50° C. and 0.2×SSC).

In a more preferred aspect, the present invention covers nucleotide sequences that can hybridise to the nucleotide sequence of the present invention, or the complement thereof, under high stringent conditions (e.g. 65° C. and 0.1×SSC).

Recombinant

In one aspect the sequence for use in the present invention is a recombinant sequence—i.e. a sequence that has been prepared using recombinant DNA techniques.

These recombinant DNA techniques are within the capabilities of a person of ordinary skill in the art. Such techniques are explained in the literature, for example, J. Sambrook, E. F. Fritsch, and T. Maniatis, 1989, *Molecular Cloning: A Laboratory Manual*, Second Edition, Books 1-3, Cold Spring Harbor Laboratory Press.

Synthetic

In one aspect the sequence for use in the present invention is a synthetic sequence—i.e. a sequence that has been prepared by in vitro chemical or enzymatic synthesis. It includes, but is not limited to, sequences made with optimal codon usage for host organisms—such as the methylotrophic yeasts *Pichia* and *Hansenula*.

Expression of Enzymes

The nucleotide sequence for use in the present invention may be incorporated into a recombinant replicable vector. The vector may be used to replicate and express the nucleotide sequence, in enzyme form, in and/or from a compatible host cell.

Expression may be controlled using control sequences e.g. regulatory sequences.

The enzyme produced by a host recombinant cell by expression of the nucleotide sequence may be secreted or may be contained intracellularly depending on the sequence and/or the vector used. The coding sequences may be designed with signal sequences which direct secretion of the substance coding sequences through a particular prokaryotic or eukaryotic cell membrane.

Expression Vector

The term "expression vector" means a construct capable of in vivo or in vitro expression.

Preferably, the expression vector is incorporated into the genome of a suitable host organism. The term "incorporated" preferably covers stable incorporation into the genome.

The nucleotide sequence of the present invention may be present in a vector in which the nucleotide sequence is operably linked to regulatory sequences capable of providing for the expression of the nucleotide sequence by a suitable host organism.

The vectors for use in the present invention may be transformed into a suitable host cell as described below to provide for expression of a polypeptide of the present invention.

The choice of vector e.g. a plasmid, cosmid, or phage vector will often depend on the host cell into which it is to be introduced.

The vectors for use in the present invention may contain one or more selectable marker genes such as a gene which confers antibiotic resistance e.g. ampicillin, kanamycin, chloramphenicol or tetracyclin resistance. Alternatively, the selection may be accomplished by co-transformation (as described in WO91/17243).

Vectors may be used in vitro, for example for the production of RNA or used to transfect, transform, transduce or infect a host cell.

Thus, in a further embodiment, the invention provides a method of making nucleotide sequences of the present invention by introducing a nucleotide sequence of the present invention into a replicable vector, introducing the vector into a compatible host cell, and growing the host cell under conditions which bring about replication of the vector.

The vector may further comprise a nucleotide sequence enabling the vector to replicate in the host cell in question. Examples of such sequences are the origins of replication of plasmids pUC19, pACYC177, pUB110, pE194, pAMB1 and pIJ702.

Regulatory Sequences

In some applications, the nucleotide sequence for use in the present invention is operably linked to a regulatory sequence which is capable of providing for the expression of the nucleotide sequence, such as by the chosen host cell. By way of example, the present invention covers a vector comprising the nucleotide sequence of the present invention operably linked to such a regulatory sequence, i.e. the vector is an expression vector.

The term "operably linked" refers to a juxtaposition wherein the components described are in a relationship permitting them to function in their intended manner. A regulatory sequence "operably linked" to a coding sequence is ligated in such a way that expression of the coding sequence is achieved under condition compatible with the control sequences.

The term "regulatory sequences" includes promoters and enhancers and other expression regulation signals.

The term "promoter" is used in the normal sense of the art, e.g. an RNA polymerase binding site.

Enhanced expression of the nucleotide sequence encoding the enzyme of the present invention may also be achieved by the selection of heterologous regulatory regions, e.g. promoter, secretion leader and terminator regions.

Preferably, the nucleotide sequence according to the present invention is operably linked to at least a promoter.

Examples of suitable promoters for directing the transcription of the nucleotide sequence in a bacterial, fungal or yeast host are well known in the art.

Constructs

The term "construct"—which is synonymous with terms such as "conjugate", "cassette" and "hybrid"—includes a nucleotide sequence for use according to the present invention directly or indirectly attached to a promoter.

An example of an indirect attachment is the provision of a suitable spacer group such as an intron sequence, such as the Sh1-intron or the ADH intron, intermediate the promoter and the nucleotide sequence of the present invention. The same is true for the term "fused" in relation to the present invention which includes direct or indirect attachment. In some cases, the terms do not cover the natural combination of the nucleotide sequence coding for the protein ordinarily associated with the wild type gene promoter and when they are both in their natural environment.

The construct may even contain or express a marker, which allows for the selection of the genetic construct.

For some applications, preferably the construct of the present invention comprises at least the nucleotide sequence of the present invention operably linked to a promoter.

Host Cells

The term "host cell"—in relation to the present invention includes any cell that comprises either the nucleotide sequence or an expression vector as described above and which is used in the recombinant production of an enzyme having the specific properties as defined herein.

Thus, a further embodiment of the present invention provides host cells transformed or transfected with a nucleotide sequence that expresses the enzyme of the present invention. The cells will be chosen to be compatible with the said vector and may for example be prokaryotic (for example bacterial), fungal, yeast or plant cells. Preferably, the host cells are not human cells.

Examples of suitable bacterial host organisms are gram positive or gram negative bacterial species.

Depending on the nature of the nucleotide sequence encoding the enzyme of the present invention, and/or the desirability for further processing of the expressed protein, eukaryotic hosts such as yeasts or other fungi may be preferred. In general, yeast cells are preferred over fungal cells because they are easier to manipulate. However, some proteins are either poorly secreted from the yeast cell, or in some cases are not processed properly (e.g. hyperglycosylation in yeast). In these instances, a different fungal host organism should be selected.

The use of suitable host cells—such as yeast, fungal and plant host cells—may provide for post-translational modifications (e.g. myristoylation, glycosylation, truncation, lapidation and tyrosine, serine or threonine phosphorylation) as may be needed to confer optimal biological activity on recombinant expression products of the present invention.

The host cell may be a protease deficient or protease minus strain.

The genotype of the host cell may be modified to improve expression.

Examples of host cell modifications include protease deficiency, supplementation of rare tRNA's, and modification of the reductive potential in the cytoplasm to enhance disulphide bond formation.

For example, the host cell *E. coli* may overexpress rare tRNA's to improve expression of heterologous proteins as exemplified/described in Kane (*Curr Opin Biotechnol* (1995), 6, 494-500 "Effects of rare codon clusters on high-level expression of heterologous proteins in *E. coli*"). The host cell may be deficient in a number of reducing enzymes thus favouring formation of stable disulphide bonds as exemplified/described in Bessette (*Proc Natl Acad Sci USA* (1999), 96, 13703-13708 "Efficient folding of proteins with multiple disulphide bonds in the *Escherichia coli* cytoplasm").

Organism

The term "organism" in relation to the present invention includes any organism that could comprise the nucleotide sequence coding for the enzyme according to the present invention and/or products obtained therefrom, and/or wherein a promoter can allow expression of the nucleotide sequence according to the present invention when present in the organism.

Suitable organisms may include a prokaryote, fungus, yeast or a plant.

The term "transgenic organism" in relation to the present invention includes any organism that comprises the nucleotide sequence coding for the enzyme according to the present invention and/or the products obtained therefrom, and/or wherein a promoter can allow expression of the nucleotide sequence according to the present invention within the organism. Preferably the nucleotide sequence is incorporated in the genome of the organism.

The term "transgenic organism" does not cover native nucleotide coding sequences in their natural environment when they are under the control of their native promoter which is also in its natural environment.

Therefore, the transgenic organism of the present invention includes an organism comprising any one of, or combinations of, the nucleotide sequence coding for the enzyme according to the present invention, constructs according to the present invention, vectors according to the present invention, plasmids according to the present invention, cells according to the present invention, tissues according to the present invention, or the products thereof.

For example the transgenic organism may also comprise the nucleotide sequence coding for the enzyme of the present invention under the control of a heterologous promoter.

Transformation of Host Cells/Organism

As indicated earlier, the host organism can be a prokaryotic or a eukaryotic organism. Examples of suitable prokaryotic hosts include *E. coli* and *Bacillus subtilis*.

Teachings on the transformation of prokaryotic hosts is well documented in the art, for example see Sambrook et al (Molecular Cloning: A Laboratory Manual, 2nd edition, 1989, Cold Spring Harbor Laboratory Press). If a prokaryotic host is used then the nucleotide sequence may need to be suitably modified before transformation—such as by removal of introns.

Filamentous fungi cells may be transformed using various methods known in the art—such as a process involving protoplast formation and transformation of the protoplasts followed by regeneration of the cell wall in a manner known. The use of *Aspergillus* as a host microorganism is described in EP 0 238 023.

Another host organism can be a plant. A review of the general techniques used for transforming plants may be found in articles by Potrykus (*Annu Rev Plant Physiol Plant Mol Biol* [1991] 42:205-225) and Christou (Agro-Food-Industry Hi-Tech March/April 1994 17-27). Further teachings on plant transformation may be found in EP-A-0449375.

General teachings on the transformation of fungi, yeasts and plants are presented in following sections.

Transformed Fungus

A host organism may be a fungus—such as a filamentous fungus. Examples of suitable such hosts include any member belonging to the genera *Thermomyces, Acremonium, Aspergillus, Penicillium, Mucor, Neurospora, Trichoderma* and the like.

Teachings on transforming filamentous fungi are reviewed in U.S. Pat. No. 5,741,665 which states that standard techniques for transformation of filamentous fungi and culturing the fungi are well known in the art. An extensive review of techniques as applied to *N. crassa* is found, for example in Davis and de Serres, *Methods Enzymol* (1971) 17A:79-143.

Further teachings on transforming filamentous fungi are reviewed in U.S. Pat. No. 5,674,707.

In one aspect, the host organism can be of the genus *Aspergillus*, such as *Aspergillus niger*.

A transgenic *Aspergillus* according to the present invention can also be prepared by following, for example, the teachings of Turner G. 1994 (Vectors for genetic manipulation. In: Martinelli S. D., Kinghorn J. R. (Editors) *Aspergillus: 50 years on*. Progress in industrial microbiology vol 29. Elsevier Amsterdam 1994. pp. 641-666).

Gene expression in filamentous fungi has been reviewed in Punt et al. (2002) Trends Biotechnol 2002 May; 20(5):200-6, Archer & Peberdy *Crit Rev Biotechnol* (1997) 17(4):273-306.

Transformed Yeast

In another embodiment, the transgenic organism can be a yeast.

A review of the principles of heterologous gene expression in yeast are provided in, for example, *Methods Mol Biol* (1995), 49:341-54, and *Curr Opin Biotechnol* (1997) October; 8(5):554-60

In this regard, yeast—such as the species *Saccharomyces cerevisiae* or *Pichia pastoris* (see FEMS Microbiol Rev (2000 24(1):45-66), may be used as a vehicle for heterologous gene expression.

A review of the principles of heterologous gene expression in *Saccharomyces cerevisiae* and secretion of gene products is given by E Hinchcliffe E Kenny (1993, "Yeast as a vehicle for the expression of heterologous genes", *Yeasts*, Vol 5, Anthony H Rose and J Stuart Harrison, Eds., 2nd edition, Academic Press Ltd.).

For the transformation of yeast, several transformation protocols have been developed. For example, a transgenic *Saccharomyces* according to the present invention can be prepared by following the teachings of Hinnen et al., (1978, *Proceedings of the National Academy of Sciences of the USA* 75, 1929); Beggs, J D (1978, *Nature*, London, 275, 104); and Ito, H et al (1983, J Bacteriology 153, 163-168).

The transformed yeast cells may be selected using various selective markers—such as auxotrophic markers dominant antibiotic resistance markers.

Transformed Plants/Plant Cells

A host organism suitable for the present invention may be a plant. A review of the general techniques may be found in articles by Potrykus (*Annu Rev Plant Physiol Plant Mol Biol* [1991] 42:205-225) and Christou (Agro-Food-Industry Hi-Tech March/April 1994 17-27).

Culturing and Production

Host cells transformed with the nucleotide sequence of the present invention may be cultured under conditions conducive to the production of the encoded enzyme and which facilitate recovery of the enzyme from the cells and/or culture medium.

The medium used to cultivate the cells may be any conventional medium suitable for growing the host cell in questions and obtaining expression of the enzyme.

The protein produced by a recombinant cell may be displayed on the surface of the cell.

The enzyme may be secreted from the host cells and may conveniently be recovered from the culture medium using well-known procedures.

Secretion

Often, it is desirable for the enzyme to be secreted from the expression host into the culture medium from where the enzyme may be more easily recovered. According to the present invention, the secretion leader sequence may be selected on the basis of the desired expression host. Hybrid signal sequences may also be used with the context of the present invention.

Typical examples of heterologous secretion leader sequences are those originating from the fungal amyloglucosidase (AG) gene (glaA—both 18 and 24 amino acid versions e.g. from *Aspergillus*), the a-factor gene (yeasts e.g. *Saccharomyces, Kluyveromyces* and *Hansenula*) or the α-amylase gene (*Bacillus*).

By way of example, the secretion of heterologous proteins in *E. coli* is reviewed in Methods Enzymol (1990) 182:132-43.

Detection

A variety of protocols for detecting and measuring the expression of the amino acid sequence are known in the art. Examples include enzyme-linked immunosorbent assay (ELISA), radioimmunoassay (RIA) and fluorescent activated cell sorting (FACS).

A wide variety of labels and conjugation techniques are known by those skilled in the art and can be used in various nucleic and amino acid assays.

A number of companies such as Pharmacia Biotech (Piscataway, N.J.), Promega (Madison, Wis.), and US Biochemical Corp (Cleveland, Ohio) supply commercial kits and protocols for these procedures.

Suitable reporter molecules or labels include those radionuclides, enzymes, fluorescent, chemiluminescent, or chromogenic agents as well as substrates, cofactors, inhibitors, magnetic particles and the like. Patents teaching the use of such labels include U.S. Pat. Nos. 3,817,837; 3,850,752; 3,939,350; 3,996,345; 4,277,437; 4,275,149 and 4,366,241.

Also, recombinant immunoglobulins may be produced as shown in U.S. Pat. No. 4,816,567.

Fusion Proteins

The amino acid sequence for use according to the present invention may be produced as a fusion protein, for example to aid in extraction and purification. Examples of fusion protein partners include glutathione-S-transferase (GST), 6×His, GAL4 (DNA binding and/or transcriptional activation domains) and (β-galactosidase). It may also be convenient to include a proteolytic cleavage site between the fusion protein partner and the protein sequence of interest to allow removal of fusion protein sequences.

Preferably, the fusion protein will not hinder the activity of the protein sequence.

Gene fusion expression systems in *E. coli* have been reviewed in *Curr Opin Biotechnol* (1995) 6(5):501-6.

In another embodiment of the invention, the amino acid sequence may be ligated to a heterologous sequence to encode a fusion protein. For example, for screening of peptide libraries for agents capable of affecting the substance activity, it may be useful to encode a chimeric substance expressing a heterologous epitope that is recognised by a commercially available antibody.

Large Scale Application

In one preferred embodiment of the present invention, the amino acid sequence is used for large scale applications.

Preferably the amino acid sequence is produced in a quantity of from 1 g per liter to about 2 g per liter of the total cell culture volume after cultivation of the host organism.

Preferably the amino acid sequence is produced in a quantity of from 100 mg per liter to about 900 mg per liter of the total cell culture volume after cultivation of the host organism.

Preferably the amino acid sequence is produced in a quantity of from 250 mg per liter to about 500 mg per liter of the total cell culture volume after cultivation of the host organism.

Food

The composition of the present invention may be used as—or in the preparation of—a food. Here, the term "food" is used in a broad sense—and covers food for humans as well as food for animals (i.e. a feed). In a preferred aspect, the food is for human consumption.

The food may be in the form of a solution or as a solid—depending on the use and/or the mode of application and/or the mode of administration.

Food Ingredient

The composition of the present invention may be used as a food ingredient.

As used herein the term "food ingredient" includes a formulation, which is or can be added to functional foods or foodstuffs and includes formulations which can be used at low levels in a wide variety of products that require, for example, acidifying or emulsifying.

The food ingredient may be in the form of a solution or as a solid—depending on the use and/or the mode of application and/or the mode of administration.

Food Products

The composition of the present invention can be used in the preparation of food products such as one or more of: confectionery products, dairy products, poultry products, fish products and bakery products.

The present invention also provides a method of preparing a food or a food ingredient, the method comprising admixing a lipolytic enzyme according to the present invention with another food ingredient.

EXAMPLES

The present invention will now be described, by way of example only, in which reference may be made to the following figures:

FIG. 7 shows alignment of amino acid sequences of all CBS peptides to the lipase of the Japanese strain of *F. heterosporum* (Nagao et al. 1994). Identical and similar (well-conserved) amino acids are marked below the alignment with * and ·, respectively.

FIG. 8 shows a nucleotide sequence and translated amino acid sequence of the synthetic *F. heterosporum* (CBS 782.83) lipolytic enzyme gene fused to the synthetic alpha-signal sequence. The amino acid sequence is presented above the nucleotide sequence. The nucleotides containing the restriction enzyme sites Eco RI and Bam HI are underlined and the translational start and stop codons are double underlined. An arrowhead marks the position of the fusion between the alpha-signal sequence and the lipolytic enzyme gene. Arrows indicate the primers used for the assembly of the gene.

Figure 9:
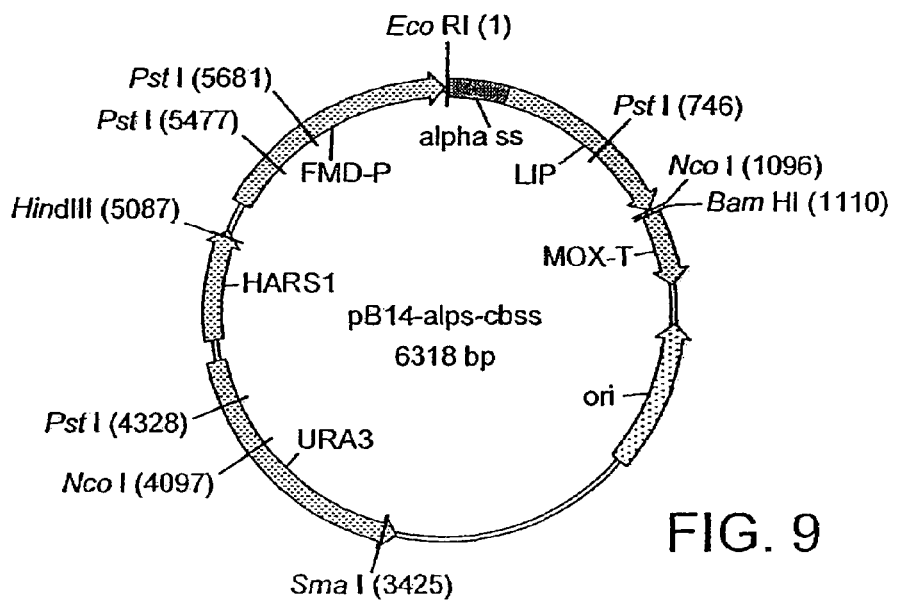

FIG. 9 shows a schematic representation of the *Hansenula* expression vector pB14 containing the synthetic *F. heterosporum* (CBS 782.83) lipolytic enzyme gene (LIPASE) fused to a synthetic alpha-signal sequence (alpha ss). URA3, orotidine-5'-phosphate-decarboxylase gene for uracil complementation for selection in *Hansenula*. HARS, Autonomously replicating sequence for replication in *Hansenula*. FMD-P, FMD promoter for expression in *Hansenula*.

Figure 10:
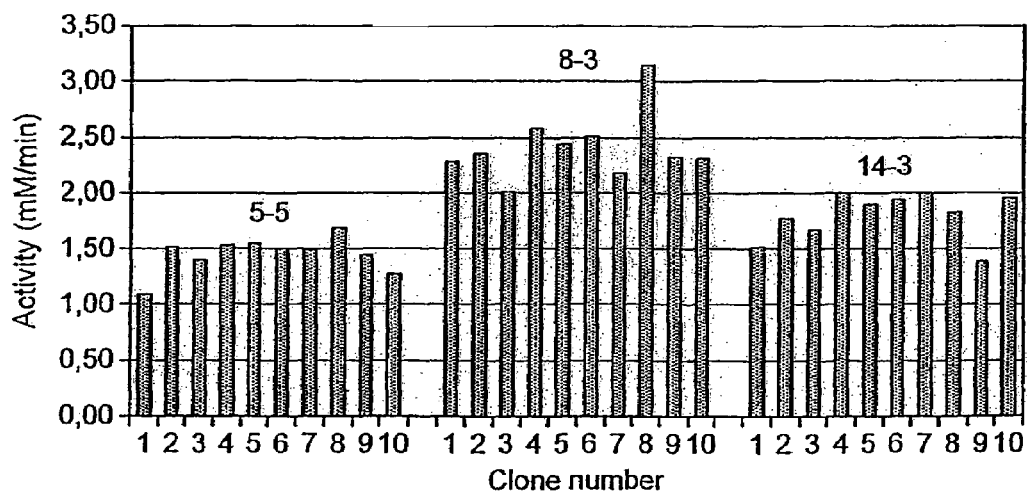

FIG. 10 shows phospholipase activity of selected *Hansenula polymorpha* clones containing the synthetic *F. heterosporum* lipolytic enzyme gene. Lecithin was used as substrate and the free fatty acid was determined using the NEFA kit (Roche).

Figure 11:
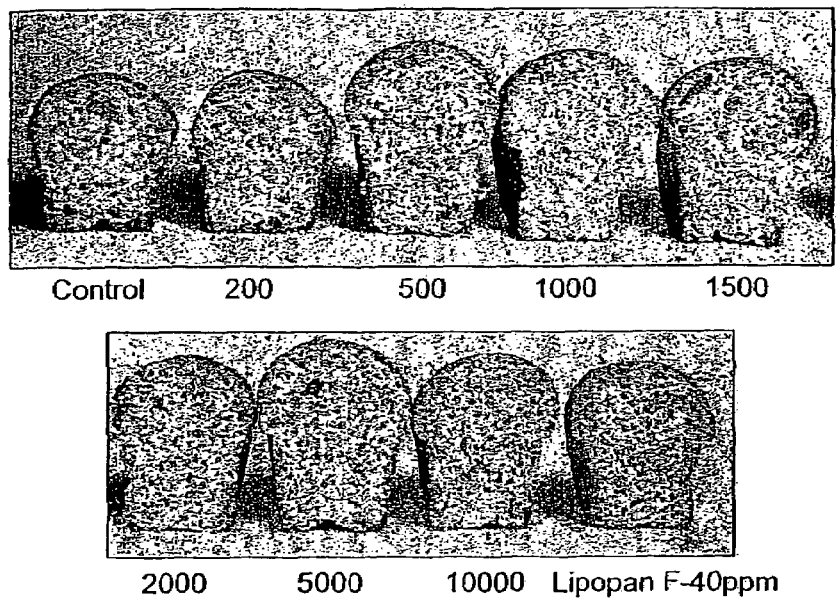

FIG. 11 shows a minibread baked with increased dosage (PLU) of phospholipase sample 205 and Lipopan F™.

Figure 12:
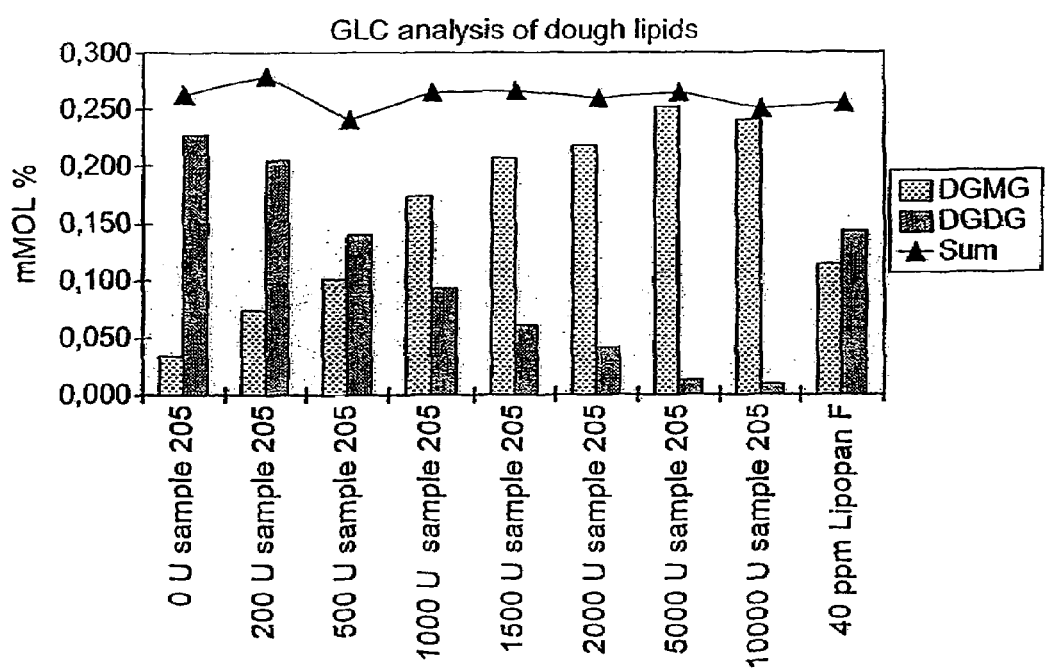

FIG. 12 shows GLC analysis of dough lipids. DGDG=digalactosyldiglyceride. DGMG digalactosylmonoglyceride. Sum=DGDG+DGMG (Example 3).

Figure 13:
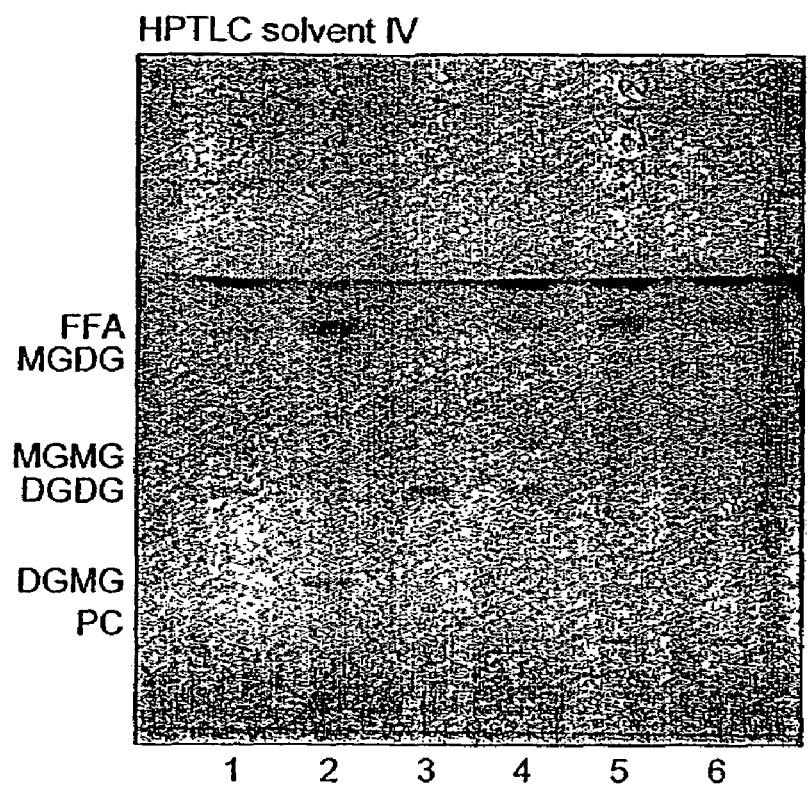

FIG. 13 shows a HPTLC chromatogram of A) References: 1. Fractionated flour lipid, 2. Hydrolyzed DGDG, 3. DGDG. B) Lipids extracted from dough: 4. Control, 5. 2000 PLU-7/kg sample 205, and 6.40 ppm Lipopan F™.

Figure 14:
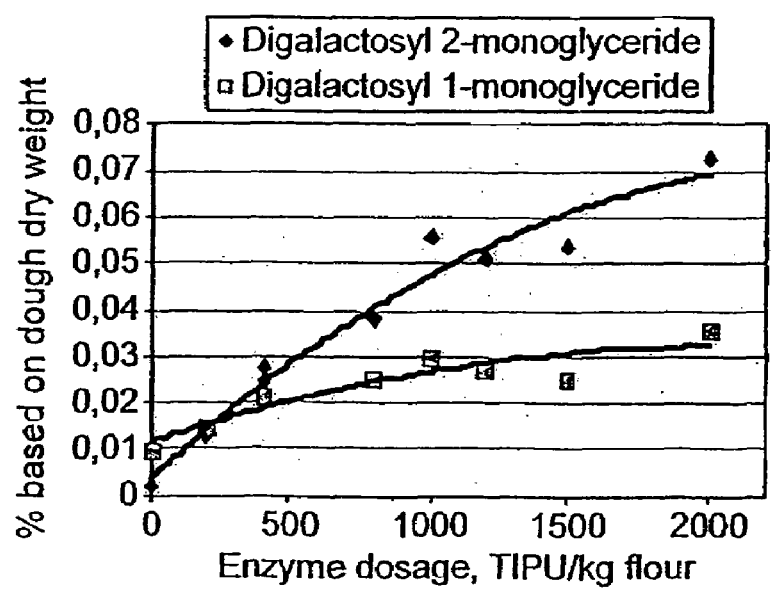

FIG. 14 shows GLC analysis of isomer digalactosyl-monoglyceride in dough treated with a lipolytic enzyme derived from *Fusarium heterosporum*.

Figure 15:
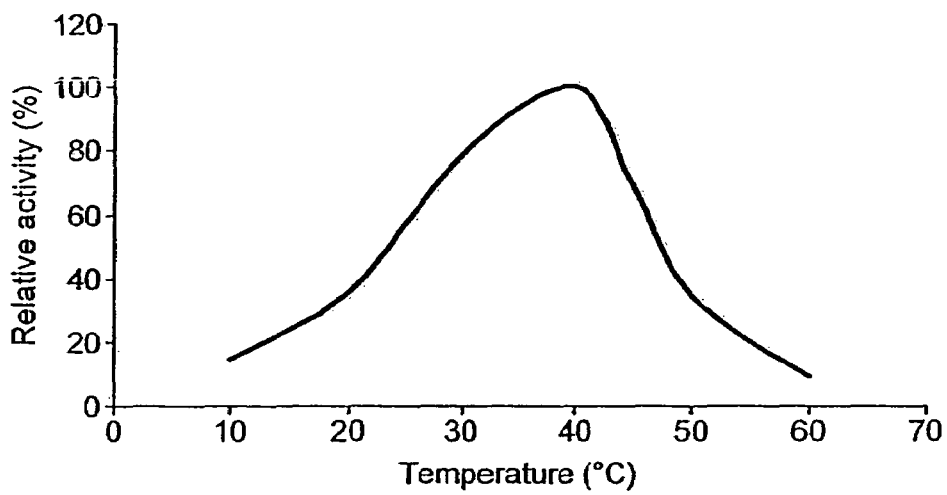

FIG. 15 shows activity of lipolytic enzyme derived from *Fusarium heterosporum* determined by 10 minutes of enzymation on lecithin substrate, pH 7.0, at various temperatures and subsequent determination of free fatty acids by the NEFA C method.

Figure 16:
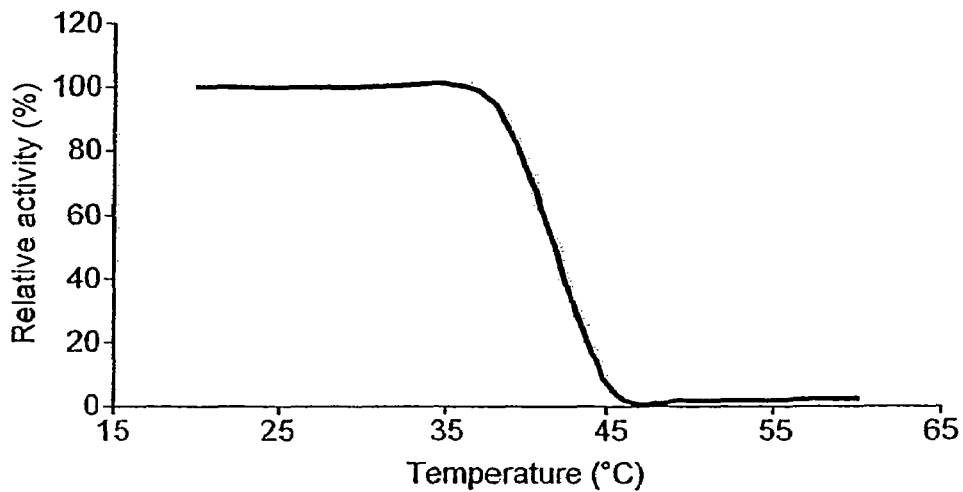

FIG. 16 shows activity of lipolytic enzyme derived from *Fusarium heterosporum* determined after 30 minutes of incubation in 50 mM phosphate buffer at 3 TIPU/ml and various temperatures (50 mM phosphate buffer, pH 7.0) by 10 minutes of enzymation on lecithin substrate (without CaCl$_2$) at 37° C. and pH 7.0 and subsequent determination of free fatty acids by the NEFA C method.

Figure 17:
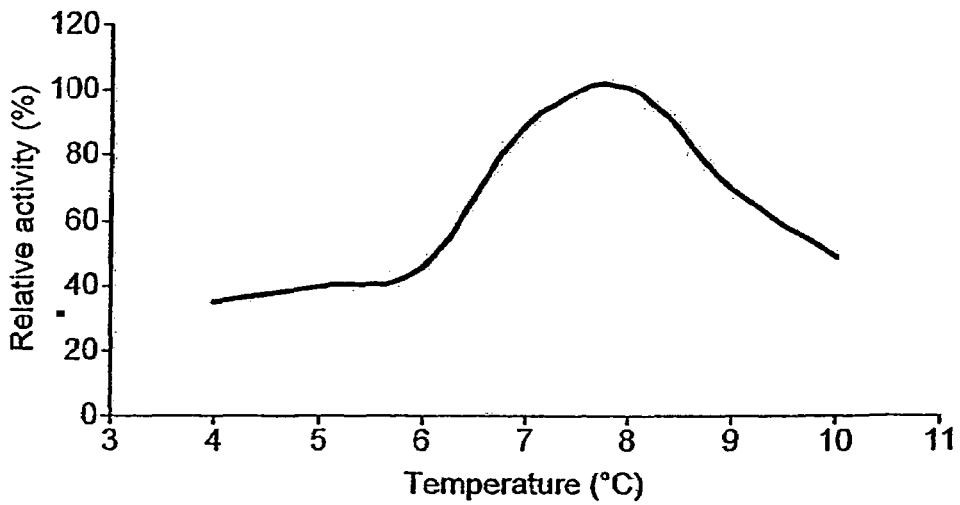

FIG. 17 shows activity of lipolytic enzyme derived from *Fusarium heterosporum* determined after 10 minutes of enzymation on lecithin substrate (without CaCl$_2$) at 37° C. and various pH (50 mM phosphate buffer) and subsequent determination of free fatty acids by the NEFA C method.

Figure 18:
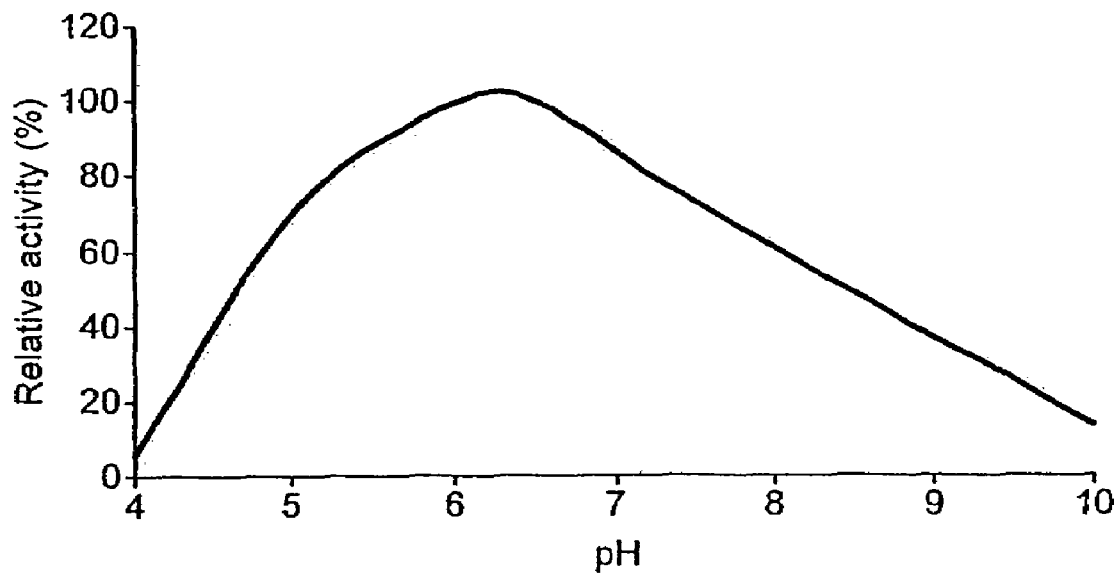

FIG. 18 shows activity of lipolytic enzyme derived from *Fusarium heterosporum* determined after 30 minutes of incubation in 50 mM phosphate buffer at 3 TIPU/ml and various pH (50 mM phosphate buffer) by 10 minutes of enzymation on lecithin substrate (without CaCl$_2$) at 37° C. and pH 7.0 and subsequent determination of free fatty acids by the NEFA C method.

Figure 19A:
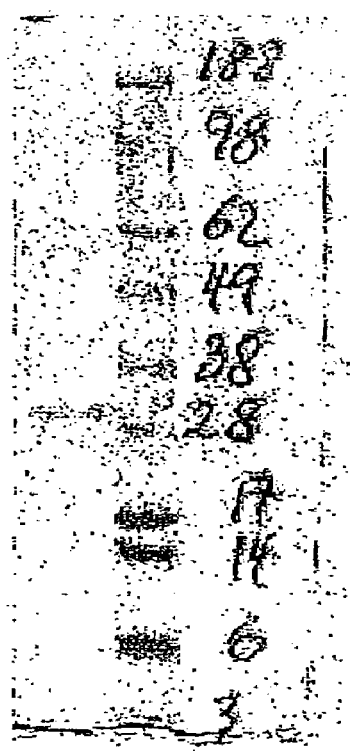
Figure 19B:
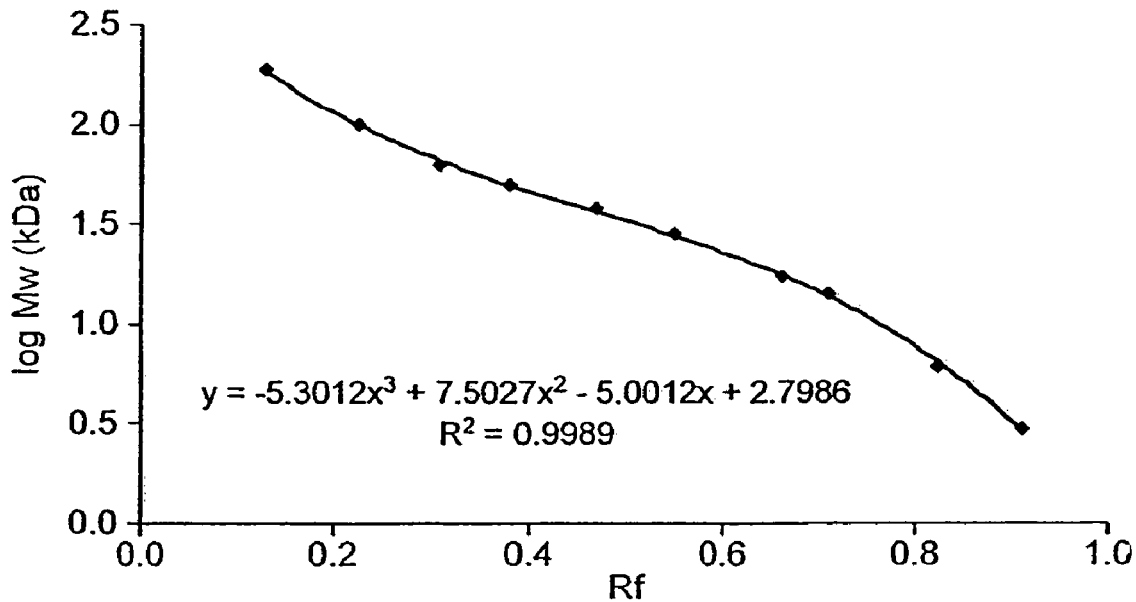

FIGS. 19a and 19b show the determination of the molecular weight, as determined by SDS-PAGE, of a lipolytic enzyme derived from *Fusarium heterosporum*

Figure 20:
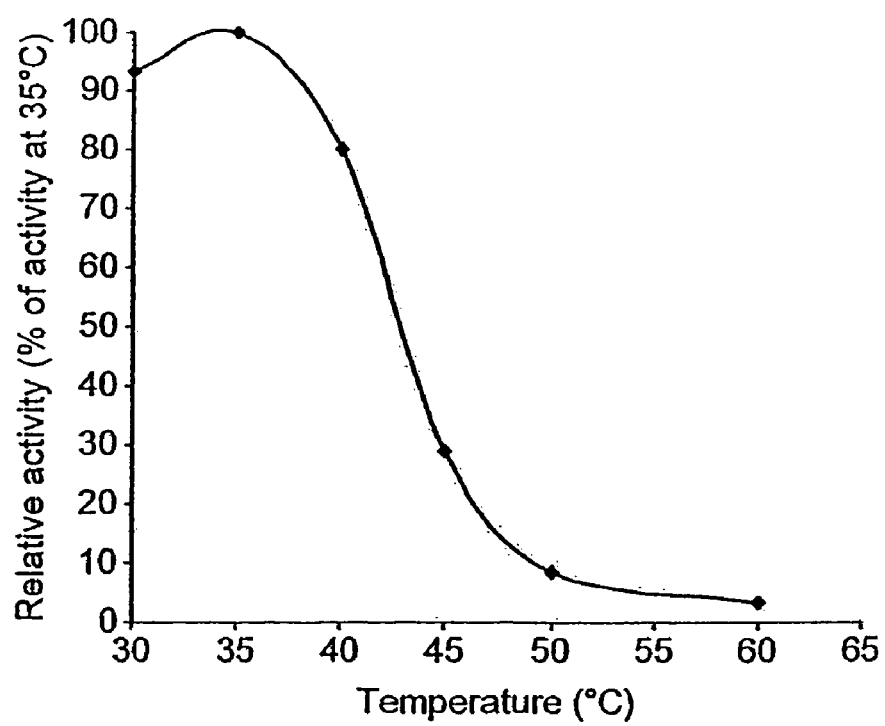

FIG. 20 depicts the temperature optimum for a lipolytic enzyme according to the present invention. The enzyme reaction was carried out at various temperatures.

Figure 21:
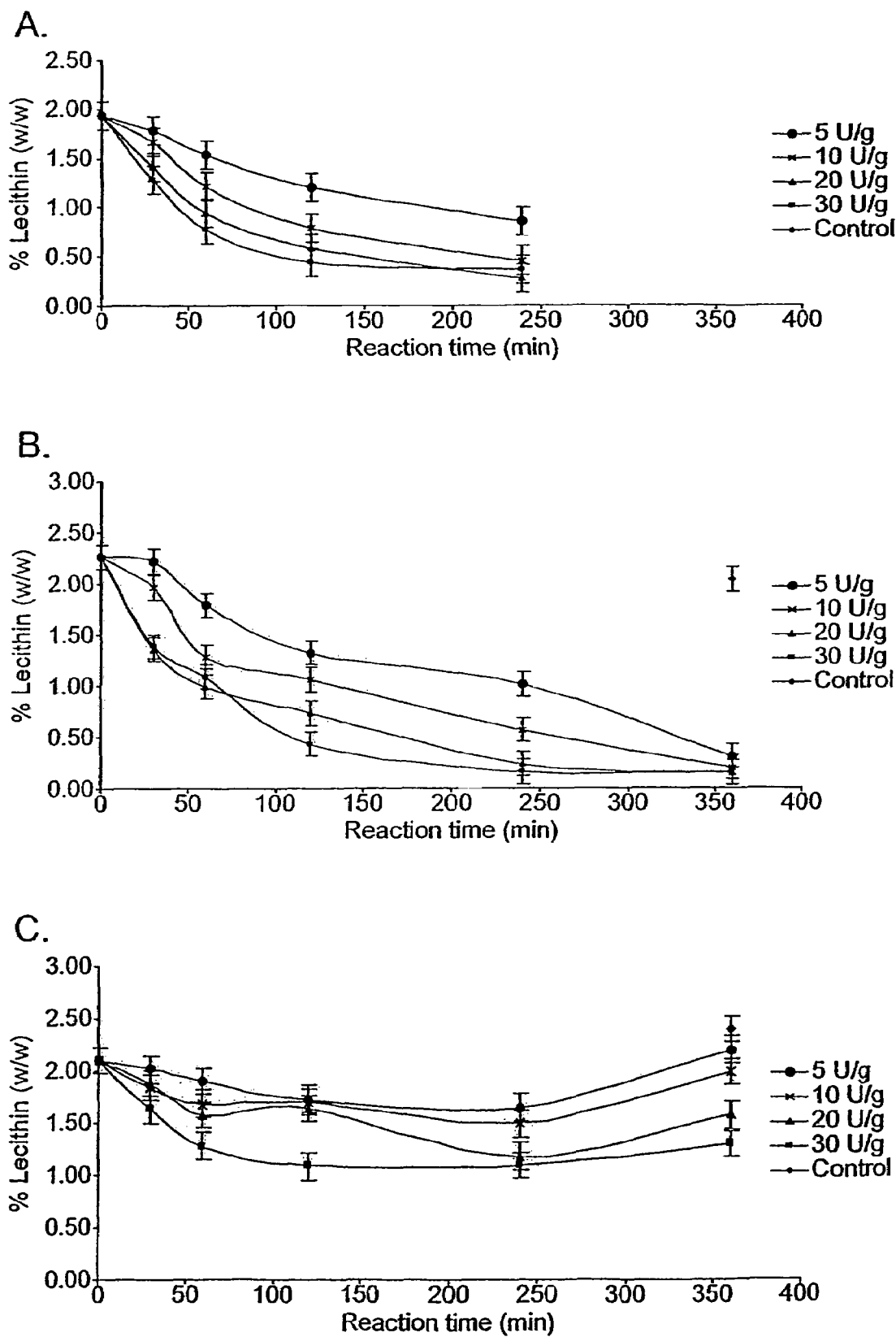

FIG. 21 depicts the amount of lecithin in enzyme-modified egg yolk as a function of reaction time at A: 30° C., B: 40° C., and C: 50° C. The amount of lecithin was analysed by LC/MS-MS and is expressed as percentage of egg yolk.

FIG. 22 depicts the amount of lyso-lecithin in enzyme-modified egg yolk as a function or reaction time at A: 30° C., B: 40° C., and C: 50° C. The amount of lyso-lecithin was analysed by LC/MS-MS and is expressed as percentage of egg yolk.

Figure 23:
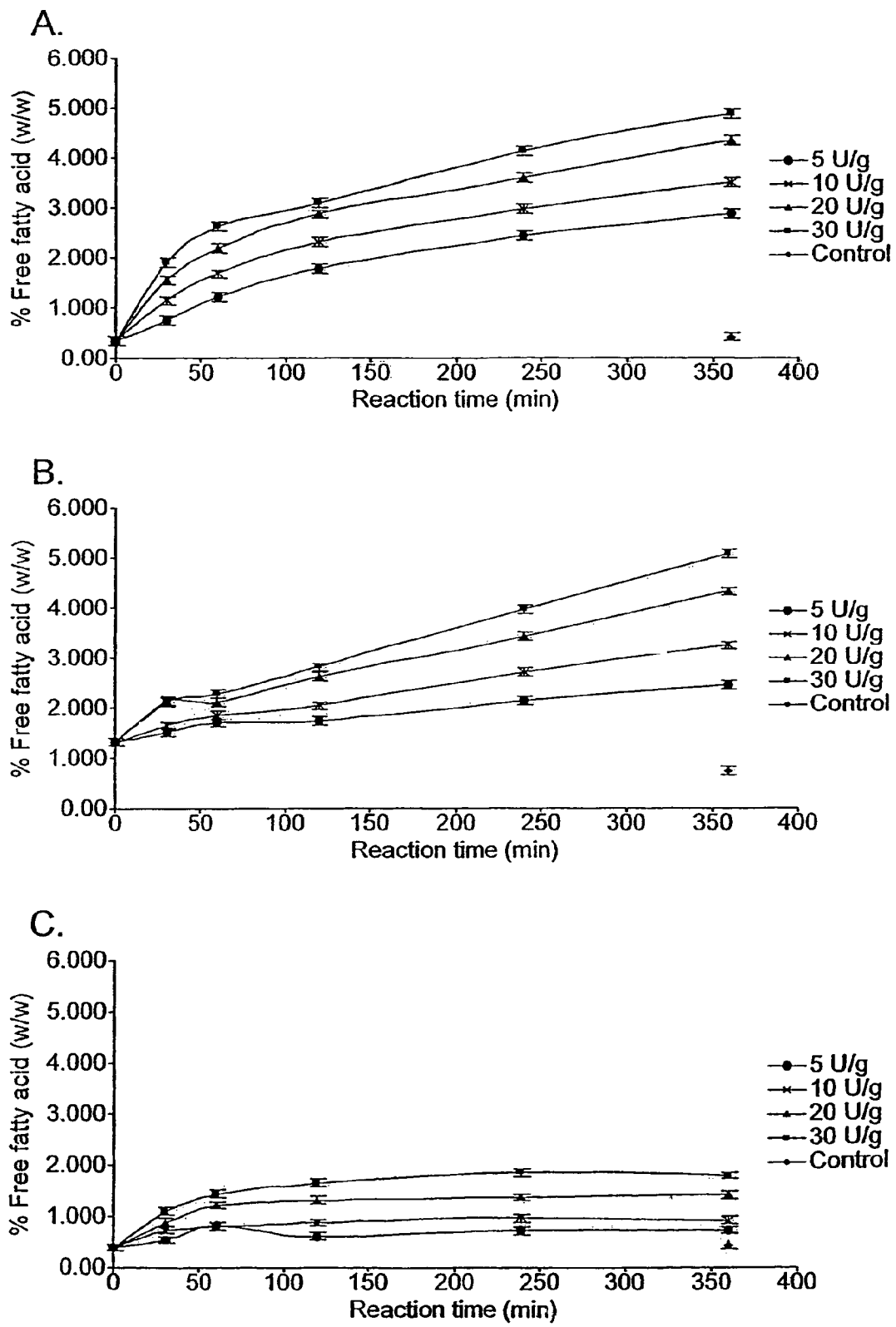

FIG. 23 depicts the amount of free fatty acid in enzyme modified egg yolk as a function of reaction time at A: 30° C., B: 40° C., and C: 50° C. The amount of free fatty acid was analysed by the NEFA C method and is expressed as percentage of egg yolk.

Figure 24:
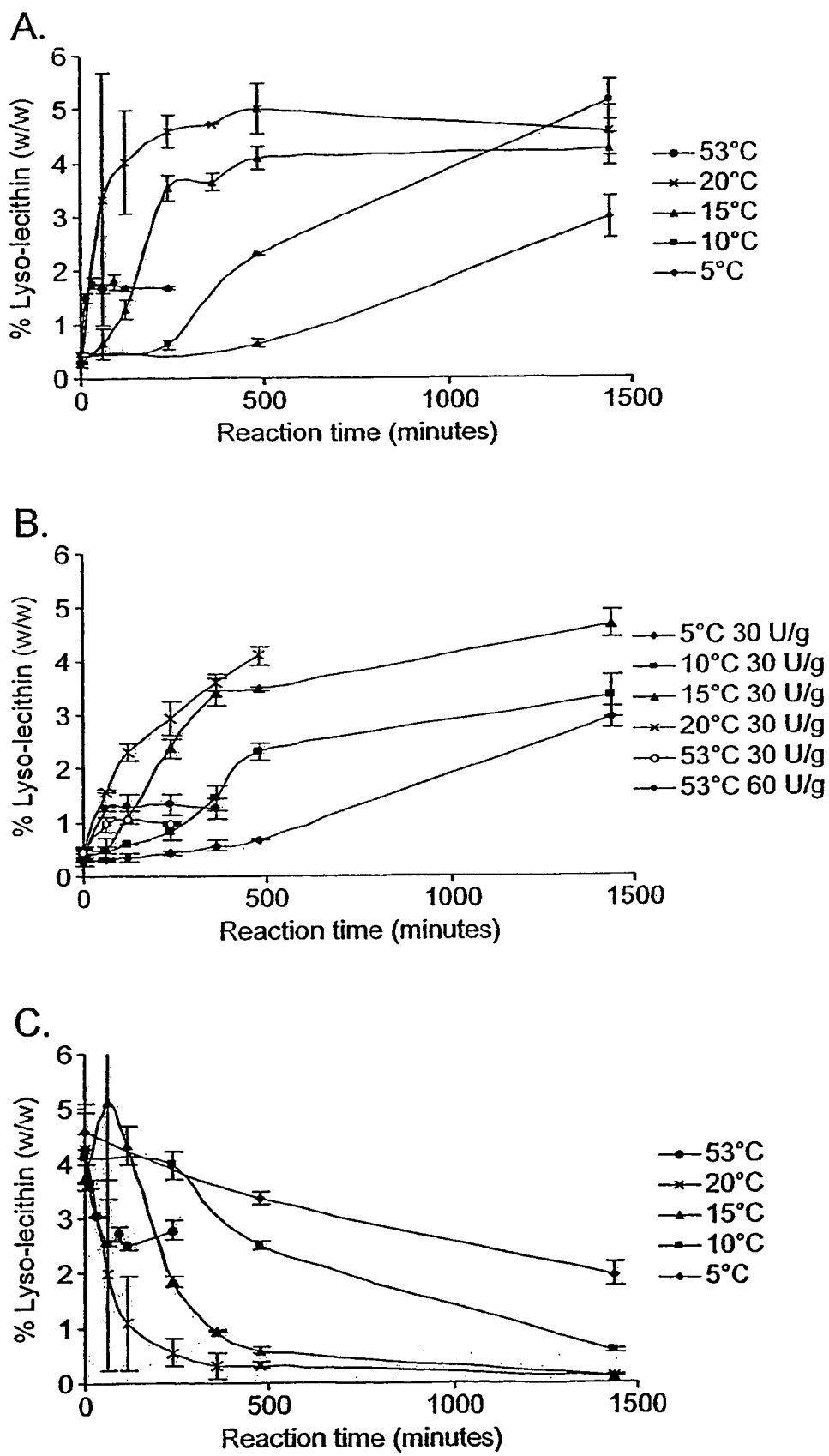

FIG. 24 depicts the enzymatic conversion of egg yolk with a lipolytic enzyme according to the present invention (Example 4). The amounts of lyso-lecithin (A), free fatty acid (B), and lecithin (C) as a function of reaction time. The error bars indicate the standard deviation of the double determinations (n=2). The amount of lecithin and lysolecithin were determined by LC/MS-MS and the amount of free fatty acid was determined by the NEFA C method. Results are expressed as percentage of egg yolk.

Figure 25:
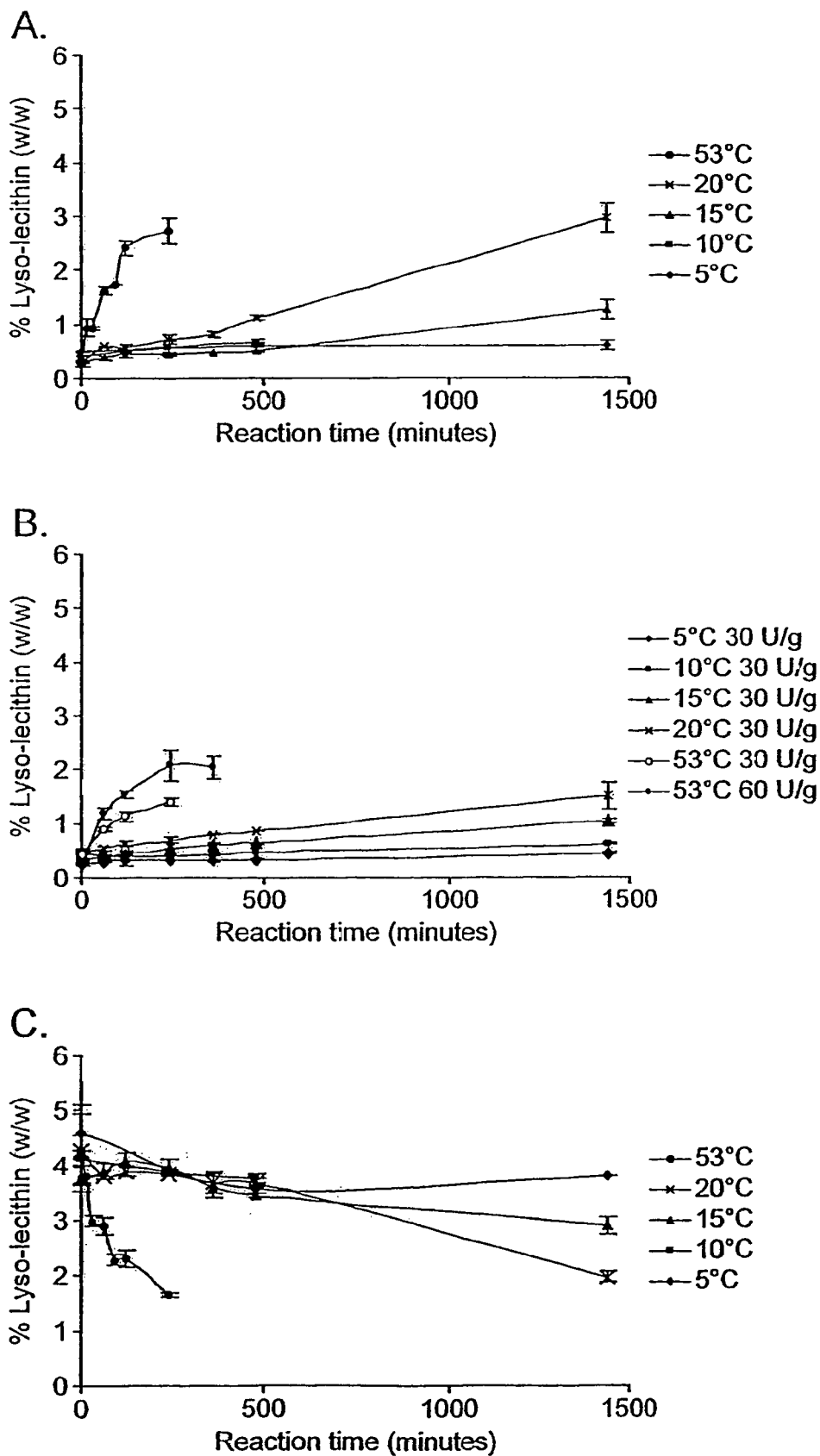

FIG. 25 depicts the enzymatic conversion of egg yolk with Lecitase® Ultra phospholipase from Novozymes A/S (Example 4). The amounts of lyso-lecithin (A), free fatty acid (B), and lecithin (C) as a function of reaction time. The error bars indicate the standard deviation of the double determinations (n=2). The amount of lecithin and lysolecithin were determined by LC/MS-MS and the amount of free fatty acid was determined by the NEFA C method. Results are expressed as percentage of egg yolk.

Figure 26:
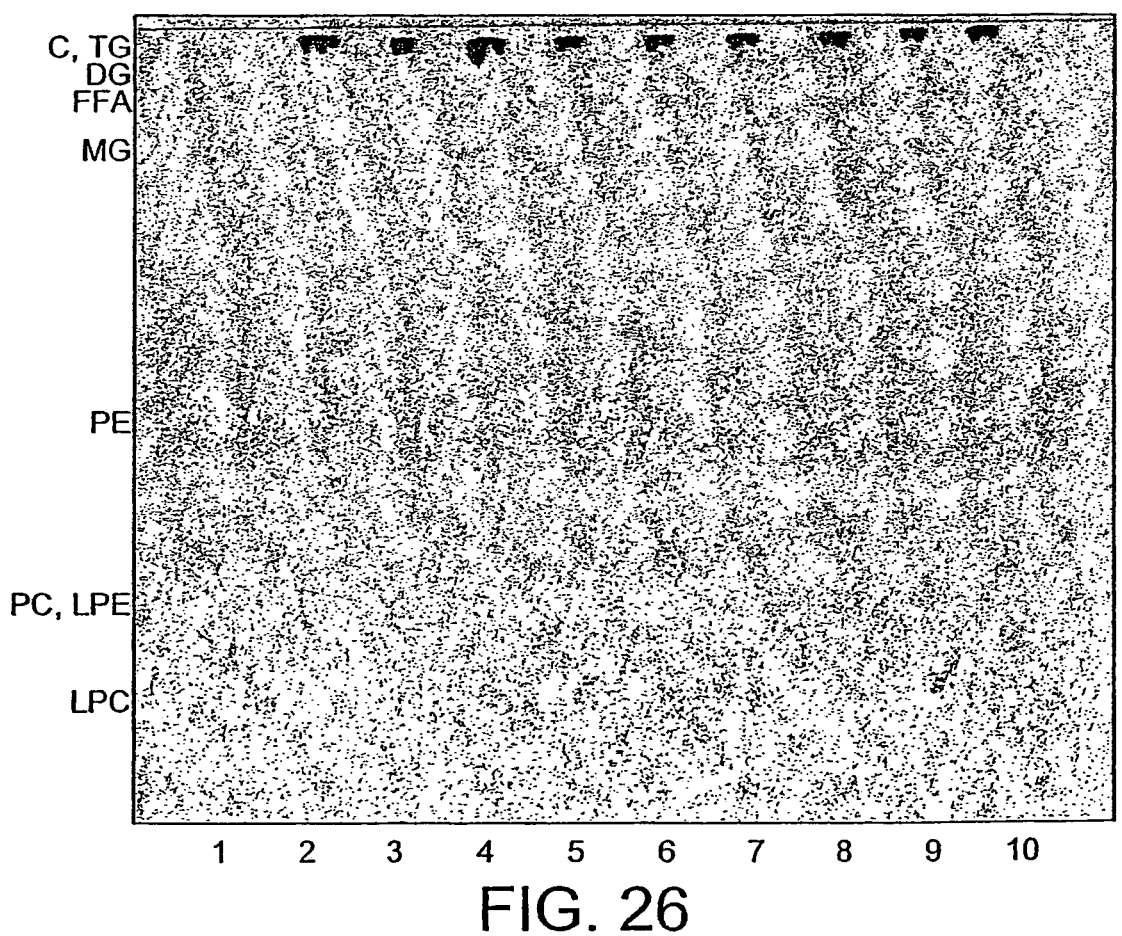

FIG. 26 shows TLC analysis (the solvent was chloroform:methanol:water (65:24:4)) of lipid extract from modified egg yolk (Example 4). 1: PC and LPC standard. 2: Lipolytic enzyme according to the present invention, 10° C., 240 min. 3: Lipolytic enzyme according to the present invention, 20° C., 240 min. 4: Lipolytic enzyme according to the present invention, 53° C., 240 min. 5: Lipolytic enzyme according to the present invention, 20° C., 1440 min. 6: Lecitase® Ultra, 10° C., 4 h. 7: Lecitase® Ultra, 20° C., 240 min. 8: Lecitase® Ultra, 53° C., 4 h. 9: Lecitase® Ultra, 20° C., 1440 min. 10: Control sample. The compounds listed to the left of the TLC plate are cholesterol (C), triacylglyceride (TG), diacylglyceride (DG), free fatty acid (FFA), monoacylglyceride (MG), phosphatidylethanolamine (PE), phosphatidylcholine (PC), lyso-phosphatidylethanolamine (LPE), and lyso-phosphatidylcholine (LPC).

Figure 27:
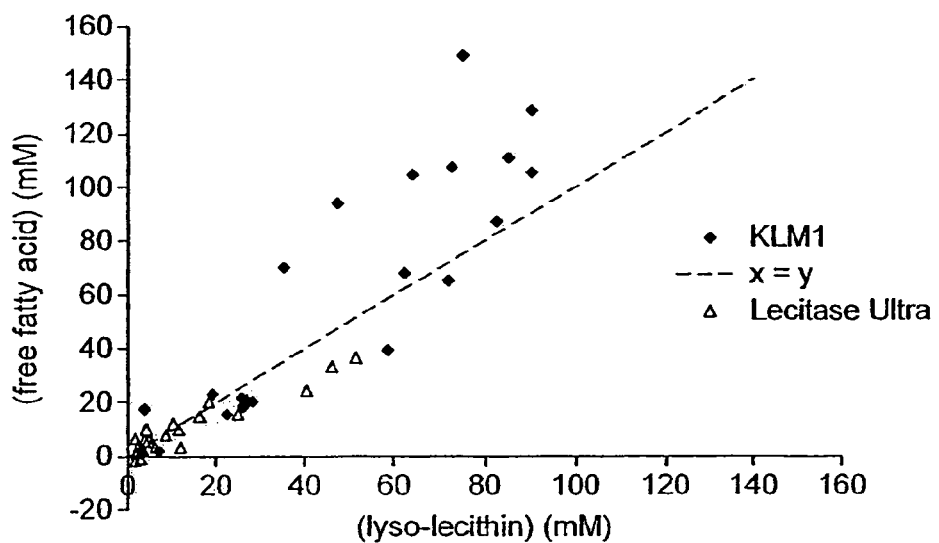

FIG. 27 depicts the relation between change in lyso-lecithin and free fatty acid content during enzymation of egg yolk with a lipolytic enzyme according to the present invention and Lecitase® Ultra phospholipases, respectively (Example 4). The results are based on a molar weight of lyso-lecithin of 523 and a molar weight of free fatty acids of 283. Free fatty acid was determined by the NEFA C method. lysolecithin and lecithin was determined by LC/MS-MS.

Figure 28:
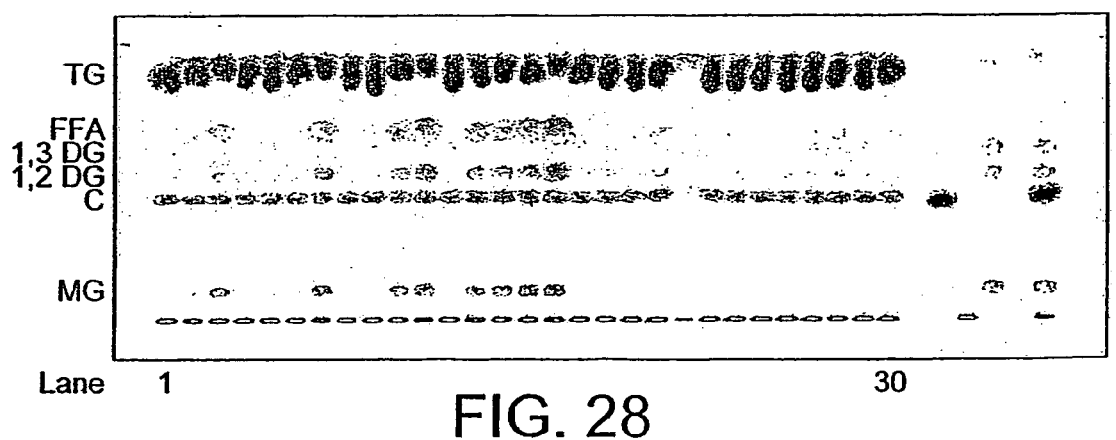

FIG. 28 shows HPTLC analysis (the solvent was p-ether:MTBE:acetic acid (50:50:1)) of lipid extract from modified egg yolk (Example 4). The compounds listed to the left of the TLC plate are triacylglyceride (TG), free fatty acid (FFA), 1,3 diacylglyceride (1,3 DG), 1,2 diacylglyceride (1,2 DG),cholesterol (C), monoacylglyceride (MG), phosphatidylethanolamine (PE), phosphatidylcholine (PC), lyso-phosphatidylethanolamine (LPE), and lyso-phosphatidylcholine (LPC).

Figure 29:
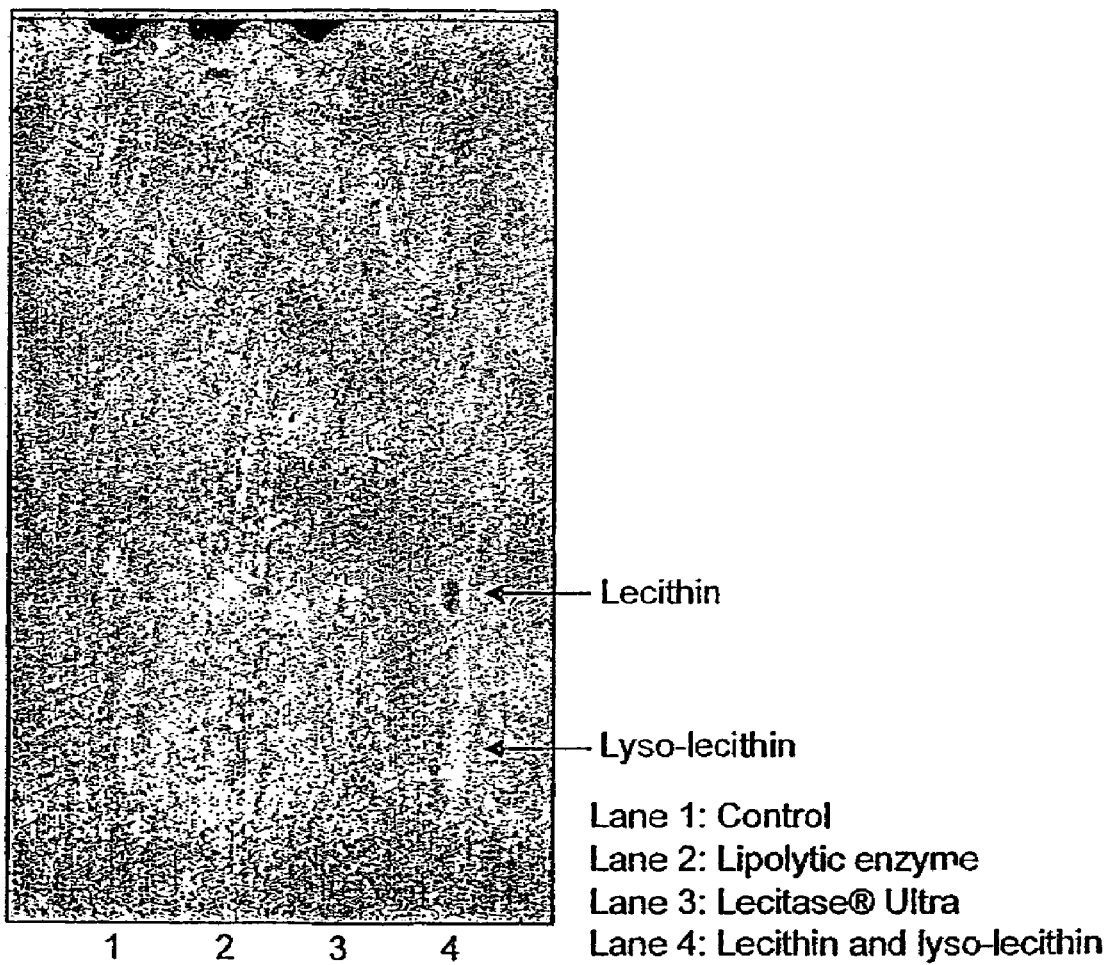

FIG. 29 shows TLC analysis (solvent IV) of mayonnaise made with enzyme-modified egg yolk from Sanofa A/S (Example 5).

Figure 30:
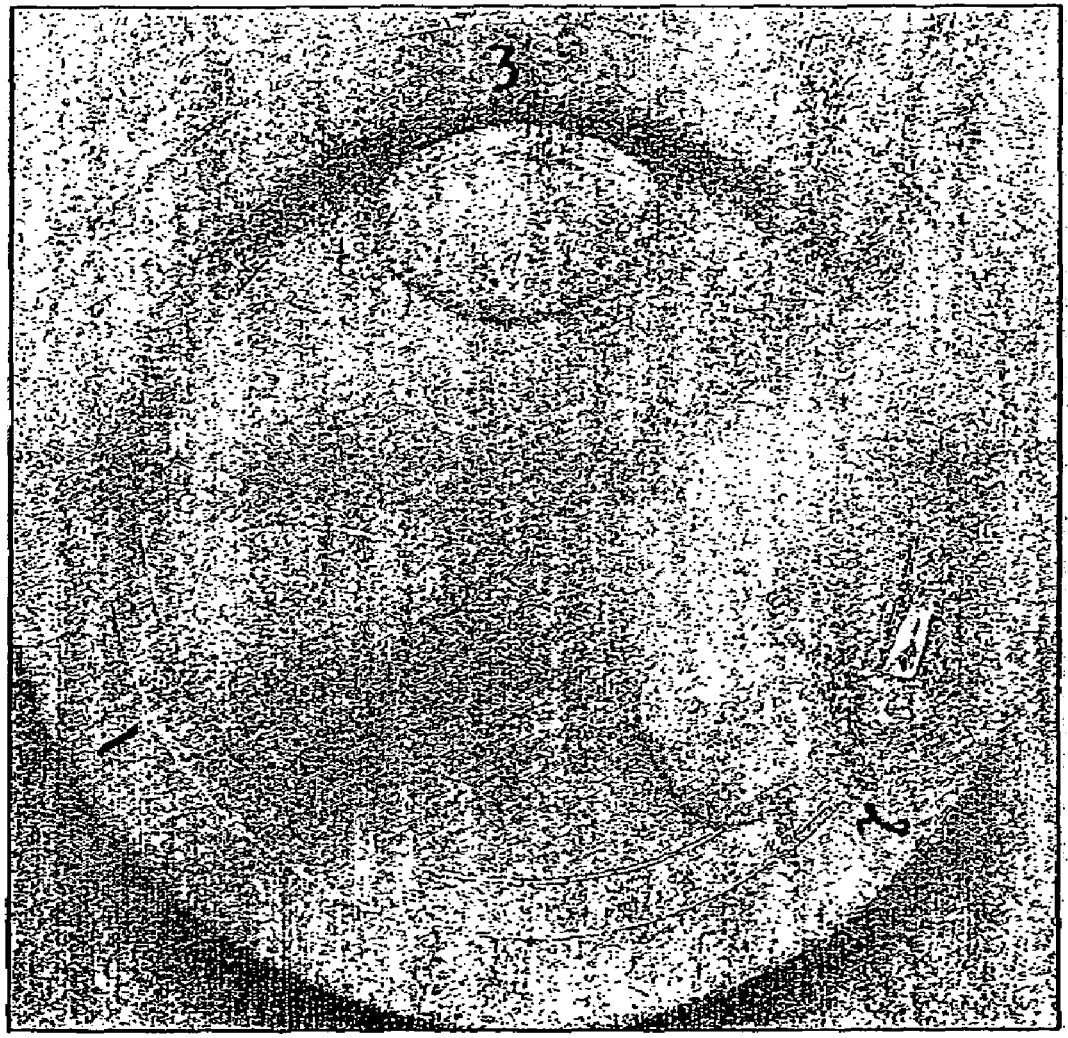

FIG. 30 shows mayonnaise prepared from enzyme-modified egg yolk from Sanofa A/S heat-treated in a microwave oven (Example 5). Sample 1 was a control with water added instead of enzyme solution, sample 2 contained 30 U/g lipolytic enzyme according to the present invention, and sample 3 contained 30 U/g Lecitase® Ultra.

Figure 31:
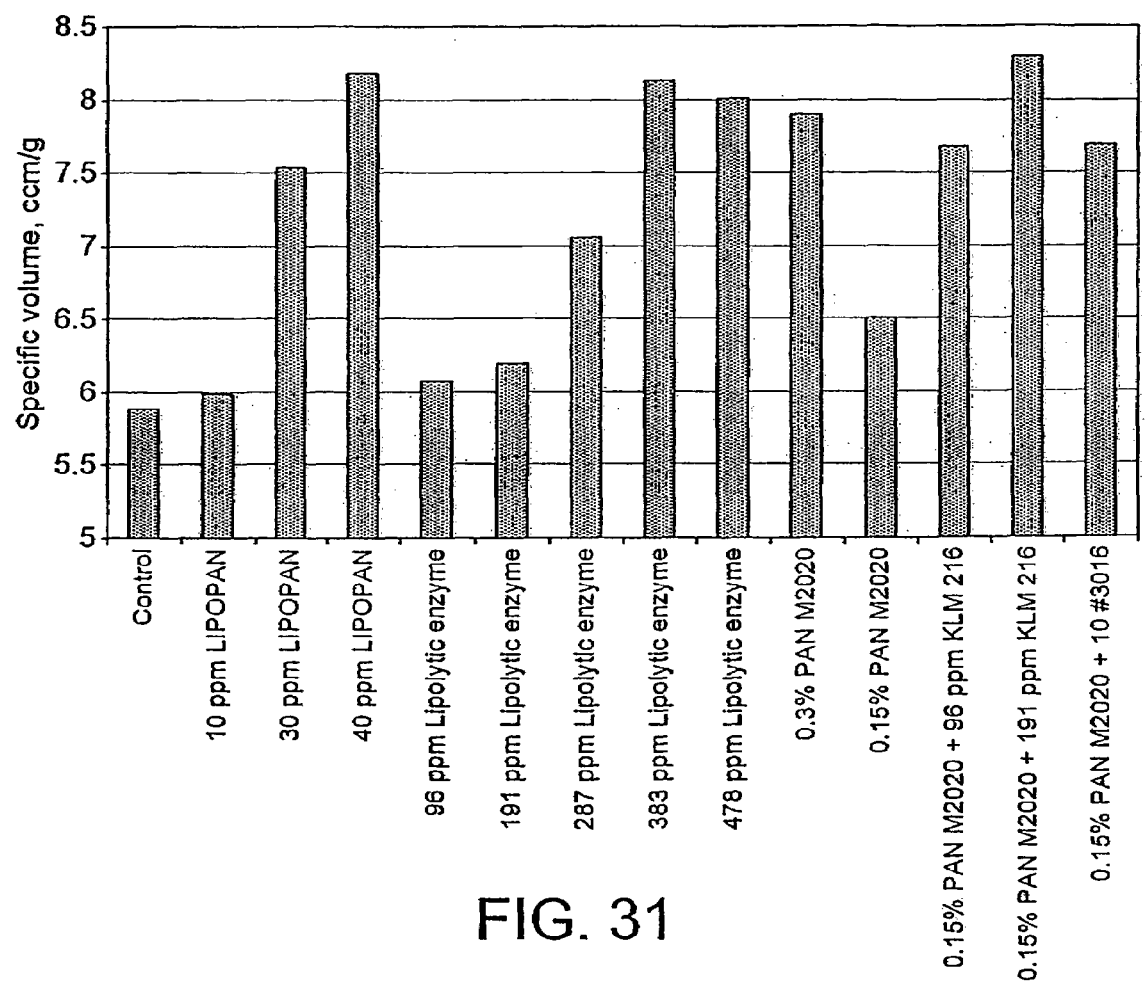

FIG. 31 shows the specific bread volume of hard crusty rolls baked with different concentrations of a lipolytic enzyme according to the present invention alone or in combination with Panodan® M2020 DATEM emulsifier and tested against a combination of Lipopan F™ and DATEM as well as pure Lipopan F™ or pure DATEM.

Figure 32:
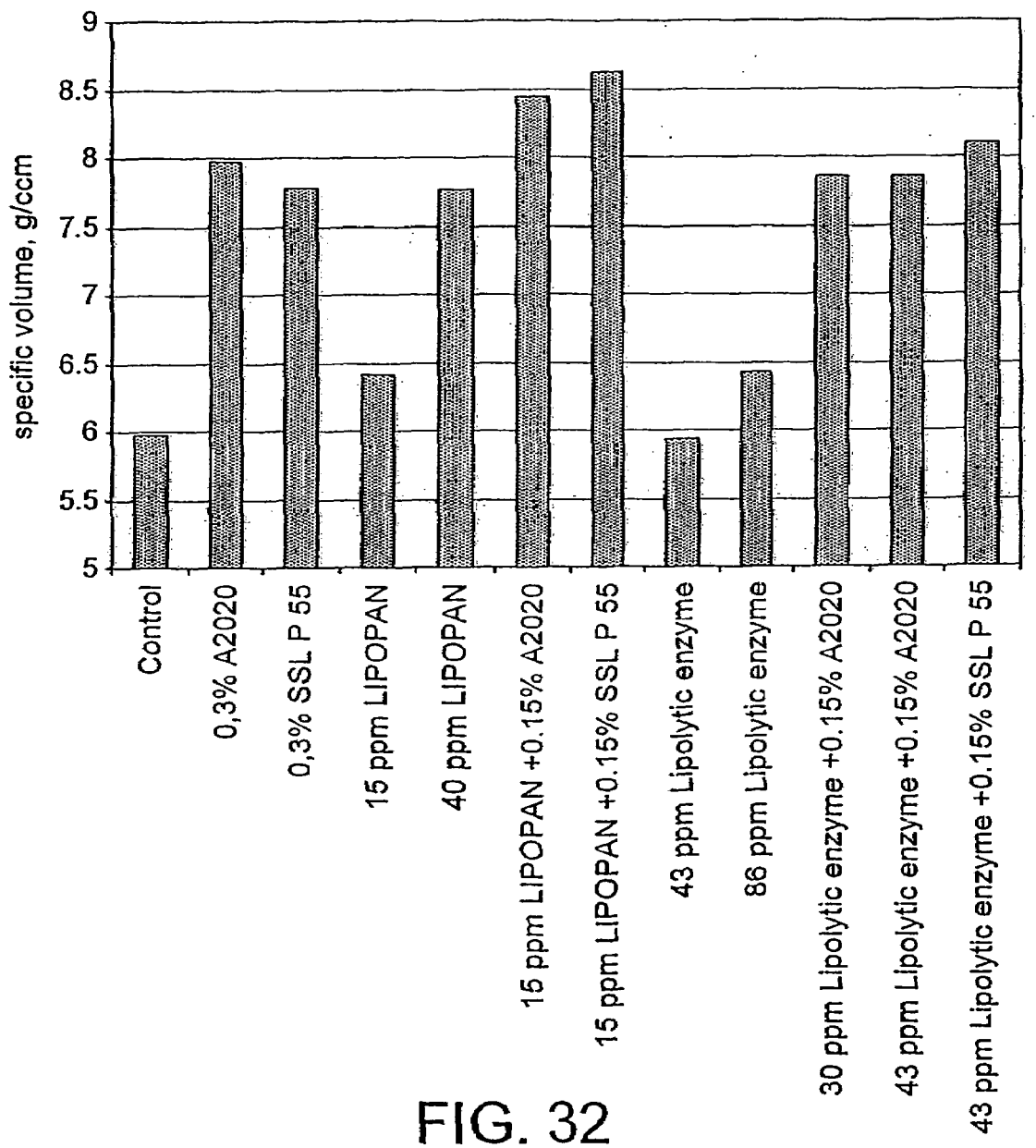

FIG. 32 shows the specific bread volume of hard crusty rolls baked with different concentrations of a lipolytic enzyme according to the present invention alone or in combination with Panodan® A2020 DATEM or SSL P 55 emulsifier and tested against a combination of Lipopan F™M/SSL P 55 or Lipopan™/DATEM as well as pure Lipopan F, pure DATEM and pure SSL P 55.

FIG. 33 shows nucleotide sequence (SEQ ID No. 5) and deduced amino acid sequence (SEQ ID No.4) of the *F. semitectum* (IBT 9507) lipase cDNA. The deduced amino acid sequence is presented above the nucleotide sequence. Arrows indicate the primers used for the amplification of the cDNA.

Figure 34:
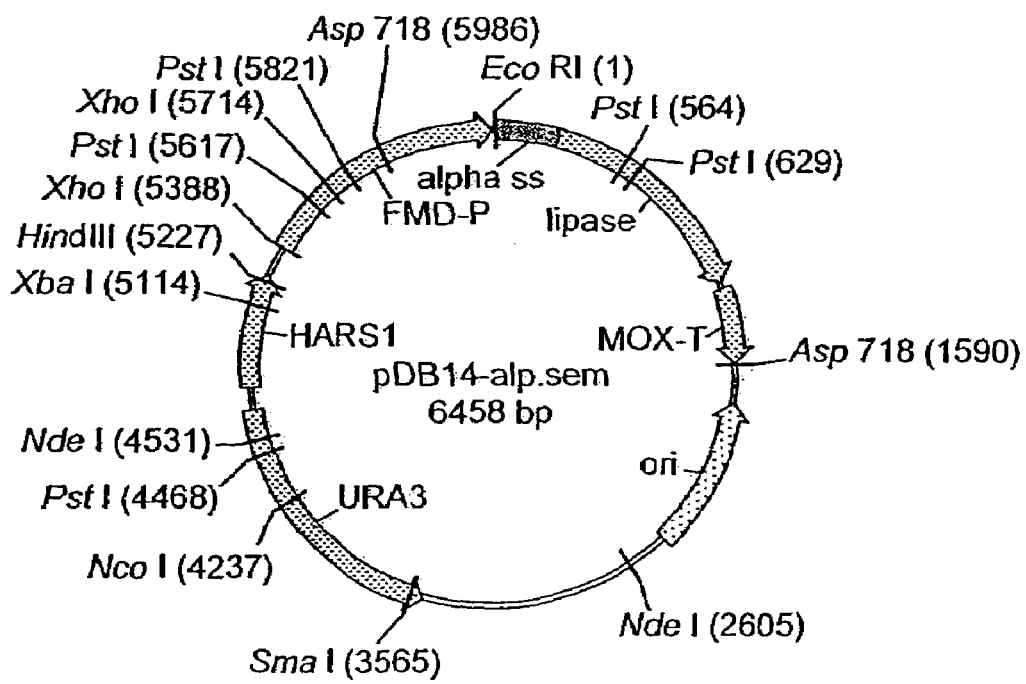

FIG. 34 shows a schematic representation of the *Hansenula* expression vector pDB14-alp-sem containing the *F. semitectum* lipase gene (Lipase) fused to the α-signal sequence (alpha ss.). AP(R), URA3, orotidine-5' phosphate-decarboxylase gene for uracil complementation for selection. HARS, Autonomously replicating sequence for replication in *Hansenula*. FMD-P, FMD promoter for expression in *Hansenula*.

Figure 35:
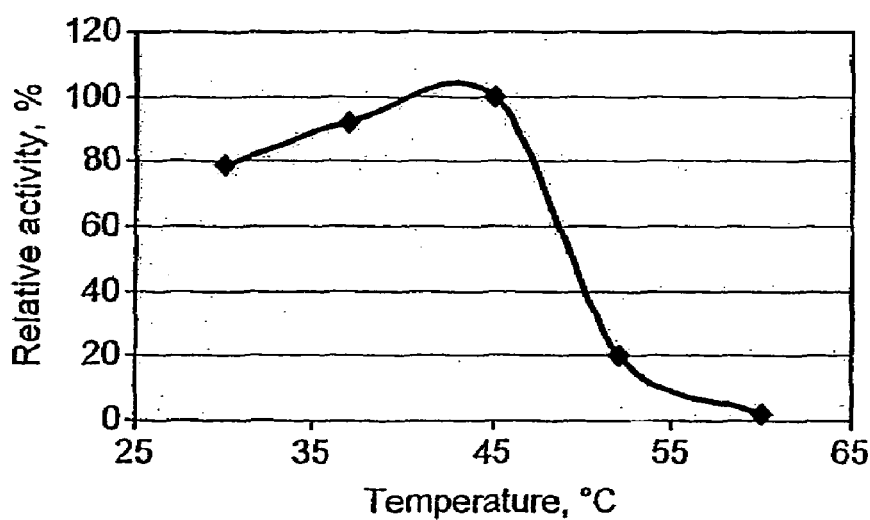

FIG. 35 shows phospholipase activity of a lipolytic enzyme from *Fusarium semitectum* IBT9507 as a function of temperature.

FIG. 36 shows phospholipase activity of a lipolytic enzyme from *Fusarium semitectum* IBT9507 as a function of pH.

FIG. 37 shows an amino acid sequence (SEQ ID No. 1) of a fungal lipolytic enzyme derived from *Fusarium heterosporum*.

FIG. 38 shows an amino acid sequence of a fungal lipolytic enzyme derived from *Fusarium heterosporum* comprising an N terminal signal sequence (underlined) (SEQ ID No. 2).

FIG. 39 shows a nucleotide sequence (SEQ ID No. 3) encoding a fungal lipolytic enzyme derived from *Fusarium heterosporum* in accordance with the present invention.

FIG. 40 shows an amino acid sequence (SEQ ID No. 4) of a lipolytic enzyme derived from *Fusarium semitectum*.

FIG. 41 shows a nucleotide sequence (SEQ ID NO. 5) encoding a lipolytic enzyme derived from *Fusarium semitectum*.

FIG. 42 shows an amino acid sequence (SEQ ID No.6) of a lipolytic enzyme derived from *Fusarium heterosporum* (EAEA is a pro-peptide originally from the α-factor signal sequence).

FIG. 43 shows a nucleotide sequence (SEQ ID No.7) of a lipolytic enzyme derived from *Fusarium heterosporum* which includes a α-factor signal sequence.

Example 1

Expression, Purification, Sequencing and Baking Trials of a *Fusarium heterosporum* Lipolytic Enzyme Fermentation

*Fusarium heterosporum* CBS 782.83 strain was obtained from Centraalbureau voor Schimmelcultures (the Netherlands).

| Growth media Glucose-yeast extract agar | |
|---|---|
| Yeast extract | 4 g/L |
| KH$_2$PO$_4$ | 1 g/L |
| MgSO$_4$, 7H$_2$O | 0.5 g/L |
| Glucose | 15 g/L |
| Agar | 20 g/L |

Glucose was added after autoclaving 1.4 Pre-Fermentation Medium

| | |
|---|---|
| Soy flour | 50 g/L |
| Glucose monohydrate | 50 g/L |
| KH$_2$PO$_4$ | 2 g/L |
| Na$_2$HPO$_4$ | 3 g/L |
| Soy oil | 1 g/L |

The medium was prepared in 500 mL shake flasks with baffles and 100 mL was added pr shake flask. The soy oil was added to each flask separately.

Glucose was added after autoclaving.

| Production medium | |
|---|---|
| Peptone | 10 g/L |
| Tween TM-80 | 12 g/L |
| MgSO$_4$, 7H$_2$O | 2 g/L |
| CaCl$_2$, 2H$_2$O | 0.1 g/L |

The medium was prepared in 500 mL shake flasks with baffles and 100 mL was added pr shake flask. The Tween TM-80 was added to each flask separately.

pH was adjusted to 6.0 before autoclaving.

Culture Conditions

*Fusarium heterosporum* CBS 782.83 was inoculated on glucose-yeast extract agar plates, which were incubated at 24° C. until development of spores.

A shake flask containing pre-fermentation medium was inoculated with 4 cm$^2$ of agar plate containing a well sporulating culture. The shake flask was incubated at 30° C. and 200 RPM. After three days of growth, 30 production medium shake flasks were each inoculated with 5 mL fermentation broth from the pre-fermentation shake flask. The production medium shake flasks were incubated at 30° C. and 200 RPM.

Ten production medium shake flasks were harvested after 2, 3 and 4 days of growth. The biomass was removed by centrifugation followed by sterile filtration of the supernatant through 0.2 μm filters (VacuCap 90 Filter Unit w/0.2 μm Supor Membrane) from Gelman Laboratory. After filtration, the filtrate was frozen at −80° C. and stored until analysis.

Analytical Procedures

Phospholipase activity was determined according to the "PLU assay" previously described herein.

Application

TLC Analysis

TLC-plate was activated in a heat cupboard (110° C.) for ½ h.

100 mL running buffer was poured into a chromatography chamber with lid. The walls of the chamber were covered with filter paper (Whatman 2) in order to saturate the chamber with the solvent vapor.

The TLC-plate was placed in a frame and the sample was applied onto the TLC plate 2 cm from the bottom. The TLC plate was then placed in the TLC chamber with the chosen running buffer. When the running buffer reached 14 cm from the bottom of the plate, the TLC plate was taken out and dried in fume board, and then placed in the heat cupboard at 110° C. for 10 minutes.

The TLC-plate was then immersed in the developing reagent, and dried in the heat cupboard at 110° C. for 15 minutes Running-Buffer:

Nr. IV: Chloroform:Methanol:H$_2$O (65:25:4)

Nr. I: P-ether:methyl-tert-butyl ether (MTBE):Acetic acid (60:40:1)

Developing Buffer (Vanadate-Buffer):

32 g Na$_2$CO$_3$ add 300 mL H$_2$O (1M)

18.2 g vanadate pentoxide (V$_2$O$_5$) was added and dissolved during gentle heating and baked in a "BACO-LINE" oven for 6 minutes.

The solution was cooled to ambient.

Carefully 460 mL 2.5 M H$_2$SO$_4$. (460 mL H$_2$O+61 mL H$_2$SO$_4$) is added

Water was added to 1000 mL.

Gas Chromatography

Perkin Elmer 8420 Capillary Gas Chromatography equipped with WCOT fused silica column 12.5 m×0.25 mm ID×0.1 μm 5% phenyl-methyl-silicone (CP Sil 8 CB from Crompack).

Carrier: Helium.

Injection: 1.5 μL with split.

| | Oven program: | | | |
|---|---|---|---|---|
| | 1 | 2 | 3 | 4 |
| Oven temperature [° C.] | 80 | 200 | 240 | 360 |
| Isothermal, time [min] | 2 | 0 | 0 | 10 |
| Temperature rate [° C./min] | 20 | 10 | 12 | |

Sample preparation: 50 mg wheat lipid was dissolved in 12 mL heptane:pyridine 2:1 containing an internal standard heptadecane, 2 mg/mL. 500 µL of the sample was transferred to a crimp vial. 100 µL MSTFA (N-Methyl-N-trimethylsilyl-trifluoracetamid) was added and the reaction incubated for 15 minutes at 90° C.

Calculation: Response factors for mono-di-triglycerides, free fatty acid and galactolipids were determined from reference mixtures of these components. Based on these response factors the lipids in the dough were calculated.

Mini Baking Test.

The following ingredients were added to a 50 g Brabrender mixing bowl and kneaded for 5 minutes at 30° C.: flour 50 g, dry yeast 10 g, sugar 0.8 g, salt 0.8 g, 70 ppm ascorbic acid and water (to a dough consistency of 400 Brabender units). Resting time was 10 min. at 34° C. The dough was scaled 15 g per dough. Then molded on a special device where the dough was rolled between a wooden plate and a Plexiglas frame. The doughs were proofed in tins for 45 min. at 34° C., and baked in a Voss household oven for 8 min. 225° C.

After baking the breads were cooled to ambient temperature and after 20 min. The breads were scaled and the volume was determined by rape-seed displacement method. The breads were also cut and crumb and crust evaluated.

Pilot Baking Tests (Hard Crust Rolls)

Flour, Danish reform 1500 g, Compressed Yeast 90 g, sugar 24 g, salt 24 g, water 400 Brabender units+2% were kneaded in a Hobart mixer with hook for 2 minutes at low speed and 9 minutes at high speed. The dough temperature was 26° C. The dough was scaled 1350 gram. The dough was rested for 10 minutes at 30° C. and molded on a Fortuna molder. The dough was then proved for 45 minutes at 34° C. The dough was baked in a Bago-oven for 18 minutes at 220° C. and steamed for 12 seconds After cooling, the rolls were scaled and the volume of the rolls was measured by the rape seed displacement method.

Specific Bread Volume $$\text{Specific volume} = \frac{\text{Volume of the bread, ml}}{\text{weight of the bread, gram}}$$

Results and Discussion

Fermentation

The fermentation samples were analyzed for phospholipase activity, and the results are shown in Table 1.

TABLE 1

Results of fermentation

| ID | Organism | Sample label | PLU-7 |
|---|---|---|---|
| 172 | Fusarium heterosporum CBS 782.83 | [a]Medium D. day 2 | 35 |
| 173 | Fusarium heterosporum CBS 782.83 | Medium D. day 3 | 33 |
| 174 | Fusarium heterosporum CBS 782.83 | Medium D. day 4 | 26 |

[a]Medium D = production medium

It was seen that the phospholipase activity was almost identical at days 2, 3 and 4, and all samples were therefore pooled and named JBS-2254-97-3.

Purification and Sequencing

Figure 1:
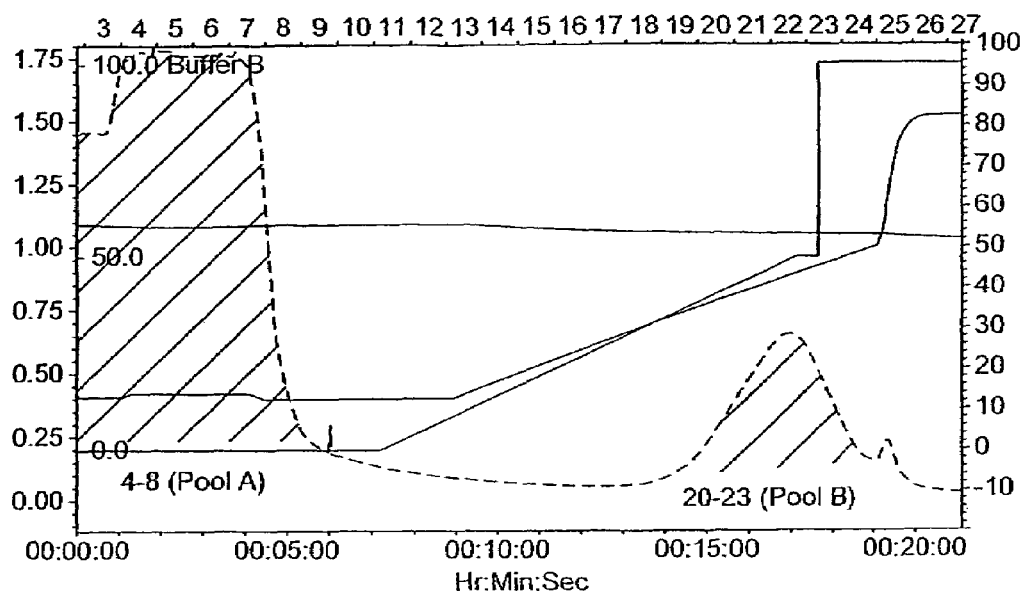
FIG. 1 shows profiles of lipase activity (indicated by hatched areas, marked as pool B) and protein (broken line) obtained after IEC chromatography.
Figure 2:
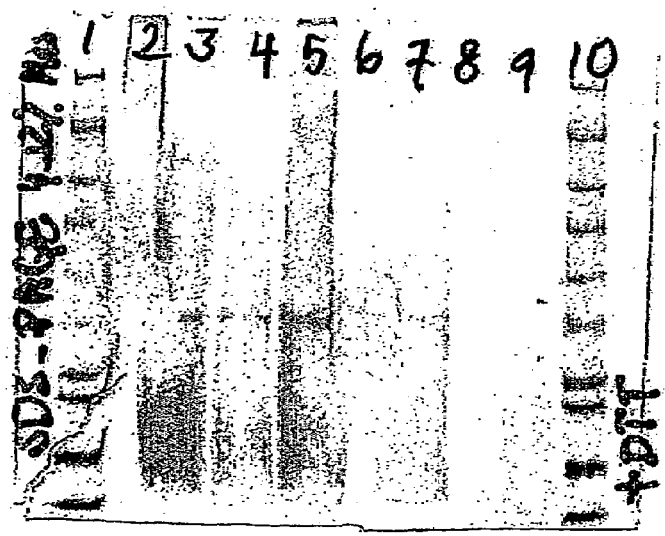
FIG. 2 shows purified fungal lipolytic enzyme (lane 3-5) applied to a gel (NU-PAGE, 4-12%, Mes-buffer, prepared as described by the manufacturer, Novex, USA), which was then commassie stained.

Purification of Phospholipase from Crude Extract Using Anion Exchange Chromatography:

The column (Q-Sepharose FF, 1.5×2.8 cm, 5 mL gel) was prepared as described by the manufacturer (Amersham Bio.), and then equilibrated in 20 mM tris/HCl buffer, 0.1 M NaCl, pH 7.5 (buffer A). The sample (15 mL) was added 0.1 M NaCl and applied to the column at a flow rate of 3.5 mL/min. The lipolytic enzyme was eluted with a linear gradient of 0-0.6 M NaCl in buffer A (See FIG. 1). Fractions of 3.5 mL were collected during the entire run. 10 µL of each fraction were subjected to spot plate assay. Lipase activity was determined by tributyrin and lecithin spot plate assay (10 µL of each fraction were transferred to the hole and the plate was incubated at 40° C. Formation of haloes in the agarose gels takes place as a function of time. A blank without enzyme was also added to one of the holes for comparison). The fractions containing lipolytic activity was then subjected to SDS-PAGE (See FIG. 2) and N-terminal analyses.

Enzymatic Fingerprinting by MALDI-TOF and Amino Acid Sequencing

The protein was reduced with Dithiothreitol and the cysteine residues were protected by carboxymethylation using iodoacetamide. The protein was cleaved by trypsin and the fragmentation pattern of the tryptic peptides were examined by MALDI-TOF analysis. The peptides were separated by chromatography on a $C_{18}$-reverse-phase HPLC column, and the degree of purification was monitored by MALDI-TOF analysis. The amino acid sequence was determined by Edman degradation as previously described in details in TR6452.

The entire amino acid sequence of Fusarium heterosporum lipolytic enzyme has been determined. The digestion with trypsin gave very specific peptides where the MW (MALDI-TOF) could be determined conclusively. The amino acid sequences for all the peptides were also determined by Edman degradation. The amino acid sequence determined by Edman degradation covers 99.64% of the polypeptides chain of the F. heterosporum lipolytic enzyme.

Summary of the MALDI-TOF and Edman degradation studies is shown in Table 2.

TABLE 2

Enzymatic fingerprinting and MW of the tryptic peptides from the Fusarium heterosporum lipolytic enzyme, and determination of the entire amino acid sequence by Edman degradation.

| Fusarium heterosporum Lipolytic enzyme (2254-97-3) | | | M + H | M + H |
|---|---|---|---|---|
| nr | From | Sequence | calc | obs |
| 1 | 1-13 | AVGVTSTDFTNFK | 1387.5 | |
| 2+ | 14-33 | FYIQHGAAAYCNSGTAAGAK | 2059.2 | 2059.0 |
| 3+ | 34-59 | ITCSNNGCPTIESNGVTVVASFTG SK | 2701.9 | |
| 4+ | 60-72 | TGIGGYVSTDSSR | 1300.4 | |
| 5+ | 73-73 | K | 147.2 | |
| 6+ | 74-80 | EIVVAIR | 780.0 | 780.0 |

TABLE 2-continued

Enzymatic fingerprinting and MW of the tryptic
peptides from the Fusarium heterosporum
lipolytic enzyme, and determination of the
entire amino acid sequence by Edman degradation.

Fusarium heterosporum Lipolytic enzyme
(2254-97-3)

| nr | From | Sequence | M + H calc | M + H obs |
|---|---|---|---|---|
| 7 | 81-86 | GSSNIR | 632.7 | |
| 8+ | 87-128 | NWLTNLDFDQSDCSLVSGCGVHSG FQNAWAEISAQASAAVAK | 4514.8 | |
| 9 | 129-130 | AR | 246.3 | |
| 10 | 131-131 | K | 147.2 | |
| 11 | 132-137 | ANPSFK | 663.8 | |
| 12+ | 138-158 | VVATGHSLGGAVATLSAANLR | 1966.3 | 1966.1 |
| 13+ | 159-173 | AAGTPVDIYTYGAPR | 1552.7 | 1552.6 |
| 14+ | 174-192 | VGNAALSAFISNQAGGEFR | 1910.1 | 1910.0 |
| 15 | 193-197 | VTHDK | 599.7 | |
| 16 | 198-202 | DPVPR | 583.7 | |
| 17+ | 203-211 | LPPLIFGYR | 1076.3 | 1076.3 |
| 18+ | 212-226 | HTTPEYWLSGGGGDK | 1605.7 | |
| 19+ | 227-235 | VDYAISDVK | 1010.1 | |
| 20a | 236-274 | VCEGAANLMCNGGTLGLDIDAHLH YFQATDACNAGGFSW* | 4231.5 | 4233.2 |
| 20b+ | 236-275 | VCEGAANLMCNGGTLGLDIDAHLH YFQATDACNAGGFSW*R | 4387.7 | 4387.8 |

+= Confirmed by Edman sequencing
*= oxidised Tryptophan Sequence coverage = 99.64%

The complete amino acid sequence of *Fusarium heterosporum* lipolytic enzyme is shown as SEQ ID No. 1 (see FIG. 37).

Application Trials

Figure 3:
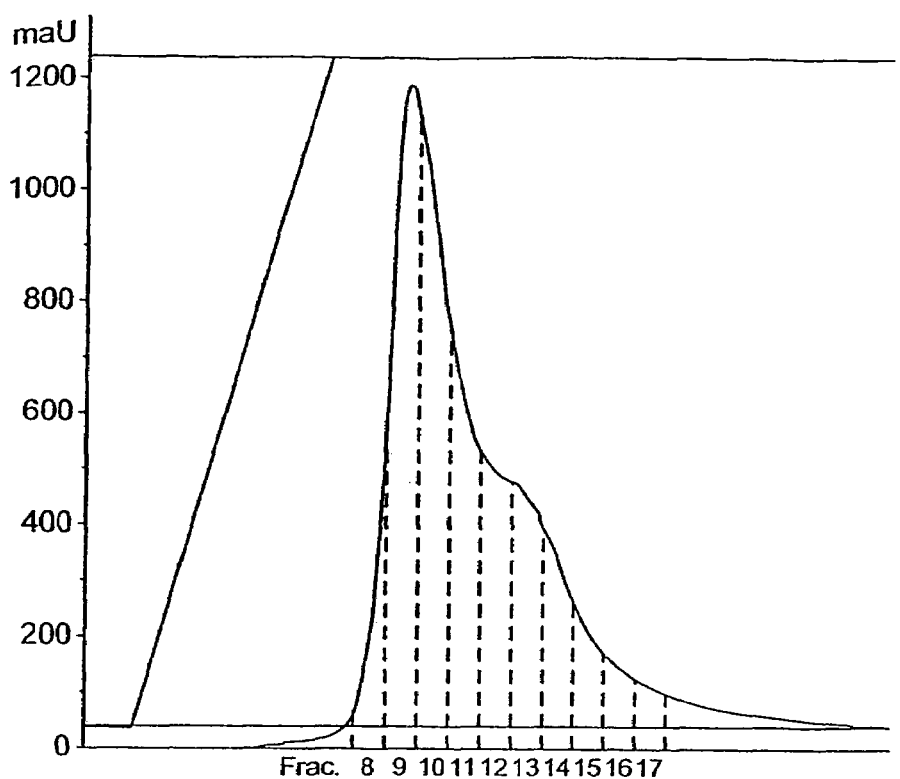
FIG. 3 shows chromatogram #61.

A pool of 2 liters from the three samples of *F. heterosporum* (Table 1), labeled Pool #172-174, was concentrated by ultra-filtration (10 kDa filter) on an Amicon Ultra Filtration unit. 250 ml of the retentate contained approx. 100 PLU-7/ml. The retentate was adjusted to 1 M Ammonium-acetate and applied onto a 27 ml Butyl Sepharose column (2.5 cm id.) and eluted with A-buffer 1M $NH_4$-acetate in 20 mM TEA pH 7.4 and B-buffer 20 mM TEA pH 7.4. The chromatogram (#61) from the purification is shown in FIG. 3.

Figure 4:
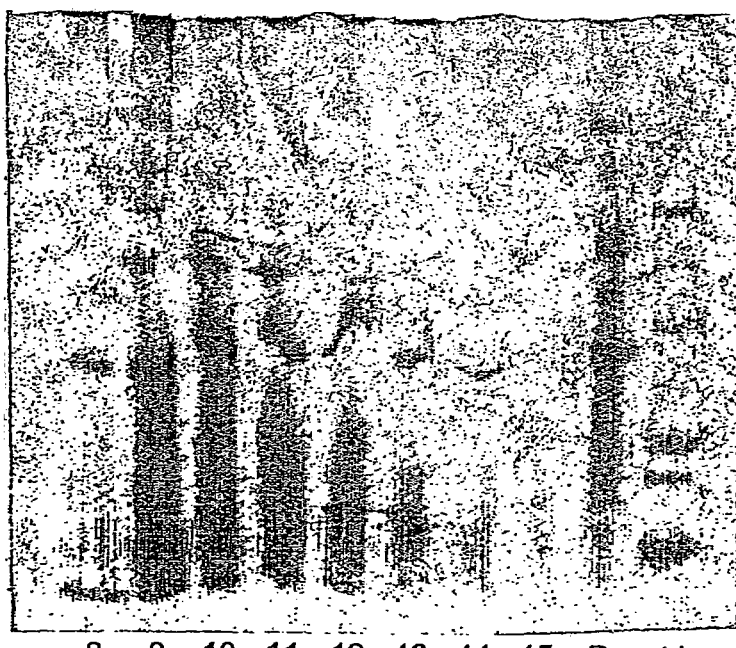
FIG. 4 shows SDS-PAGE of fractions from the Butyl Sepharose column (P: Pool #172-174 100 U/mL diluted 1:10; Std=standard protein series).

Fractions from the chromatogram #61 were analyzed by SDS-PAGE as shown in FIG. 4.

10 mL fractions from this chromatography were collected and analyzed for phospholipase activity as shown in Table 3. These results indicate a quite high amount of phospholipase activity in the fractions eluted in the main peak of the chromatogram. Small amount of activity is not bound to the column but is eluted in the front. Although the SDS gel did not run so nicely, it is observed that the fractions contain several proteins but fraction 14 and 15 contain one main band, which is expected to be the fungal lipolytic enzyme.

TABLE 3

| Chromatogram #61. | PLU-7 |
|---|---|
| Frac. 8 | 32 |
| Frac. 9 | 89 |
| Frac. 10 | 69 |
| Frac. 11 | 51 |
| Frac. 12 | 39 |
| Frac. 13 | 81 |
| Frac. 14 | 23 |
| Frac. 15 | 17 |

Figure 5:
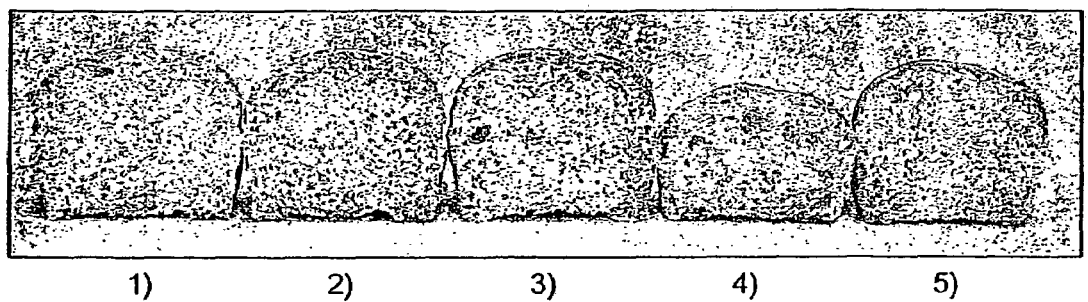
FIG. 5 shows mini baking experiments with 1) Chr #61 frac. 9. 2) Pool #172-#174. 3) Chr. #61 frac. 14. 4) Control. 5) Lipase #3044.

Fraction 9 and fraction 14 from chromatogram #61 were used for a mini baking test and also the non-purified pool #172-174 was tested in mini baking test. Results from this baking experiment are shown in Table 4. This clearly shows that purified lipolytic enzyme from *F. heterosporum* CBS 782.83 gives very good baking results in term of improved bread volume. Also the non-purified sample contributed to a very nice bread volume. The crumb structure of the breads were also improved very much by *F. heterosporum* lipolytic enzyme as indicated in FIG. 5 and evaluated better than a lipase from *Pseudomonas cepacia* #3044.

TABLE 4

| Sample | Enzyme | PLU-7/50 g flour | Bread volume, mL/g |
|---|---|---|---|
| 1 | Chr #61 frac 9 | 100 U | 4.33 |
| 2 | Pool #172-174 | 100 U | 4.33 |
| 3 | Chr #61 frac. 14 | 100 U | 4.60 |
| 4 | Control | 0 | 3.29 |
| 5 | Lipase, #3044 | 40 ppm | 4.38 |

Dough from this mini-baking experiment were extracted with water-saturated-butanol and the lipids were analysed by TLC. TLC analysis confirmed that Lipase #3044 is more active on triglyceride than the lipolytic enzyme from *F. heterosporum* samples. The amount of free fatty acids (FFA), are also higher with lipase #3044. TLC in solvent IV indicates a component (DGMG), which is clearly higher in the samples of dough lipids treated with *F. heterosporum* compared with a triglyceride hydrolysing lipase #3044.

The purified fractions from *F. heterosporum* were also tested in pilot baking experiment with the results shown in Table 5.

TABLE 5

Use of purified chromatography fractions from *Fusarium heterosporum* in pilot baking test and effects on bread volume.

| No. | | Specific volume (ccm/g) |
|---|---|---|
| 1 | Control | 5.11 |
| 2 | 500 U *F. het.* Pool #172-#174 | 6.28 |
| 3 | 1000 U *F. het* Pool #172-#174 | 6.79 |
| 4 | 40 ppm #3044 (*Pseudomonas*) | 5.27 |
| 5 | 2000 U *F. het.* Pool #172-#174 | 6.24 |
| 6 | 4000 U *F. het.* Pool #172-#174 | 4.95 |
| 7 | 1000 U 2254-97 C61 | 6.95 |
| 8 | 40 ppm #3016 (Lipopan F ™) | 6.97 |

Dough from this baking test were extracted with water-saturated-butanol and the dough lipids analyzed by GLC analysis with results shown in Table 6.

TABLE 6

GLC analysis of dough lipids.

| | GL | FFA | MGMG | DAG | DGMG | MGDG | DGDG | TRI |
|---|---|---|---|---|---|---|---|---|
| Control | 0.120 | 0.152 | 0.0015 | 0.0771 | 0.0195 | 0.0644 | 0.172 | 0.770 |
| 500 U F. het. Pool #172-#174 | 0.121 | 0.250 | 0.012 | 0.059 | 0.057 | 0.030 | 0.139 | 0.792 |
| 1000 U F. het Pool #172-#174 | 0.121 | 0.277 | 0.018 | 0.056 | 0.087 | 0.010 | 0.102 | 0.738 |
| 40 ppm #3044 | 0.127 | 0.368 | 0.002 | 0.132 | 0.022 | 0.066 | 0.173 | 0.276 |
| 2000 U F. het. Pool #172-#174 | 0.122 | 0.320 | 0.018 | 0.060 | 0.119 | 0.013 | 0.062 | 0.723 |
| 4000 U F. het. Pool #172-#174 | 0.128 | 0.332 | 0.021 | 0.065 | 0.146 | 0.010 | 0.033 | 0.739 |
| 1000 U 2254-97 C61 | 0.125 | 0.287 | 0.019 | 0.067 | 0.088 | 0.016 | 0.099 | 0.655 |
| 40 ppm#3016 | 0.124 | 0.284 | 0.017 | 0.058 | 0.086 | 0.014 | 0.101 | 0.723 |

GL = glycerol.
FFA = free fatty acid.
MGMG = monogalactosylmonoglyceride.
DAG = Diglyceride.
DGMG digalactosylmonoglyceride.
MGDG = monogalactosyldiglyceride.
DGDG = digalactosyldiglyceride.
TRI = triglyceride.

The ratio of DGDG hydrolysis compared to triglyceride hydrolysis is shown in Table 7.

Figure 6:
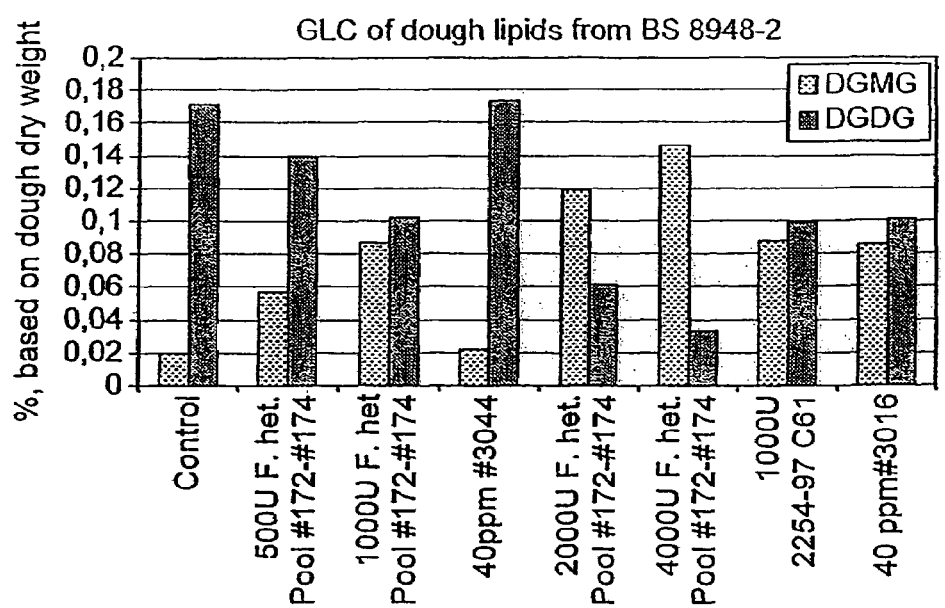
FIG. 6 shows GLC analysis of dough lipids digalactosyldiglyceride (DGDG) and digalactosylmonoglyceride (DGMG) from BS8948-2

The GLC analysis of galactolipids, are also illustrated graphically in FIG. 6.

The GLC results confirm that the amount of DGMG produced in dough by F. heterosporum is higher than the amount produced by 40 ppm Lipopan F (#3016). The results also indicate a higher degree of hydrolysis of MGDG than DGDG. The results also indicate that the amount of hydrolyzed triglyceride is low compared with a normal triglyceride-hydrolyzing enzyme like #3044 from P. cepacia. The pilot scale baking results and the lipid analysis confirmed that the lipolytic enzyme from F. heterosporum CBS 782.83 has clear hydrolytic activity on digalactosyldiglyceride (DGDG) and the formation of digalactosylmonoglyceride (DGMG) in a dough.

TABLE 7

Ratio of DGDG hydrolysis compared to triglyceride hydrolysis of purified chromatography fractions from Fusarium heterosporum

| | dTRI | dDGDG | dDGDG/dTRI |
|---|---|---|---|
| Control | | | |
| 500 U F. het. Pool #172-#174 | 0 | 0.033 | n/a |
| 1000 U F. het Pool #172-#174 | 0.032 | 0.07 | 2.19 |
| 40 ppm #3044 | 0.494 | 0 | n/a |
| 2000 U F. het. Pool #172-#174 | 0.047 | 0.11 | 2.34 |
| 4000 U F. het. Pool #172-#174 | 0.031 | 0.139 | 4.4 |
| 1000 U 2254-97 C61 | 0.115 | 0.073 | 0.63 |
| 40 ppm#3016 | 0.047 | 0.071 | 1.5 |

4. Conclusions

In this study, a fungal lipolytic enzyme from F. heterosporum CBS 782.83 was produced by fermentation in shake flasks. The enzyme was purified and the amino acid sequence was determined. The enzyme has about 83% homology to a commercial lipase from F. oxysporum (LipopanF™). The enzyme gave very good results in baking trial in terms of improved bread volume and improved crumb structure. Lipid analysis from dough confirmed that the enzyme was active on galactolipids during production of galactomonoglycerides. Without any optimization of dosage, the baking results indicate that the fungal lipolytic enzyme from F. heterosporum CBS 782.83 is at least equivalent to the commercial enzyme LipopanF, and the comparative DGDG to triglycerides activity indicate that this enzyme has a superior enzymatic activity in a dough environment compared to LipopanF™.

Example 2

Construction and Expression of a Synthetic Gene Encoding a Lipolytic Enzyme from Fusarium heterosporum (CBS 782.83) in Hansenula polymorpha The amino acid sequence of a fungal lipolytic enzyme isolated from Fusarium heterosporum (CBS 782.83) was determined and used to design and clone a synthetic lipolytic enzyme gene for expression in Hansenula polymorpha. To favour high expression, the codons of the synthetic gene were optimised to be in accordance with the codon preferences of Hansenula polymorpha. A codon optimised alpha-factor signal sequence was synthesised as Well and cloned in front of the synthetic lipolytic enzyme gene. The assembled construct was transferred into the expression vector pB14 and transformed into Hansenula polymorpha. pB14 is a plasmid without genes conferring antibiotic resistance and can therefore be used in production facilities.

A number of lipolytic enzyme producing Fusarium strains were screened for activities with a high ratio of activity on of galactolipids and/or phospholipids when compared to triglycerides.

Several of the strains have been selected as producing lipolytic enzymes of interest. Among these is the Fusarium heterosporum (CBS 782.83). The lipolytic enzyme from this strain has therefore been isolated and the amino acid sequence has been determined. The amino acid sequence was back translated into a nucleic acid sequence that was used to design and construct a synthetic gene for expression in Hansenula polymorpha.

Experimental

The strain of Hansenula used in this study was the uracil-auxotrophic Hansenula polymorpha strain RB11 (odc1) obtained from Rhein Biotech GmbH (Düsseldorf, Germany).

Enzymatic Fingerprinting by MALDI-TOF and Amino Acid Sequencing.

A protein having lipolytic enzyme activity was isolated from Fusarium heterosporum (CBS 782.83). The protein was reduced with dithiothreitol and the cysteine residues were protected by carboxymethylation using iodoacetamide. The protein was cleaved by trypsin and the fragmentation pattern of the tryptic peptides were examined by MALDI-TOF analysis. The peptides were separated by chromatography on a $C_{18}$-reverse-phase HPLC column, and the degree of purification was monitored by MALDI-TOF analysis. The amino acid sequence was determined by Edman degradation as previously described in details in TR6452.

cbss.t (Table 8). The PCR product was cloned into the vector pCR 2.1-TOPO (Invitrogen) and the nucleotide sequence of the inserts were determined using a BigDye Terminator v3.0 cycle sequencing kit (Applied Biosystems) and an ABI Prism 3100 Genetic Analyzer (Applied Biosystems).

TABLE 8

Primer sequences used for the amplification and assembly of the synthetic F. heterosporum (CBS 782.83) lipolytic enzyme gene and the synthetic alpha-signal sequence. The restriction enzyme sites introduced for cloning purposes in each primer are underlined. The nucleotides included allowing fusion of the synthetic lipolytic enzyme gene and the synthetic alpha-signal are double underlined.

| Gene | | Primer sequence | Restriction site |
|---|---|---|---|
| CBSLip | 5'-alps.cbss | 5'-TCCTTGGACAAGAGAGCCGTTGGAGTGACCTCTACTG | None |
|  | 3'-cbss.t | 5'-AGGATCCAATTCTCTCCATGGCCTATCTCCAGGAGAAACCTCCG | Bam HI |
| α-signal | 5'-alpsynt | 5'-AGAATTCAAACGATGAGATTCCCATCCATCTTTACCG | Eco RI |
|  | 3'-cbss.alps | 5'-AGGTCACTCCAACGGCTCTCTTGTCCAAGGAAACACCTTCC | None |

Design and Construction of a Synthetic Lipolytic Enzyme Gene.

The amino acid sequences of the peptide fragments were ordered by alignment with the Japanese strain of F. heterosporum (Nagao et al. 1994). The complete amino acid sequence thus obtained was back translated into a nucleic acid sequence to reveal all possible codons. For each codon the codon most favourable for expression in Hansenula polymorpha was chosen according to the codon preference table of genes expressed in Hansenula polymorpha. Synthetic oligonucleotides, each about 100 nucleotides long, comprising the complete gene, were synthesised, and the gene was assembled by PCR. For the final amplification of the gene was used an upstream primer (alps.cbss) designed with the most 5' nucleotides from the 3'-end of the alpha-factor signal sequence to allow in frame fusion, and a downstream primer (cbss.t) designed with a Bam HI restriction enzyme site for cloning purposes (Table 8).

A nucleotide sequence encoding the signal sequence from the yeast alpha mating factor was similarly synthesised with favourable codons by oligonucleotides and amplified by PCR. For the final amplification of the alpha-signal sequence was used an upstream primer (alpsynt) designed with an Eco RI restriction enzyme site for cloning purposes, and a downstream primer (cbss.alps) designed with the most 5' sequences from the 5'-end of the synthetic lipolytic enzyme gene to allow in frame fusion (Table 8).

To fuse the synthetic alpha-factor signal sequence to the synthetic lipolytic enzyme gene the two fragments were mixed and re-amplified with the outer primers alpsynt and Expression of Lipolytic Enzyme in Hansenula Polymorpha.

To express the synthetic F. heterosporum (CBS 782.93) lipolytic enzyme gene in Hansenula the combined alpha-signal sequence/lipolytic enzyme gene was inserted behind the FMD-promoter into the Hansenula expression vector pB14, a plasmid without genes conferring antibiotic resistance. After conformation of the expected structure of the assembled plasmid in E. coli, the plasmid was transformed into competent Hansenula polymorpha cells by electroporation. Transformants were selected on YND plates and colonies were further selected for multiple integration of the gene by 3 and 8 passages of 1:200 dilutions in liquid cultures of YND. Finally, the selected cultures were stabilised by transferring twice in YPD medium. To further select for high expressers each cultures showing high level of expression were plated for single colonies, which each were assayed for expression level.

To determine the level of expression of the lipolytic enzyme gene the selected clones were grown in YPD with 1.8% glycerol and 0.2% glucose for 2 days at 24° C.

Enzyme Activity

Samples of the culture medium were analysed for lipolytic enzyme activity with Lecithin or DGDG as substrates and using the NEFA Kit (Roche) scaled down to volumes suitable for micro titre plates for determination of the liberated free fatty acids.

Results

Enzymatic Fingerprinting by MALDI-TOF and Amino Acid Sequencing.

The entire amino acid sequence of Fusarium heterosporum lipolytic enzyme has been determined (See SEQ ID No.

1—FIG. 37). The digestion with trypsin gave very specific peptides where the MW (MALDI-TOF) could be determined conclusively. The amino acid sequences for all the peptides were also determined by Edman degradation. The amino acid sequences determined by Edman degradation covers 99.64% of the polypeptide chain of the F. heterosporum (CBS 782.83) lipolytic enzyme. The amino acid sequences of all peptides were aligned to the lipase of the Japanese strain of F. heterosporum (Nagao et al. 1994 J. Biochem. 116: 536-540) thus revealing the order of the peptides identifying the amino acid sequence of the mature protein. The alignment is shown in FIG. 7. Summary of the MALDI-TOF and Edman degradation studies is shown in Table 9 with the peptides order according to the alignment with the Nagao sequence.

Identity to Other *Fusarium* Lipases

Alignments of the amino acid and nucleotide sequence of F. heterosporum (CBS 782.83) lipolytic enzyme with sequences from other *Fusarium* lipases show the relationships between some of the *Fusarium* lipases (Table 10).

TABLE 10

Amino acid and nucleotide identity of F. heterosporum (CBS 782.83) lipolytic enzyme compared to other *Fusarium* lipases.

| LIPASE IDENTITIES | F. heterosporum (Nagao supra) | F. oxysporum (Lipopan F ™) |
|---|---|---|
| F. heterosporum (CBS 782.83) amino acid (SEQ ID No. 1) | 58.7% | 85.1% |

TABLE 9

Enzymatic fingerprinting, MW determination of the entire amino acid sequence by Edinan degradation of the tryplic peptides from the Fusarium heterosporum (CBS 782.83) lipolytic enzyme.

Fusarium heterosporum Phospholipase (2254-97-3)      Partial cleavage

| Nr | From | Sequence | M + H calc | M + H obs | Peptides | M + H calc | M + H obs |
|---|---|---|---|---|---|---|---|
| 1 | 1-13 | AVGVTSTDFTNFK | 1387.5 | | | | |
| 2+ | 14-33 | FYIQHGAAAYCNSGTAAGAK | 2059.2 | 2059 | 1 + 2 | 3427 | 3427 |
| 3+ | 34-59 | ITCSNNGCPTIESNGVTVVASFTGSK | 2701.9 | | | | |
| 4+ | 60-72 | TGIGGYVSTDSSR | 1300.4 | | 3 + 4 + 5 | 4111 | 4112 |
| 5+ | 73-73 | K | 147.2 | | | | |
| 6+ | 74-80 | EIYVAIR | 780.0 | 780.0 | 4 + 5 + 6 | 2209 | 2209 |
| 7 | 81-86 | GSSNIR | 632.7 | | | | |
| 8+ | 87-128 | NWLTNLDFDQSDCSLVSGCGVHSGFQ NAWAEISAQASAAVAK | 4514.8 | | 7 + 8 | 5129 | 5129 |
| 9 | 129-130 | AR | 246.3 | | 8 + 9 | 4743 | 4743 |
| 10 | 131-132 | K | 147.2 | | | | |
| 11 | 132-137 | ANPSFK | 663.8 | | | | |
| 12+ | 138-158 | VVATGHSLGGAVATLSAANLR | 1966.3 | 1966 | 10 + 11 + 12 | 2739 | 2739 |
| 13+ | 159-173 | AAGTPVDIYTYGAPR | 1552.7 | 1552 | | | |
| 14+ | 174-192 | VGNAALSAFISNQAGGEFR | 1910.1 | 1910 | | | |
| 15 | 193-197 | VTHDK | 599.7 | | | | |
| 16 | 198-202 | DPVPR | 583.7 | | | | |
| 17+ | 203-211 | LPPLIFGYR | 1076.3 | 1076 | 15 + 16 + 17 | 2221 | 2221 |
| 18+ | 212-226 | HTTPEYWLSGGGGDK | 1605.7 | | | | |
| 19+ | 227-235 | VDYAISDVK | 1010.1 | | 18 + 19 | 2596 | 2596 |
| 20a | 236-274 | VCEGAANLMCNGGTLGLDIDAH LHYFQATDACNAGGFSW* | 4231.5 | 4232 | | | |
| 20b+ | 236-275 | VCEGAANLMCNGGTLGLDIDAHL HYFQATDACNAGGFSW*R | 4387.7 | 4387 | | | |

Peptide sequences confirmed by Edman degradation are marked +.
Oxidised Tryptophan is marked by *.
Sequence coverage = 99.64%

TABLE 10-continued

Amino acid and nucleotide identity of *F. heterosporum* (CBS 782.83) lipolytic enzyme compared to other *Fusarium* lipases.

| LIPASE IDENTITIES | *F. heterosporum* (Nagao supra) | *F. oxysporum* (Lipopan F ™) |
|---|---|---|
| *F. heterosporum* (CBS 782.83) nucleotide sequence (SEQ ID No. 3) | 61.8% | 69.2% |

Mixing and amplification by PCR of the synthetic oligonucleotides for the lipolytic enzyme gene and the alpha-signal sequence resulted in DNA fragments, which were cloned and sequenced. Fragments containing the correct sequences were used to assemble the complete gene by re-amplification using the primers shown in Table 8. The assembled nucleotide sequence is shown in FIG. 8 with its translated amino acid sequence, and the primers used are indicated with arrows.

The DNA fragment containing the assembled gene construct was transferred to the *Hansenula* expression vector pB14 using the introduced restriction enzyme sites. The resulting plasmid pB14-alps.cbss is schematically shown in FIG. 9.

Expression of Fungal Lipolytic Enzyme Activity in Selected Clones.

The clones, which have been through the selection process, were analysed for expression of lipolytic enzyme. 10-microliter samples of the supernatant of 2 day cultures were incubated with either DGDG or lecithin for 10 minutes and 10 microliters of these reactions were analysed with the NEFA kit. The results after single colony isolation of 3 of the clones are shown in FIG. 10.

The amino acid sequence of a lipolytic enzyme from a strain of *Fusarium heterosporum* (CBS 782.83) has been determined and a synthetic gene encoding this lipolytic enzyme has been constructed and optimised for expression in *Hansenula polymorpha*. The gene that encoded the mature enzyme was fused to a synthetic signal sequence derived from the yeast mating alpha-factor. The combination of the alpha-signal sequence with the FMD promoter of the *Hansenula* pB14 vector has previously been shown to be suitable for expression of *Fusarium* lipases.

Example 3

Expression of a *Fusarium heterosporum* CBS 782.83 Lipolytic Enzyme in *Hansenula polymorpha* and Characterization of the Product in Baking Trials The *Hansenula polymorpha* strain B14:8-3, 8 (DCDK0172), containing a lipolytic enzyme-encoding gene from the filamentous fungus *Fusarium heterosporum* CBS782.83, was fermented in the fed-batch mode. After 160 hours of fermentation the phospholipase activity reached 1200 U/mL. Based on the fermentations three products were made and tested further. The products are named the following: sample 205, –206 and –209.

A lipolytic enzyme sample 205 from *F. heterosporum* expressed in *H. polymorpha* was tested in miniscale baking experiments. Dough from the baking experiment was analyzed by GLC and HPTLC.

The baking results from mini scale baking confirm a very strong improvement of lipolytic enzyme sample 205 on bread volume and improvement of crumb structure. Lipolytic enzyme analysis confirmed a strong hydrolytic activity of lipolytic enzyme sample 205 on digalactosyldiglyceride (DGDG) concomitant with the accumulation of digalactosylmonoglyceride (DGMG).

The enzyme had only minor activity on triglycerides in the dough.

Samples 206 and 209 were tested in pilot scale baking trials and confirmed the good baking performance of the lipolytic enzymes both with respect to increased bread volume and improved crumb structure. From the baking trials it is indicated that sample 206 perform a bit better compared to sample 209 in a straight dough procedure, however the two products have not been compared directly to each other and more baking trials has to confirm this.

2. Experimental

Fermentation

Microorganism

The strain of *H. polymorpha* transformed with the plasmid containing the lipolytic from *F. heterosporum* CBS 782.83 as described in EXAMPLE 2 was used in this study. The promoter used in the construct was the formate dehydrogenase promoter from *H. polymorpha*.

Growth Media and Culture Conditions

YNB-Glycerol Medium

The medium used for preparation of inoculum for the bioreactor fermentations and for growth in shake flasks contained: 1.7 g/L Yeast Nitrogen Base (DIFCO, Detroit, USA, 0335-15-9), 5 g/L $(NH_4)_2SO_4$, 10 g/L glycerol, and 0.1 M 2-[N-Morpholino]ethanesulfonic acid (MES) as a buffer. The pH was adjusted to 6.1 (the pKa of MES) with 4 M NaOH (before autoclaving). Yeast Nitrogen Base and $(NH_4)_2SO_4$ were filter-sterilized to the medium after autoclaving. This medium was used for growth in shake flasks (250 mL medium in a shake flask with a total volume of 500 mL).

YNB Agar

The defined medium used for plating of stock cultures (kept at –80° C. in 25% (w/v) glycerol) contained: 1.7 g/L Yeast Nitrogen Base (DIFCO, Detroit, USA, 0335-15-9), 5 g/L $(NH_4)_2SO_4$, 10 g/L glycerol, and 20 g/L agar (DIFCO, Detroit, USA, 0140-01). Yeast Nitrogen Base and $(NH_4)_2SO_4$ were filter-sterilized to the medium after autoclaving.

YPD Medium

The rich medium was used for contamination check in the fermentors. The medium contained: 10 g/L yeast extract, 10 g/L peptone and 20 g/L glycerol.

Fermentations

Three fermentations were carried out in this study: HET0401, HET0402 and HET0410, all with the strain described above. The variations between the three fermentations are in the composition of the batch medium and the feed medium. All other parameters were identical for the three fermentations.

The batch medium (3 L) used for the fermentation in 6 L fermentor contained: 13.3 g/L $NH_4H_2PO_4$, 3.0 g/L $MgSO_4.H_2O$, 3.3 g/L KCl, 0.3 g/L NaCl, 15 g/L glycerol, and 3 mL/L ADD APT® Foamstop Sin 260 (ADD APT Chemicals AG, Helmond, The Netherlands), 1.0 g/L $CaCl_2.2H_2O$, 67 mg/L $(NH_4)_2Fe(SO_4)_2.6H_2O$, 5 mg/L $CuSO_4.5H_2O$, 20 mg/L $ZnSO_4.7H_2O$, 21 mg/L $MnSO_4.H_2O$, and 67 mg/L EDTA), 0.65 mg/L $NiSO_4.6H_2O$, 0.65 mg/L $CoCl_2$, 0.65 mg/L $H_3BO_4$, 0.65 mg/L KI, 0.65 mg/L $Na_2MoO_4.2H_2O$), 2 mg/L D-biotin and 0.67 g/L thiaminchloride-hydrochloride.

In addition to the batch medium described above, fermentation HET0402 contained 10 g/L peptone in the batch medium.

In addition to the batch medium described above, fermentation HET0410 contained 10 g/L Bacto tryptone in the batch medium.

Feed Medium HET0401 and HET0402:

The feed medium contained 635 g/kg glycerol and 130 g/kg formic acid.

Feed Medium HET0410:

The feed medium contained 570 g/kg glycerol, 120 g/kg formic acid and 95 g/kg Bacto tryptone.

The pH was controlled by adding 25% (w/v) $NH_3$-water.

The fermentation was carried out in the fed-batch mode in an in house build 6 L fermentor. The following fermentation conditions were used: pH 5, aeration 1 vvm, temperature 26° C., and stirring from 400 to 700 rpm.

The fermentor was inoculated with 2*250 mL YNB-glycerol culture grown at 25° C. and 180 rpm, and with an OD-600 of approximately 10.

The feed flow in the fermentation was controlled by the accumulated $CO_2$ evolution, and based on the following equations:

$$\text{Feed-flow}[g/h]=0, \text{AcCO}_2<0.45$$

$$\text{Feed-flow}[g/h]=1.33 \cdot V \cdot \text{AccCO}_2, \quad 0.45 \leq \text{AccCO}_2 \leq 3.25$$

$$\text{Feed-flow}[g/h]=4.33 \cdot V, \quad 3.25 \leq \text{AccCO}_2$$

V: The fermentation broth volume [L]

$AccCO_2$: The accumulated $CO_2$ evolution [moles]

Harvest

The fermentations were harvested by centrifugation for 10 minutes at 16000×g followed by sterile filtration of the supernatant through 0.2 μm filters (VacuCap 90 Filter Unit w 0.8/0.2 μm Supor Membrane) from Gelman Laboratory. The product was kept at 4° C. until use in baking trials.

Analytical Procedures

Determination of Lipase Activity

A fermentation sample (10 mL) was centrifuged 9000×g for 10 minutes, and the supernatant was used for the analysis of phospholipase activity according to the "PLU assay" taught previously herein.

Biomass Growth

The biomass concentration in a culture fluid was determined by centrifugation of 10 mL of culture fluid at 9000×g for 10 minutes in a pre weighed container. After centrifugation, the supernatant was removed and the biomass was dried for 24 hours at 100° C. and then weighed. The biomass concentration was calculated as g dry weight of cells per L culture fluid.

Enzyme Characterisation and Mini Baking

Enzymes and Flour

Sample 205: Sample 7 (161 hours fermentation) from HET0401

Phospholipase Lipopan F, #2938

Flour: Reform 2003055

Minibaking

The following ingredients were added to a 50 g Brabrender mixing bowl and kneaded for 5 minutes at 30° C.: flour 50 g, dry yeast 10 g, sugar 0.8 g, salt 0.8 g, 70 ppm ascorbic acid and water (to a dough consistency of 400 Brabender units). Resting time was 10 min. at 34° C. The dough was scaled 15 g per dough. Then molded on a special device where the dough was rolled between a wooden plate and a Plexiglas frame. The doughs were proofed in tins for 45 min. at 34° C., and baked in a Voss household oven for 8 min. 225° C.

After baking the breads were cooled to ambient temperature and after 20 min. The breads were scaled and the volume was determined by rape-seed displacement method. The breads were also cut and crumb and crust evaluated Lipid Extraction 10 g of fully proofed dough was immediately frozen and freeze dried. The freeze-dried dough was milled in a coffee mill and passed through a 800 micron screen. 1.5 g freeze-dried dough was scaled in a 15 mL centrifuge tube with screw lit. 7.5 ml water saturated butanol (WSB) was added. The centrifuge tube was placed in a boiling water bath for 10 min. The tubes were placed in a Rotamix and turned at 45 rpm for 20 min. at ambient temperature. Then place in boiling water bath again for 10 min. and turn on the Rotamix for 30 min. at ambient temperature. The tubes were centrifuged at 3500 g for 5 min. 5 ml supernatant was transferred into a vial. WSB was evaporated to dryness under a steam of nitrogen.

Gas Chromatography

Gas chromatography was performed as described under analytical procedures in example 1 above.

HPTLC

Applicator: LINOMAT 5, CAMAG applicator.

HPTLC plate: 10×10 cm, Merck no. 1.05633

The plate is dried before use in an oven at 180° C. for 20-30 minutes.

Application: 1.0 μL of a 1% solution in CHCl3:MeOH85:15 is applied to the HPTLC plate using LINOMAT 5 applicator.

Running-Buffer:

No. IV: Chloroform:Methanol:$H_2O$ (65:25:4)

No. I: P-ether:methyl-tert-butylether (MTBE):Acetic acid (60:40:1)

Application/Elution time: 11 minutes for running buffer 1 and 18 minutes for running buffer IV.

The plate is dried in an oven at 180° C. for 10 minutes, cooled and developed in 6% cupri acetate in 16% $H_3PO_4$. Dried additional 10 minutes at 180° C. and evaluated directly.

Baking Trials

Products Tested:

3016—Lipopan F containing 8700 LIPU/g

| ID | Strain/host | Fermentation |
| --- | --- | --- |
| Sample 206 | containing 390 LIPU/g | F. heterosporum/H. polymorpha HET0401 + HET0402 |
| Sample 209 | containing 950 LIPU/g | F. heterosporum/H. polymorpha HET0410 |

Recipe:

Hard crusty rolls performed with Reform flour: 2003159

|  | Bakers % | Amount, g |
| --- | --- | --- |
| Flour-reform 2003159 | 100 | 2000 |
| Water | 58.5 | 1170 |
| Compressed yeast | 6 | 120 |
| Salt | 1.6 | 32 |
| Sugar | 1.6 | 32 |

-continued

|  | Bakers % | Amount, g |
|---|---|---|
| Ascorbic acid | 10 ppm | 0.02 |
| Standard alpha-amylase GRINDAMYL ™ A 1000 | 90 ppm | 0.180 |

Baking Procedure:

Diosna Mixer System
  Dry mix for 1 min slow
  Mix 2 min slow+4 min fast
  Dough temperature: 26° C.
  Scaling: 1350 g
  Resting: 10 min. at 30° C. in heating cabinet
  Moulding: Fortuna 3/17/7
  Proofing: 45 min. at 34° C., 85% RH.
  Baking: Bago oven: 13 min. at 220° C., 13 sec. steam+5 min damper open
  MIWE stone deck: prog. nr 1
  After baking the rolls are cooled for 25 min before weighing and measuring of volume Results and Discussion Fermentation Physiology and Phospholipase Production The addition of tryptone to the batch and feed medium of HET0410 resulted in a faster production of biomass and a higher final level of biomass compared to HET0401-0402.

HET0401 and HET0402 are almost identical with respect to the phospholipase activity development, whereas the phospholipase productivity is significantly higher in HET0410.

Harvest

The fermentations were harvested after 168 hours (HET0401-0402) and 161 hours (HET0410) of fermentation. The product was kept at 4° C. until use in baking trials. Some of the product of HET0401 was named sample 205, and contained approximately 700 PLU-7/mL. Some of the product from HET0401 and HET0402 was pooled and named sample 206. This product contained approximately 390 PLU-7/mL. The lower enzyme activity of sample 206 compared to the end product of HET0401 and HET0402 may be caused by storage and sterile filtration. The product of HET0410 was named sample 209 and contained approximately 950 PLU-7/mL.

Enzyme Characterization and Mini Baking

Lipolytic enzyme sample 205 from fermentation HET0401 was tested in a minibaking experiment.

In different dosage and compared with a control and Lipopan F™. The specific bread volume of bread from this baking test is shown in Table 11. Picture of the bread are shown in FIG. 11.

TABLE 11

Lipolytic enzyme from *Fusarium heterosporum* (sample 205) in minibaking experiments. Effect on bread volume.

| Sample | Dosage PLU-7/kg flour | Bread volume mL/g |
|---|---|---|
| 205 | 0 | 3.56 |
| 205 | 200 U/kg | 3.98 |
| 205 | 500 U/kg | 4.87 |
| 205 | 1000 U/kg | 5.05 |
| 205 | 1500 U/kg | 5.13 |
| 205 | 2000 U/kg | 4.82 |
| 205 | 5000 U/kg | 5.05 |
| 205 | 10000 U/kg | 4.51 |
| Lipopan F | 40 ppm | 4.57 |

The baking results confirmed a very strong effect of sample 205 on improvement of bread volume, and the volume effect was better than Lipopan F™ in a standard dosage of 40 ppm.

From FIG. 11 it is also seen that sample 205 contributes to a strong improvement in crumb structure and color.

Fully proofed dough from this baking experiment was freeze-dried and extracted with water saturated butanol, and the isolated lipids analyzed by GLC and HPTLC.

The GLC analysis of the dough lipids (Table 12) confirms the hydrolytic effect of lipolytic enzyme sample 205 on digalactosyldiglyceride (DGDG) concomitant with an accumulation of digalactosylmonoglyceride (DGMG). The activity of the enzyme on DGMG is quite low because the total molar amount of DGDG (mmol %=mmol/100 g freeze-dried dough) and DGMG (mmol %) remains constant at increased enzyme dosage (FIG. 12). The GLC results also indicate a very low activity of sample 205 on triglyceride.

TABLE 12

GLC analysis of dough lipids.

| Sample (S-) | % FFA | % MGMG | % DGMG | % MGDG | % DGDG | % TRI | mmol % DGMG | mmol % DGDG | mmol % DGMG + DGDG |
|---|---|---|---|---|---|---|---|---|---|
| 0 U S-205 | 0.232 | 0.002 | 0.023 | 0.013 | 0.214 | 0.641 | 0.034 | 0.228 | 0.262 |
| 200 U S-205 | 0.321 | 0.007 | 0.050 | 0.038 | 0.193 | 0.660 | 0.074 | 0.205 | 0.279 |
| 500 U S-205 | 0.384 | 0.012 | 0.069 | 0.021 | 0.132 | 0.610 | 0.101 | 0.140 | 0.241 |
| 1000 U S-205 | 0.418 | 0.014 | 0.117 | 0.008 | 0.087 | 0.614 | 0.173 | 0.093 | 0.265 |
| 1500 U S-205 | 0.444 | 0.016 | 0.140 | 0.011 | 0.057 | 0.600 | 0.206 | 0.060 | 0.267 |
| 2000 U S-205 | 0.438 | 0.026 | 0.148 | 0.011 | 0.039 | 0.594 | 0.218 | 0.041 | 0.259 |
| 5000 U S-205 | 0.456 | 0.022 | 0.171 | 0.011 | 0.012 | 0.533 | 0.252 | 0.013 | 0.264 |

TABLE 12-continued

GLC analysis of dough lipids.

| Sample (S-) | % FFA | % MGMG | % DGMG | % MGDG | % DGDG | % TRI | mmol % DGMG | mmol % DGDG | mmol % DGMG + DGDG |
|---|---|---|---|---|---|---|---|---|---|
| 10000 U S-205 | 0.453 | 0.017 | 0.163 | 0.013 | 0.009 | 0.547 | 0.241 | 0.010 | 0.251 |
| 40 ppm Lipopan F | 0.372 | 0.017 | 0.077 | 0.027 | 0.134 | 0.577 | 0.114 | 0.142 | 0.256 |

FFA = free fatty acid.
MGMG = monogalactosylmonoglyceride.
DGMG digalactosylmonoglyceride.
MGDG = monogalactosyldiglyceride.
DGDG = digalactosyldiglyceride.
TRI = triglyceride
mmol % = mmol/100 g freeze-dried dough Comparing the baking results and the lipid analysis it is interesting to observe that the best baking effect is not obtained by a complete hydrolysis of DGDG to DGMG, but the results indicate that a partly hydrolysis of DGDG to DGMG may give the best baking performance.

The high enzyme dosage produces more DGMG but also more free fatty acid is produced which is expected to give a negative baking effect, which might be another explanation why only a partly hydrolysis of DGDG is preferable. Table 13 shows the ratio of DGDG and triglycerides hydrolysis, calculated from Table 12. The results illustrates that the best baking performance is obtained when at a dosage where the ratio of DGDG to triglycerides activity is greatest.

TABLE 13

Ratio of DGDG and triglyceride hydrolysis from GLC analysis of dough lipids.

| Sample (S) | dTRI | dDGDG | dDGDG/dTRI | Bread volume mL/g |
|---|---|---|---|---|
| 0 U S-205 | | | | 3.56 |
| 200 U S-205 | 0 | 0.023 | | 3.98 |
| 500 U S-205 | 0.031 | 0.088 | 2.84 | 4.87 |
| 1000 U S-205 | 0.027 | 0.135 | 0.030 | 5.05 |
| 1500 U S-205 | 0.041 | 0.168 | 4.1 | 5.13 |
| 2000 U S-205 | 0.047 | 0.187 | 3.98 | 4.82 |
| 5000 U S-205 | 0.108 | 0.215 | 1.99 | 5.05 |
| 10000 U S-205 | 0.094 | 0.218 | 2.3 | 4.51 |
| 40 ppm Lipopan F | 0.064 | 0.086 | 1.34 | 4.57 |

Some of the lipid samples were also analyzed by HPTLC as shown in FIG. 13. Sample 4, 5 and 6 are dough lipids from the baking experiment. The HPTLC analysis confirms the hydrolysis of DGDG and formation of DGMG by lipolytic enzyme sample 205.

The relative polar lipid:triglyceride activity ratio of Lipopan F and Sample 209 using the assays taught hereinabove are:

Phospholipid/triglyceride (PLU/LIPU) Lipopan
   F=3
   Sample 209=9
Galactolipid/triglyceride (GLU/LIPU) Lipopan
   F=1
   Sample 209=4

*Fusarium heterosporum* CBS 782.83 lipolytic enzyme gave very strong effects in miniscale baking experiments with strong increase in bread volume and improvement of crumb structure. Lipid analysis confirms strong hydrolytic activity on DGDG in dough concomitant with the accumulation of DGMG. *Fusarium heterosporum* CBS 782.83 lipolytic enzyme showed low activity on triglycerides in a dough.

Example 4

Characterization of Activity on Lipid Substrates and Position Specificity of a *Fusarium heterosporum* CBS 782.83 Lipolytic Enzyme Expressed in *Hansenula polymorpha*

A lipolytic enzyme according to the present invention from *Fusarium heterosporum* was expressed in *Hansenula polymorpha* as described in Example 3.

Analytical Procedures

Phospholipase activity was determined using the PLU assay described previously herein.

Galactolipase activity was determined using the galactolipase assay described previously herein.

Activity on triglyceride (tributyrin) was determined using the LIPU assay described previously herein.

Activity on Sunflower Oil (LUSol, pH-Stat pH 6):

Reagents:

8.4 g gum arabic is dissolved in 100 ml deionized water and 100 ml 30 mM $CaCl_2$ is added. 36 g sunflower oil is slowly added during mixing with a Turrax mixer (20000 rpm)

Assay:

20 ml sunflower oil emulsion in a beaker is equilibrated at 30° C. for 5 min. pH is adjusted to 6,3-6,5 using a pH stat. 2 ml enzyme solution is added, and 0.05 N NaOH is continuously added keeping the pH at 6.5 for 10 minutes. The slope of the curve for the addition of 0.05 NaOH as a function of time is calculated.

1 LUSol is defined as the quantity of enzyme, which can liberate 1 μmol fatty acid per min. under assay conditions The lipolytic enzyme was analysed for activity on different substrates according to procedures mentioned above. The results are shown in Table 14.

TABLE 14

Activity of a lipolytic enzyme *Fusarium heterosporum* according to the present invention on different lipid substrates.

| Activity | Substrate | pH | Temperature | UNIT/ml |
|---|---|---|---|---|
| LIPU | Tributyrin | 5.5 | 30 | 754 |
| LUSol | Sunflower oil | 6.5 | 30 | 48 |
| PLU-7 | Phosphatidylcholine | 7 | 37 | 4650 |
| GLU | Digalactosyldiglyceride | 7 | 37 | 1600 |

The lipolytic enzyme from *Fusarium heterosporum* expressed in *Hansenula polymorha* hydrolysis primarily fatty acids in the sn-1 position of galactolipid and phospholipids in dough. The specificity of the enzyme was investigated by adding different concentrations of the enzyme to a bread dough. The fully proofed dough was frozen and freeze dried, and the dough lipids were extracted with water saturated butanol.

The dough lipids were analysed by GLC and HPLC analysis.

By GLC analysis it was possible to analyse digalactosyl diglyceride (DGDG) and digalactosylmonoglyceride (DGMG). Further it was possible to analyse the position isomers of digalactosyl monoglyceride (1:digalactosyl 1-monoglyceride and 2: digalactosyl 2-monoglyceride, see structure below). These components were separated and quantified by GLC.

1: R1=H and R2=Fatty acyl

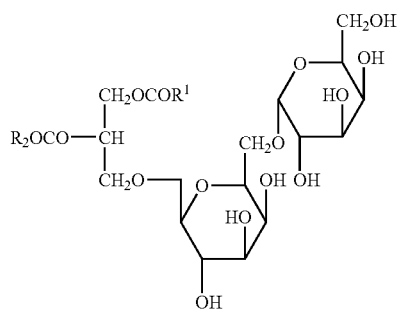

2: R1=Fatty acyl and R2=H

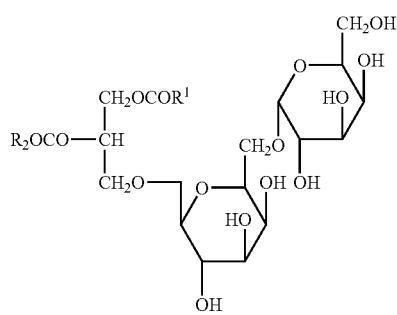

In a baking test for production of hard crust rolls different dosages of the lipolytic enzyme were added and galactolipids in the fully proofed dough were analysed. The amount of the isomer digalactosylmonoglycerides are shown in Table 15 and illustrated graphically in FIG. 14.

TABLE 15

Amount of isomer digalactosylmonoglycerides in a baking test using lipolytic enzyme from *Fusarium heterosporum*

| Enzyme dosage TIPU/kg flour | Digalactosyl 2-monoglyceride %, based on dough dry weight | Digalactosyl 1-monoglyceride %, based on dough dry weight |
|---|---|---|
| 0 | 0.0102 | 0.0399 |
| 200 | 0.0092 | 0.0167 |
| 400 | 0.0071 | 0.0100 |
| 400 | 0.0067 | 0.0057 |
| 800 | 0.0103 | 0.0063 |

TABLE 15-continued

Amount of isomer digalactosylmonoglycerides in a baking test using lipolytic enzyme from *Fusarium heterosporum*

| Enzyme dosage TIPU/kg flour | Digalactosyl 2-monoglyceride %, based on dough dry weight | Digalactosyl 1-monoglyceride %, based on dough dry weight |
|---|---|---|
| 1000 | 0.0071 | 0.0060 |
| 1200 | 0.0081 | 0.0053 |
| 1500 | 0.0064 | 0.0057 |
| 2000 | 0.0084 | 0.0047 |

Conclusion

From the results in Table 15 and FIG. 14 it is concluded that digalactosyl diglyceride is primarily hydrolysed in 1-position during production of digalactosyl 2-monoglyceride. A smaller increase in the amount of digalactosyl 1-monoglyceride is also observed. It is well known that acyl migration from 2 to 1 position of acyl fatty acid in lipids will occur. This acyl migration depends on temperature and as a function of time an equilibrium between digalactosyl-2-monoglyceride and digalactosyl 1-monoglyceride will occur. This phenomena explains the fact that a small increase in digalactosyl 1-monoglyceride also is observed.

Example 5

Determination of Temperature Optimum and Stability of Lipolytic Enzyme Derived from *Fusarium heterosporum*

The enzyme activity of spray dried lipolytic enzyme derived from *F. Heterosporum* and expressed in *Hansenula Polymorpha* was determined at various temperatures according to PLU-7 with modifications as described below. The substrate was an emulsion of 0.6% phosphatidylcholin, 0.4% Triton X-100, 6 mM $CaCl_2$, and 50 mM HEPES, pH 7.0. The spray dried lipolytic enzyme ferment was diluted with demineralised water to 3 TIPU/ml. 400 µl of substrate was thermostatted for 5 minutes at 10, 20, 30, 40, 50, 45, 50 and 60° C. and 50 µl sample was added. After exactly 10 minutes, the enzymation was stopped by incubation at 99° C. for another 10 minutes. Finally, the amount of free fatty acids was determined by NEFA C method (Wako Chemicals GMbH, Neuss, Germany). Colour reagent A and B was made according to manufacturers protocol. 10 µl redispersed extracted lipid and 100 µl reagent A were pipetted to a microtiter plate and incubated at 37° C. for 10 minutes. 200 µl reagent B was added to the microtiter plate and incubated at 37° C. for 10 minutes. The optical density at 540 nm was measured. The amount of free fatty acid was determined, using the read absorbance and a standard curve based on oleic acid. Results are shown in FIG. 15.

Enzyme stability of spray dried lipolytic enzyme ferment was determined at various temperatures. Spray dried lipolytic enzyme ferment was diluted with 50 mM phosphate buffer, pH 7.0 to 3 TIPU/ml. After 30 minutes of incubation at 20, 30, 37, 40 and 45° C. the sample was stored on ice. Subsequently, phospholipase activity was determined according to PLU-7 with modifications as described below. The substrate was an emulsion of 0.6% phosphatidylcholin, 0.4% Triton X-100, and 50 mM phosphate buffer. $CaCl_2$ was left out to prevent precipitation of calcium phosphate and does not affect the enzyme activity. 400 µl of substrate was thermostatted for 5 minutes at 37° C. and 50 µl sample was added. After exactly 10 minutes, the enzymation was stopped by incubation at 99° C. for another 10 minutes. Finally, the amount of free fatty acids was determined by the NEFA C method (Wako Chemicals GmbH, Neuss, Germany). Colour reagent A and B was made according to manufacturer's protocol. 10 μl redispersed extracted lipid and 100 μl reagent A were pipetted to a microtiter plate and incubated at 37° C. for 10 minutes. 200 μl reagent B was added to the microtiter plate and incubated at 37° C. for 10 minutes. The optical density at 540 nm was measured. The amount of free fatty acid was determined using the red absorbance and a standard curve based on oleic acid. Results are shown in FIG. 16.

Example 6

Determination of pH Optimum and Stability of a Lipolytic Enzyme Derived from *Fusarium heterosporum*

The enzyme activity of spray dried lipolytic enzyme derived from *F. heterosporum* and expressed in *Hansenula Polymorpha* was determined at various pH. The substrate was an emulsion of 0.6% phosphatidylcholin, 0.4% Triton X-100, and 50 mM phosphate buffer pH 4.0, 5.0, 6.0, 6.5, 7.0, 7.5, 8.0, 8.5, 9.0 and 10.0. $CaCl_2$ was left out to prevent precipitation of calcium phosphate and does not affect the enzyme activity. The spray dried lipolytic enzyme ferment was diluted with demineralised water to 3 TIPU/ml. 400 μl of substrate was thermostatted for 5 minutes at 37° C. and 50 μl sample was added. After exactly 10 minutes, the enzymation was stopped by incubation at 99° C. for another 10 minutes. Finally, the amount of free fatty acids was determined by NEFA C method (Wako Chemicals GMbH, Neuss, Germany). Colour reagent A and B was made according to manufacturers protocol. 10 μl redispersed extracted lipid and 100 μl reagent A were pipetted to a microtiter plate and incubated at 37° C. for 10 minutes. 200 μl reagent B was added to the microtiter plate and incubated at 37° C. for 10 minutes. The optical density at 540 nm was measured. The amount of free fatty acid was determined, using the read absorbance and a standard curve based on oleic acid. Results are shown in FIG. [17].

The enzyme stability of spray dried lipolytic enzyme ferment was determined at various pH. Spray dried lipolytic enzyme ferment was diluted with 50 mM phosphate buffer at pH 4.0, 5.0, 6.0, 6.5, 7.0, 7.5, 8.0, 8.5, 9.0 and 10.0 to 3 TIPU/ml. After 30 minutes of incubation at 37° C. the sample was stored on ice. Subsequently, the phospholipase activity was determined according to PLU-7 with modifications as described below. The substrate was an emulsion of 0.6% phosphatidylcholin, 0.4% Triton X-100, and 50 mM phosphate buffer, pH7. $CaCl_2$ was left out to prevent precipitation of calcium phosphate and does not affect the enzyme activity. 400 μl of substrate was thermostatted for 5 minutes at 37° C. and 50 μl sample was added. After exactly 10 minutes, the enzymation was stopped by incubation at 99° C. for another 10 minutes. Finally, the amount of free fatty acids was determined by the NEFA C method (Wako Chemicals GmbH, Neuss, Germany). Colour reagent A and B was made according to manufacturers protocol. 10 μl redispersed extracted lipid and 100 μl reagent A were pipetted to a microtiter plate and incubated at 37° C. for 10 minutes. 200 μl reagent B was added to the microtiter plate and incubated at 37° C. for 10 minutes. The optical density at 540 nm was measured. The amount of free fatty acid was determined using the read absorbance and a standard curve based on oleic acid. Results are shown in FIG. 18.

Example 7

Determination of Molecular Weight of Purified Lipolytic Enzyme Derived from *Fusarium heterosporum*

Purified lipolytic enzyme according to the present invention derived from *Heterosporum Fusarium* was run on an SDS-PAGE gel, FIGS. 19a and 19b. Based on a Novex standard marker, the molecular weight was calculated as shown in Table 15

TABLE 15

Determination of the molecular weight of the lipolytic enzyme according to the present invention

| Sample | $R_f$ | $M_w$ (kDa) | log $M_w$ | Calculations |
|---|---|---|---|---|
| Novex standard | 0.91 | 3.0 | 0.48 | Log $M_w$ (kDa) = $-5.30 \cdot R_f^3$ + |
|  | 0.82 | 6.0 | 0.78 | $7.50 \cdot R_f^2 - 5.00 \cdot R_f + 2.7986$ |
|  | 0.71 | 14 | 1.15 | $r^2 = 0.9989$ |
|  | 0.66 | 17 | 1.23 |  |
|  | 0.55 | 28 | 1.45 |  |
|  | 0.47 | 38 | 1.58 |  |
|  | 0.38 | 49 | 1.69 |  |
|  | 0.31 | 62 | 1.79 |  |
|  | 0.23 | 98 | 1.99 |  |
|  | 0.13 | 188 | 2.27 |  |
| Lipolytic enzyme according to the present invention |  |  |  | log $M_w = -5.30 \cdot 0.52^3$ + $7.50 \cdot 0.52^2 - 5.00 \cdot 0.52 + 0.52$ 2.80- $\Rightarrow M_w = 29.9$ kDa |

The weight of the lipolytic enzyme was calculated to 29.9 kDa.

Example 8

Determination of the Isoelectrical Point (pI) of Lipolytic Enzyme Derived from *Fusarium heterosporum*

The isoelectrical point (pI) of a lipolytic enzyme derived from *F. heterosporum* was determined theoretically based on the amino acid sequence SEQ ID NO. 6.

The calculation was made using the software Vector NTI Suite 9 from Informax (Invitrogen, CA, USA) and resulted in a pI of 6.40.

Example 9

Characterization of Enzymatic Conversion of Lecithin to Lysolecithin in Egg Yolk at Different Temperatures by a *Fusarium heterosporum* CBS 782.83 Lipolytic Enzyme Lipolytic enzymes can convert lecithin (phosphatidylcholine) to lyso-lecithin (lyso-phosphatidylcholine) with release of a free fatty acid. Enzymatic conversion of lecithin to lysolecithin in egg yolk creates better emulsifying properties because lysolecithin is a better emulsifier than lecithin. Good emulsifying properties of egg yolks are of importance when making heat stable mayonnaise and other foods and food applications, such as, but not limited to, cakes and maturation of cheese.

Enzyme Preparation:

A lipolytic enzyme from *Fusarium heterosporum*, CBS 782.83, expressed in *Hansenula polymorpha* from fermentation HET0420 was spray dried on wheat starch. The resulting enzyme preparation had a phospholipase activity of 1265 U/g, determined by TIPU assay previously described herein. A 10% (w/v) or 20% (w/v) enzyme stock solution was prepared by dissolving the spray dried enzyme powder in demineralised water. After 15 minutes of stirring, the solution was centrifuged for five minutes at 1370×g. The supernatant was used as the enzyme stock solution.

Enzymation:

Two different experiments were set up to determine the optimal combination of enzyme dosage, reaction temperature and time for the enzymatic conversion of lecithin to lysolecithin in egg yolk. In the first, enzymation was carried out with a lipolytic enzyme according to the present invention at the three following temperatures: 30° C., 40° C. and 50° C., each with the four following dosages: 5 U/g egg yolk, 10 U/g egg yolk, 20 U/g egg yolk and 30 U/g egg yolk.

In the second experiment, enzymation was carried out for a lipolytic enzyme according to the present invention and with Lecitase® Ultra from Novozymes A/S (Denmark), respectively, at the following five temperatures: 5° C., 10° C., 15° C., 20° C., and 53° C. with an enzyme dosage of 30 U/g egg yolk. At 53° C. the enzyme dosage of 60 U/g egg yolk was also tested.

In both experiments, 10.0 g pasteurised egg yolk from DanAEg (Christiansfeld, Denmark) was transferred to a Wheaton tube and placed in a heating block thermostatted to the appropriate temperature. The samples were continuously mixed on a magnetic stirrer. At time t=0 enzyme stock solution was added to the egg yolk according to Table 16. Each experiment was made in duplicate. 1.0 g samples were taken from the egg yolk/enzyme solutions according to Table 17. After incubation times according to Table 17, the enzymatic reaction in the samples was stopped by adding 7.5 ml organic solvent (CHCl$_3$:MeOH, 2:1).

TABLE 16

Enzyme stock solution was added to egg yolk to obtain different enzyme dosages, including a control. Demineralised water was added to a total of 2.35 ml to disregard any difference in volume upon addition of different volumes of enzyme stock solution.

| Sample | Amount egg yolk | Enzyme activity | Enzyme activity of stock solution | Volume enzyme stock solution added | Volume dem. H$_2$O added |
|---|---|---|---|---|---|
| Control | 10.0 g | 0 U | — | 0 ml | 2.35 ml |
| | 10.0 g | 50 U | 127 U/ml | 0.40 ml | 1.95 ml |
| Lipolytic enzyme | 10.0 g | 100 U | 127 U/ml | 0.80 ml | 1.55 ml |
| | 10.0 g | 200 U | 127 U/ml | 1.60 ml | 0.75 ml |
| | 10.0 g | 300 U | 127 U/ml | 2.35 ml | 0 ml |
| | 10.0 g | 600 U | 253 U/ml | 2.35 ml | 0 ml |
| Lecitase® Ultra | 10.0 g | 300 U | 3620 U/ml | 83 µl | 2.25 ml |
| | 10.0 g | 300 U | 3620 U/ml | 165 µl | 2.20 ml |

TABLE 17

Reaction times at sample extraction in the different experiments.

| Reaction temperature | Enzyme dosage | Reaction time (min) | | | | | | |
|---|---|---|---|---|---|---|---|---|
| 5° C., 10° C., 15° C., 20° C. | 30 U/g | 60 | 120 | 240 | 360 | 480 | 1440 | — |
| 30° C. | 5, 10, 20 and 30 U/g | 30 | 60 | 120 | 240 | 360 | — | — |
| 40° C. | 5, 10, 20 and 30 U/g | 30 | 60 | 120 | 240 | 360 | — | — |
| 50° C. | 5, 10, 20 and 30 U/g | 30 | 60 | 120 | 240 | 360 | — | — |
| 53° C. | 30 U/g | 15 | 30 | 60 | 90 | 120 | 240 | — |
| 53° C. | 60 U/g | 15 | 30 | 60 | 90 | 120 | 240 | 330 |

Lipid Extraction:

Addition of 7.5 ml organic solvent (CHCl$_3$:MeOH, 2:1) to the sample not only stopped the enzyme reaction but also extracted the lipids. Furthermore, 0.2 ml demineralised H$_2$O was added to the sample before it was dispersed, using a Whirley mixer for 1 minute. The sample was then centrifuged for ten minutes at 110×g. Approximately 3 ml of the organic phase was transferred to another tube and this extracted lipid was used for various analyses. The samples were stored at −18° C.

Determination of Free Fatty Acids:

100 µl of the extracted lipid solution was evaporated under nitrogen at 50° C. 1.0 ml demineralised H$_2$O was added and the lipid was dispersed using a Whirley mixer. The amount of free fatty acid was determined using the NEFA C kit from WAKO Chemicals GmbH (Neuss, Germany). Colour reagent A and B were made according to manufacturers protocol. 10 µl redispersed extracted lipid and 100 µl solution A were pippetted to a microtiter plate. The plate was incubated at 37° C. for 15 minutes. 200 µl solution B was added to the microtiter plate, and the plate was incubated at 37° C. for 10 minutes. The optical density at 540 nm was measured. The amount of free fatty acid was determined, using the read absorbance and a standard curve based on oleic acid.

Determination of Lecithin and Lyso-Lecithin by LC/MS-MS:

Materials

Acetone, methanol, chloroform were all from Lab Scan, Dublin, Ireland, ethanol 96% was from De Danske Spritfabrikker, and formic acid was from AppliChem, Darmstadt, Germany.

Instrumentals

The HPLC system consisted of a quarternary pump (G1311A), a capillary pump (G1376A), an autosampler (G1377A), and a column compartment (G1316A) all from Agilent Technologies (Waldbronn, Germany). An Acurate™ flowsplitter (ACM-CU-CR) from LC Packings (Amsterdam, Netherlands) was used to split the column effluent to the mass spectrometer and to introduce polar make-up solvent. The mass spectrometer was an LCQ Deca Ion Trap from Thermo Finnigan (San Jose, Calif., USA).

The column was a Hypersil SI, 100×4.6 mm id, 5 µm from Thermo Hypersil-Keystone.

Chromatographic and MS Conditions

Mobile Phases
- A: - - - not used
- B: Chloroform
- C: Methanol/Formic Acid (1000/0,190)
- D: Chloroform/Methanol/Water/Formic Acid (300/550/150/0,190)
- Make-up: Ethanol 96%

| Flow [ml/min] | Time [min] | B [%] | C [%] | D [%] |
|---|---|---|---|---|
| 0.6 | 0 | 40 | 60 | 0 |
| 0.6 | 2 | 0 | 0 | 100 |
| 0.6 | 8 | 0 | 0 | 100 |
| 0.6 | 9 | 40 | 60 | 0 |
| 0.6 | 16 | 40 | 60 | 0 |

The injection volume was 5 µl and the column temperature was 45° C.

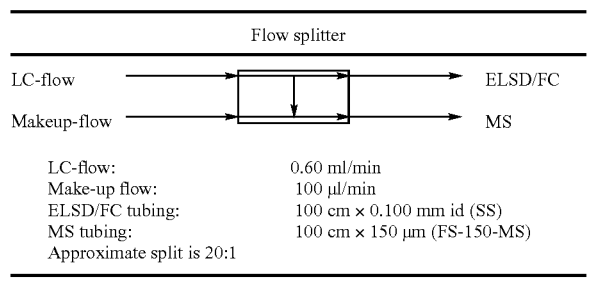

LC-flow: 0.60 ml/min
Make-up flow: 100 µl/min
ELSD/FC tubing: 100 cm × 0.100 mm id (SS)
MS tubing: 100 cm × 150 µm (FS-150-MS)
Approximate split is 20:1

MS conditions
MS parameter settings:

| Parameter | Value |
|---|---|
| Capillary temp [° C.] | 325 |
| Sheath gas flow | 70 |
| Auxiliary gas flow | 4 |
| Source | ESI |
| Polarity | Positive |
| Source voltage [kV] | 6.0 |
| SIM micro Scans | 5 |
| SIM Max Ion Time [ms] | 200 |

MS detector setting:

| Parameter | Value |
|---|---|
| Duration [min] | 15 |
| Tune method | LPC__544__SIM__00.LCQTune |

| Scan Event 1 - SIM Ranges | Mass Interval |
|---|---|
| LPC (16:0) - H+ | 494.0-498.0 |
| LPC (18:2) - H+ | 517.0-527.0; 541.0-549.0 |
| PC (34:2) - H+ | 778.0-786.0 |
| PC (36:4) - H+ | 801.0-813.0 |

Standard and Sample Preparation

Lyso-phosphatidylcholine (LPC) (Egg, chicken) (89865) and phosphatidylcholin (PC) (plant) (441601) were from Avanti Polar Lipids, Inc, Alabaster, Ala., USA. A stock solution of PC and LPC (10 mg/20 ml $CHCl_3$/MeOH) was prepared. Dilutions hereof were prepared to cover the concentrations from 50 µg/ml to 2.5 µg/ml.

7.5 µl lipid extract from 1 g of egg yolk was reconstituted in 1.5 ml $CHCl_3$:MeOH (1:1).

TLC Analysis:

The TLC analysis was carried out as described in Example 1.

For visualisation of the different glycerides, 2 µl lipid extract was applied in 3 mm bands to a HPTLC silica 60 plate (Merck) by an automatic TLC sampler 4 (CAMAG). The silica plate was placed in a horizontal developing chamber (CAMAG) with running buffer I (P-ether:methyl tertiary butyl ether:acetic acid (50:50:1)). 20 ml running buffer was used for the gas phase and 5 ml for the through and the plate was eluted until approx. 5 cm from the application position. The plate was dried in a heating cupboard (160° C.) for 5 minutes. Finally, the TLC plate was immersed in the developing reagent (6% $Cu(CH_3COO)_2$ in 16% aqueous $H_3PO_4$) and carbonised in a heating cupboard (160° C.) for 10 minutes.

Results

To determine the optimal combination of enzyme dosage, reaction temperature and time for the enzymatic conversion of lecithin to lyso-lecithin in egg yolk four different enzyme dosages were tested at three different temperatures and five different reaction times.

The four enzyme dosages used, 5 U/g, 10 U/g, 20 U/g, and 30 U/g, as well as the reaction times used, 30 minutes, 60 minutes, 120 minutes, 240 minutes, and 360 minutes, were based on initial trials not covered herein. The three temperatures, 30° C., 40° C., and 50° C., were chosen based on the temperature optimum curve for the lipolytic enzyme, see FIG. 20.

The amount of lecithin and lyso-lecithin in enzyme modified egg yolk was analyzed by HPLC and depicted in FIG. 21 and FIG. 22 as a function of reaction time. In FIG. 23, the amount of free fatty acid in enzyme modified egg yolk is depicted as a function of reaction time.

The experiment shows that conversion of lecithin to lyso-lecithin by a lipolytic enzyme according to the present invention was optimal using 20 U/g egg yolk of the lipolytic enzyme at 30° C. for 120 minutes. The dosage of 20 U/g egg yolk is chosen due to an observed decrease in LPC levels at 30 U/g egg yolk from 120 minutes of reaction to 240 minutes of reaction.

Based on this result, it was examined whether the lipolytic enzyme according to the present invention and Lecitase® Ultra have an effect on egg yolk lipids at temperatures lower than 30° C. and to compare their activities at 53° C., which is the temperature currently used industrially for Lecitase® Ultra.

The enzymatic conversion of lecithin to lyso-lecithin in egg yolk was tested at five different temperatures (5° C., 10° C., 15° C., 20° C., and 53° C.) and six different reaction times. An enzyme dosage of 30 U/g egg yolk was tested because this would be the highest dosage of commercial interest due to cost of the enzyme and because reaction rates were expected to be low at the temperatures tested. All enzyme units mentioned have been determined by TIPU. 30 U/g egg yolk is also the recommended dosage of Lecitase® Ultra. In addition, a dosage of 60 U/g egg yolk was tested at 53° C. The reaction times used were 60 minutes, 120 minutes, 240 minutes, 360 minutes, 480 minutes and 1440 minutes. However, at 53° C. the reaction times were 15 minutes, 30 minutes, 60 minutes, and 90 minutes, 120 minutes and 240 minutes. At 53° C. using 60 U/g a sample was also taken at 330 minutes of reaction.

In FIGS. 24 and 25 the amount of lyso-lecithin, free fatty acid, and lecithin in enzyme-modified egg yolk is depicted as a function of reaction time using the lipolytic enzyme according to the present invention and Lecitase® Ultra phospholipases, respectively. The lecithin and lyso-lecithin contents of the samples were determined by LC-MS and the free fatty acid content was determined by the NEFA C method. The amount of FFA in the control samples (results not shown) and the sum of lyso-lecithin and lecithin remained constant during the experiments shown in FIGS. 24 and 25.

FIG. 24 shows the results of enzymation of egg yolk with the lipolytic enzyme according to the present invention. At 53° C. the activity of the lipolytic enzyme ceased after 30 minutes of reaction reaching a level of LPC of 1.7% (w/w) with 30 U/g egg yolk (FIG. 24b). The levels of FFA were 1.0% (w/w) and 1.3% (w/w) with 30 U/g egg yolk and 60 U/g egg yolk, respectively. Using Lecitase® Ultra, the amounts of LPC and FFA increased during the period 15-240 minutes (FIG. 19), yielding 2.7% LPC (w/w) after 240 minutes of reaction with 30 U/g egg yolk. The levels of FFA were 1.4% (w/w) and 2.1% (w/w) after 240 minutes of reaction using 30 and 60 U/g egg yolk, respectively. The activity of Lecitase® Ultra ceased after 330 minutes of reaction using 60 U/g egg yolk. The lipolytic enzyme of the present invention had a higher initial reaction rate than Lecitase® Ultra.

At 20° C. and 53° C. the initial reaction rates were similar with the lipolytic enzyme of the present invention (FIG. 24). At temperatures 5-20° C. the amount of LPC and FFA increased during the experiment. Although at temperatures below 20° C. the initial velocity decreased markedly with decreasing temperatures. At 20° C. a LPC level of 3.3% (w/w) and a FFA level of 1.6% (w/w) was reached after 60 minutes of reaction with 30 U/g egg yolk. This level was similar to 240 minutes of reaction at 53° C. with Lecitase® Ultra. It was not possible to resuspend the solvent-free lipid extract for FFA analysis after 1440 of reaction at 20° C. After 1440 minutes at 5° C. and 10° C. the samples with the lipolytic enzyme had a high viscosity which made stirring impossible. This was most likely due to crystallisation of FFA. The decrease in LPC levels which was seen in TN 6642 at 30 U/g egg yolk, 30° C. from 120 to 240 minutes of reaction was not observed in any of these experiments.

Enzymation of egg yolk with Lecitase® Ultra phospholipase gives significantly decreasing initial velocities at 20° C. and temperatures below compared to the initial velocity of Lecitase® Ultra at 53° C. (FIG. 25). At 20° C. a LPC level of 3.0% (w/w) and a FFA level of 1.5% (w/w) was reached after 1440 minutes of reaction with 30 U/g egg yolk. This level was similar to 240 minutes of reaction at 53° C.

FIG. 26 shows TLC analysis of extracted lipid from enzyme modified egg yolk. This analysis confirmed the results from LC-MS and showed that the lipolytic enzyme according to the present invention and Lecitase® Ultra phospholipase increased the amount of lyso-lecithin.

The enzymatic reaction, which is catalysed by lipolytic enzymes, produces equivalent amounts of lyso-lecithin and free fatty acids. A possible and unwanted side reaction is hydrolysis of triacylglycerides. The relation between change in amount of lyso-lecithin and free fatty acids during the enzymatic reaction is shown in FIG. 27.

With Lecitase® Ultra there is a good correlation of equivalent formation of lyso-lecithin and free fatty acids (FIG. 27). However, in most samples treated with Lecitase® Ultra there was very little reaction. Enzymation of egg yolk with the lipolytic enzyme of the present invention results in production of more than one free fatty acid per lyso-lecithin formed at lyso-lecithin levels above 40 mM and free fatty acid levels above 60 mM. The maximal conversion with Lecitase® Ultra is 30 mM lyso-lecithin and 25 mM free fatty acid. Samples with a free fatty acid to lyso-lecithin ratio below 0.8 or above 1.2 (n/n) and LPC content above 1.0% (w/w) are shown in table 18.

TABLE 18

Samples with free fatty acid (FFA) to lyso-lecithin (LPC) ratios below 0.8 or above 1.2 (n/n) and LPC content above 1% (w/w). The samples were treated with lipolytic enzyme or Lecitase ® Ultra. FFA was determined by the NEFA C method. LPC and PC was determined by LC-MS.

| Enzyme | Temp. (° C.) | Reaction time (min) | ΔFFA/ΔLPC (n/n) | % LPC (w/w) | % FFA (w/w) | % PC (w/w) |
|---|---|---|---|---|---|---|
| Lipolytic enzyme | 5 | 1440 | 1.99 | 3.0 | 2.9 | 2.0 |
| Lipolytic enzyme | 10 | 480 | 1.97 | 2.3 | 2.3 | 2.5 |
| Lipolytic enzyme | 15 | 480 | 1.48 | 4.1 | 3.5 | 0.6 |
| Lipolytic enzyme | 15 | 360 | 1.64 | 3.6 | 3.4 | 1.0 |
| Lipolytic enzyme | 15 | 1440 | 1.98 | 4.2 | 4.7 | 0.1 |
| Lipolytic enzyme | 20 | 60 | 0.67 | 3.3 | 1.6 | 2.0 |
| Lipolytic enzyme | 20 | 360 | 1.30 | 4.7 | 3.6 | 0.3 |
| Lipolytic enzyme | 20 | 480 | 1.43 | 5.0 | 4.1 | 0.3 |
| Lecitase ® Ultra | 20 | 1440 | 0.72 | 3.0 | 1.5 | 2.0 |
| Lipolytic enzyme | 53 | 15 | 0.69 | 1.5 | 0.9 | 3.7 |
| Lipolytic enzyme | 53 | 60 | 0.70 | 1.7 | 1.0 | 2.6 |
| Lipolytic enzyme | 53 | 90 | 0.71 | 1.8 | 1.0 | 2.7 |
| Lipolytic enzyme | 53 | 240 | 0.72 | 1.7 | 1.0 | 2.8 |
| Lipolytic enzyme | 53 | 30 | 0.72 | 1.8 | 1.0 | 3.0 |
| Lecitase ® Ultra | 53 | 120 | 0.61 | 2.4 | 1.1 | 2.3 |
| Lecitase ® Ultra | 53 | 60 | 0.62 | 1.6 | 0.9 | 2.9 |

Samples with a free fatty acid to lyso-lecithin ratio above 1.2 (n/n) and LPC content above 1.0% (w/w) (FIG. 27) are generally seen at prolonged reaction times or in samples containing less than 1.0% PC (w/w). The lipolytic enzyme sample at 15° C. has elevated free fatty acid to lyso-lecithin ratios in all samples. This indicates that the enzymes change substrate specificity at prolonged reaction times or when the content of PC is low. This could be due to hydrolysis of phosphatidylethanolamine, digalactosyl diacylglyceride, or triacylglycerides that are found in egg yolk. Samples with a free fatty acid to lyso-lecithin ratio below 0.8 (n/n) and LPC content above 1.0% (w/w) are generally seen at a reaction temperature of 53° C. (Table 18). This could be explained by interesterifications.

FIG. 28 shows that the lipolytic enzyme of the present invention does have hydrolytic activity on triacylglycerides and 1,3 diacylglycerides at prolonged reaction times or low concentrations of PC. The accumulation of 1,2 diacylglycerides shows that the lipase activity is 1,3-specific. The formation of monoglycerides shows that Lecitase® Ultra had a hydrolytical effect on tri- or diacylglycerides at 20° C. It is not possible to determine whether the lipolytic enzyme of the present invention or Lecitase® Ultra phospholipase has the highest degree of hydrolysis of triacylglycerides because the levels of formation of LPC differ significantly. Lowering the enzyme dosage and reaction time of lipolytic enzyme could reduce the hydrolysis. Table 18A shows the reaction time, temperature and dosage applied to the subjects of lanes 1-30 in FIG. 28.

thorough optimization of conditions of treatment for each product in question. At 53° C. interesterifications can explain that less than one equivalent free fatty acid per lyso-lecithin is produced with lipolytic enzyme and Lecitase® Ultra.

In conclusion, the lipolytic enzyme according to the present invention is a potential candidate for enzymation of egg yolk at low temperatures. The observed activity at low temperatures is also of interest in other applications.

TABLE 18A

| | Lane number | | | | | | | | | | | | | | | | | | | | |
|---|---|---|---|---|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 | 16 | 17 | 18 | 19 | 20 | 21 |
| Enzyme* | B | K | K | L | B | K | K | L | B | K | K | B | K | K | K | K | L | L | L | L | B |
| Reaction time (h) | | 8 | 24 | 24 | | 8 | 24 | 24 | | 8 | 24 | | 4 | 6 | 8 | 24 | 4 | 6 | 8 | 24 | |
| Temperature (° C.) | 5 | 5 | 5 | 5 | 10 | 10 | 10 | 10 | 15 | 15 | 15 | 20 | 20 | 20 | 20 | 20 | 20 | 20 | 20 | 20 | 53 |
| Dosage (U/g) | 30 | 30 | 30 | 30 | 30 | 30 | 30 | 30 | 30 | 30 | 30 | 30 | 30 | 30 | 30 | 30 | 30 | 30 | 30 | 30 | 30 |

| | Lane number | | | | | | | | | | | | | | |
|---|---|---|---|---|---|---|---|---|---|---|---|---|---|---|---|
| | 22 | 23 | 24 | 25 | 26 | 27 | 28 | 29 | 30 | | | | | | |
| Enzyme* | K | K | K | L | L | L | B | K | L | Chol. | PC | LPC | MG.DG | FFA | Mix |
| Reaction time (h) | 1 | 2 | 4 | 1 | 2 | 4 | | 4 | 4 | | | | | | |
| Temperature (° C.) | 53 | 53 | 53 | 53 | 53 | 53 | 53 | 53 | 53 | | | | | | |
| Dosage (U/g) | 30 | 30 | 30 | 30 | 30 | 30 | 60 | 60 | 60 | | | | | | |

*B: Blank, K: Lipolytic protein according to the present invention, L: Lecitase ® Ultra phospholipase It will be apparent to the skilled person that, using routine experimentation, optimisation of enzyme dosage, reaction temperature and reaction time may be readily determined for any given food application.

Conclusion

Enzymation of egg yolk from DanAEg A/S of a lipolytic enzyme according to the present invention and Lecitase® Ultra phospholipases was carried out to determine the conversion of lecithin to lyso-lecithin. This was done using an enzyme dosage 30 U/g egg yolk at five temperatures (5-20° C., and 53° C.), and six different reaction times (60-1440 minutes, however at 53° C., 15-240 min) was carried out to examine the enzyme activity. 53° C. is the temperature currently used in the industry for modifying egg yolk with Lecitase® Ultra.

The lipolytic enzyme according to the present invention had a higher initial reaction rate than Lecitase® Ultra at all temperatures tested. At 53° C. reaction with lipolytic enzyme ceased after only 30 minutes of reaction. At a dosage of 30 U/g egg yolk at 53° C. the LPC level was 1.7 and 2.7% (w/w) with lipolytic enzyme and Lecitase® Ultra, respectively. A level of 3.3% (w/w) LPC was reached after only 60 minutes of reaction at 20° C. with lipolytic enzyme.

At low temperatures (5-20° C.) the conversion of lecithin to lyso-lecithin with lipolytic enzyme was significantly better than with Lecitase® Ultra. The reaction velocity of the lipolytic enzyme was markedly lower at 10° C. and below compared to at 15° C. and above. The lipolytic enzyme was active at 5° C. and formation of more than 2% (w/w) lyso-lecithin was detectable after 24 hours of reaction. Also, the samples with the lipolytic enzyme were more viscous at 10° C. and below compared to higher temperatures.

The lipolytic enzyme was found to change substrate specificity and hydrolyse phosphatidyl-ethanolamine, digalactosyl diacylglyceride, or triacylglycerides in addition to phospholipids at prolonged reaction times or when the content of PC is low. This may be avoided by using a lower enzyme dosage and shorter reaction times and substantiates the need for Example 10

Production of Mayonnaise by Use of a *Fusarium heterosporum* CBS 782.83 Lipolytic Enzyme Production of Mayonnaise:

6.25 g lipolytic enzyme prepared as described in Example 4 was dissolved in 50 mL demineralised $H_2O$ corresponding to a phospholipase activity of 150 U/mL. After 15 minutes of stirring, the solution was centrifuged for five minutes at 1370×g. The supernatant was used for enzymation of 150 g egg yolk from Sanofa A/S according to Table 19. Another 150 g egg yolk from Sanofa A/S was treated with Lecitase® Ultra (Novozymes A/S, Denmark) according to Table. The enzymations were carried out at 30° C. for 180 minutes with slow agitation. Lipid extraction was carried out as described in Example 4.

TABLE 19

Enzymation of egg yolk from Sanofa A/S using lipolytic enzyme according to the present invention and Lecitase ® Ultra, respectively. The lipolytic enzyme solution used had an activity of 150 U/mL, and the Lecitase ® Ultra had a phospholipase activity of 34500 U/mL.

| Sample | Amount egg yolk | Lipolytic enzyme added | Lecitase ® Ultra added | Dem $H_2O$ added | U/g egg yolk |
|---|---|---|---|---|---|
| Control | 150 g | | | 30.0 mL | 0 |
| Lipolytic enzyme | 150 g | 30.0 mL | | | 30 |
| Lecitase ® Ultra | 150 g | | 0.13 mL | 29.9 mL | 30 |

Mayonnaise with enzyme-modified egg yolk from Sanofa A/S was produced using a Koruma mixer (Disho V60/10). During processing the mayonnaise was heated to 95° C. for five minutes.

TABLE 20

Ingredients used to produce mayonnaise.

| Ingredient | Mayonnaise Control | Mayonnaise Lipolytic enzyme | Mayonnaise Lecitase ® Ultra |
|---|---|---|---|
| Water | 34.5% | 34.5% | 34.5% |
| Oil | 50.0% | 50.0% | 50.0% |
| Salt | 1.0% | 1.0% | 1.0% |
| Sugar | 3.0% | 3.0% | 3.0% |
| Potassium Sorbate | 0.1% | 0.1% | 0.1% |
| Grindsted FF 1102 | 1.7% | 1.7% | 1.7% |
| Egg yolk 1 | 4.23% | | |
| Egg yolk 2 | | 4.23% | |
| Egg yolk 3 | | | 4.23% |
| Vinegar 10% | 4.00% | 4.00% | 4.00% |
| Mustard | 1.50% | 1.50% | 1.50% |
| Sum | 100% | 100% | 100% |

TLC-Analysis:

TLC analysis was carried out as described above.

Particle Size Determination in Mayonnaise:

2.0 g mayonnaise sample was dissolved in 22.5 g 0.2% SDS and stirred for minimum 30 minutes at 300 rpm. The particle size distribution was then measured on a Malvern Mastersizer.

Results

For production of mayonnaise with enzyme-modified egg yolk, egg yolk from Sanofa A/S was used. This egg yolk contained 8% salt (compared to 0% in egg yolk from Dan-AEg). Initial trials (not shown) showed that the higher salt concentration in egg yolk from Sanofa A/S influenced the lipolytic activity and, therefore, an enzyme dosage of 30 U/g was used instead of 20 U/g.

TLC analysis of extracted lipid from enzyme modified egg yolk from Sanofa A/S (FIG. 29) showed that the lipolytic enzyme according to the present invention reduced the amount of lecithin concurrent with increasing the amount of lyso-lecithin (FIG. 29). In comparison, the conversion of lecithin to lyso-lecithin when using Lecitase® Ultra was negligible. The high conversion of lecithin to lyso-lecithin shown by TLC correlated well with the free fatty acid determination made on extracted lipid from enzyme modified egg yolk from Sanofa A/S (Table 21). The amount of free fatty acid liberated using lipolytic enzyme was 3.5 times higher than the amount of free fatty acid liberated using Lecitase® Ultra.

TABLE 21

Amount of free fatty acid in enzyme modified egg yolk from Sanofa A/S. The amount of free fatty acid was analysed by the NEFA C method and is expressed as percentage of egg yolk.

| Sample | Free fatty acid (% (w/w)) |
|---|---|
| Control | 0.39 |
| Lipolytic enzyme | 2.4 |
| Lecitase ® Ultra | 0.68 |

The size distribution of oil droplets in mayonnaise was analysed in order to evaluate the emulsification properties of the differently enzyme-modified egg yolk from Sanofa A/S. As can be seen in, the mayonnaise produced with egg yolk treated with the lipolytic enzyme according to the present invention had the smallest mean particle size as well as the narrowest particle size distribution compared to mayonnaise produced with either Lecitase® Ultra treated egg yolk or non-treated egg yolk. A small mean particle size as well as a narrow particle size distribution indicates good emulsification properties, hence the egg yolk modified with lipolytic enzyme had the best emulsification properties.

TABLE 22

Particle size distribution in mayonnaise made with enzyme modified egg yolk from Sanofa A/S.

| Sample | Mean particle size (μm) | 10% quantile (μm) | 90% quantile (μm) |
|---|---|---|---|
| Control | 13.7 | 2.0 | 21.5 |
| Lipolytic enzyme | 4.4 | 1.2 | 7.3 |
| Lecitase ® Ultra | 13.3 | 1.8 | 21.9 |

To evaluate the heat stability of emulsions made with enzyme modified egg yolk from Sanofa A/S, the mayonnaises were heated in a microwave oven for 4 seconds. As can be seen in FIG. 30, the mayonnaises containing enzyme-modified egg yolk produced heat stable emulsions, whereas the control containing non-treated egg yolk separated upon the heat treatment in the microwave oven and the emulsion was therefore not heat stable.

Conclusion

Results from TLC analysis and free fatty acid determination of enzyme modified egg yolk from Sanofa A/S, and particle size distribution and heat stability test of the mayonnaises produced with the enzyme modified egg yolk from Sanofa A/S correlated well. Egg yolk modified using a lipolytic enzyme according to the present invention had the highest conversion rate of lecithin to lyso-lecithin and the highest amount of free fatty acid. As expected, this change in the lecithin:lyso-lecithin ratio resulted in a mayonnaise, which was heat stable and had the most optimal particle size distribution.

Using Lecitase® Ultra to modify egg yolk from Sanofa A/S did not result in a very large change in the lecithin:lyso-lecithin ratio or a high amount of free fatty acids. This less pronounced conversion of lecithin to lyso-lecithin was reflected in the particle size distribution of the mayonnaise, which was similar to that of the non-modified egg yolk. The change in lecithin:lyso-lecithin ratio that occurred using Lecitase® Ultra was enough, though, to make the mayonnaise heat stable.

Egg yolk from Sanofa A/S modified with 30 U/g of lipolytic enzyme at 30° C. for 120 minutes showed a high conversion rate of lecithin to lyso-lecithin, and the mayonnaise produced with this egg yolk was heat stable and had an optimal particle size distribution. In comparison, egg yolk from Sanofa A/S treated with 30 U/g Lecitase® Ultra at 30° C. for 120 minutes showed only a minor change in the lecithin:lysolecithin ratio, and the mayonnaise produced had a particle size distribution similar to mayonnaise with non-treated egg yolk, but it was in fact heat stable. Hence the lipolytic enzyme according to the present invention was superior to Lecitase® Ultra in the production of mayonnaise.

Example 11

Application Test of a Lipolytic Enzyme Derived from *Fusarium heterosporum* in Combination with Emulsifier for Preparation of Hard Crusty Rolls In this test ferments of lipolytic enzyme according to the present invention and derived from *Fusarium heterosporum* was used alone or in combination with Panodan® A2020

DATEM and GRINDSTED® SSL P55, both emulsifiers from Danisco A/S, for the baking of hard crusty rolls. The effect on specific bread volume was compared to the effect of Lipopan F™ from Novozymes alone or in combination with emulsifier on specific bread volume.

Application

Hard crusty rolls were baked using the following recipe and baking procedure.

| Baking recipe | Amount | Bakers % of flour |
|---|---|---|
| Flour-Danish Reform 2004002 | 2000 g | 100 |
| Water | 1140 g | 57 |
| Compressed yeast | 120 g | 6 |
| Salt | 32 g | 1.6 |
| Sugar | 32 g | 1.6 |
| Ascorbic acid | 0 ppm | 0 |
| Standard alpha amylase/GRINDAMYL ™ A 1000 from Danisco A/S | 75 ppm | 0.150 |

Baking Procedure

Diosna Mixer System
1. Dry mix for 1 min slow
2. Mix 2 min slow+4 min fast
3. Dough temperature: 26° C.
4. Scaling of the dough: 1350 g
5. Resting: 10 min. at 30° C. in heating cabinet
6. Moulding: Fortuna 3/17/7 molder
7. Proofing: 45 min. at 34° C., 85% RH.
8. Baking in a Bago oven: 13 min. at 220° C., 13 sec. steam+5 min damper open
9. MIWE stone deck: prog. nr 1
10. After baking the rolls are cooled for 25 min before weighing. The volume of the rolls was measured by the rape seed displacement method.

Specific Bread Volume:

Specific volume=Volume of the bread, ccm/weight of the bread, g

Addition of spray dried lipolytic enzyme is based on flour. The enzyme is added to flour after first mixing together with water, ascorbic acid and compressed yeast. All other dry ingredients are mixed in step 1.

Results

Spray dried lipolytic enzyme derived from *Fusarium heterosporum* is used in combination with Panodan® M2020 DATEM from Danisco A/S and tested against a combination of Lipopan F™/DATEM as well as pure Lipopan F™ or pure DATEM. The results are shown in Table 23 and FIG. 31.

TABLE 23

| Sample | Amount | Specific volume, g/ccm |
|---|---|---|
| Control | | 5.89 |
| Lipopan F ™ | 10 ppm | 5.98 |
| | 30 ppm | 7.54 |
| | 40 ppm | 8.18 |
| Lipolytic enzyme | 96 ppm | 6.07 |
| | 191 ppm | 6.2 |
| | 287 ppm | 7.06 |
| | 383 ppm | 8.13 |
| | 478 ppm | 8.01 |
| PAN M2020 | 0.3% | 7.89 |
| | 0.15% | 6.5 |
| PAN M2020 + Lipolytic | 0.15% | 7.68 |

TABLE 23-continued

| Sample | Amount | Specific volume, g/ccm |
|---|---|---|
| enzyme | 96 ppm | |
| PAN M2020 + Lipolytic enzyme | 0.15% 191 ppm | 8.29 |
| PAN M2020 + Lipopan F ™ | 0.15% 10 ppm | 7.69 |

Freeze dried lipolytic enzyme derived from *Fusarium heterosporum* was used in combination with Panodan® A2020 DATEM and GRINDSTED® SSL P55 and tested against a combination of Lipopan F™/SSL or Lipopan F™M/DATEM as well as pure Lipopan F™, pure DATEM and pure SSL.

The results are shown in Table 24 and FIG. 32

TABLE 24

| Sample | Amount | Specific volume, g/ccm |
|---|---|---|
| Control | | 5.98 |
| 0.3% Panodan ® A2020 | 0.3% | 7.98 |
| 0.3% SSL P 55 | 0.3% | 7.78 |
| Lipopan F ™ | 15 ppm | 6.42 |
| | 40 ppm | 7.77 |
| Lipopan F ™ + 0.15% Panodan ® A2020 | 15 ppm 0.15% | 8.44 |
| Lipopan F ™ + 0.15% SSL P 55 | 15 ppm 0.15% | 8.62 |
| Lipolytic enzyme | 43 ppm | 5.93 |
| | 86 ppm | 6.43 |
| Lipolytic enzyme + 0.15% Panodan ® A2020 | 30 ppm 0.15% | 7.86 |
| Lipolytic enzyme + 0.15% Panodan ® A2020 | 43 ppm 0.15% | 7.86 |
| Lipolytic enzyme + GRINDSTED ® SSL P55 | 43 ppm 0.15% | 8.1 |

Conclusion

The conclusion of Table 23 and FIG. 31 is that an optimal dosage of spray dried lipolytic enzyme according to the present invention is approximately 383 ppm lipolytic enzyme and that the product can be used in a low dosage in combination with a low dosage of the DATEM emulsifier. In a parallel experiment it was shown that at dosages from 574 ppm to 1912 ppm lipolytic enzyme the specific bread volume decreased (data not shown). The performance of 383 ppm lipolytic enzyme according to the present invention is similar to 40 ppm Lipopan F™. When used in combination with emulsifier the lipolytic enzyme according to the present invention also performs on level with Lipopan F™. According to determination of phospholipase activity using the TIPU assay described previously herein, 10 ppm Lipopan F™ is approx. 120 TIPU per kg flour and 96 ppm lipolytic enzyme of the present invention correspond to 117 TIPU per kg flour.

In addition, based on the trial results of Table 24 and FIG. 32, we conclude that a lipolytic enzyme according to the present invention can be used in combination with SSL as well as DATEM and thereby boost the effect of a low emulsifier level. The functionality of lipolytic enzyme according to the present invention can be compared to the functionality of Lipopan F™ when dosed equally. Again the optimal level of phospholipase activity in combination with an emulsifier is determined to be approx. 100-150 TIPU per kg flour.

Conclusively, an optimal dosage of the pure lipolytic enzyme according to the present invention is around 500 TIPU per kg flour and in combination with emulsifier the level of lipolytic enzyme should be ⅕ to ¼ of the optimal level of lipolytic enzyme, meaning approx. 120 TIPU per kg flour.

Example 12

Application Test of a Lipolytic Enzyme Derived from *Fusarium heterosporum* for Preparation of Wheat Tortilla The effect of a lipolytic enzyme according to the present invention and derived from *Fusarium heterosporum* on rollability of wheat tortilla made with fumaric acid (US procedure) has been tested as explained in the following example.

Wheat tortilla was baked using the ingredients in Table 25:

TABLE 25

Recipe for preparation of wheat tortilla.

| Recipe: | Type: | Dosage (% of flour) | Grams |
|---|---|---|---|
| Flour | Classic (no. 2004068) | 100 | 3000 |
| Sugar | | 1.0 | 30 |
| Fat (shortening, margarine, oil) | Shortening | 8.7 | 267 |
| Salt | | 1.5 | 45 |
| Potassium sorbate | | 0.3 | 9 |
| Ca-propionate | | 0.3 | 9 |
| Sodium bicarbonate | | 0.9 | 27 |
| Acid | Fumaric | 0.8 | 24 |
| Water | | 48 | 144 |

The procedure for making the wheat tortilla dough:
1. Desired dough temperature: 32° C.
2. Kneading is conducted at ambient temperature in a Kemper mixer.
3. Place all dry ingredients in mixer bowl (optionally including lipolytic enzymes and/or emulsifiers).
4. Dry mix for 1 min.
5. Add Water
6. Mixing: 11 min at speed 1
7. Scaling: 1350 g×3
8. Shaping: into dough balls on glimek divider/rounder
9. Resting for 10 min at 32° C.
10. Baking: in a tortilla oven CFO 40, with the following setting: Top: 230° C., middle: 228° C. and bottom: 160° C.
11. Cooling: 12 min at 20° C., 80% RH A lipolytic enzyme according to the present invention was added to the dough at increasing concentrations (Trial no. 3-7). For comparison, a control (Trial no. 1) and a trial with the Panodan® 205 emulsifier from Danisco A/S (Trial no. 2) were included. See Table 26.

The lipolytic enzyme, Panodan® 205, and L-cystein, when added, are added to the first mixing process (steps 3 and 4 above). L-cystein may be added to increase the extensibility of the dough made and thereby improve the pressing process of the dough before baking.

TABLE 26

Trial set-up

| Ingredients Trial no. | Lipolytic enzyme | PANODAN® 205 | L'cystein (ppm) |
|---|---|---|---|
| 1 | | | 10 |
| 2 | | 1.03% | 10 |

TABLE 26-continued

Trial set-up

| Ingredients Trial no. | Lipolytic enzyme | PANODAN® 205 | L'cystein (ppm) |
|---|---|---|---|
| 3 | 100 ppm | | 10 |
| 4 | 200 ppm | | 10 |
| 5 | 400 ppm | | 10 |
| 6 | 1200 ppm | | 10 |
| 7 | 2400 ppm | | 10 |

The tortillas are evaluated by means of a cold rollability test performed at room temperature, where the tortilla is rolled around different wooden sticks of different diameters, starting with the wooden stick with the biggest diameter. The rollability is indicated by the number of wooden sticks around which the tortilla can be rolled without breaking. The higher the number the better the rollability.

| Sample | Visual evaluation Rollability | Penetration Force (g) |
|---|---|---|
| 1-day 7 | 2-1-1 | 432 |
| 2-day 7 | 1-1-1 | 421 |
| 3-day 7 | 1-1-1 | 369 |
| 4-day 7 | 2-2-2 | 439 |
| 5-day 7 | 2-2-1 | 489 |
| 6-day 7 | 2-1-2 | 448 |
| 7-day 7 | 2-2-2 | 533 |

From the results we conclude that a dosage of 200 ppm or more of a lipolytic protein according to the present invention seems to give an improved rollability compared to the control system. Using the TIPU assay described previously herein it was determined that the level of activity needed in order to improve the rollability (in a dosage of 200 ppm) corresponds to approximately 650 TIPU units per kg flour. From the results it can also be concluded that the force for making the penetration test is increased at a higher level of lipolytic enzyme, meaning that the resistance of the tortilla is improved. The penetration test is conducted by use of the texture analyser TAXT2 produced by Stable Micro System, where the force needed in order to penetrate/break the tortilla is measured.

This equipment is set up with the following parameters:

| Force is measured in Compression | |
|---|---|
| Pre-test Speed | 10 mm/s |
| Test Speed | 2 mm/s |
| Post Test Speed | 10 mm/s |
| Rupture Test Dist. | 1 mm |
| Distance | 25 mm |
| Force | 1 g |
| Time | 5 sec |
| Load Cell | 5 kg |
| Temperature | 20-22 deg C. (room temperature) |

Example 13

Molecular Cloning, Sequence Analysis and Heterologous Expression of a Synthetic Gene Encoding a Lipolytic Enzyme from *Fusarium semitectum* (IBT9507) in *Hansenula polymorpha*

A fragment of a *F. semitectum* lipolytic enzyme gene was cloned from genomic DNA using PCR with primers designed from conserved blocks of amino acids within aligned protein sequences of lipolytic enzymes from different *Fusarium* strains. The degenerate PCR primers were designed using the computer programs CODEHOP (Rose et al. 2003 (Nucleic Acid Res., 18:3763-3766)).

To clone the ends of the gene the methods for 5'- and 3'-RACE (Frohman et al. 1988 Proc. Natl. Acad. Sci. USA 85:8998-9002) were used. Total RNA was isolated from a culture of the *F. semitectum* strain induced with 1% sunflower oil and the primers used were designed from the sequence of the gene fragment obtained with the CODEHOP primers.

The three fragments obtained by the above procedures were assembled in silico to reveal the full-length cDNA sequence. Analysis of the 1236 nucleotides long cDNA sequence showed an open reading frame comprising 352 amino acids (FIG. 33).

To express the *F. semitectum* lipolytic enzyme gene in *Hansenula* the gene was furnished with a signal sequence form the yeast α mating factor and inserted behind the FMD-promoter into the *Hansenula* expression vector pB14. The resulting plasmid, pB14-alp.sem (schematically shown in FIG. 34) was transformed into competent *Hansenula polymorpha* cells by electroporation. Transformants were selected on YND plates and colonies were further selected for multiple integration of the gene by 10 passages of 1:200 dilutions in liquid cultures of YND. Finally, the selected cultures were transferred twice in YPD medium.

To determine the level of expression of the lipolytic enzyme gene the selected clones were grown in YPD with 1.8% glycerol and 0.2% glucose for 2 days at 37° C.

Example 14

Determination of Optimum pH and Temperature for Activity of a *Fusarium semitectum* Lipolytic Enzyme A lipolytic enzyme according to the present invention from *Fusarium semitectum* IBT 9507 and expressed in *Hansenula polymorpha* as described in Example 8 was used in functional assays in dough slurry for determination of phospholipase and galactolipase activity and the activity of this enzyme was studied in relation to variations in pH and temperature.

Analytical Procedures

Gas Chromatography 0.8 gram Wheat flour is scaled in a 12 ml centrifuge tube with lid. 1.5 ml water containing the enzyme is added. The sample is mixed on a Whirley and placed in a heating cabinet at 30° C. for 60 minutes. 6 ml n-Butanol:Ethanol 9:1 is added, and the sample is mixed again until the flour is finely distributed in the solvent. The tubes are then placed in a water bath at 95° C. for 10 minutes. Then mixed again and placed on a rotation device 45 rpm, for 45 minutes. The sample is then centrifuged at 2000 g for 10 minutes and 2 ml supernatant is transferred to a 10 ml dram glass. The solvent is evaporated at 70° C. under a steam of nitrogen. The isolated lipids are analysed by GLC.

Gas Chromatograph and Galactolipase activity assay were performed as described in Example 1.

Temperature Optimum

Phospholipase Activity

For the determination of activity as a function of temperature the Phospholipase assay was conducted as in Example 1 but the temperature was set at 30° C., 37° C., 45° C., 52° C. or 60° C.

PH Optimum

Phospholipase Activity

For the determination of activity as a function of pH the Phospholipase assay was conducted as in Example 1 but the 0.6% L-α Phosphatidylcholine 95% Plant (Avanti #441601) and 0.4% Triton-X 100 (Sigma X-100) was dissolved in 0.05M phosphate buffer pH 5, pH 6, pH 7, pH 8 or pH 9.

Results

A lipolytic enzyme according to the present invention from *Fusarium semitectum* IBT9507 was analysed for phospholipase activity PLU-7 and galactolipase activity GLU with results shown in table 27

TABLE 27

Enzyme activity of *Fusarium semitectum*.

| Assay | Activity |
|---|---|
| Phospholipase | 0.8 PLU-7/ml |
| Galactolipase | 1.3 GLU/ml |

*Fusarium semitectum* EBT9507 was tested in dough slurry experiments by adding 1 PLU-7 to 0.8 gram flour according to the procedure mentioned. A control sample with water instead of enzyme and a sample with Lipopan F™ was also prepared. Lipids extracted from the dough was analysed by GLC with results shown in table 28.

TABLE 28

GLC of dough lipid, % based on flour weight.

| Enzyme | Dosage | FFA % | MGMG % | DGMG % | MGDG % | DGDG % | TRI % |
|---|---|---|---|---|---|---|---|
| Control | 0 | 0.148 | 0.007 | 0.025 | 0.047 | 0.160 | 0.516 |
| *F. semitectum* | 1 PLU-7/g g flour | 0.268 | 0.001 | 0.120 | 0.033 | 0.045 | 0.446 |
| Lipopan F ™ | 1 PLU-7/g g flour | 0.229 | 0.027 | 0.090 | 0.016 | 0.069 | 0.415 |

FFA = free fatty acids
MGMG = monogalactosylmonoglyceride,
DGMG = digalactosylmonoglyceride
MGDG = monogalactosyldiglyceride,
DGDG = digalactosyldiglyceride,
TRI = triglyceride.

The results in table 28 indicate that the lipase from *F. semitectum* has significant activity on galactolipids, and relative less activity on triglyceride compared with Lipopan F™.

*Fusarium semitectum* IBT9507 was also analysed with regard to activity as a function of temperature (table 29) and pH (table 30).

TABLE 29

Phospholipase activity as a function of temperature for *F. semitectum*.

| Temperature, ° C. | Relative activity, PLU |
|---|---|
| 30 | 79 |
| 37 | 92 |
| 45 | 100 |
| 52 | 20 |
| 60 | 2 |

TABLE 30

Phospholipase activity as a function of pH for *F. semitectum*.

| pH | Relative activity, PLU |
|---|---|
| 5 | 67 |
| 6 | 83 |
| 7 | 100 |
| 8 | 80 |
| 9 | 17 |

The activities listed in table 29 and 30 are also illustrated graphically in FIGS. 35 and 36.

Conclusion

Lipolytic enzyme according to the present invention from *Fusarium semitectum* has shown very strong activity on galactolipids in dough and the activity on triglyceride is less than the triglyceride activity of Lipopan F™. Temperature optimum for activity of this enzyme is approx. 45° C. and the pH optimum is 7.

Example 15

Use of a Lipolytic Enzyme According to the Present Invention in Animal Feed

To assess the efficacy of a lipolytic enzyme according to the present invention at various dose levels used in normal feed for the full production period of broiler chickens.

Summary:

Preliminary results suggest that addition of a lipolytic enzyme according to the present invention in the diets of broiler chickens is an effective nutritional strategy to improve the performance of the birds, to improve nutrient retention and to reduce nitrogen excretion. Specifically, preliminary investigations suggest that addition of a lipolytic enzyme according to the present invention to the animal's diet improves the body weight gain, feed conversion efficiency, and metabolisability of dry matter and of nitrogen of the animal.

Treatment details

| Number of treatments | 8 |
|---|---|
| Replicates per Treatment | 0-21 d, 13 replicates |
| | 22-42 d, 9 replicates |
| Birds per Replicate | 0-21 d, 8 birds/replicate |
| | (6 in large cage, 2 in small cage) |
| | 22-42 d, 2 birds/replicate |
| | (2 in large cage) |
| Species of bird | Broiler |
| Breed of bird | Ross or Cobb |
| Sex of bird | Male |
| Range of trial | 0-42 days |
| Diet form (pellet/mash) | Mash |
| Diet Coccidiostat/Growth promoter used | None |
| Age at which birds/feed are weighed | 0, 21 and 42 days/0, 21 and 42 days |
| Stocking density (birds/m2) | |
| Lighting programme | 23 h light days 0-4, 16 h light days 4-21, 20 h light days 22-31 and 23 h light days 32-42. |
| House temperature programme | |
| House humidity programme | |
| Vaccination programme | Elancoban (starter ration) |
| Ventilation - Air changes/hr | |

| Ingredients | Starter (%) | Finisher (%) |
|---|---|---|
| Diet formulation and feeding schedule | | |
| Maize | 55.55 | 59.22 |
| Rye | 5.00 | 9.00 |
| SBM (48% CP) | 33.47 | 24.79 |
| Soy Oil | 1.85 | 3.06 |
| Salt | 0.41 | 0.33 |
| DL Methionine | 0.21 | 0.14 |
| Lysine HCl | 0.05 | 0.10 |
| Limestone | 1.18 | 1.15 |
| Dicalcium Phosphate | 1.48 | 1.41 |
| Vit/Min | 0.50 | 0.50 |
| TiO2 | 0.30 | 0.30 |
| TOTAL | 100.00 | 100.00 |
| Nutrient Provision (calculated) | | |
| CP (%) | 21.50 | 18.06 |
| ME (kcal/kg) | 3000.0 | 3125.0 |
| ME (MJ/kg) | 12.55 | 13.08 |
| Calcium (%) | 0.90 | 0.85 |
| Phos (%) | 0.68 | 0.63 |
| Av. Phos (%) | 0.40 | 0.38 |
| Fat (%) | 4.48 | 5.73 |
| Fibre (%) | 2.59 | 2.48 |
| Met (%) | 0.55 | 0.43 |
| Cys (%) | 0.36 | 0.32 |
| Met + Cys (%) | 0.91 | 0.75 |
| Lys (%) | 1.20 | 1.00 |
| Try (%) | 0.25 | 0.20 |
| Na (%) | 0.18 | 0.15 |

The feed is prepared as a mash, either with or without a lipolytic enzyme according to the present invention.

Diets and water are offered ad libitum. Test diets are fed continuously throughout the trial period. The feed samples are optionally supplemented with a lipolytic enzyme according to the present invention at 330 g/tonne. The enzyme may be added as a dry enzyme whilst mixing the feed.

Observations are taken at:

| Live weight (cage basis): | day 0, 21 and 42 |
|---|---|
| Weight gain: | 0-21 d, 22-42 d, 0-42days |

-continued

| | |
|---|---|
| Feed Intake: | 0-21 d, 22-42 d, 0-42days |
| FCR (food conversion rate): | 0-21 d, 22-42 d, 0-42days |
| Collection of ileal contents: | day 21 and 42 |

Total cage weights for feed and birds are determined, as well as total mortality weight and number of birds for each cage per period analysed. Feed consumption per cage is determined uncorrected for mortality. Feed conversion efficiency data is determined as total consumption per live weight and total weight (including mortality weight) basis.

Prior to the study start the animals are examined for signs of ill health and injury. Any that appear to be in poor condition are removed from the study.

Study animals are assigned to their treatment groups using a randomisation technique. Animals and their storage pens are uniquely identified before the start of administration of test feed.

Data from the treated groups are compared with those of their relevant control group using the appropriate statistical tests and accepting a level of probability of less than 0.05 as indicating significance.

Body weights, food intakes and food conversion rates are analysed by analysis of variance and least significant difference tests.

| Animals | |
|---|---|
| Treatment Number | 2 |
| Number of replicates | 13 to 21 days and 9 to 42 days |
| Animals per replicate | 8 to 21 days and 2 to 42 days |
| Species of Animal | Broiler |
| Breed of animal | Ross |
| Sex | Male |
| Age of test animals | 0-42 d |
| Weights of test animals | ~40 g |
| Diet/Housing | |
| Diet Information | See above |
| Diet Form | Mash |
| Coccidiostat Starter | None |
| Coccidiostat Finisher | None |
| Growth Promoter Starter | None |
| Growth Promoter Finisher | None |

Main Measurements made

| | |
|---|---|
| Variables | weight gain, feed conversion, nutrient digestibility |
| When Enzymes/additives | 0-21 d, 22-42 d |
| Enzymes used (1) | Lipolytic enzyme from *Fusarium semitectum* and/or *Fusarium heterosporum* - 330 g/Tonne |

Example 16

Evaluation of the Effect of a *Fusarium heterosporum* CBS 782.83 Lipolytic Enzyme on Instant Noodle Duality Made from Chinese Flour Introduction The instant noodle (IN) market has seen a phenomenal growth in the last 5-8 years in SE Asia, and to some extent in Europe and USA. This growth is evident even in regions that are traditionally rice and/or pasta based markets (Food Navigator, 2000). The recent popularity of IN can be mainly attributed to its very affordable cost, convenience and clean production procedures.

Flour with an average protein content (9-11%), low ash value (~0.50%), high $L^*$ (85) brightness and $b^*$ (>8.0) yellowness and high starch paste viscosity (<750 BU) produces a creamy/yellow coloured instant noodle (IN) and has the desired mouth feel characteristics. There are several different types of noodles consumed, each with specific flour quality characteristics that impact on end product quality.

Meeting end user demands is challenging in the flour industry owing to the large number of end products and wide range of customer expectations. Specifically designed ingredients and additives at the right doses play a very important role in improving taste, texture, appearance, shelf life and/or nutritive value of the final end product.

Whilst the importance of colour and texture of cooked IN cannot be underestimated, customers are getting increasingly discerning and health conscious and are seeking low fat alternatives without compromising on quality.

A lipolytic enzyme according to the present invention was tested on Chinese flour in order to evaluate the effect on fat content of IN and study the changes to texture and colour during processing.

Materials and Methods

The standard Agrifood Technology procedure for IN production and an extended evaluation method was used for this project. Chinese flour was used as the control flour and was run at the start of each day. The protein content, moisture, ash, colour, wet gluten and diastatic activity of the Chinese flour were measured using AACC (American Association for Clinical Chemistry) approved methods. Dough rheology tests included: farinogram, extensogram (45 min pull), alveogram and amylogram.

The IN production can be summarized as follows:

Each batch of IN was made from 350 g flour and mixed at low speed during which 33 parts of aqueous salt solution containing 1% sodium chloride and 0.2% alkaline salts (potassium carbonate:sodium carbonate in the ratio 6:4) was gradually added. For dosed samples, the flour was mixed thoroughly with the measured amount of ingredient prior to the addition of the aqueous salty solution.

The crumbly dough was mixed for a further 4 minutes at medium speed and sheeted 8 times. Sheeting commenced with a steel compactor, followed by two plastic fluted rollers and finally by five stainless steel smooth rollers, with a 30% reduction ratio between each roll. The final dough sheet thickness was 1.35 mm. The dough sheet was sheeted once more prior to cutting. The differential in speed between the cutting rolls and the conveyor belt resulted in tight curls being formed. The tightly curled noodle strands were steamed for two minutes, fried in palm oil on both sides at 180° C. for 1 minute. The noodle blocks were cooled and packed in clip seal bags for further analyses.

Samples were collected at several stages of production for analyses. The colour and particle size of the crumb were measured using the Minolta Chromameter and the vernier calipers, respectively. The colour of the dough sheet and the final product were recorded with the Minolta Chromameter and a digital photo was taken of both (not shown). Water activity measurements were conducted on the steamed noodles. Water activity may be measured by determining the weight of the steamed noodles, both immediately after steaming and after complete removal of water content by drying in an oven at 90° C.—the water content can then be determined by dividing the weight difference before and after drying by the weight after drying.

Optimal cooking time, cooking yield, cooking losses (gravimetric method), colour and texture (firmness) of cooked noodles were measured using standard Agrifood Technology procedures known to a person skilled in the art. Texture profile analysis (TPA) was also conducted on cooked noodle texture in order to measure cohesiveness, springiness and chewiness.

Cohesiveness is defined as how well the product withstands a second deformation relative to how it behaved under the first deformation. It is measured as the area of work during the second compression divided by the area of work during the first compression and hence has no units of measurements. Cohesiveness, in this instance relates to product 'al-dente', which is not a desirable attribute for IN.

Springiness is defined as how well a product physically springs back after it has been deformed during the first compression. Springiness is measured in several ways, but most typically, by the distance of the detected height of the product on the second compression.

Chewiness only applies to solid products, and is calculated as gumminess multiplied by springiness. Chewiness is mutually exclusive with gumminess.

One noodle block representing each dosage rate was ground in a coffee grinder and a homogenous sub sample was used for fat analysis by acid hydrolysis method (alternative standard methods for determining fat content may be used).

Results and Discussion

The protein content and colour (with respect to brightness, L*) of the flour was within the acceptable range for the production of instant noodles. The water absorption was slightly on the higher end for IN production; however, as the noodle dough is quite crumbly it did not impact machinability.

The flour had good single (extensogram) and bi-axial (alveogram) extensibility, which would have a positive impact on the eating qualities of the noodle. Peak viscosity of the amylograph was 870 BU, which is desirable for IN.

Cooking loss of IN containing the second highest dose of lipolytic enzyme was higher than the control and the 1N containing the least amount of the lipolytic enzyme according to the present invention. The fat content of IN with the highest amount of the lipolytic enzyme was significantly lower than the control and the experimental IN with the lowest amount of lipolytic enzyme. Springiness and chewiness of some experimental IN were better than the control. Based on this data, the lipolytic enzyme should be investigated further at different dosages.

Conclusions

Some of the salient points that can be made from this study are:

The addition to IN of a lipolytic enzyme according to the present invention did not dramatically impact on crumb size, dough stickiness, machinability or processing characteristics. Importantly, increasing dosages of lipolytic enzyme resulted in a reduction in fat content of IN. Lipolytic enzyme improved noodle firmness at increasing doses compared to control while cohesiveness was not affected. Lipolytic enzyme had a positive effect on yellowness of cooked noodles.

Thus, lipolytic enzyme reduced fat content in IN, improved texture and increased yellowness of cooked noodles.

All publications mentioned in the above specification are herein incorporated by reference. Various modifications and variations of the described methods and system of the present invention will be apparent to those skilled in the art without departing from the scope and spirit of the present invention. Although the present invention has been described in connection with specific preferred embodiments, it should be understood that the invention as claimed should not be unduly limited to such specific embodiments. Indeed, various modifications of the described modes for carrying out the invention which are obvious to those skilled in biochemistry and biotechnology or related fields are intended to be within the scope of the following claims.

The invention will now be further described by the following numbered paragraphs:

1. A fungal wild-type lipolytic enzyme having a higher ratio of activity on polar lipids compared with triglycerides.
2. A fungal lipolytic enzyme according to paragraph 1 wherein the enzyme has a phospholipid:kiglyceride hydrolysing activity ratio of at least 4.
3. A fungal lipolytic enzyme according to paragraph 1 wherein the enzyme has a glycolipid:kiglyceride hydrolysing activity ratio of at least 1.5.
4. A fungal lipolytic enzyme wherein the enzyme comprises an amino acid sequence as shown in SEQ ID No. 1 or SEQ ID No. 2 or an amino acid sequence which has at least 90% identity thereto.
5. A fungal lipolytic enzyme according to any one of the preceding paragraphs wherein the enzyme is obtainable from a filamentous fungus
6. A fungal lipolytic enzyme according to any one of the preceding paragraphs wherein the enzyme is obtainable from *Fusarium* spp.
7. A fungal lipolytic enzyme according to paragraph 6, wherein the enzyme is obtainable from *Fusarium heterosporum*.
8. A fungal, lipolytic enzyme according to paragraph 7 wherein the enzyme is obtainable from *Fusarium heterosporum* CBS 782.83.
9. A nucleotide sequence encoding a fungal lipolytic enzyme according to any one of paragraphs 4-8.
10. A nucleic acid encoding a fungal lipolytic enzyme, which nucleic acid is selected from the group consisting of: a) a nucleic acid comprising a nucleotide sequence shown in SEQ ID No. 3; b) a nucleic acid which is related to Me nucleotide sequence of SEQ ID No. 3 by the degeneration of the genetic code; and c) a nucleic acid comprising a nucleotide sequence which has at least 90% identity with the nucleotide sequence shown in SEQ ID No. 3.
11. A method of making a foodstuff comprising adding the fungal lipolytic enzyme according to any one of paragraphs 1-8 to one or more ingredients of the foodstuff.
12. A method of making a baked product comprising adding a fungal lipolytic enzyme according to any one of paragraphs 1-8 to a dough and baking the dough to make the baked product.
13. A method according to paragraph 11 wherein the foodstuff is one or more of: egg or an egg-based product; a baked product; confectionery; a frozen product; a dairy product including a cheese; a mousse; a whipped vegetable cream; an edible oil and fat; an aerated and non-aerated whipped product; an oil-in-water emulsions and water-in-oil emulsions; margarine; shortening, a spread, including low fat and very low fat spreads; a dressing; mayonnaise; a dip; a cream based sauce; a cream based soup; a beverage; a spice emulsion and a sauce.

14. A method of preparing a lyso-phospholipid comprising treating a phospholipid with the fungal lipolytic enzyme according to any one of paragraphs 1-8 to produce the lyso-phospholipid.
15. A method of preparing a lyso-glycolipid comprising treating a glycolipid with a fungal lipolytic enzyme according to any one of paragraphs 1-8 to produce a lyso glycolipid.
16. A process of enzymatic degumming of vegetable or edible oils, comprising treating the edible or vegetable oil with a fungal lipolytic enzyme according to any one of paragraphs 1-8 so as to hydrolyse a major part of the polar lipids present therein.
17. A foodstuff obtained by the method according to paragraph 11.
18. A baked product obtained by the method of paragraph 12.
19. A fungal lipolytic enzyme as generally hereinbefore described with reference to the description and drawings.

The invention claimed is:

1. An isolated fungal lipolytic enzyme wherein the fungal lipolytic enzyme comprises:
   a) the amino acid sequence as shown in SEQ ID NO: 1,
   b) the amino acid sequence as shown in SEQ ID NO: 2,
   c) the amino acid sequence as shown in SEQ ID NO: 4,
   d) the amino acid sequence as shown in SEQ ID NO: 6,
   e) an amino acid sequence which has at least 90% identity to SEQ ID NO: 1,
   f) an amino acid sequence which has at least 90% identity to SEQ ID NO: 2,
   g) an amino acid sequence which has at least 90% identity to SEQ ID NO: 4, or
   h) an amino acid sequence which has at least 90% identity to SEQ ID NO: 6.

2. The isolated fungal lipolytic enzyme according to claim wherein the enzyme has a phospholipid:triglyceride hydrolysing activity ratio of at least 4.

3. The isolated fungal lipolytic enzyme according to claim 1 wherein the enzyme has a glycolipid:triglyceride hydrolysing activity ratio of at least 1.5.

4. The isolated fungal lipolytic enzyme according to claim 1 wherein the enzyme is obtained from a filamentous fungus.

5. The isolated fungal lipolytic enzyme according to claim 4 wherein the enzyme is obtained from *Fusarium spp.*

6. The isolated fungal lipolytic enzyme according to claim 5, wherein the enzyme is obtained from *Fusarium heterosporum*.

7. The isolated fungal lipolytic enzyme according to claim 6 wherein the enzyme is obtained from *Fusarium heterosporum* CBS 782.83.

8. A method of making a foodstuff comprising adding the fungal lipolytic enzyme according to claim 1 to one or more ingredients of the foodstuff.

9. A method of making a baked product comprising adding a fungal lipolytic enzyme according to claim 1 to a dough and baking the dough to make the baked product.

10. A method according to claim 8 wherein the foodstuff is one or more of: egg or an egg-based product; a baked product; confectionery; a frozen product; a dairy product including a cheese; a mousse; a whipped vegetable cream; an edible oil and fat; an aerated and non-aerated whipped product; an oil-in-water emulsions and water-in-oil emulsions; margarine; shortening, a spread, including low fat and very low fat spreads; a dressing; mayonnaise; a dip; a cream based sauce; a cream based soup; a beverage; a spice emulsion and a sauce.

11. A method of preparing a lyso-phospholipid comprising treating a phospholipid with the fungal lipolytic enzyme according to claim 1 to produce the lyso-phospholipid.

12. A method of preparing a lyso-glycolipid comprising treating a glycolipid with a fungal lipolytic enzyme according to claim 1 to produce a lyso glycolipid.

13. A process of enzymatic degumming of vegetable or edible oils, comprising treating the edible or vegetable oil with a fungal lipolytic enzyme according to claim 1 so as to hydrolyse a major part of the polar lipids present therein.

* * * * *

UNITED STATES PATENT AND TRADEMARK OFFICE
CERTIFICATE OF CORRECTION

PATENT NO. : 7,622,290 B2
APPLICATION NO. : 11/519734
DATED : November 24, 2009
INVENTOR(S) : Brunstedt et al.

It is certified that error appears in the above-identified patent and that said Letters Patent is hereby corrected as shown below:

Column 95, Claim 2, line 28 should read

2. The isolated fungal lipolytic enzyme according to claim --1-- wherein the enzyme has a phospholipid:triglyceride hydrolysing activity ratio of at least 4.

Signed and Sealed this

Sixteenth Day of March, 2010

David J. Kappos
*Director of the United States Patent and Trademark Office*

SEQUENCE LISTING

<160> NUMBER OF SEQ ID NOS: 11

<210> SEQ ID NO 1
<211> LENGTH: 275
<212> TYPE: PRT
<213> ORGANISM: Fusarium heterosporum

<400> SEQUENCE: 1

```
Ala Val Gly Val Thr Ser Thr Asp Phe Thr Asn Phe Lys Phe Tyr Ile
1               5                   10                  15

Gln His Gly Ala Ala Ala Tyr Cys Asn Ser Gly Thr Ala Ala Gly Ala
            20                  25                  30

Lys Ile Thr Cys Ser Asn Asn Gly Cys Pro Thr Ile Glu Ser Asn Gly
        35                  40                  45

Val Thr Val Val Ala Ser Phe Thr Gly Ser Lys Thr Gly Ile Gly Gly
    50                  55                  60

Tyr Val Ser Thr Asp Ser Ser Arg Lys Glu Ile Val Val Ala Ile Arg
65                  70                  75                  80

Gly Ser Ser Asn Ile Arg Asn Trp Leu Thr Asn Leu Asp Phe Asp Gln
                85                  90                  95

Ser Asp Cys Ser Leu Val Ser Gly Cys Gly Val His Ser Gly Phe Gln
            100                 105                 110

Asn Ala Trp Ala Glu Ile Ser Ala Gln Ala Ser Ala Ala Val Ala Lys
        115                 120                 125

Ala Arg Lys Ala Asn Pro Ser Phe Lys Val Val Ala Thr Gly His Ser
    130                 135                 140

Leu Gly Gly Ala Val Ala Thr Leu Ser Ala Ala Asn Leu Arg Ala Ala
145                 150                 155                 160

Gly Thr Pro Val Asp Ile Tyr Thr Tyr Gly Ala Pro Arg Val Gly Asn
                165                 170                 175

Ala Ala Leu Ser Ala Phe Ile Ser Asn Gln Ala Gly Gly Glu Phe Arg
            180                 185                 190

Val Thr His Asp Lys Asp Pro Val Pro Arg Leu Pro Pro Leu Ile Phe
        195                 200                 205

Gly Tyr Arg His Thr Thr Pro Glu Tyr Trp Leu Ser Gly Gly Gly Gly
    210                 215                 220

Asp Lys Val Asp Tyr Ala Ile Ser Asp Val Lys Val Cys Glu Gly Ala
225                 230                 235                 240

Ala Asn Leu Met Cys Asn Gly Gly Thr Leu Gly Leu Asp Ile Asp Ala
                245                 250                 255

His Leu His Tyr Phe Gln Ala Thr Asp Ala Cys Asn Ala Gly Gly Phe
            260                 265                 270

Ser Trp Arg
    275
```

```
<210> SEQ ID NO 2
<211> LENGTH: 360
<212> TYPE: PRT
<213> ORGANISM: Fusarium heterosporum

<400> SEQUENCE: 2

Met Arg Phe Pro Ser Ile Phe Thr Ala Val Leu Phe Ala Ala Ser Ser
1               5                   10                  15

Ala Leu Ala Ala Pro Val Asn Thr Thr Thr Glu Asp Glu Thr Ala Gln
            20                  25                  30

Ile Pro Ala Glu Ala Val Ile Gly Tyr Ser Asp Leu Glu Gly Asp Phe
        35                  40                  45

Asp Val Ala Val Leu Pro Phe Ser Asn Ser Thr Asn Asn Gly Phe Leu
    50                  55                  60

Phe Ile Asn Thr Thr Ile Ala Ser Ile Ala Ala Lys Glu Glu Gly Val
65                  70                  75                  80

Ser Leu Asp Lys Arg Ala Val Gly Val Thr Ser Thr Asp Phe Thr Asn
                85                  90                  95

Phe Lys Phe Tyr Ile Gln His Gly Ala Ala Ala Tyr Cys Asn Ser Gly
            100                 105                 110

Thr Ala Gly Ala Lys Ile Thr Cys Ser Asn Asn Gly Cys Pro Thr
        115                 120                 125

Ile Glu Ser Asn Gly Val Thr Val Ala Ser Phe Thr Gly Ser Lys
130                 135                 140

Thr Gly Ile Gly Gly Tyr Val Ser Thr Asp Ser Ser Arg Lys Glu Ile
145                 150                 155                 160

Val Val Ala Ile Arg Gly Ser Ser Asn Ile Arg Asn Trp Leu Thr Asn
                165                 170                 175

Leu Asp Phe Asp Gln Ser Asp Cys Ser Leu Val Ser Gly Cys Gly Val
            180                 185                 190

His Ser Gly Phe Gln Asn Ala Trp Ala Glu Ile Ser Ala Gln Ala Ser
        195                 200                 205

Ala Ala Val Ala Lys Ala Arg Lys Ala Asn Pro Ser Phe Lys Val Val
    210                 215                 220

Ala Thr Gly His Ser Leu Gly Gly Ala Val Ala Thr Leu Ser Ala Ala
225                 230                 235                 240

Asn Leu Arg Ala Ala Gly Thr Pro Val Asp Ile Tyr Thr Tyr Gly Ala
                245                 250                 255

Pro Arg Val Gly Asn Ala Ala Leu Ser Ala Phe Ile Ser Asn Gln Ala
            260                 265                 270

Gly Gly Glu Phe Arg Val Thr His Asp Lys Asp Pro Val Pro Arg Leu
        275                 280                 285

Pro Pro Leu Ile Phe Gly Tyr Arg His Thr Thr Pro Glu Tyr Trp Leu
    290                 295                 300

Ser Gly Gly Gly Gly Asp Lys Val Asp Tyr Ala Ile Ser Asp Val Lys
305                 310                 315                 320

Val Cys Glu Gly Ala Ala Asn Leu Met Cys Asn Gly Thr Leu Gly
                325                 330                 335

Leu Asp Ile Asp Ala His Leu His Tyr Phe Gln Ala Thr Asp Ala Cys
            340                 345                 350

Asn Ala Gly Gly Phe Ser Trp Arg
        355                 360
```

-continued

```
<210> SEQ ID NO 3
<211> LENGTH: 825
<212> TYPE: DNA
<213> ORGANISM: Fusarium heterosporum

<400> SEQUENCE: 3
gccgttggag tgacctctac tgacttcact aactttaagt tctacattca gcatggtgct      60
gccgcatact gtaactccgg taccgccgca ggtgcaaaga tcacttgttc gaataacggt     120
tgccctacta tcgagtccaa cggcgtgact gtggtcgcct ccttcactgg ttcgaagact     180
ggcatcggcg gttacgtgtc caccgatagc tcgagaaaag agatcgtggt cgcaatcaga     240
ggttccagca acatccggaa ttggctgact aatcttgact ttgaccagtc cgactgttcc     300
cttgtttcgg gctgtggtgt tcactccggt ttccagaacg cttgggccga gatctccgca     360
caggcctcgg ctgccgtggc aaaagctaga aaggccaacc catccttcaa ggttgtcgcc     420
actggccact cgctcggcgg cgctgtggcg accctgtccg ctgccaacct tcgagctgca     480
ggtactccag tcgacatcta cacttatggt gcacctagag ttggcaacgc cgcactgtct     540
gctttcatct cgaaccaagc aggcggtgaa tttagagtca ctcacgacaa ggacccagtg     600
cctcggcttc cacctctgat cttcggttac agacacacta ccccagagta ctggctgtca     660
ggtggcggcg gagacaaggt ggactacgca atctccgacg tgaaggtctg cgagggagcc     720
gcaaacctca tgtgtaacgg cggtacactg ggactggaca tcgacgcaca cttgcactac     780
ttccaggcaa ctgatgcttg caacgccgga ggtttctcct ggaga                     825

<210> SEQ ID NO 4
<211> LENGTH: 352
<212> TYPE: PRT
<213> ORGANISM: Fusarium semitectum

<400> SEQUENCE: 4

Met Arg Val Leu Ser Leu Leu Ser Val Ala Thr Phe Ala Val Ala Ser
1               5                   10                  15

Pro Leu Ser Val Glu Asp Tyr Ala Lys Ala Leu Asp Glu Arg Ala Val
            20                  25                  30

Ala Val Ser Asn Gly Asp Phe Gly Asn Phe Lys Phe Tyr Ile Gln His
        35                  40                  45

Gly Ala Ala Ser Tyr Cys Asn Ser Asn Ala Ala Ala Gly Ala Lys Ile
    50                  55                  60

Thr Cys Gly Asn Asn Gly Cys Pro Thr Val Gln Ser Asn Gly Ala Thr
65                  70                  75                  80

Ile Val Ala Ser Phe Thr Gly Ser Lys Thr Gly Ile Gly Gly Tyr Val
                85                  90                  95

Ser Thr Asp Ser Ser Arg Lys Glu Ile Val Leu Ser Val Arg Gly Ser
            100                 105                 110

Ile Asn Ile Arg Asn Trp Leu Thr Asn Leu Asp Phe Gly Gln Glu Asp
        115                 120                 125

Cys Ser Leu Thr Ser Gly Cys Gly Val His Ser Gly Phe Gln Asn Ala
    130                 135                 140

Trp Lys Glu Ile Ser Ala Ala Ala Thr Ala Ala Val Ala Lys Ala Arg
145                 150                 155                 160

Lys Ala Asn Pro Ser Phe Lys Val Ile Ala Thr Gly His Ser Leu Gly
                165                 170                 175

Gly Ala Val Ala Thr Leu Ala Gly Ala Asn Leu Arg Val Gly Gly Thr
            180                 185                 190
```

```
Pro Val Asp Ile Tyr Thr Tyr Gly Ser Pro Arg Val Gly Asn Ser Gln
            195                 200                 205

Leu Ala Gly Phe Ile Ser Asn Gln Ala Gly Gly Glu Phe Arg Val Thr
        210                 215                 220

Asn Ala Lys Asp Pro Val Pro Arg Leu Pro Pro Leu Val Phe Gly Tyr
225                 230                 235                 240

Arg His Thr Ser Pro Glu Tyr Trp Leu Ser Gly Ala Gly Gly Asp Lys
                245                 250                 255

Val Asp Tyr Thr Ile Asn Asp Ile Lys Val Cys Glu Gly Ala Ala Asn
            260                 265                 270

Leu Lys Cys Asn Gly Gly Thr Leu Gly Leu Asp Ile Asp Ala His Leu
        275                 280                 285

His Tyr Phe Gln Glu Thr Asp Ala Cys Ser Gly Gly Gly Ile Ser Trp
    290                 295                 300

Arg Ser Arg Arg Tyr Arg Ser Ala Lys Arg Glu Asp Ile Ser Glu Arg
305                 310                 315                 320

Ala Ala Pro Met Thr Asp Ala Glu Leu Glu Lys Lys Leu Asn Asn Tyr
                325                 330                 335

Val Glu Met Asp Lys Glu Tyr Val Lys Asn Asn Ala Ala Arg Thr Ser
            340                 345                 350

<210> SEQ ID NO 5
<211> LENGTH: 1236
<212> TYPE: DNA
<213> ORGANISM: Fusarium semitectum

<400> SEQUENCE: 5
gggggggata tcttcgccag tttcagtgtt cagtatcctt tctgagggag tcgcacttgt      60
cacagcttgt ctatcactta taccttgat ccatacccct gcctgtcaag atgcgtgtcc     120
```

<210> SEQ ID NO 6
<211> LENGTH: 279
<212> TYPE: PRT
<213> ORGANISM: Fusarium heterosporum

<400> SEQUENCE: 6

| Glu | Ala | Glu | Ala | Ala | Val | Gly | Val | Thr | Ser | Thr | Asp | Phe | Thr | Asn | Phe |
|-----|-----|-----|-----|-----|-----|-----|-----|-----|-----|-----|-----|-----|-----|-----|-----|
| 1 | | | | 5 | | | | | 10 | | | | | 15 | |

| Lys | Phe | Tyr | Ile | Gln | His | Gly | Ala | Ala | Tyr | Cys | Asn | Ser | Gly | Thr |
|-----|-----|-----|-----|-----|-----|-----|-----|-----|-----|-----|-----|-----|-----|-----|
| | | | 20 | | | | 25 | | | | 30 | | | |

| Ala | Ala | Gly | Ala | Lys | Ile | Thr | Cys | Ser | Asn | Asn | Gly | Cys | Pro | Thr | Ile |
|-----|-----|-----|-----|-----|-----|-----|-----|-----|-----|-----|-----|-----|-----|-----|-----|
| | | 35 | | | | 40 | | | | | 45 | | | | |

| Glu | Ser | Asn | Gly | Val | Thr | Val | Val | Ala | Ser | Phe | Thr | Gly | Ser | Lys | Thr |
|-----|-----|-----|-----|-----|-----|-----|-----|-----|-----|-----|-----|-----|-----|-----|-----|
| | 50 | | | | | 55 | | | | | 60 | | | | |

| Gly | Ile | Gly | Gly | Tyr | Val | Ser | Thr | Asp | Ser | Ser | Arg | Lys | Glu | Ile | Val |
|-----|-----|-----|-----|-----|-----|-----|-----|-----|-----|-----|-----|-----|-----|-----|-----|
| 65 | | | | | 70 | | | | | 75 | | | | | 80 |

| Val | Ala | Ile | Arg | Gly | Ser | Ser | Asn | Ile | Arg | Asn | Trp | Leu | Thr | Asn | Leu |
|-----|-----|-----|-----|-----|-----|-----|-----|-----|-----|-----|-----|-----|-----|-----|-----|
| | | | | 85 | | | | | 90 | | | | | 95 | |

| Asp | Phe | Asp | Gln | Ser | Asp | Cys | Ser | Leu | Val | Ser | Gly | Cys | Gly | Val | His |
|-----|-----|-----|-----|-----|-----|-----|-----|-----|-----|-----|-----|-----|-----|-----|-----|
| | | | | 100 | | | | | 105 | | | | | 110 | |

| Ser | Gly | Phe | Gln | Asn | Ala | Trp | Ala | Glu | Ile | Ser | Ala | Gln | Ala | Ser | Ala |
|-----|-----|-----|-----|-----|-----|-----|-----|-----|-----|-----|-----|-----|-----|-----|-----|
| | | | 115 | | | | | 120 | | | | | 125 | | |

| Ala | Val | Ala | Lys | Ala | Arg | Lys | Ala | Asn | Pro | Ser | Phe | Lys | Val | Val | Ala |
|-----|-----|-----|-----|-----|-----|-----|-----|-----|-----|-----|-----|-----|-----|-----|-----|
| | | 130 | | | | | 135 | | | | | 140 | | | |

| Thr | Gly | His | Ser | Leu | Gly | Gly | Ala | Val | Ala | Thr | Leu | Ser | Ala | Ala | Asn |
|-----|-----|-----|-----|-----|-----|-----|-----|-----|-----|-----|-----|-----|-----|-----|-----|
| 145 | | | | | 150 | | | | | 155 | | | | | 160 |

| Leu | Arg | Ala | Ala | Gly | Thr | Pro | Val | Asp | Ile | Tyr | Thr | Tyr | Gly | Ala | Pro |
|-----|-----|-----|-----|-----|-----|-----|-----|-----|-----|-----|-----|-----|-----|-----|-----|
| | | | | 165 | | | | | 170 | | | | | 175 | |

| Arg | Val | Gly | Asn | Ala | Ala | Leu | Ser | Ala | Phe | Ile | Ser | Asn | Gln | Ala | Gly |
|-----|-----|-----|-----|-----|-----|-----|-----|-----|-----|-----|-----|-----|-----|-----|-----|
| | | | 180 | | | | | 185 | | | | | 190 | | |

| Gly | Glu | Phe | Arg | Val | Thr | His | Asp | Lys | Asp | Pro | Val | Pro | Arg | Leu | Pro |
|-----|-----|-----|-----|-----|-----|-----|-----|-----|-----|-----|-----|-----|-----|-----|-----|
| | | | 195 | | | | | 200 | | | | | 205 | | |

| Pro | Leu | Ile | Phe | Gly | Tyr | Arg | His | Thr | Thr | Pro | Glu | Tyr | Trp | Leu | Ser |
|-----|-----|-----|-----|-----|-----|-----|-----|-----|-----|-----|-----|-----|-----|-----|-----|
| | 210 | | | | | 215 | | | | | 220 | | | | |

| Gly | Gly | Gly | Gly | Asp | Lys | Val | Asp | Tyr | Ala | Ile | Ser | Asp | Val | Lys | Val |
|-----|-----|-----|-----|-----|-----|-----|-----|-----|-----|-----|-----|-----|-----|-----|-----|
| 225 | | | | | 230 | | | | | 235 | | | | | 240 |

| Cys | Glu | Gly | Ala | Ala | Asn | Leu | Met | Cys | Asn | Gly | Gly | Thr | Leu | Gly | Leu |
|-----|-----|-----|-----|-----|-----|-----|-----|-----|-----|-----|-----|-----|-----|-----|-----|
| | | | | 245 | | | | | 250 | | | | | 255 | |

| Asp | Ile | Asp | Ala | His | Leu | His | Tyr | Phe | Gln | Ala | Thr | Asp | Ala | Cys | Asn |
|-----|-----|-----|-----|-----|-----|-----|-----|-----|-----|-----|-----|-----|-----|-----|-----|
| | | | 260 | | | | | 265 | | | | | 270 | | |

| Ala | Gly | Gly | Phe | Ser | Trp | Arg |
|-----|-----|-----|-----|-----|-----|-----|
| | | | 275 | | | |

<210> SEQ ID NO 7
<211> LENGTH: 1257
<212> TYPE: DNA
<213> ORGANISM: Fusarium heterosporum

<400> SEQUENCE: 7

| agaattcaaa cgatgagatt cccatccatc tttaccgctg ttctgttcgc cgcttcctcc | 60 |
| gccctggctg ccccagtcaa cactaccact gaggacgaga ctgctcagat tccagctgag | 120 |
| gctgtcatcg ttactctgaa cctggagggt gacttcgatg ttgctgtttt gccattctcc | 180 |
| aactccacca caacggtttt cttgttcatc aacactacca ttgcctccat tgctgccaag | 240 |

```
gaggaaggtg tttccttgga caagagagct gttgctgtct ccaacggtga ctttggtaac      300
ttcaagttct acatccagca cggtgctgct tcatactgca actccaatgc cgcagctggt      360
gcaaagatca cctgtggaaa caatggctgt ccaacagtcc agtccaacgg tgctactatc      420
gtcgcatcct tcactggttc caagactggc atcggcggtt acgtttcgac cgactcttca      480
cgaaaggaaa tcgtcctctc cgttcgaggc agcataaaca ttcgaaactg gctcaccaac      540
ctcgacttcg gccaggagga ctgcagcttg acctcaggtt gtggagtaca cagcggtttc      600
cagaatgcct ggaaagagat tccgctgca gcaaccgctg ctgtcgcaaa ggcccgcaag       660 gcgaacccctt cgttcaaggt cattgccaca ggccactccc ttggtggtgc cgtcgctaca     720
ctcgccggcg caaatcttcg agttggtgga acaccgttg acatctacac ctacggctcc      780
ccccgagttg gaaactccca gctcgctggc ttcatctcga accaagctgg tggagagttc      840
cgcgttacca atgccaagga ccctgttccc agacttcccc ctctggtctt tggttaccga      900
cacacatccc ccgagtactg gctgtctggt gcgggaggtg acaaggttga ctacaccatc      960
aatgacatca aggtctgtga gggtgctgcc aacctcaagt gcaacggtgg aaccccttgga    1020 ttggatattg atgctcacct gcactacttc caggagactg atgcttgctc tggtggcggt    1080
atctcttgga gaagccgaag atacagaagc gccaagcgtg aggacatctc tgagagggct    1140
gctcctatga cggatgctga gcttgagaag aagctcaaca actatgtcga gatggataag    1200
gagtatgtca agaacaatgc cgcacgcacg tcatagtatg acatttacgc ggatcct       1257

<210> SEQ ID NO 8
<211> LENGTH: 37
<212> TYPE: DNA
<213> ORGANISM: Artificial Sequence
<220> FEATURE:
<223> OTHER INFORMATION: Oligonucleotide primer for CBSLip

<400> SEQUENCE: 8
tccttggaca agagagccgt tggagtgacc tctactg                              37

<210> SEQ ID NO 9
<211> LENGTH: 44
<212> TYPE: DNA
<213> ORGANISM: Artificial Sequence
<220> FEATURE:
<223> OTHER INFORMATION: Oligonucleotide primer for CBSLip

<400> SEQUENCE: 9
aggatccaat tctctccatg gcctatctcc aggagaaacc tccg                      44

<210> SEQ ID NO 10
<211> LENGTH: 37
<212> TYPE: DNA
<213> ORGANISM: Artificial Sequence
<220> FEATURE:
<223> OTHER INFORMATION: Oligonucleotide primer for alpha-signal

<400> SEQUENCE: 10
agaattcaaa cgatgagatt cccatccatc tttaccg                              37

<210> SEQ ID NO 11
<211> LENGTH: 41
<212> TYPE: DNA
<213> ORGANISM: Artificial Sequence
```

```
-continued

<220> FEATURE:
<223> OTHER INFORMATION: Oligonucleotide primer for alpha-signal

<400> SEQUENCE: 11
aggtcactcc aacggctctc ttgtccaagg aaacaccttc c                    41
```